United States Patent
Gallagher et al.

(10) Patent No.: US 10,806,717 B2
(45) Date of Patent: *Oct. 20, 2020

(54) METHODS AND COMPOSITIONS FOR IMPROVING COGNITIVE FUNCTION

(71) Applicant: The Johns Hopkins University, Baltimore, MD (US)

(72) Inventors: Michela Gallagher, Baltimore, MD (US); Rebecca Haberman, Baltimore, MD (US); Ming Teng Koh, Baltimore, MD (US); Arnold Bakker, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,576

(22) PCT Filed: Mar. 14, 2014

(86) PCT No.: PCT/US2014/029170
§ 371 (c)(1),
(2) Date: Sep. 14, 2015

(87) PCT Pub. No.: WO2014/144663
PCT Pub. Date: Sep. 18, 2014

(65) Prior Publication Data
US 2016/0038463 A1    Feb. 11, 2016

Related U.S. Application Data

(60) Provisional application No. 61/794,909, filed on Mar. 15, 2013.

(51) Int. Cl.
| | | |
|---|---|---|
| A61K 31/4015 | (2006.01) | |
| A61P 25/28 | (2006.01) | |
| A61K 31/19 | (2006.01) | |
| A61K 45/06 | (2006.01) | |
| A61B 5/00 | (2006.01) | |
| C12Q 1/6883 | (2018.01) | |
| G01N 33/68 | (2006.01) | |
| G01N 33/74 | (2006.01) | |
| G09B 3/06 | (2006.01) | |

(52) U.S. Cl.
CPC ........ *A61K 31/4015* (2013.01); *A61B 5/4088* (2013.01); *A61K 31/19* (2013.01); *A61K 45/06* (2013.01); *A61P 25/28* (2018.01); *C12Q 1/6883* (2013.01); *G01N 33/6896* (2013.01); *G01N 33/74* (2013.01); *G09B 3/06* (2013.01); *C12Q 2600/118* (2013.01); *C12Q 2600/158* (2013.01); *G01N 2333/4703* (2013.01); *G01N 2333/575* (2013.01); *G01N 2800/2814* (2013.01); *G01N 2800/52* (2013.01)

(58) Field of Classification Search
CPC .............. A61B 5/4088; A61K 31/4015; G01N 33/6996; A61P 25/28
See application file for complete search history.

(56) References Cited

U.S. PATENT DOCUMENTS

| | | |
|---|---|---|
| 2,701,225 A | 2/1955 | Lorenz et al. |
| 4,118,396 A | 10/1978 | Pifferi et al. |
| 4,145,347 A | 3/1979 | L'Italien et al. |
| 4,173,569 A | 11/1979 | Banfi et al. |
| 4,221,789 A | 9/1980 | Rodriguez et al. |
| 4,372,960 A | 2/1983 | L'Italien |
| 4,476,308 A | 10/1984 | Aschwanden et al. |
| 4,558,070 A | 12/1985 | Bauer et al. |
| 4,595,695 A | 6/1986 | Ladkani et al. |
| 4,650,878 A | 3/1987 | Aschwanden et al. |
| 4,654,370 A | 3/1987 | Marriott, III et al. |
| 4,663,318 A | 5/1987 | Davis |
| 4,668,687 A | 5/1987 | Yevich et al. |
| 4,678,801 A | 7/1987 | Kurono et al. |
| 4,696,943 A | 9/1987 | Gobert et al. |
| 4,816,456 A | 3/1989 | Summers |
| 4,837,223 A | 6/1989 | Gobert et al. |
| 4,837,224 A | 6/1989 | Gobert et al. |
| 4,895,841 A | 1/1990 | Sugimoto et al. |
| 4,895,873 A | 1/1990 | Schäfer |
| 4,913,906 A | 4/1990 | Friedman et al. |
| 4,914,102 A | 4/1990 | Glamkowski |
| 4,939,126 A | 7/1990 | Kurono et al. |
| 4,943,639 A | 7/1990 | Gobert et al. |
| 4,948,807 A | 8/1990 | Rosin et al. |
| 4,950,658 A | 8/1990 | Becker et al. |
| 4,981,870 A | 1/1991 | Koe |
| 5,017,613 A | 5/1991 | Aubert et al. |
| 5,019,398 A | 5/1991 | Daste |
| 5,034,402 A | 7/1991 | Aschwanden et al. |
| 5,049,586 A | 9/1991 | Ortega et al. |
| 5,061,725 A | 10/1991 | Giannessi et al. |
| 5,100,901 A | 3/1992 | Sugimoto et al. |

(Continued)

FOREIGN PATENT DOCUMENTS

| | | |
|---|---|---|
| AU | 08/904016 | 8/2008 |
| AU | 08/904021 | 8/2008 |

(Continued)

OTHER PUBLICATIONS

Brivaracetam, CAS Reg. No. 357336-20-0 (retrieved from STN on May 1, 2019). (Year: 2019).*

(Continued)

*Primary Examiner* — Theodore R. West
(74) *Attorney, Agent, or Firm* — Haley Guiliano LLP; James F. Haley, Jr.; Sarah E. Tully

(57) ABSTRACT

This invention relates to methods and compositions for treating cognitive impairment associated with central nervous system (CNS) disorders. In particular, it relates to the use of inhibitors of synaptic vesicle glycoprotein 2A (SV2A), alone or in combination with valproate, in treating cognitive impairment associated with central nervous system (CNS) disorders in a subject in need or at risk thereof, including, without limitation, subjects having or at risk for age-related cognitive impairment.

3 Claims, 30 Drawing Sheets

(56) References Cited

U.S. PATENT DOCUMENTS

| | | |
|---|---|---|
| 5,102,891 A | 4/1992 | Effland et al. |
| 5,106,856 A | 4/1992 | Kosley, Jr. et al. |
| 5,162,573 A | 11/1992 | Chiesi et al. |
| 5,166,181 A | 11/1992 | Cottens |
| 5,187,165 A | 2/1993 | Hamer et al. |
| 5,231,093 A | 7/1993 | Flanagan et al. |
| 5,238,945 A | 8/1993 | Perregaard et al. |
| 5,246,947 A | 9/1993 | Effland et al. |
| 5,288,758 A | 2/1994 | Vidaluc et al. |
| 5,300,517 A | 4/1994 | Hasegawa et al. |
| 5,302,593 A | 4/1994 | Alisi et al. |
| 5,338,548 A | 8/1994 | Kochinke et al. |
| 5,364,864 A | 11/1994 | Bigg et al. |
| 5,389,629 A | 2/1995 | Shutske et al. |
| 5,391,553 A | 2/1995 | Shutske et al. |
| 5,439,930 A | 8/1995 | Seredenin et al. |
| 5,440,023 A | 8/1995 | Cheng et al. |
| 5,447,952 A | 9/1995 | Wulfert et al. |
| 5,455,245 A | 10/1995 | Effland et al. |
| 5,574,046 A | 11/1996 | Chen et al. |
| 5,602,176 A | 2/1997 | Enz |
| 5,622,976 A | 4/1997 | Takasugi et al. |
| 5,663,448 A | 9/1997 | Collard et al. |
| 5,668,117 A | 9/1997 | Shapiro |
| 5,693,668 A | 12/1997 | Schirlin et al. |
| 5,744,476 A | 4/1998 | Locke et al. |
| 5,750,542 A | 5/1998 | Villalobos et al. |
| 5,856,569 A | 1/1999 | Santaniello et al. |
| 5,886,008 A | 3/1999 | Macor |
| 5,886,023 A | 3/1999 | Otomo et al. |
| 5,965,569 A | 10/1999 | Camps Garcia et al. |
| 5,965,571 A | 10/1999 | Hutchinson |
| 5,985,864 A | 11/1999 | Imai et al. |
| 6,131,106 A | 10/2000 | Steele, Jr. |
| 6,140,321 A | 10/2000 | Imai et al. |
| 6,245,911 B1 | 6/2001 | Imai et al. |
| 6,277,866 B1 | 8/2001 | Takeuchi et al. |
| 6,372,760 B1 | 4/2002 | Kato et al. |
| 6,479,523 B1 | 11/2002 | Puskas |
| 6,495,700 B1 | 12/2002 | Bruening |
| 6,555,544 B2 | 4/2003 | Francois et al. |
| 6,610,326 B2 | 8/2003 | Chen et al. |
| 6,620,802 B1 | 9/2003 | Schatzberg et al. |
| 6,706,741 B2 | 3/2004 | Iimura et al. |
| RE39,198 E | 7/2006 | Strupczewski et al. |
| 7,090,985 B2 | 8/2006 | Lynch et al. |
| 7,091,218 B1 | 8/2006 | Iimura et al. |
| 7,378,425 B2 | 5/2008 | Iimura et al. |
| 7,544,705 B2 | 6/2009 | Farina et al. |
| 7,557,137 B2 | 7/2009 | Decicco et al. |
| 7,563,808 B2 | 7/2009 | Pratt |
| 7,635,709 B2 | 12/2009 | Korsten et al. |
| 7,678,808 B2 | 3/2010 | Barlow et al. |
| 7,732,162 B2 | 6/2010 | Hoffman et al. |
| 7,846,930 B2 | 12/2010 | Keith |
| 7,858,611 B2 | 12/2010 | Barlow et al. |
| 7,863,316 B2 | 1/2011 | Kshirsagar |
| 8,058,291 B2 | 11/2011 | Went et al. |
| 8,211,936 B2 | 7/2012 | Quere |
| 8,604,075 B2 * | 12/2013 | Gallagher ............... A61K 31/19 514/424 |
| 1,015,498 A1 | 12/2018 | Gallagher |
| 10,154,988 B2 * | 12/2018 | Gallagher .......... A61K 31/4015 |
| 10,624,875 B2 | 4/2020 | Gallagher |
| 2001/0036949 A1 | 11/2001 | Coe et al. |
| 2002/0119963 A1 | 8/2002 | Sanner et al. |
| 2003/0069289 A1 | 4/2003 | Iimura et al. |
| 2003/0078252 A1 | 4/2003 | Sanner et al. |
| 2004/0063776 A1 | 4/2004 | Ueda et al. |
| 2004/0082644 A1 | 4/2004 | Korsten |
| 2004/0106147 A1 | 6/2004 | Lynch et al. |
| 2004/0116505 A1 | 6/2004 | Krauss et al. |
| 2004/0116506 A1 | 6/2004 | Krusz |
| 2004/0204388 A1 | 10/2004 | Lynch et al. |
| 2005/0124642 A1 | 6/2005 | Iimura et al. |
| 2005/0245504 A1 | 11/2005 | Corbett et al. |
| 2006/0052428 A1 | 3/2006 | Chez |
| 2006/0063707 A1 | 3/2006 | Baudry et al. |
| 2006/0165796 A1 | 7/2006 | Kshirsagar et al. |
| 2006/0276412 A1 | 12/2006 | Tollefson |
| 2007/0031513 A1 | 2/2007 | Kikuchi et al. |
| 2007/0135514 A1 | 6/2007 | Lynch et al. |
| 2007/0212428 A1 | 9/2007 | Wittlin |
| 2007/0213337 A1 | 9/2007 | Zhao |
| 2007/0244143 A1 | 10/2007 | Barlow et al. |
| 2007/0264358 A1 | 11/2007 | Wittlin |
| 2007/0275959 A1 | 11/2007 | Verheijen et al. |
| 2007/0298098 A1 | 12/2007 | Jenkins et al. |
| 2008/0014264 A1 | 1/2008 | Goffin et al. |
| 2008/0076820 A1 | 3/2008 | Otomo et al. |
| 2008/0103105 A1 | 5/2008 | Barlow et al. |
| 2008/0167291 A1 | 7/2008 | Barlow et al. |
| 2008/0242698 A1 | 10/2008 | Flor et al. |
| 2008/0261950 A1 | 10/2008 | Rupniak et al. |
| 2008/0269316 A1 | 10/2008 | Deelers |
| 2008/0045583 A1 | 12/2008 | Delmarre et al. |
| 2009/0030403 A1 | 1/2009 | Leyde |
| 2009/0074854 A1 | 3/2009 | Caron et al. |
| 2009/0123541 A1 | 5/2009 | Zala |
| 2009/0124659 A1 | 5/2009 | Moebius |
| 2009/0131508 A1 | 5/2009 | Verdru |
| 2009/0176740 A1 | 7/2009 | Phillips, II |
| 2009/0306051 A1 | 12/2009 | Meyerson et al. |
| 2010/0048634 A1 | 2/2010 | Cha |
| 2010/0087422 A1 | 4/2010 | Bird |
| 2010/0099735 A1 | 4/2010 | Gallagher et al. |
| 2010/0125096 A1 | 5/2010 | Farina et al. |
| 2010/0151018 A1 | 6/2010 | Brochart |
| 2010/0152108 A1 | 6/2010 | Hung et al. |
| 2010/0172979 A1 | 7/2010 | Yu et al. |
| 2010/0216734 A1 | 8/2010 | Barlow et al. |
| 2010/0227852 A1 | 9/2010 | Moebius |
| 2010/0297181 A1 | 11/2010 | Hanada |
| 2010/0311697 A1 | 12/2010 | Went et al. |
| 2011/0206767 A1 | 8/2011 | Zala |
| 2011/0212928 A1 | 9/2011 | Gallagher |
| 2011/0262442 A1 | 10/2011 | Hamilton |
| 2012/0046336 A1 | 2/2012 | Gallagher et al. |
| 2012/0171125 A1 | 7/2012 | Kenda et al. |
| 2012/0214859 A1 | 8/2012 | Gallagher et al. |
| 2012/0245215 A1 | 9/2012 | Quere |
| 2014/0206667 A1 | 7/2014 | Gallagher |
| 2015/0094352 A1 | 4/2015 | Gallagher |
| 2015/0313876 A1 | 11/2015 | Gallagher |
| 2016/0030391 A1 | 2/2016 | Gallagher |
| 2018/0015109 A1 | 1/2018 | Gallagher |
| 2018/0140555 A1 | 5/2018 | Gallagher |

FOREIGN PATENT DOCUMENTS

| | | |
|---|---|---|
| CA | 2180703 | 1/1998 |
| CN | 101647789 | 8/2011 |
| EP | 162036 | 11/1985 |
| EP | 0165919 | 12/1985 |
| EP | 0381959 | 8/1990 |
| EP | 0236684 | 5/1992 |
| EP | 0298202 | 8/1994 |
| EP | 0611769 | 8/1994 |
| EP | 0409676 | 3/1995 |
| EP | 0411534 | 3/1995 |
| EP | 0487071 | 7/1995 |
| EP | 0477903 | 4/1996 |
| EP | 0468187 | 3/1998 |
| EP | 1050303 | 11/2000 |
| EP | 0481429 | 1/2001 |
| EP | 1731149 | 12/2006 |
| EP | 1878844 | 1/2008 |
| EP | 2018874 | 1/2009 |
| EP | 2260839 | 12/2010 |
| EP | 2486918 | 8/2012 |
| EP | 2533645 | 7/2016 |
| JP | 4-187674 | 7/1992 |
| JP | 7-252216 | 10/1995 |
| JP | 2000-319257 | 11/2000 |

(56) References Cited

FOREIGN PATENT DOCUMENTS

| | | |
|---|---|---|
| JP | 2001-139547 | 5/2001 |
| RU | 2359675 C2 | 6/2009 |
| WO | WO1988/008708 | 11/1988 |
| WO | WO1991/003467 | 3/1991 |
| WO | WO1992/017475 | 10/1992 |
| WO | WO1992/019238 | 11/1992 |
| WO | WO1993/003034 | 2/1993 |
| WO | WO1993/003041 | 2/1993 |
| WO | WO1993/007140 | 4/1993 |
| WO | WO1993/013100 | 7/1993 |
| WO | WO1993/016690 | 9/1993 |
| WO | WO1994/019356 | 9/1994 |
| WO | WO1994/020476 | 9/1994 |
| WO | WO1994/029255 | 12/1994 |
| WO | WO1994/029272 | 12/1994 |
| WO | WO1996/040682 | 12/1996 |
| WO | WO1997/008146 | 3/1997 |
| WO | WO1997/013754 | 4/1997 |
| WO | WO1997/019059 | 5/1997 |
| WO | WO1997/021681 | 6/1997 |
| WO | WO1997/029750 | 8/1997 |
| WO | WO1997/038993 | 10/1997 |
| WO | WO1998/003510 | 1/1998 |
| WO | WO1998/030243 | 7/1998 |
| WO | WO1998/039000 | 9/1998 |
| WO | WO1999/007359 | 2/1999 |
| WO | WO1999/008672 | 2/1999 |
| WO | WO1999/047131 | 9/1999 |
| WO | WO2000/002549 | 1/2000 |
| WO | WO2000/007600 | 2/2000 |
| WO | WO2000/009483 | 2/2000 |
| WO | WO2000/015205 | 3/2000 |
| WO | WO2000/023057 | 4/2000 |
| WO | WO2000/030446 | 6/2000 |
| WO | WO2000/033840 | 6/2000 |
| WO | WO2001/000215 | 1/2001 |
| WO | WO2001/021590 | 3/2001 |
| WO | WO 2001/39779 | 6/2001 |
| WO | WO2001/066096 | 9/2001 |
| WO | WO2001/066114 | 9/2001 |
| WO | WO2001/078728 | 10/2001 |
| WO | WO2002/032412 | 4/2002 |
| WO | WO2002/074293 | 9/2002 |
| WO | WO2003/020289 | 3/2003 |
| WO | WO 2003/032981 | 4/2003 |
| WO | WO2003/082794 | 10/2003 |
| WO | WO2003/082820 | 10/2003 |
| WO | WO2003/091220 | 11/2003 |
| WO | WO2003/101458 | 12/2003 |
| WO | WO2004/032929 | 4/2004 |
| WO | WO2004/034963 | 4/2004 |
| WO | WO2004/037234 | 5/2004 |
| WO | WO2004/052348 | 6/2004 |
| WO | WO2004/080393 | 9/2004 |
| WO | WO2004/084884 | 10/2004 |
| WO | WO2004/105682 | 12/2004 |
| WO | WO2005/027975 | 3/2005 |
| WO | WO2005/035523 | 4/2005 |
| WO | WO2005/039580 | 5/2005 |
| WO | WO2005/072713 | 8/2005 |
| WO | WO2005/074535 | 8/2005 |
| WO | WO2005/079789 | 9/2005 |
| WO | WO2005/092009 | 10/2005 |
| WO | WO 2005/108358 | 11/2005 |
| WO | WO 2005/121082 | 12/2005 |
| WO | WO2006/040688 | 4/2006 |
| WO | WO2006/044176 | 6/2006 |
| WO | WO2006/060082 | 6/2006 |
| WO | WO2006/070394 | 7/2006 |
| WO | WO2006/071274 | 7/2006 |
| WO | WO2006/097588 | 9/2006 |
| WO | WO 2006/113937 | 10/2006 |
| WO | WO2007/019312 | 2/2007 |
| WO | WO 2007/104035 | 9/2007 |
| WO | WO2007/107846 | 9/2007 |
| WO | WO2007/127474 | 11/2007 |
| WO | WO2008/006528 | 1/2008 |
| WO | WO2008/062446 | 5/2008 |
| WO | WO2008/073452 | 6/2008 |
| WO | WO2008/074896 | 6/2008 |
| WO | WO 2008/095221 | 8/2008 |
| WO | WO2008/097546 | 8/2008 |
| WO | WO2009/008769 | 1/2009 |
| WO | WO 2009/011412 | 1/2009 |
| WO | WO 2009/038412 | 3/2009 |
| WO | WO 2009/109547 | 9/2009 |
| WO | WO 2010/006929 | 1/2010 |
| WO | WO 2010/015029 | 2/2010 |
| WO | WO2010/057088 | 5/2010 |
| WO | WO 2010/057870 | 5/2010 |
| WO | WO 2010/086315 | 8/2010 |
| WO | WO 2010/089372 | 8/2010 |
| WO | WO 2011/015349 | 2/2011 |
| WO | WO2011/143721 | 11/2011 |
| WO | WO2012/070785 | 5/2012 |
| WO | WO2012/109491 | 8/2012 |
| WO | WO2012/159609 | 11/2012 |
| WO | WO2013/007698 | 1/2013 |
| WO | WO 2014/078568 | 5/2014 |
| WO | WO 2014/144546 | 9/2014 |
| WO | WO 2014/144663 | 9/2014 |
| WO | WO 2014/144801 | 9/2014 |

OTHER PUBLICATIONS

Cramer et al., "Tolerability of levetiracetam in elderly patients with CNS disorders," Epilepsy Research, 56(2-3):135-145 (2003).

Fattouch et al., "Intravenous Levetiracetam as first-line treatment of status epilepticus in the elderly," Acta. Neurol. Scand., 121(6):418-421 (2010).

French et al., "Levetiracetam overall safety profile," Epilepsia, 42(S7):151 (2001).

Gaudenzi et al., "[Levetiracetam therapy in patients with epilepsy and dementia]," Bollettino—Lega Italiana contro l'Epilessia, 125-126:215-216 (2004) (English Abstract only).

Glien et al., "Effects of the novel antiepileptic drug levetiracetam on spontaneous recurrent seizures in the rat pilocarpine model of temporal lobe epilepsy," Epilepsia, 43(4):350-357 (2002).

Klatte et al., "The quality of life with levetiracetam in benign rolandic epilepsy," Epilepsia, 49 (S7):220, p. 2.108 (2008) (Abstract).

Klitgaard et al., "Evidence for a unique profile of levetiracetam in rodent models of seizures and epilepsy," Eur. J. Pharmacol., 353(2-3):191-206 (1998).

Kopp et al., "Cognitive side affects of levetiracetam in monotherapy: comparison with carbamazepine and valproate," Epilepsia, 48(S3):39-40 (2007) (Abstract).

Löscher et al., "Profile of ucb L059, a novel anticonvulsant drug, in models of partial and generalized epilepsy in mice and rats," Eur. J. Pharmacol., 232(2-3):147-158 (1993).

Meo et al., "Use of levetiracetam monotherapy in patients with post-traumatic epilepsy: Preliminary data," Epilepsia, 47(S4):162, p. 2135 (2006) (Abstract).

Shorvon et al., "Multicenter double-blind, randomized, placebo-controlled trial of levetiracetam as add-on therapy in patients with refractory partial seizures. European Levetiracetam Study Group," Epilepsia, 41(9):1179-1186 (2000).

UCB Keppra® Injectable Formulation Label Approved on Sep. 12, 2007.

UCB Keppra® Label Approved on Apr. 23, 2009.

UCB Keppra® XR Label Approved on Apr. 23, 2009.

Agam et al., "Levetiracetam does not interfere with attention to novel and targeted stimuli: An psychophysiological study," Neurology, 68(12), S1, p. 06.051 (2007) (Abstract).

Brandt et al., "Prophylactic treatment with levetiracetam after status epilepticus: lack of effect on epileptogenesis, neuronal damage, and behavioral alterations in rats," Neuropharmacology, 53(2):207-221 (2007).

Brown et al., "Impact of levetiracetam on mood and cognition during prednisone therapy," European Psychiatry, 22(7):448-452 (2007).

(56) References Cited

OTHER PUBLICATIONS

Cicolin et al., "[Levetiracetam and cognitive functions: A single blind, crossover, placebo controlled study in healthy volunteers]," Bolletinno Lega Italiana contro l'Epilessia, No. 113-114:79-81 (2001) (English Abstract only).
Cumbo et al., "Levetiracetam, lamotrigine, and phenobarbital in patients with epileptic seizures and Alzheimer's disease," Epilepsy & Behavior, 17(4):461-466 (2010).
Cumbo, "Effects of levetiracetam, phenobarbital and lamotrigine on neuropsychological performance and mood in patients with alzheimer's disease and epilepsy," Epilepsia, 50(S4):101-102 (2009).
Detrait et al., "Brivaracetam does not alter spatial learning and memory in both normal and amygdala-kindled rats," Epilepsy Research, 91(1):74-83 (2010).
Detrait et al., "Brivaracetam does not impair cognitive performance of rats in the morris water maze test," Epilepsia, 49(S7):111, p. 1.253 (2008) (Abstract).
Detrait et al., "Brivaracetam does not impair cognitive performance in normal and kindled rats," Epilepsia, 50(S10):96, p. 450 (2009) (Abstract).
Dinapoli et al., "Quality of life and seizure control in patients with brain tumor-related epilepsy treated with levetiracetam monotherapy: preliminary data of an open-label study," Neurological Sciences, 30(4):353-359 (2009).
Edelbroek et al., "Evaluation of the pharmacokinetic and neuropsychometric parameters in chronic comedicated epileptic patients of three increasing dosages of a novel, antiepileptic drug, UCB L059 250-mg capsules per Os each dose for one week followed by two-weeks of placebo," Epilepsia, 34(S2):7 (1993) (Abstract).
Fritz et al., "Effects of add-on treatment with topiramate or levetiracetam on cognition and health related quality of life in patients with epilepsy," European Journal of Neurology, 12 (S2):121 p. 1341 (2005) (Abstract).
Fritz et al., "Effects of add-on treatment with topiramate or levetiracetam on cognition and health related quality of life for patients with epilepsy," Epilepsia, 46(S6):106-107 (2005) (Abstract).
Gevins et al., "Neuropsychological and neurophysiological effects of carbamazepine and levetiracetam," Epilepsia, 47(S4):157-158,p. 2112 (2006) (Abstract).
Gomer et al., "The influence of antiepileptic drugs on cognition: a comparison of levetiracetam with topiramate," Epilepsy & Behavior, 10(3):486-494 (2007).
Guido et al., "Event-related potential sin the evaluation of the effect of levetiracetam and carbamazepine on cognitive functions in newly diagnosed epilepsy patients; preliminary results of a randomized trial," Epilepsia, 48(S7):107, p. 244 (2007) (Abstract).
Guido et al., "Event-related potentials (ERPs) in the evaluation of the effect of levetiracetam and carbamazepine on cognitive functions in adult patients with newly diagnosed epilepsy," European Journal of Neurology, 15(S3):305 (2008) (Abstract).
Haber et al., "Cognitive effects of levetiracetam in patients treated for interactable epilepsy," Epilepsia, 47( S4):97-98, p. 1.197 (2006) (Abstract).
Huang et al., "Comparative cognitive effects of levetiracetam and topiramate in intractable epilepsy," Psychiatry and Clinical Neurosciences, 62(5):548-553 (2008).
Kong et al., "Effect of antiepileptic drugs on cognitive functions and expressions of glutamate receptor 2 and synaptophysin of the hippocampus in rats," Journal of Shandong University (Health Science), 48(7):14-18 (2010) (Chinese language, English Abstract).
Lamberty et al., "Absence of negative impact of levetiracetam on cognitive function and memory in normal and amygdala-kindled rats," Epilepsy & Behavior, 1:333-342 (2000).
Lamberty et al., "Cognitive performance is unaltered by levetiracetam (ucb L059) in the pilocarpine model of chronic epilepsy," Epilepsia, 39(S2):85 (1998) (Abstract).
Lamberty et al., "Lack of negative impact on cognitive function differentiates levetiracetam (UCB L059) from other antiepileptic drugs," Epilepsia, 39(S6):45, p. 2.053 (1998) (Abstract).
Leeman et al., "Cognitive effects of treatment of focal interictal discharges with levetiracetam," Epilepsia, 49(S7):136-137, p. 1.312 (2008) (Abstract).
Levisohn et al., "Neurocognitive effects of adjunctive levetiracetam in children with partial-onset seizures: a randomized, double-blind, placebo-controlled, noninferiority trial," Epilepsia 50(11):2377-2389 (2009).
Meador et al., "Cognitive and behavioral effects of carbamazepine and levetiracetam in healthy volunteers: S09.002: 2:15 pm," Neurology, 66(S2) p. A72 (2006) (Abstract).
Meador et al., "Neurocognitive effects of brivaracetam, levetiracetam, and lorazepam," Epilepsia, 52(2):264-272 (2011).
Meador et al., "Neuropsychological and neurophysiologic effects of carbamazepine and levetiracetam," Neurology, 69(22):2076-2084 (2007).
Mechtler et al., "Efficacy of intravenous levetiracem in the treatment of status migrainosus," Headache, 48( S1):S45-S46, S16 (2008) (Abstract).
Minervini et al., "Mild cognitive impairment, focal epilepsy and levetiracetam," Epilepsia, 49(S7):110, p. 256 (2007) (Abstract).
Mintz et al., "Double-blind, placebo-controlled, non-inferiority study to evaluate the cognitive and neuropsychological effects of levetiracetam 20-60 mg/kg/day as adjunctive treatment versus placebo in pediatric patients with partial-onset seizures," Epilepsia, 48(S6):356, p. 3.292 (2007) (Abstract).
Neyens et al., "Cognitive effects of a new pyrrolidine derivative (levetiracetam) in patients with epilepsy," Prog. Neuro-Psychopharmacol. & Biol. Psychiat., 19(3):411-419 (1995).
Neyens et al., "Cognitive side effects of levetiracetam (UCB LO59) in epilepsy," Epilepsia, 35(S7):76 (1994) (Abstract).
Nghiemphu et al., "Levetiracetam monotherapy in patients with malignant glioma," Neuro-Oncology, p. 566, QL-11 (2007).
Rugino et al., "Levetiracetam in autistic children: an open-label study," Journal of Development and Behavioral Pediatrics, 23(4)225-230 (2002).
Sargentini-Maier et al., "The pharmacokinetics, CNS pharmacodynamics and adverse event profile of brivaracetam after single increasing oral doses in healthy males," British Journal of Clinical Pharmacology, 63(6):680-688 (2007).
Schoenberg et al., "Results of a randomized double-blind placebo controlled cross-over study of the cognitive and mood effects of levetiracetam in healthy older adults," Epilepsia, 48(56):339, p. 3.246 (2007) (Abstract).
Shannon et al., "Effects of antiepileptic drugs on attention as assessed by a five-choice serial reaction time task in rats," Epilepsy Behavior, 7:620-628 (2005).
Shannon et al., "Effects of antiepileptic drugs on learning as assessed by a repeated acquisition of response sequences task in rats," Epilepsy Behavior, 10(1):16-25 (2007).
Shannon et al., "Effects of antiepileptic drugs on working memory as assessed by spatial alternation performance in rats," Epilepsy Behavior, 5(6):857-865 (2004).
Specchio et al., "Event-related potentials (erps) in the evaluation of the effect of levetiracetam and carbamazepine on cognitive functions in adult newly diagnosed epileptic patients. preliminary results of a randomized open trial," Epilepsia, 50(S4):98, T189 (2009) (Abstract).
Walker et al., "Early experience with UCB L059 in refractory epilepsy," European Congress Proceedings, 35(S7):76 (1994) (Abstract).
Wojda et al., "Isobolographic characterization of interactions of levetiracetam with the various antiepileptic drugs in the mouse 6Hz psychomotor seizure model," Epilepsy Research, 86(2-3):163-174 (2009).
Zhao et al., "Effect of levetiracetam on visual-spatial memory impairment following status epilepticus," Epilepsia, 47(S4):201 (2006) (Abstract).
Zhou et al., "Effect of levetiracetam on visual-spatial memory following status epilepticus," Epilepsy Research, 73(1):65-74 (2006).
Zou et al., "Effects of chronic treatment of levetiracetam on cognitive and motor recovery after experimental traumatic brain injury," Journal of Neurotrauma, 26:A67, p. 262 (2009) (Abstract).

(56) References Cited

OTHER PUBLICATIONS

Aeby et al., "Levetiracetam efficacy in epileptic syndromes with continuous spikes and waves during slow sleep: experience in 12 cases," Epilepsia, 46(12):1937-1942 (2005).
Altenmüller et al., "Termination of absence status epilepticus by low-dose intravenous levetiracetam—a case report," Epilepsia, 48(S6):336, p. 3.238 (2007) (Abstract).
Arcas et al., "Levetiracetaminn children and adolescents with refractory epilepsy: A clinical experience," Epilepsia, 47(S3):179 Absp696 (2006) (Abstract).
Bootsma et al., "The effect of antiepileptic drugs on cognition: patient perceived cognitive problem of topiramate versus levetiracetam in clinical practice," Epilepsia, 47(S2):24-27 (2006).
Cercy et al., "Gelastic epilepsy and dysprosodia in a case of late-onset right frontal seizures," Epilepsy & Behavior, 16(2):360-365 (2009).
Chaisewikul et al., "Levetiracetam add-on for drug-resistant localization related (partial) epilepsy (review)," Cochrane Database of Systematic Reviews Issue 1 (2010).
Ciesielski et al., "Neuropsychological and psychiatric impact of add-on titration of pregabalin versus levetiracetam: A comparative study," Epilepsia, 47(S3):Absp518 (2006).
Ciesielski et al., "Neuropsychological and psychiatric impact of add-on titration of pregabalin versus levetiracetam: a comparative short-term study," Epilepsy & Behavior, 9(3):424-431 (2006).
Cramer et al., "Effect of levetiracetam on epilepsy-related quality of life. N132 Study Group," Epilepsia, 41(7):868-874 (2000).
Diaz Negrillo et al., "[Levetiracetam efficacy in patients with Lennox-Gastaut syndrome. Presentation of a case]," Neurologia, 26(5):285-290 (2011) (Spanish language article, English Abstract Only).
Dyzdarer et al., "Levetiracetam in the treatment of refractory epilepsy in children," Epilepsia, 50(S 4)244:AbsE720 (2009) (Abstract).
Ehtisham et al., "Cognitive outcomes following seizure prophylaxis for intracranial hemorrhages of different subtypes with levetiracetam versus phenytoin," Annals of Neurology, 64(S12):S30, M-110 (2008).
Fauser et al., "Effect of levetiracetam in limbic encephalitis: A case report," Epilepsia, 44(S 8):111-112 p. 298 (2003) (Abstract).
Feleppa et al., "Epileptogenic Kluver-Bucy syndrome (EKBS) treated with nasogastric levetiracetam (LVT) as adjunctive therapy: A case of excellent neurological recovery at 4 months after discharge," European Journal of Neurology, 14(S1):214 Absp2206 (2007) (Abstract).
French et al., "A systematic review of the safety profile of levetiracetam: a new antiepileptic drug," Epilepsy Research, 47(1-2):77-90 (2001).
Frings et al., "Early detection of behavioral side effects of antiepileptic treatment using handheld computers," Epilepsy & Behavior, 13(2):402-406 (2008).
Frings et al., "Effects of add-on treatment with levetiracetam on cognition in epilepsy patients," Epilepsia, 44, S 8, p. 111, p. 297 (2003) (Abstract).
Garcia-Penas et al., "Efficacy and safety of levetiracetam monotherapy for children with epilepsy," Epilepsia, 48(S7):150 Absp390 (2007) (Abstract).
Guo et al., "Effects of levetiracetam on quality of life in children with refractory epilepsy," Changjiang Daxue Xuebao, Ziran Kexueban, 8(1):151-155 (2011) (English Abstract only).
Helmstaedter et al., "Cognitive outcome of antiepileptic treatment with levetiracetam versus carbamazepine monotherapy: a non-interventional surveillance trial," Epilepsy & Behavior, 18(1-2):74-80 (2010).
Helmstaedter et al., "Positive and negative psychotropic effects of levetiracetam," Epilepsy & Behavior, 13(3):535-541 (2008).
Helmstaedter et al., "The effects of levetiracetam on cognition: a non-interventional surveillance study," Epilepsy & Behavior, 13(4):642-649 (2008).
Helmstaedter, "'Real life' cohort study on levetiracetam versus carbamazepine monotherapy: a controlled surveillance study," Epilepsia, 50(S10):100, p. 465 (2009) (Abstract).
Helmstaedter, "'real life' cohort study on levetiracetam versus carbamazepine monotherapy—a controlled surveillance study on cognition," Epilepsia, 50(S6):47, p. 210 (2009) (Abstract).
Herranz et al., "Effectiveness and tolerability of levetiracetam in 43 children and adolescents with epilepsy," Revisa de neurologia, 37(11):1005-1008 (2003) (English Abstract only).
Herranz et al., "Levetiracetam: efficacy and tolerability in children and adolescents with epilepsy," Epilepsia, 44(S 8):152, p. 457 (2003) (Abstract).
Herranz et al.,"Effectiveness and safety of levetiracetam in 133 children with medication resistant epileptic seizures," Revista de neurologia, 43(7):393-397 (2006) (English Abstract only).
Higgins et al., "Comparative study of five antiepileptic drugs on a translational cognitive measure in the rat: relationship to antiepileptic property," Psychopharmacology, 207(4):513-527 (2010).
Himi et al., "Levetiracetam prevents the attention deficit induced by bilateral carotid artery occlusion in mice," Journal of Pharmacological Sciences, 109(S1):226P (2009) (English Abstract only).
Ioannidis et al., "Transient epileptic amnesia in a memory clinic setting: A report of three cases," Epilepsy and Behavior, 20(2):414-417 (2011).
Junemann et al., "Cognitive performance in patients with focal and primary generalized epilepsy under levetiracetam or topiramate monotherapy: a prospective pseudo-randomized study," Epilepsia,50(S6):47, p. 209 (2009) (Abstract).
Kossoff et al., "A pilot study transitioning children onto levetiracetam monotherapy to improve language dysfunction associated with benign rolandic epilepsy," Epilepsy & Behavior, 11(4):514-517 (2007).
Lagae et al., "Clinical experience with levetiracetam in childhood epilepsy: an add-on and mono-therapy trial," Seizure, 14:66-71 (2005).
Lagae et al., "Effect of levetiracetam on behavior and alertness in children with refractory epilepsy," Epilepsia, 44(S9):92, p. 1.258 (2003) (Abstract).
Lindholm, "Levetiracetam levels correlating with successful treatment of epilepsy, headaches, cognitive effects, and adverse reactions in pediatric age group," Epilepsia, 43(S7):60 (2002) (Abstract).
Lippa et al., "Levetiracetam: a practical option for seizure management in elderly patients with cognitive impairment," American Journal of Alzheimer's Disease & Other Dementias, 25(2):149-154 (2010).
Lippa et al., "Levetiracetam: seizure management for elderly patients with cognitive impairment," Neurology, 70(11, S1) Absp02-185 (2008) (Abstract).
Lopez-Gongora et al., "Cognitive function and quality of life after six months treatment with levetiracetam (LEV)," Epilepsia, 46(S 6):156, p. 136 (2005) (Abstract).
López-Góngora et al., "Effect of levetiracetam on cognitive functions and quality of life: a one-year follow-up study," Epileptic Disord, 10(4):297-305 (2008).
Mecarelli et al., "Clinical cognitive, and neurophysiologic correlates of short-term treatment with carbamazepine, oxcarbazepine, and levetiracetam in healthy volunteers," Annual Pharmacotherapy, 38(11):1816-1822 (2004).
Minervini et al., "Mild cognitive impairment, focal epilepsy and levetiracetam," Epilepsia, 48:(S7):110, p. 256 (2007) (Abstract).
Mintz et al., "The underrecognized epilepsy spectrum: the effects of levetiracetam on neuropsychological functioning in relation to subclinical spike production," Journal of Child Neurology, 24(7):807-815 (2009).
Mintz et al., "The effects of levetiracetam on neuropsychological functioning in relation to "subclinical" spike production," Epilepsia, 47, S4, p. 112, 1.237 (2006) (Abstract).
Palmer et al., "Correlation between behavioural adverse events and cognitive functions in epilepsy patients receiving levetiracetam," Epilepsia, 44(S8):172, p. 537 (2003) (Abstract).
Park et al., "Increased EEG current-source density in the high Beta frequency band induced by levetiracetam adjunctive therapy in refractory partial epilepsy," Journal of Clinical Neurology (Seoul, Korea) 5(4):178-185 (2009).

(56) References Cited

OTHER PUBLICATIONS

Piazzini et al., "Levetiracetam: an improvement of attention and of oral fluency in patients with partial epilepsy," Epilepsy Research, 68(3):181-188 (2005).
Quiske et al., "Add-on treatement with LEV and its influence on cognition," Epilepsia, 46(S6):311, p. 986 (2005).
Ravagnan et al., "ESES: 4 cases treated with levetiracetam," Bollettino—Lega Italiana contro l'Epilessia, 138:77-78 (2008) (English Abstract only).
Rudakova et al., "Levetiracetam (keppra) in the treatment of different epileptic syndromes in adults," Zhurnal nevrologii i psikhiatrii imeni S.S. Korsakova / Ministerstvo zdravookhraneniia i meditsinskoi promyshlennosti Rossiiskoi Federatsii, Vserossiiskoe obshchestvo nevrologov [i] Vserossiiskoe obshchestvo psikhiatrov, 109(10):25-29 (2009) (English Abstract only).
Ryzhkov et al., "Levetiracetam treatment in rare epileptic syndromes of early childhood: a case series," Epilepsia, 47(S3):180,p. 701 (2006) (Abstract).
Ryzhkov, "Advantages of levetiracetam as monotherapy in treating epileptic syndromes of early childhood, characterized by psychological disorders," European Journal of Neurology, 14(S1):90, p. 1224 (2007) (Abstract).
Salas-Puig et al., "Self-reported memory problems in everyday activities in patients with epilepsy treated with antiepileptic drugs," Epilepsy & Behavior, 14(4):622-627 (2009).
Tozzi et al., "[Levetiracetam in children and adolescents: Generalised vs partial seizures]," Bollettino—Lega Italiana contro l'Epilessia, 133-134:257-258 (2006) (English Abstract only).
Verloes et al., "Effects of nootropic drugs in a scopolamine-induced amnesia model in mice," Psychopharmacology, 95(2):226-230 (1988).
Vicenzini et al., "[Clinical and neuropsycological effects of carbamazepine, oxcarbazepine and levetiracetam in healthy volunteers]"—Bollettino—Lega Italiana contro l'Epilessia, 118:173-175 (2002) (Italian-English abstract only).
Von Stüulpnagel et al., "Levetiracetam as add-on therapy in different subgroups of "benign" idiopathic focal epilepsies in childhood," Epilepsy & Behavior, 17(2):193-198 (2010).
Wheless et al., "Levetiracetam in refractory pediatric epilepsy," Journal of Child Neurology, 17(6):413-415 (2002).
Witt et al., "The impact of antiepileptic drug treatment on attention and executive functions," Epilepsia, 51(S4):20 (2010) (Abstract).
Witt, "The effects of levetiracetam on cognition—a noninterventional surveillance study," Epilepsia, 50(S4):227 (2009) (Abstract).
Wu et al., "Clinical efficacy and cognitive and neuropsycholoical effects of levetiracetam in epilepsy: an open-label multicenter study," Epilepsy & Behavior, 16(3):468-474 (2009) (Abstract).
Yang et al., "Adjunctive levetiracetam in children and adolescents aged 4-16 years with partial-onset seizures: A long-term, multicenter, noncomparative, open-label, follow-up study," Epilepsia, 50(S10):102, p. 471 (2009) (Abstract).
Yang et al., "Therapeutic effect of levetiracetam for epilepsy combined with electrical status epilepticus during sleep in children," Shiyong Erke Linchuang Zazhi, 25(12):937-939 (2010) (English Abstract only).
Zhou et al., "Cognitive and quality of life effects of levetiracetam as an add-on therapy for partial seizures," Epilepsia, 48(S7):70, p. 116 (2007) (Abstract).
Zhou et al., "Levetiracetam: an improvement of attention and of oral fluency in patients with partial epilepsy," Epilepsy & Behavior, 12:305-310 (2008).
Banfi et al., "Cyclic GABA-GABOB analogs. IV. Activity on learning and memory," Farmaco, Edizione Scientifica, 39(1):16-22 (1984).
Bartolini et al., "Aniracetam restores object recognition impaired by age, scopolamine, and nucleus basalis lesions," Pharmacol. Biochem. Behav., 53(2):277-283 (1996).
Bartolini et al., "Effect of scopolamine and nootropic drugs on rewarded alternation in a T-maze," Pharmacol. Biochem. Behav., 43(4):1161-1164 (1992).
Bhattacharya et al., "Latency of memory consolidation induced in mice by piracetam, a nootropic agent," Indian J. Exp. Biol., 31(11):898-901 (1993).
Bottini et al., "Oxiracetam in dementia: a double-blind, placebo-controlled study," Acta. Neurol. Scand., 86(3):237-241 (1992).
Butler et al., "Amnesia-reversal activity of a series of N-[(disubstituted-amino)alkyl]-2-oxo-1-pyrrolidineacetamides, including pramiracetam," Journal of Medicinal Chemistry, 27:684-691 (1984).
Cavoy et al., "Relationships between arousal and cognition-enhancing effects of oxiracetam," Pharmacol. Biochem. Behav., 47(2):283-287 (1994).
Claus et al., "Nootropic drugs in Alzheimer's disease: symptomatic treatment with pramiracetam," Neurology, 41(4):570-574 (1991).
Croisile et al., "Long-term and high-dose piracetam treatment of Alzheimer's disease," Neurology, 43(2):301-305 (1993).
De Vreese et al., "Memory training and drug therapy act differently on memory and metamemory functioning: evidence from a pilot study," Arch. Gerontol. Geriatr., 22(S 1):9-22 (1996).
Ennaceur et al., "A new one-trial test for neurobiological studies of memory in rats. II: Effects of piracetam and pramiracetam," Behav. Brain Research, 33(2):197-207 (1989).
Fedi et al., "Long-term efficacy and safety of piracetam in the treatment of progressive myoclonus epilepsy," Arch. Neurol., 58(5):781-786 (2001).
Firstova et al., "Effects of nootropic drugs on hippocampal and cortical BDNF levels in mice with different exploratory behavior efficacy," Eksperimental'naya i Klinicheskaya Farmakologiya, 72(6):3-6 (2009) (English Abstract only).
Gallai et al., "A clinical and neurophysiological trial on nootropic drugs in patients with mental decline," Acta. Neurol. (Napoli), 13(1):1-12 (1991).
Gamzu, "Animal behavioral models in the discovery of compounds to treat memory dysfunction," Annals of the New York Academy of Sciences, 444:370-393 (1985).
Ghelardini et al., "The novel nootropic compound DM232 (unifiram) ameliorates memory impairment in mice and rats," Drug Development Research, 56:23-32 (2002).
Green et al., "Treatment trial of oxiracetam in Alzheimer's disease," Arch. Neurol., 49(11):1135-1136 (1992).
Gualtieri et al., "Design and study of piracetam-like nootropics, controversial members of the problematic class of cognition-enhancing drugs," Current Pharmaceutical Design, 8(2):125-138 (2002).
Hlinak et al., "Kynurenic acid and 5,7-dichlorokynurenic acids improve social and object recognition in male rats," Psychopharmacology (Berl), 120(4):463-469 (1995).
Hlinak et al., "Oxiracetam prevented the scopolamine but not the diazepam induced memory deficits in mice," Behav. Brain Research, 133(2):395-399 (2002).
Israel et al., "Drug therapy and memory training programs: A double-blind randomized trial of general practice patients with age-associated memory impairment," International Psychogeriatrics, 6(2):155-170 (1994).
Lebrun et al., "Effects of S 18986-1, a novel cognitive enhancer, on memory performances in an object recognition task in rats," European Journal of Pharmacology, 401(2):205-212 (2000).
Magnani et al., "Oxiracetam antagonizes the disruptive effects of scopolamine on memory in the radial maze," Psychopharmacology (Berl), 106(2):175-178 (1992).
Maina et al., "Oxiracetam in the treatment of primary degenerative and multi-infarct dementia: a double-blind, placebo-controlled study," Neuropsychobiology, 21(3):141-145 (1989).
Maresova et al., "Pramiracetam and epileptic after-discharges in young rats after hypoxia," Act. Nerv. Super (Praha), 31(1):68-69 (1989).
Marini et al., "Placebo-controlled double-blind study of pramiracetam (CI-879) in the treatment of elderly subjects with memory impairment," Advances in Therapy 9(3):136-146 (1992).
Mauri et al., "Pramiracetam effects on scopolamine-induced amnesia in healthy volunteers," Arch. Gerontol. Geriatr., 18(2):133-139 (1994).

(56) References Cited

OTHER PUBLICATIONS

Mondadori et al., "Elevated corticosteroid levels block the memory-improving effects of nootropics and cholinomimetics," Psychopharmacology (Berl), 108(1-2):11-15 (1992).
Mondadori et al., "The GABAB receptor antagonist CGP 36,742 and the nootropic oxiracetam facilitate the formation of long-term memory," Behav. Brain Research, 77(1-2):223-225 (1996).
Mondadori et al., "The pharmacology of the nootropics; new insights and new questions," Behavioural Brain Research, 59(1-2):1-9 (1993).
Mondadori et al., "Delayed emergence of effects of memory-enhancing drugs: implications for the dynamics of long-term memory," Proceedings of the National Academy of Science USA, 91(6):2041-2045 (1994).
Murphy et al., "Chronic exposure of rats to cognition enhancing drugs produces a neuroplastic response identical to that obtained by complex environment rearing," Neuropsychopharmacology, 31(1):90-100 (2006).
Murray et al., "The effect of pramiracetam (CI-879) on the acquisition of a radial arm maze task," Psychopharmacology (Berl), 89(3):378-381 (1986).
Nakamoto et al., "Nootropic nefiracetam inhibits proconvulsant action of peripheral-type benzodiazepines in epileptic mutant EL mice," Annals New York Academy of Science, 1025:135-139 (2004).
Nikolova et al., "Effects of ACE-inhibitors on learning and memory processes in rats," Folia Med. (Plovdiv), 42(1):47-51 (2000).
Parnetti et al., "Neuropsychological results of long-term therapy with oxiracetam in patients with dementia of Alzheimer type and multi-infarct dementia in comparison with a control group," Neuropsychobiology, 22(2):97-100 (1989).
Perini et al., "Use of valproate in treatment of behavioural and psychological disturbances of dementia," European Neuropsychopharmacology, 15:S565, p. 5.017 (Abstract).
Petkov et al., "Effect of CDP-choline on learning and memory processes in rodents," Methods Find Exp. Clin. Pharamcol., 14(8):593-605 (1992).
Pitsikas et al., "Effect of oxiracetam on scopolamine-induced amnesia in the rat in a spatial learning task," Pharmacology Biochemistry and Behavior, 43(3):949-951 (1992).
Platel et al., "Habituation of exploratory activity in mice: effects of combinations of piracetam and choline on memory processes," Pharmacol. Biochem. Behav., 21(2):209-212 (1984).
Poschel et al., "Pharmacologic therapeutic window of pramiracetam demonstrated in behavior, EEG, and single neuron firing rates," Experientia., 41(9):1153-1156 (1985).
Poschel et al., "Pharmacology of the cognition activator pramiracetam (CI-879)," Drugs under Experimental and Clinical Research, 9(12):853-872 (1983).
Preda et al., "Effects of acute doses of oxiracetam in the scopolamine model of human amnesia," Psychopharmacology (Berl), 110(4):421-426 (1993).
Pugsley et al., "Some neurochemical properties of pramiracetam (CI-879) a new cognition enhancing agent," Drug Development Research, 3(5):407-420 (1983).
Rao et al., "Effects of intrahippocampal aniracetam treatment on Y-maze avoidance learning performance and behavioral long-term potentiation in dentate gyrus in rat," Neuroscience Letters, 298(3):183-186 (2001).
Rozzini et al., "Treatment of cognitive impairment secondary to degenerative dementia. Effectiveness of oxiracetam therapy," Acta. Neurol. (Napoli), 15(1):44-52 (1993).
Saletu et al., "Pharmaco-EEG and Brain Mapping in Cognitive Enhancing Drugs," Clin. Neuropharamacol., 13(S 2):575-576 (1990).
Salimov et al., "Effect of chronic piracetam on age-related changes of cross-maze exploration in mice," Pharmacol. Biochem. Behav., 52(3):637-640 (1995).
Sansone et al., "Effects of oxiracetam, physostigmine, and their combination on active and passive avoidance learning in mice," Pharmacol. Biochem. Behav., 44(2):451-455 (1993).
Sara et al., "Piracetam facilitates retrieval but does not impair extinction of bar-pressing in rats," Psychopharmacology (Berl.), 61(1):71-75 (1979).
Sara, "Memory retrieval deficits: alleviation by etiracetam, a nootropic drug," Psychopharmacology, 68(3):235-241 (1980).
Villardita et al., "Clinical studies with oxiracetam in patients with dementia of Alzheimer type and multi-infarct dementia of mild to moderate degree," Neuropsychobiology, 25(1):24-28 (1992).
Waegemans et al., "Clinical efficacy of piracetam in cognitive impairment: a meta-analysis," Dement. Geriatr. Cogn. Disord., 13(4):217-224 (2002).
Wolthuis et al., "Behavioural effects of etiracetam in rats," Pharmacology Biochemistry & Behavior, 15:247-255 (1981).
Wolthuis, "Experiments with UCB 6215, a drug which enhances acquisition in rats: its effects compared with those of metamphetamine," Eur. J. Pharmacol., 16(3):283-297 (1971).
Yamada et al., "Prolongation of latencies for passive avoidance responses in rats treated with aniracetam or piracetam," Pharmacol. Biochem. Behav., 22(4):645-648 (1985).
Aarts et al., "Selective cognitive impairment during focal and generalized epileptiform EEG activity," Brain, 107(Pt. 1):293-308 (1984).
Boido et al., "Cortico-hippocampal hyperexcitability in synapsin I/II/III knockout mice: age-dependency and response to the antiepileptic drug levetiracetam," Neuroscience, 171(1):268-283 (2010).
Bridgman et al., "Memory during subclinical hippocampal seizures," Neurology, 39(6):853-856 (1989).
Campos-Castello, "Neuropsychology and epilepsy," Revista de Neurologia, 39(2):166-177 (2004) (English Abstract only).
Coras et al., "Low proliferation and differentiation capacities of adult hippocampal stem cells correlate with memory dysfunction in humans," Brain, 133(11):3359-3372 (2010).
Heidegger et al., "Effects of antiepileptic drugs on associative LTP-like plasticity in human motor cortex," European Journal of Neuroscience, 32:1215-1222 (2010).
Himi et al., "Levetiracetam prevents attentional deficits induced by bilateral common artery occlusion in mice," Epilepsia, 48(S6):323, 3.203 (2007) (Abstract).
Krakow et al., "Effects of antiepileptic drugs on cortical plasticity and motor learning: a double blind, placebo-controlled transcranial magnetic stimulation study," Epilepsia, 46(8):212-213 (2005).
Lamberty et al., "Behavioural phenotyping reveals anxiety-like features of SV2A deficient mice," Behavioural Brain Research, 198(2):329-333 (2009).
Lukyanetz et al., "Selective blockade of N-type calcium channels by levetiracetam," Epilepsia, 43(1):9-18 (2002).
Manthey et al., "Sulthiame but not levetiracetam exerts neurotoxic effect in the developing rat brain," Experimental Neurology, 193(2):497-503 (2005).
Martella et al., "Seletracetam (ucb 44212) inhibits high-voltage-activated Ca2+ currents and intracellular Ca2+ increase in rat cortical neurons in vitro," Epilepsia, 50(4):702-710 (2009).
Nagarkatti et al., "Levetiracetam inhibits both ryanodine and IP3 receptor activated calcium induced calcium release in hippocampal neurons in culture," 436(3):289-293 (2008).
Niespodziany et al., "Levetiracetam inhibits the high-voltage-activated Ca2+ current in pyramidal neurons of rat hippocampal slices," Neuroscience Letters, 306:5-8 (2001).
Paulson et al., "Effect of levetiracetam on hippocampal protein expression and cell proliferation in rats," Epilepsy Research, 90(1-2):110-120 (2010).
Provinciali et al., "Recognition impairment correlated with short bisynchronous epileptic discharges," 32(5):684-689 (1991).
Sohn et al., "Effect of levetiracetam on rapid motor learning in humans," Annals of Neurology, 50:S31-S32 (2001).
Sohn et al., "Effect of levetiracetam on rapid motor learning in humans," Archives of Neurology, 59:1909-1912 (2002).
Sugaya et al., "Levetiracetam suppresses development of spontaneous EEG seizures and aberrant neurogenesis following kainate-induced status epilepticus," Brain Research, 1352:187-199 (2010).
Veauthier et al., "Impact of levetiracetam add-on therapy on different Eeg occipital frequencies in epileptic patients," Seizure: the journal of the British Epilepsy Association,18(6):392-395 (2009).

(56) References Cited

OTHER PUBLICATIONS

Abou-Khalil, "Benefit-risk assessment of levetiracetam in the treatment of partial seizures," Drug Safety, 28(10):871-890 (2005).
Abou-Khalil, "Levetiracetam in the treatment of epilepsy," Neuropsychiatric Disease and Treatment, 4(3):507-523 (2008).
Adam et al., "Symptomatic Treatment of Huntington Disease," The Journal of the American Society for Experimental NeuroTherapeutics 5(2):181-197 (2008).
Aldenkamp et al., "Newer antiepileptic drugs and cognitive issues," Epilepsia, 44(S4):21-29 (2003).
Asconapé, "Some common issues in the use of antiepileptic drugs," Seminars in Neurology, 22(1):27-39 (2002).
Béatrice Brunner et al., Neurocognitive effects of antiepileptic drugs frequently used in long term treatement of epilepsies: A review, Epileptologie, 25:118-130 (2008).
Bourgeois, "Determining the effects of antiepileptic drugs on cognitive function in pediatric patients with epilepsy," Journal of Child Neurology, 19(S1):S15-S24 (2004).
Carreno et al., "Cognitive disorders associated with epilepsy: Diagnosis and treatment," The Neurologist, 14(65):S26-S34 (2008).
Chaisewikul et al., "Levetiracetam add-on for drug-resistant localization related (partial) epilepsy," Cochrane Collaboration, Issue 1, p. 1-25 (2010).
Cramer et al., "A systematic review of the behavioral effects of levetiracetam in adults with epilepsy, cognitive disorders, or an anxiety disorder during clinical trials," Epilepsy & behavior, 4(2):124-132 (2003).
Czubak et al., "Cognitive effects of GABAergic antiepileptic drugs," Arzneimittel-Forschung, 60:(1)1-11 (2010).
Frostl et al., "The families of cognition enhancers," Pharmacopsychiatry, 22(2):54-100 (1989).
Gamzu et al., "Drug improvement of cognition: Hope and reality," Psychiatrie et Psychobiologie, 3(No. SPEC. ISS B):115-123 (1988).
Gamzu et al., "Recent developments in 2-pyrrolidinone-containing nootropics," Drug Development Research, 18(3):177-189 (1989).
Genton et al., "Piracetam and levetiracetam: close structural similarities but different pharmacological and clinical profiles," Epileptic disorders, 2(2):99-105 (2000) (Abstract).
Goldberg et al., "Cognitive side effects of anticonvulsants," Journal of Clinical Psychiatry, 62(S14):27-33 (2001).
Gouliaev et al., "Piracetam and other structurally related nootropics," Brain Research Review, 19(2):180-222 (1994).
Hamed, "The aspects and mechanisms of cognitive alterations in epilepsy: the role of antiepileptic medications," CNS Neuroscience & Therapeutics, 15(2):134-156 (2009).
Hermann et al., "Cognition across the lifespan: antiepileptic drugs, epilepsy, or both?" Epilepsy Behavior, 17:1-5 (2010).
Jelic et al., "Clinical trials in mild cognitive impairment: lessons for the future," J. Neurol. Neurosurg. Psychiatry., 77(4):429-438 (2006).
Jetter et al., "Epilepsy in the elderly," Seminars in Neurology, 28(3):336-341 (2008).
Kaindl et al., "Antiepileptic drugs and the developing brain," Cellular and Molecular Life Sciences, 63(4): 399-413 (2006).
Kalinin, "Suicidality and antiepileptic drugs. Is there a link?" Drug Safety, 30(2):123-142 (2007).
Kamada Kyousuke, "Are clinical features derived from evidences and experiences outside of Japan applicable to clinical practices in Japan? Comparisons of results among studies conducted in US, Europe, Asian Countries and Japan," Brain and nerve = Shinkei kenkyu no shinpo, 63(3):247-54 (2011) (English Abstract only).
Klitgaard et al., "Use of epileptic animals for adverse effect testing," Epilepsy Research, 50(1-2):55-65 (2002).
Lagae, "Cognitive side effects of anti-epileptic drugs. The relevance in childhood epilepsy," Seizure, 5(4):235-241 (2006).
Loring et al., "Neuropsychological and behavioral effects of antiepilepsy drugs," Neuropsychol Rev, 17(4):413-425 (2007).
Lyseng-Williamson, "Levetiracetam: a review of its use in epilepsy," Drugs, 71(4):489-514 (2011).
Maguire et al., "Epilepsy (generalised)," Neurological disorders, Clinical evidence, 6(1201):1-14 (2009).
Maguire et al., "Epilepsy (partial)," Neurological disorders,Clinical evidence, 5(1214):1-42 (2011).
Malik et al., "Towards better brain management: Nootropics," Current Medicinal Chemistry, 14:123-131 (2007).
Malykh et al., "Piracetam and piracetam-like drugs: from basic science to novel clinical applications to CNS disorders," Drugs, 70(3):287-312 (2010).
Meador, "Cognitive and memory effects of the new antiepileptic drugs," Epilepsy Research, 68(1):63-67 (2006).
Meador, "Cognitive effects of levetiracetam versus topiramate," Epilepsy Currents, 8(3):64-65 (2008).
Merlini et al., "Trends in searching for new cognition enhancing drugs," Progress in Neuro-Psychopharmacology and Biological Psychiatry, 13: S61-S75 (1989).
Mondadori et al., "The Effects of Nootropics on Memory: New Aspects for Basic Research," Pharmacopsychiatry, 22(S 2):102-106 (1989).
Mula et al., "Antiepileptic Drug-Induced Cognitive Adverse Effects Potential Mechanisms and Contributing Factors," CNS Drugs, 23(2):121-137 (2009).
Nicholson, "Pharmacology of nootropics and metabolically active compounds in relation to their use in dementia," Psychopharmacology, 101(No. 2):147-159 (1990).
Onuma Teiichi, "Cognitive Dysfunction and Antiepileptic Drugs," Brain and Nerve (Tokyo), 63( 4):379-383 (2011) (Abstract—Japanese and English translation ).
Sankar et al., "Mechanisms of action for the commonly used antiepileptic drugs: relevance to antiepileptic drug-associated neurobehavioral adverse effects," Journal of Child Neurology, 19 (S1):S6-S14 (2004).
Sarter et al., "Behavioral screening for cognition enhancers: From indiscriminate to valid testing: Part I," Psychopharmacology, 107:144-159 (1992).
Schmidt et al., "Strategies and new aspects in the pharmacology of drugs for the treatment of senile dementia," Drug Development Research, 14(3-4):251-262 (1988).
Schmitz et al., "Assessing the unmet treatment need in partial-onset epilepsy: looking beyond seizure control," Epilepsia, 51(11):2231-2240 (2010).
Shorvon, "Pyrrolidone derivatives," Lancet, 358(9296):1885-1892 (2001).
Stepien et al., "Profile of anticonvulsant activity and neuroprotective effects of novel and potential antiepileptic drugs—an update," Pharmacological Reports, 57(6):719-733 (2005).
Vecht et al., "Seizures in low- and high-grade gliomas: current management and future outlook," Expert Review Anticancer Therapy, 10(5):663-669 (2010).
Wang et al., "Effect of commonly used new antiepileptic drugs on cognition," Zhongguo Xinyao Yu Linchuang Zazhi, China 27(9):705-709 (2008) (English Abstract only).
Wheless, "Levetiracetam in the treatment of childhood epilepsy," Neuropsychiatric Disease and Treatment, 3(4):409-421 (2007).
Wilby et al., "Clinical effectiveness, tolerability and cost-effectiveness of newer drugs for epilepsy in adults: a systematic review and economic evaluation," Health Technology Assessment, Executive Summary—Newer drugs for epilepsy in adult, 9(15) (2005).
Winnicka et al., "Piracetam—An old drug with novel properties," Acta Pol.Pharm., Drug Research, 62(5):405-409 (2005).
Wu, "The effects of antiepileptic drugs on cognitive function," Erke Yaoxue Zazhi, China, 13(6):7-9 (2007) (English Abstract only).
Zaccara et al., "Central nervous system adverse effects of new antiepileptic drugs. A meta-analysis of placebo-controlled studies," Seizure, 17(5):405-421 (2008).
Aisen et al., "Clinical Core of the Alzheimer's Disease Neuroimaging Initiative: progress and plans," Alzheimer's & Dementia, 6(3):239-246 (2010).
Ashe et al., "Probing the biology of Alzheimer's disease in mice," Neuron. 66:631-645 (2010).
Barner et al., "Donepezil use in Alzheimer disease," Ann. Pharmacotherapy, 32:70-77 (1998).
Bores et al., "Galanthamine derivatives for the treatment of alzheimer's disease," Drugs of the future, 21(6):15- (1996).

(56) References Cited

OTHER PUBLICATIONS

Buschke et al., "Evaluating storage, retention, and retrieval in disordered memory and learning," Neurology, 24:1019-1025 (1974).
Chang et al., "SV2 renders primed synaptic vesicles competent for Ca2+-induced exocytosis," Journal of Neuroscience, 29(4):883-897 (2009).
Chappell et al., "A re-examination of the role of basal forebrain cholinergic neurons in spatial working memory," Neuropharmacology, 37(4-5):481-487 (1998).
Crook et al., "Age-associated memory impairment: Proposed diagnostic criteria and measures of clinical change—Report of a National Institute of Mental Health workgroup," Developmental Neuropsychology, 2:261-276 (1986).
De Smedt et al., "Levetiracetam: the profile of a novel anticonvulsant drug-part I: preclinical data," CNS Drug Review, 13(1):43-56 (2007).
Dietrich et al., "Clinical patterns and biological correlates of cognitive dysfunction associated with cancer therapy," Oncologist, 13:1285-1295 (2008).
Estimating the Safe Starting Dose in Clinical Trials for Therapeutics in Adult Healthy Volunteers, Dec. 2002, Center for Biologics Evaluation and Research.
Hassel et al., "Up-regulation of hippocampal glutamate transport during chronic treatment with sodium valproate," Journal of Neurochemistry, 77:1285-1292 (2001).
Herholz et al., "Discrimination between Alzheimer dementia and controls by automated analysis of multicenter FDG PET," NeuroImage, 17:302-316 (2002).
Kenda et al., "Discovery of 4-Substituted Pyrrolidone Butanamidesas New Agents with Significant Antiepileptic Activity," Journal of Medicinal Chemistry, 47(3):530-549 (2004).
Khan et al., "Topiramate attenuates exaggerated acoustic startle in an animal model of PTSD," Psychopharmacology 172:225-229 (2004).
Kim et al., "Transient impairment of hippocampus-dependent learning and memory in relatively low-dose of acute radiation syndrome is associated with inhibition of hippocampal neurogenesis," J. Radiat. Res., 49:517-526 (2008).
Kobayashi et al. "Behavioral phenotypes of amyloid-based genetically modified mouse models of Alzheimer's disease," Genes Brain Behav., 4:173-196 (2005).
Larrabee, "Age-Associated Memory Impairment: Definition and psychometric characteristics," Aging, Neuropsychology, and Cognition, 3:118-131 (1996).
Liberzon et al., "Stress-restress: effects on ACTH and fast feedback," Psychoneuroendocrinology, 22:443-453 (1997).
Loscher, "Valproate: a reappraisal of its pharmacodynamic properties and mechanisms of action," Progress in Neurobiology, 58:31-59 (1999).
Maggini M, Vanacore N, Raschetti R (2006) Cholinesterase Inhibitors: Drugs Looking fora Disease? PLoS Med 3(4): e140.doi:10.1371/journal.pmed.0030140.
Nicolle et al., "In vitro autoradiography of ionotropic glutamate receptors in hippocampus and striatum of aged Long-Evans rats: relationship to spatial learning," Neuroscience, 74(3):741-756 (1996).
Owens et al., "Pharmacology of Divalproex," Psychopharmacology Bulletin 37 Suppl 2:17-24. (2003).
Padwa et al., "Cyclization-cycloaddition casade of rhodium carbenoids using different carbonyl groups. Highlighting the position of interaction," J. Org. Chem., 65:5223-5232 (2000).
Petersen et al., "Mild cognitive impairment, clinical characterization and outcome," Arch. Neurology, 56:303-308 (1999).
Petersen et al., "Vitamin E and Donepezil for the Treatment of Mild Cognitive Impairment. Alzheimer's Disease Cooperative Study Group," N. Engl. J. Med., 52:2379-2388 (2005).
Rogers et al., "Long-term efficacy and safety of donepezil in the treatment of Alzheimer's disease: an interim analysis of the results of a US multicentre open label extension study," Eur. Neuropsych. 8:67-75 (1998).

Smith et al., "Age-associated memory impairment diagnoses: problems of reliability and concerns for terminology," Psychology and Aging, 6(4):551-558 (1991).
Soussain et al., "CNS complications of radiotherapy and chemotherapy," Lancet 374:1639-1651 (2009).
Wang et al., "Magnetic resonance imaging of hippocampal subfields in posttraumatic stress disorder," Arch. Gen. Psychiatry, 67:296-303 (2010).
Woon et al., "Hippocampal volume deficits associated with exposure to psychological trauma and posttraumatic stress disorder in adults: a meta-analysis," Prog Neuropsychopharmacol Biol Psychiatry, 34:1181-1188 (2010).
Yaffe et al., "Post-Traumatic Stress Disorder and Risk of Dementia among U.S. Veterans," Arch. Gen. Psych., 678:608-613 (2010).
Yang et al., "Cyclophosphamide impairs hippocampus-dependent learning and memory in adult mice: Possible involvement of hippocampal neurogenesis in chemotherapy-induced memory deficits," Neurobiology of Learning and Memory, Epilepsia, 93:487-494 (2010).
Yassa et al., "Ultrahigh-resolution microstructural diffusion tensor imaging reveals perforant path degradation in aged humans in vivo," PNAS, 107:12687-12691 (2010).
Yehuda et al., "Longitudinal assessment of cognitive performance in Holocaust survivors with and without PTSD," Bio. Psych., 60:714-721 (2006).
Youngjohn et al., "Stability of everyday memory in age-associated impairment: A longitudinal study," Neuropsychology, 7(3);406-416 (1993).
Doheny et al., "Blood and cerebrospinal fluid pharmacokinetics of the novel anticonvulsant levetiracetam (ucb L059) in the rat," Epilepsy Research, 34: 161-168 (1999).
Gillard et al., "Binding characteristics of brivaracetam, a selective, high affinity SV2A ligand in rat, mouse and human brain: relationship to anti-convulsant properties," European Journal of Pharmacology, 664:36-44 (2011).
Patsalos, "Pharmacokinetic profile of levetiracetam: toward ideal characteristics," Pharmacol. Ther., 85(2):77-85 (2000).
Patsalos, "Clinical pharmacokinetics of levetiracetam," Clin. Pharmacokinet., 43(11):707-724 (2004).
Sargentini-Maier et al., "Brivaracetam Disposition in Renal Impairment," J. Clin. Pharmacol., published online Jan. 10, 2012.
Sargentini-Maier et al., "Pharmacokinetics and metabolism of $^{14}$C-brivaracetam, a novel SV2A ligand, in healthy subjects," Drug Metab Dispos, 36(1):36-45 (2008).
Bakker et al., "Reduction of hippocampal hyperactivity improves cognition in amnestic mild cognitive impairment," Neuron, 74(3): 467-474 (2012).
Koh et al., "Treatment strategies targeting excess hippocampal activity benefit aged rats with cognitive impairment," Neuropsychopharmacology, 35(4):1016-1025 (2010).
Halgren et al., "Recall deficits produced by afterdischarges in the human hippocampal formation and amygdale," Electroencephalogr. Clin. Neurophysiol., 61(5):375-380 (1985).
Irizaary et al., "Incidence of new-onset seizures in mild to moderate Alzheimer disease," Arch. Neurol., 69(3):368-372 (2012).
Ito et al., "A case series of epilepsy-derived memory impairment resembling Alzheimer disease," Alzheimer Dis. Assoc. Disord., 23(4):406-409 (2009).
Kasteleijn-Nolst Trenite et al., "On-line detection of transient neuropsychological disturbances during EEG discharges in children with epilepsy," Dev. Med. Child Neurol., 32(1):46-50 (1990).
Kooi et al., "Alterations in mental function and paroxysmal cerebral activity," AMA Arch. Neurol. Psychiarty, 78(3):264-271 (1957).
Liedorp et al., "Prevalence and clinical significance of epileptiform EEG discharges in a large memory clinic cohort," Dement. Geriatr. Cogn. Disord., 29(5):432-437 (2010).
Mendez et al., "Seizures in Alzheimer's disease: clinicopathologic study," J. Geriatr. Psychiatry Neurol., 7(4):230-233 (1994).
Rao et al., "Recurrent seizures in patients with dementia: frequency, seizure types, and treatment outcome," Epilepsy Behav., 14(1):118-120 (2008).
Scarmeas et al., "Seizures in Alzheimer disease: who, when, and how common?" Arch. Neurol., 66(8):992-997 (2009).

(56) References Cited

OTHER PUBLICATIONS

Albert et al., "The diagnosis of mild cognitive impairment due to Alzheimer's disease: Recommendations from the National Institute on Aging-Alzheimer's Association workgroups," Alzheimer's & Dementia 1-10 (2011).
Bertolucci et al., "Proposta de uma versão brasileira para a escala adcs-cgic," Arq Neuropsiquiatr 61(3-B):881-890 (2003) (Portuguese language, English Abstract only).
Schneider et al., "Validity and reliability of the Alzheimer's Disease Cooperative Study-Clinical Global Impression of Change," The Alzheimer's Disease Cooperative Study, Alzheimer Dis. Assoc. Disord., 11 Suppl. 2:S22-S32 (1997).
Levetiracetam American journal of health-system pharmacy, 57:1484 (2000).
Muscas et al., "[Efficacy and tolerability of Levetiracetam in epileptic patients with acquired progressive cognitive impairment]," Bollettino—Lega Italiana contro l'Epilessia, 129-130:233-234 (2005) (full text English translation).
Takahashi et al., "Case report of sodium valproate treatment of aggression associated with Alzheimer's disease," Brain and Nerve (Tokyo), 48(8):757-760 (1996) (English Abstract only).
Chen, Yangmei et al., "Epilepsy Therapeutics," Sichuan Publishing Group, Sichuan Science and Technology Press, Jun. 2004 (Full-text English translation).
Lee et al., "Levetiracetam inhibits glutamate transmission through presynaptic P/Q-type calcium channels on the granule cells of the dentate gyrus," British J. Pharmacol., 158:1753-1762 (2009).
Li, Jinjin et al., "Patient Discharge Guidance, Internal Medicine Section," Zhejiang Science and Technology Publishing House, Jun. 2007 (Full-text English translation).
Nygaard et al., "Brivaracetam, but not ethosuximide, reverses memory impairments in an Alzheimer's disease mouse model," Alzheimer's Research & Therapy, 7:25 (2015) (12 pages).
Pastor et al., "Tolerability and efficacy of the combination of piracetam and citicoline in acute ischemic stroke. A randomized comparative open study," p. e286, top right-hand column, paragraph 1 of Abstract of the 5th World Stroke Conference, Jan. 2004, Retrieved from the Internet: http://stroke.ahajournals.org/content/35/6/e276.full.pdf#page=1$view=Fith.
Xie et al., "Observation for the effects of nicergoline for treating aging low-grade cognitive disorders," Chinese Community Physician, 11(3):20-21 (2009) (Chinese Language and English Abstract only).
Yuede et al., Anti-dementia drugs and hippocampal-dependent memory in rodents, Behav. Pharmacol., 18:347-363 (2007).
Zhu et al., "Progress in the research of Alzheimer's disease and its drug therapies," Guangzhou Chemistry, 29(2):35-44 (2004) (Chinese Language and English Abstract only; machine English translation of full text; and English translation of paragraphs 1.2, 1.2.3 and 2.1.
The Oct. 10, 2013 Office Action issued by the Chinese Patent Office in a corresponding Chinese Application No. 201180014664.8 (Chinese Language and the full-text English translation).
Ito et al., "The efficiency of donepezil in Alzheimer's Disease," J. Nippon Med Sch, 69(4): 379-382 (Japanese language, English Abstract).
Smith et al., "Circuit-specific alterations in hippocampal synaptophysin immunoreactivity predict spatial learning impairment in aged rats," J. Neuroscience, 20(17):6587-6593 (2000).
Scheff et al., "Hippocampal synaptic loss in early Alzheimer's disease and mild cognitive impairment," Neurobiology of Aging, 27:1372-1384 (2006).
Bennett, "Seletracetam (UCB 44212)," Neurotherapeutics: The Journal of the American Society for Experimental NeuroTherapeutics, 117-122 (2007).
Hamann et al., "Brivaracetam and seletracetam, two new SV2A ligands, improve paroxysmal dystonia in the dtsz mutant hamster," European Journal of Pharmacology, 601:99-102 (2008).
Rogawski, "Diverse mechanisms of antiepileptic drugs in the development pipeline," Epilepsy Research, 69:273-294 (2006).
Taylor et al., "Levetiracetam is associated with improved cognitive outcome for patients with intracranial hemorrhage," Neurocritical Care, 15:80-84 (2011).
Von Rosenstiel, "Brivaracetam (UCB 34714)," Neurotherapeutics: The Journal of the American Society for Experimental NeuroTherapeutics, 84-87 (2007).
Schobel et al., "Differential targeting of the CA1 subfield of the hippocampal formation by schizophrenia and related psychotic disorders," Arch. Gen. Psychiatry, 66:938-946 (2009).
Tregellas et al., "Intrinsic Hippocampal Activity as a Biomarker for Cognition and Symptoms in Schizophrenia," Am. J. Psychiatry, 1-8 (2014).
Berchtold et al., "Brain gene expression patterns differentiate mild cognitive impairment from normal aged and Alzheimer's disease," Neurobiology of Aging, S0197-4580(14)00289-9 (2014).
Martinez-Coria et al., "Memantine improves cognition and reduces Alzheimer's-like neuropathology in transgenic mice," Am J Pathol, 176 (11 pages) (2010).
ADR news: Levetiracetam. Parkinsonism: case report. Reactions (Nov. 30, 2006) ISSN:0114-9954 (1 page).
Bernhard et al., "Levetiracetam add-on treatment for bipolar patients suffering from subsyndromal symptoms: preliminary data of an open 6-months longitudinal study," European Neuropsychopharmacology, Elsevier Science Publisher BV, NL, S416 p. 2055 (1 page) (2005).
Bora et al., "Theory of mind impairment: a distinct trait-marker for schizophrenia spectrum disorders and bipolar disorder?" Acta Psychiatr Scand., 120 (12 pages) (2009).
Kilgore et al., "Inhibitors of class 1 histone deacetylases reverse contextual memory deficits in a mouse model of Alzheimer's disease," Neuropsychopharmacology, 35:870-880 (2010).
"The Merck Manual", 1999, Merck Research Laboratories, (12 pages).
Sajatovic et al., "Adjunct extended-release valproate semisodium in late life schizophrenia," International Journal of Geriatric Psychiatry, 23:142-147 (2008).
Walden et al., "Levetiracetam and ethosuximide in the treatment of acute mania in an open study with an on-off-on design," Bipolar Disorders, 4(Suppl 1):114 Abstract only (1 page) (2002).
Eddy, et al. "The cognitive impact of antiepileptic drugs," Therapeutic Advances in Neurological Disorders, 4(6):385-407 (2011).
Extended Release Memantine at www.medscape.com/viewarticle/723988 (2010) (retrieved Jun. 21, 2017) (4 pages).
Rosche, et al. "Different cognitive effects of inducing levetiracetam or topiramate into an antiepileptic pharmacotherapy in patients with therapy refractory epilepsy," Neurology, Psychiatry and Brain Research, 11:109-114 (2004).
Sabbagh et al., "Progressive cholinergic decline in Alzheimer's Disease: consideration for treatment with donepezil 23 mg in patients with moderate to severe symptomatology," BMC Neurology, 11(21), pages (2011).
Bakker et al., "Response of the medial temporal lobe network in amnestic mild cognitive impairment to therapeutic intervention assessed by fMRI and memory task performance," NeuroImage Clinical, 21(7):688-698 (2015).
Farlow, "Treatment of Mild Cognitive Impairment (MCI)," Current Alzheimer Research, 6:362-367 (2009).
Huynh et al., "Therapies under investigation for treating Parkinson's disease psychosis," Clinical Investigation, 4(10):889-901 (2014).
Brivaracetam, CAS Reg. No. 357336-20-0 (retrieved from STN on May 1, 2019) (1 page).
Karakaya, et al., "Pharmacological Treatment of Mild Cognitive Impairment as a Prodromal Syndrome of Alzheimer's Disease," Current Neuropharmacology, 11(1):102-108 (2013).
Lodge, et al., "Hippocampal dysregulation of dopamine system function and the pathophysiology of schizophrenia," Trends in Pharmacological Sciences, 32(9):507-513 (2011).
Luciano et al., "Results of treatment changes in patients with apparently drug-resistant chronic epilepsy," Annals of Neurology, 62(4):375-381 (2007).
Leppik et al., "Extended-release antiepileptic drugs: a comparison of pharmacokinetic parameters relative to original immediate-release formulations," Epilepsia, 54(1):28-35 (2013).

(56) References Cited

OTHER PUBLICATIONS

Matagne et al., "Anti-convulsive and anti-epileptic properties of brivaracetam (ucb 34714), a high-affinity ligand for the synaptic vesicle protein, SV2A," British Journal of Pharmacology, 154:1662-1671 (2008).
Philips et al., "An observational assessment method for aging laboratory rats," The Journal of the American Association for Laboratory Animal Science, 49(6):792-799 (2010).
Rouits et al., "Pharmacokinetics of levetiracetam XR 500mg tablets," Epilepsy Research, 84(2-3):224-231 (2009).
Ulloa et al., "Review of levetiracetam, with a focus on the extended release formulation, as adjuvant therapy in controlling partial-onset seizures," Neuropsychiatric Disease and Treatment, 5:467-476 (2009).
Zona et al., "Brivaracetam (Ucb 34714) inhibits $Na^+$ current in rat cortical neurons in culture," Epilepsy Research, 88(1):46-54 (2009).

\* cited by examiner

Left CA3 Lures

| Group | Mean Activity | Standard Error |
|---|---|---|
| Control | -0.39129 | 0.182628 |
| MCI Placebo | 0.48440 | 0.277487 |
| MCI Drug | -0.09653 | 0.205892 |

FIG. 8C

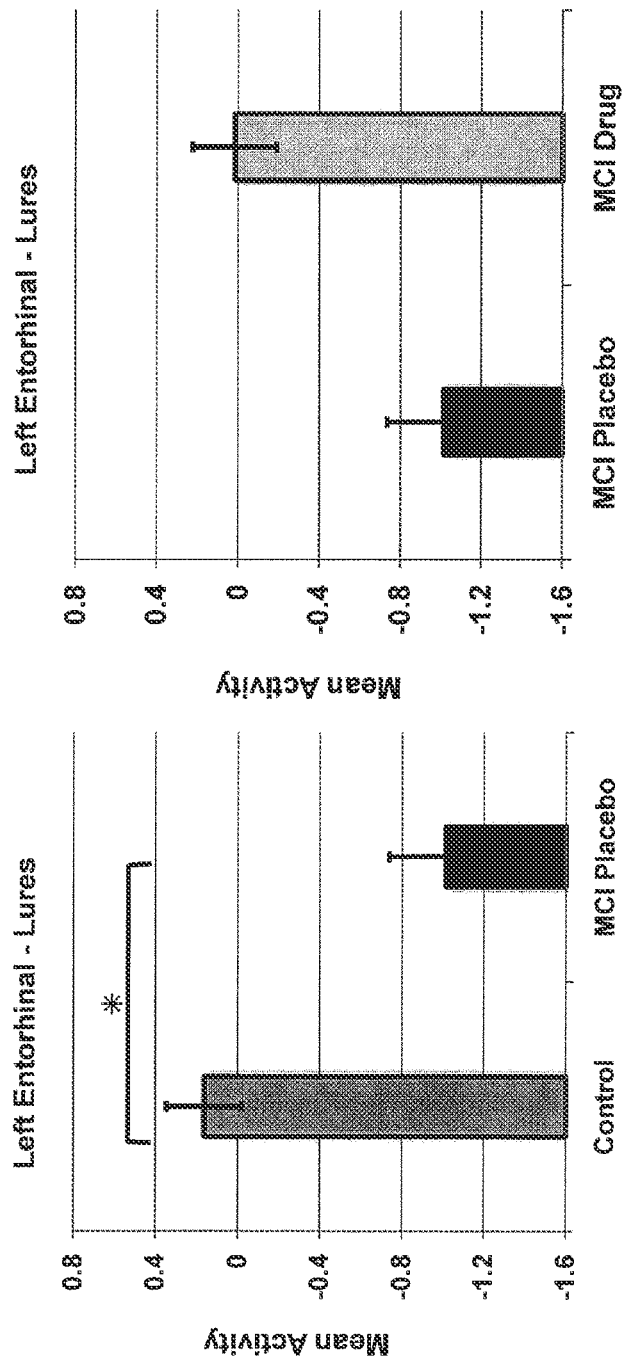

Left Entorhinal Lures

| Group | Mean Activity | Standard Error |
|---|---|---|
| Control | 0.16444 | 0.143864 |
| MCI Placebo | -1.01273 | 0.329062 |
| MCI Drug | 0.016291 | 0.411762 |

FIG. 9C

Reduced memory in task that taxes pattern separation

Behavioral Performance

| Control Subjects | Proportion of Responses | Standard Error |
|---|---|---|
| Old | 0.433676 | 0.04426 |
| Similar | 0.406771 | 0.04135 |
| New | 0.159553 | 0.03312 |
| MCI Placebo Subjects | Proportion of Responses | Standard Error |
| Old | 0.52262 | 0.04871 |
| Similar | 0.27549 | 0.03956 |
| New | 0.20188 | 0.04528 |
| MCI Drug Subjects | Proportion of Responses | Standard Error |
| Old | 0.45361 | 0.04825 |
| Similar | 0.33144 | 0.04592 |
| New | 0.21494 | 0.04202 |

FIG. 13

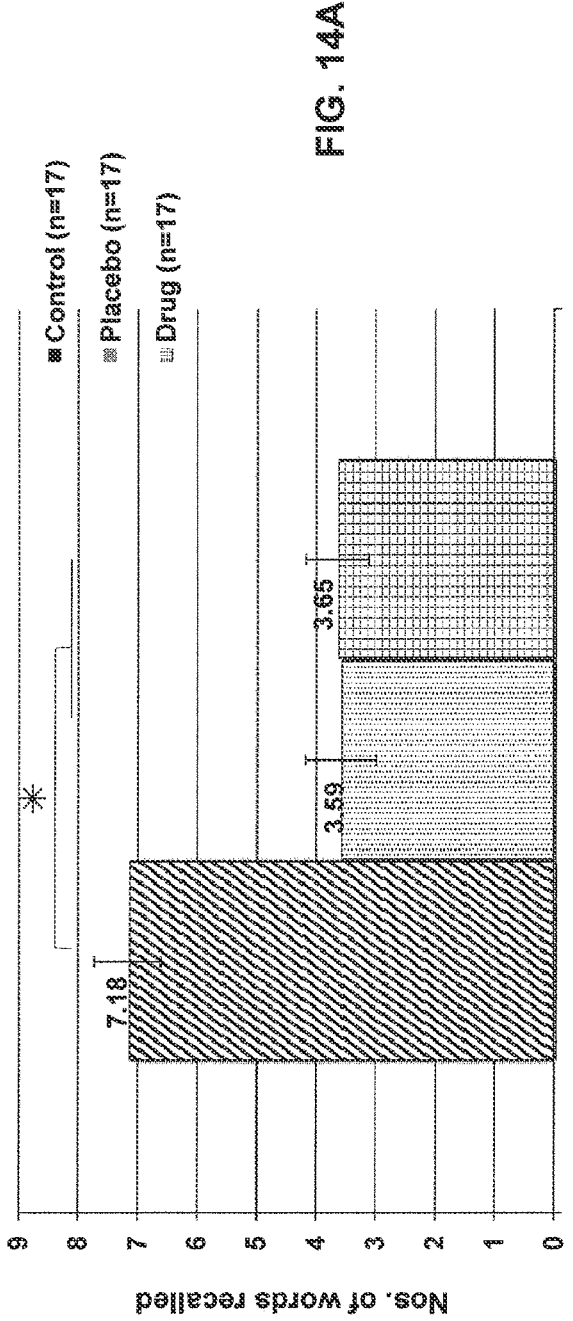

Study Status

| | Control subjects | MCI subjects | Total subjects |
|---|---|---|---|
| Participated in screening | 26 | 32 | 58 |
| Screening failures | 4 | 9 | 13 |
| Enrolled | 22 | 23 | 45 |
| Removed or withdrew from study | 5 | 6 | 11 |
| Total subjects used in analysis | 17 | 17 | 34 |

FIG. 18A

Characteristics of Study Samples

| | Control Subjects | MCI Subjects | p |
|---|---|---|---|
| N | 17 | 17 | |
| Sex (M/F) | 9/8 | 6/11 | 0.307 |
| Age (yrs) | 69.3 (7.0) | 72.9 (8.9) | 0.201 |
| Education (yrs) | 15.9 (2.6) | 15.8 (2.9) | 0.951 |
| Race (Caucasian/African American) | 17/0 | 14/3 | 0.074 |
| Hispanic or Latino (y/n) | 0/17 | 1/16 | 0.317 |

FIG. 18B

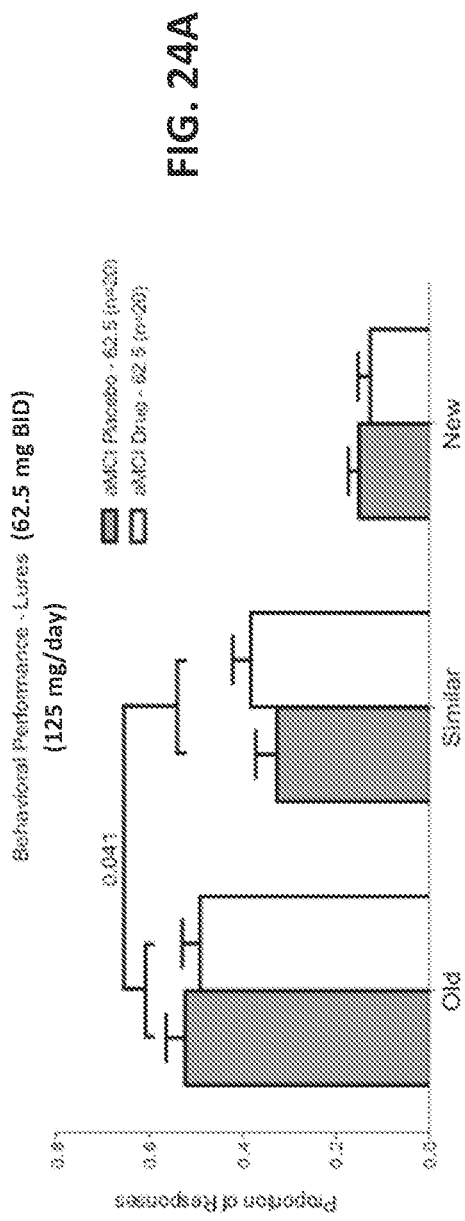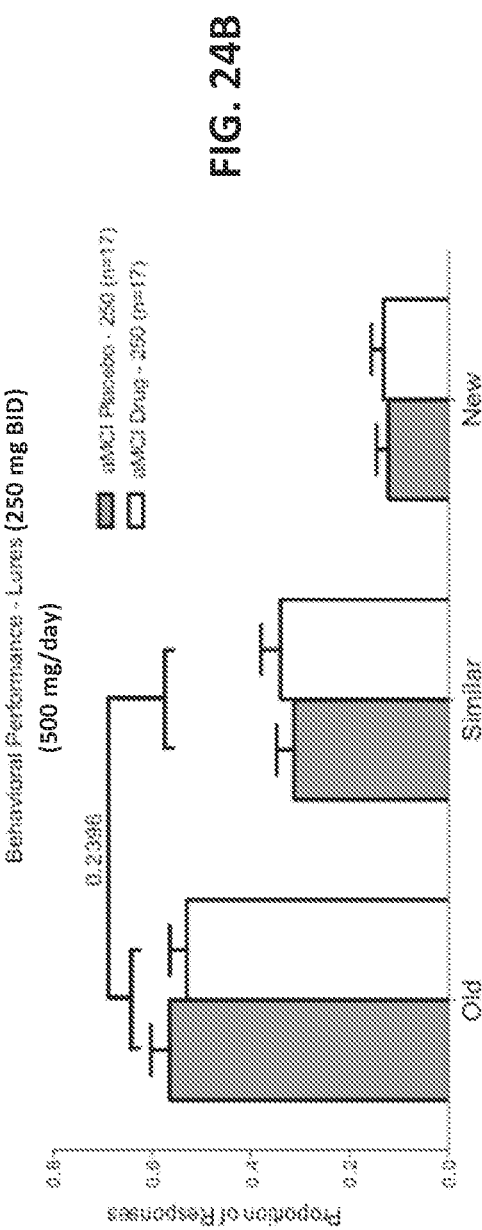

METHODS AND COMPOSITIONS FOR IMPROVING COGNITIVE FUNCTION

This application is a national stage application under 35 U.S.C. § 371 of International Application No. PCT/US2014/029170 (now pending), filed Mar. 14, 2014, which claims the benefit of and priority from U.S. provisional patent application 61/794,909, filed Mar. 15, 2013). The contents and disclosures of each of the foregoing applications are incorporated herein by reference in their entirety.

FIELD OF THE INVENTION

This invention relates to methods and compositions for improving cognitive function by using a synaptic vesicle glycoprotein 2A (SV2A) inhibitor, alone or in combination with valproate. In particular, it relates to the use of SV2A inhibitors alone or in combination with valproate in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism, compulsive behavior, and substance addiction.

BACKGROUND OF THE INVENTION

Cognitive ability may decline as a normal consequence of aging or as a consequence of a CNS disorder.

For example, a significant population of elderly adults experiences a decline in cognitive ability that exceeds what is typical in normal aging. Such age-related loss of cognitive function is characterized clinically by progressive loss of memory, cognition, reasoning, and judgment. Mild Cognitive Impairment (MCI), Age-Associated Memory Impairment (AAMI), Age-Related Cognitive Decline (ARCD) or similar clinical groupings are among those related to such age-related loss of cognitive function. According to some estimates, there are more than 16 million people with AAMI in the U.S. alone (Barker et al., 1995), and MCI is estimated to affect 5.5-7 million in the U.S. over the age of 65 (Plassman et al., 2008).

Cognitive impairment is also associated with other central nervous system (CNS) disorders, such as dementia, Alzheimer's Disease (AD), prodromal AD, post traumatic stress disorder (PTSD), schizophrenia, bipolar disorder (e.g., mania), amyotrophic lateral sclerosis (ALS), cancer-therapy-related cognitive impairment, mental retardation, Parkinson's disease (PD), autism, compulsive behavior, and substance addiction.

There is, therefore, a need for effective treatment of cognitive impairment associated with central nervous system (CNS) disorders and to improve cognitive function in patients diagnosed with, for example, age-related cognitive impairment, MCI, amnestic MCI, AAMI, ARCD, dementia, Alzheimer's Disease (AD), prodromal AD, post traumatic stress disorder (PTSD), schizophrenia, bipolar disorder (e.g., mania), amyotrophic lateral sclerosis, cancer-therapy-related cognitive impairment, mental retardation, Parkinson's disease (PD), autism, compulsive behavior, and substance addiction, and similar central nervous system (CNS) disorders associated with cognitive impairment or at risk of developing them.

SUMMARY OF THE INVENTION

In accordance with a first aspect of the present invention, there is provided a method for treating cognitive impairment or improving cognitive function, delaying or slowing the progression of cognitive impairment, or reducing the rate of decline of cognitive function, in a subject suffering from cognitive impairment associated with a central nervous system (CNS) disorder, or at risk thereof, the method comprising the step of administering to said subject a therapeutically effective amount of an SV2A inhibitor or a pharmaceutically acceptable salt, hydrate, solvate, polymorph, or prodrug thereof. In some embodiments of this aspect of the invention, the methods improve or treat cognitive function in said subject. In some embodiments of this aspect of the invention, the methods delay or slow the progression of cognitive impairment in said subject. In some embodiments of this aspect of the invention, the methods reduce the rate of decline of cognitive function in said subject. In some embodiments of this aspect of the invention, the methods prevent or slow the progression of the cognitive impairment associated with said CNS disorder in said subject. In other embodiments of this aspect of the invention, the methods alleviate, ameliorate, or slow the progression, of one or more symptoms associated with the cognitive impairment aspects of said CNS disorder in said subject.

In some embodiments of this aspect of the invention, the cognitive impairment is associated with age-related cognitive impairment, such as Mild Cognitive Impairment (MCI), Age-Associated Memory Impairment (AAMI), Age Related Cognitive Decline (ARCD). In one embodiment of this aspect of the invention, the MCI is amnestic MCI. In some embodiments of this aspect of the invention, the cognitive impairment is associated with dementia, Alzheimer's Disease (AD), prodromal AD, post traumatic stress disorder (PTSD), schizophrenia, bipolar disorder, amyotrophic lateral sclerosis, cancer-therapy-related cognitive impairment, mental retardation, Parkinson's disease, autism, compulsive behavior, or substance addiction. In one embodiment of this aspect of the invention, the subject that suffers such cognitive impairment is a human patient.

The SV2A inhibitor or the pharmaceutically acceptable salt, hydrate, solvate, polymorph, or prodrug thereof that is useful in the methods and compositions of this aspect of the invention include those disclosed in, for example, U.S. patent application Ser. No. 12/580,464 (Pub. No. US-2010-0099735), U.S. patent application Ser. No. 13/287,531 (Pub. No. US-2012-0046336), U.S. patent application Ser. No. 13/370,253 (Pub. No. US-2012-0214859), International Patent Application PCT/US2009/005647 (Pub. No. WO2010/044878), International Patent Application PCT/US12/24556 (Pub. No. WO2012/109491), U.S. Patent Application 61/105,847, U.S. Patent Application 61/152,631, U.S. Patent Application 61/175,536, and U.S. Patent Application 61/441,251. However, any SV2A inhibitor or a pharmaceutically acceptable salt, hydrate, solvate, polymorph, or prodrug thereof may be used in the methods and compositions of this aspect of the invention. In other embodiments, the SV2A inhibitor is selected from the group of SV2A inhibitors referred to in International Patent Applications WO2010/144712; WO2010/002869; WO2008/132139; WO2007/065595; WO2006/128693; WO2006/128692;

WO2005/054188; WO2004/087658; WO2002/094787; WO2001/062726; U.S. Pat. Nos. 7,465,549; 7,244,747; 5,334,720; 4,696,943; 4,696,942; U.S. Patent Application Publication Numbers 20090312333; 20090018148; 20080081832; 2006258704; and UK Patent Numbers 1,039,113; and 1,309,692 or their pharmaceutically acceptable salts, hydrates, solvates, polymorphs or prodrugs. In other embodiments, the SV2A inhibitor is selected from the group consisting of levetiracetam, brivaracetam, and seletracetam or derivatives or analogs or pharmaceutically acceptable salts, hydrates, solvates, polymorphs or prodrugs thereof. In other embodiments, the SV2A inhibitor is levetiracetam or a derivative or an analog or a pharmaceutically acceptable salt, hydrate, solvate, polymorph, or prodrug thereof. In other embodiments, the SV2A inhibitor is brivaracetam or a derivative or an analog or a pharmaceutically acceptable salt, hydrate, solvate, polymorph, or prodrug thereof. In other embodiments, the SV2A inhibitor is seletracetam or a derivative or an analog or a pharmaceutically acceptable salt, hydrate, solvate, polymorph, or prodrug thereof.

In other embodiments of this aspect of the invention, the SV2A inhibitor or the pharmaceutically acceptable salt, hydrate, solvate, polymorph, or prodrug thereof can be administered at doses as disclosed, for example, in U.S. patent application Ser. No. 12/580,464 (Pub. No. US-2010-0099735), U.S. patent application Ser. No. 13/287,531 (Pub. No. US-2012-0046336), U.S. patent application Ser. No. 13/370,253 (Pub. No. US-2012-0214859), International Patent Application PCT/US2009/005647 (Pub. No. WO2010/044878), International Patent Application PCT/US12/24556 (Pub. No. WO2012/109491), U.S. Patent Application 61/105,847, U.S. Patent Application 61/152,631, U.S. Patent Application 61/175,536, and U.S. Patent Application 61/441,251. In other embodiments of this aspect of the invention, the SV2A inhibitor or the pharmaceutically acceptable salt, hydrate, solvate, polymorph, or prodrug thereof is administered at a daily dose of about 0.1 to 0.2 mg/kg, or about 0.01 to 2.5 mg/kg, or about 0.1 to 2.5 mg/kg, or about 0.4 to 2.5 mg/kg, or about 0.6 to 1.8 mg/kg, or about 0.04 to 2.5 mg/kg, or about 0.06 to 1.8 mg/kg, or about 2.0 to 4.0 mg/kg, or about 2.0 to 3.0 mg/kg, or about 3.0 to 4.0 mg/kg, or about 0.2 to 0.4 mg/kg, or about 0.2 to 0.3 mg/kg, or about 0.3 to 0.4 mg/kg, or about 0.001-5 mg/kg, or about 0.001-0.5 mg/kg, or about 0.01-0.5 mg/kg. In some embodiments of this aspect of the invention, the SV2A inhibitor or the pharmaceutically acceptable salt, hydrate, solvate, polymorph, or prodrug thereof is administered at a daily dose of about 0.1-500 mg, 0.1-350 mg, 0.7-350 mg, 3-300 mg, 3-150 mg, 3-110 mg, 7-70 mg, 70-350 mg, 100-300 mg, or 125-250 mg; or about 0.0015-7 mg/kg, 0.0015-5 mg/kg, 0.01-5 mg/kg, 0.05-4 mg/kg, 0.05-2 mg/kg, 0.05-1.5 mg/kg, 0.1-1 mg/kg, 1-5 mg/kg, 1.5-4 mg/kg, or 1.8-3.6 mg/kg.

In accordance with a second aspect of the present invention, there is provided a method for treating cognitive impairment or improving cognitive function, delaying or slowing the progression of cognitive impairment, or reducing the rate of decline of cognitive function, in a subject suffering from cognitive impairment associated with a central nervous system (CNS) disorder, or at risk thereof, the method comprising the step of administering to said subject a therapeutically effective amount of an SV2A inhibitor or its pharmaceutically acceptable salt, hydrate, solvate, polymorph, or prodrug in combination with valproate or an analog, derivative, pharmaceutically acceptable salt, hydrate, solvate, polymorph, or prodrug thereof.

In some embodiments of this aspect of the invention, the SV2A inhibitor and/or valproate are administered at doses that are subtherapeutic as compared to the doses at which they are therapeutically effective when administered in the absence of the other.

In some embodiments of this aspect of the invention, the cognitive impairment is associated with age-related cognitive impairment, such as Mild Cognitive Impairment (MCI), Age-Associated Memory Impairment (AAMI), Age Related Cognitive Decline (ARCD). In one embodiment of this aspect of the invention, the MCI is amnestic MCI. In some embodiments of this aspect of the invention, the cognitive impairment is associated with dementia, Alzheimer's Disease (AD), prodromal AD, post traumatic stress disorder (PTSD), schizophrenia, bipolar disorder, amyotrophic lateral sclerosis, cancer-therapy-related cognitive impairment, mental retardation, Parkinson's disease, autism, compulsive behavior, or substance addiction. In one embodiment, the subject that suffers such cognitive impairment is a human patient.

The SV2A inhibitor or the pharmaceutically acceptable salt, hydrate, solvate, polymorph, or prodrug thereof that is useful in the methods and compositions of this aspect of the invention include those disclosed in, for example, U.S. patent application Ser. No. 12/580,464 (Pub. No. US-2010-0099735), U.S. patent application Ser. No. 13/287,531 (Pub. No. US-2012-0046336), U.S. patent application Ser. No. 13/370,253 (Pub. No. US-2012-0214859), International Patent Application PCT/US2009/005647 (Pub. No. WO2010/044878), International Patent Application PCT/US12/24556 (Pub. No. WO2012/109491), U.S. Patent Application 61/105,847, U.S. Patent Application 61/152,631, U.S. Patent Application 61/175,536, and U.S. Patent Application 61/441,251. However, any SV2A inhibitor or a pharmaceutically acceptable salt, hydrate, solvate, polymorph, or prodrug thereof may be used in the methods and compositions of this aspect of the invention. In other embodiments, the SV2A inhibitor is selected from the group of SV2A inhibitors referred to in International Patent Applications WO2010/144712; WO2010/002869; WO2008/132139; WO2007/065595; WO2006/128693; WO2006/128692; WO2005/054188; WO2004/087658; WO2002/094787; WO2001/062726; U.S. Pat. Nos. 7,465,549; 7,244,747; 5,334,720; 4,696,943; 4,696,942; U.S. Patent Application Publication Numbers 20090312333; 20090018148; 20080081832; 2006258704; and UK Patent Numbers 1,039,113; and 1,309,692 or their pharmaceutically acceptable salts, hydrates, solvates, polymorphs or prodrugs. In other embodiments, the SV2A inhibitor is selected from the group consisting of levetiracetam, brivaracetam, and seletracetam or derivatives or analogs or pharmaceutically acceptable salts, hydrates, solvates, polymorphs or prodrugs thereof. In other embodiments, the SV2A inhibitor is levetiracetam or a derivative or an analog or a pharmaceutically acceptable salt, hydrate, solvate, polymorph, or prodrug thereof. In other embodiments, the SV2A inhibitor is brivaracetam or a derivative or an analog or a pharmaceutically acceptable salt, hydrate, solvate, polymorph, or prodrug thereof. In other embodiments, the SV2A inhibitor is seletracetam or a derivative or an analog or a pharmaceutically acceptable salt, hydrate, solvate, polymorph, or prodrug thereof.

In other embodiments of this aspect of the invention, the SV2A inhibitor or the pharmaceutically acceptable salt, hydrate, solvate, polymorph, or prodrug thereof that is administered in combination with valproate or its analog, derivative or pharmaceutically acceptable salt can be administered at doses as disclosed, for example, in U.S. patent application Ser. No. 12/580,464 (Pub. No. US-2010-0099735), U.S. patent application Ser. No. 13/287,531 (Pub.

No. US-2012-0046336), U.S. patent application Ser. No. 13/370,253 (Pub. No. US-2012-0214859), International Patent Application PCT/US2009/005647 (Pub. No. WO2010/044878), International Patent Application PCT/US12/24556 (Pub. No. WO2012/109491), U.S. Patent Application 61/105,847, U.S. Patent Application 61/152,631, U.S. Patent Application 61/175,536, and U.S. Patent Application 61/441,251. In other embodiments of this aspect of the invention, the SV2A inhibitor or the pharmaceutically acceptable salt, hydrate, solvate, polymorph, or prodrug thereof that is administered in combination with valproate or its analog, derivative or pharmaceutically acceptable salt is administered at a daily dose of about 0.01 to 1 mg/kg, or about 0.001 to 1 mg/kg, or about 0.1 mg/kg to 5 mg/kg, or about 0.05 mg/kg to 0.5 mg/kg. In other embodiments of this aspect of the invention, the SV2A inhibitor or the pharmaceutically acceptable salt, hydrate, solvate, polymorph, or prodrug thereof that is administered in combination with valproate or its analog, derivative or pharmaceutically acceptable salt is administered at a daily dose of less than 7 mg/kg, less than 6 mg/kg, less than 5 mg/kg, less than 4 mg/kg, less than 3.6 mg/kg, less than 3 mg/kg, less than 2 mg/kg, less than 1.5 mg/kg, less than 1.5 mg/kg, less than 1 mg/kg, less than 0.1 mg/kg, less than 0.05 mg/kg, less than 0.01 mg/kg, or less than 0.0015 mg/kg, or at a daily dose of 0.0015-5 mg/kg, 0.01-5 mg/kg, 0.05-4.0 mg/kg, 0.05-2 mg/kg, 0.05-1.5 mg/kg, 0.1-1 mg/kg, 1-5 mg/kg, 1.5-4 mg/kg, or 1.8-3.6 mg/kg.

In certain embodiments of this aspect of the invention, valproate or an analog, derivative, pharmaceutically acceptable salt, hydrate, solvate, polymorph, or prodrug thereof that is administered in combination with the SV2A inhibitor or the pharmaceutically acceptable salt, hydrate, solvate, polymorph, or prodrug thereof is administered at a daily dose such that the subject maintains a blood total valproate level of 0.5 to 5 µg/ml plasma.

In other embodiments of this aspect of the invention, the SV2A inhibitor or its pharmaceutically acceptable salt, hydrate, solvate, polymorph, or prodrug and the valproate or its analog, derivative, pharmaceutically acceptable salt, hydrate, solvate, polymorph or prodrug are administered simultaneously, or sequentially, or in a single formulation or in separate formulations packaged together. In other embodiments of this aspect of the invention, the SV2A inhibitor or its pharmaceutically acceptable salt, hydrate, solvate, polymorph, or prodrug and the valproate or its analog, derivative, pharmaceutically acceptable salt, hydrate, solvate, polymorph or prodrug are administered via different routes. As used herein, "combination" includes administration by any of these formulations or routes of administration.

In certain embodiments of this aspect of the invention, the combined treatment has a longer or improved therapeutic effect in the subject than is attained by administering valproate or a derivative or an analog or a pharmaceutically acceptable salt, hydrate, solvate, polymorph or prodrug thereof in the absence of the SV2A inhibitor or a pharmaceutically acceptable salt, solvate, hydrate, or polymorph or prodrug thereof by at least about 1.5×, or 2.0×, or 2.5×, or 3.0×, or 3.5×, or 4.0×, or 4.5×, or 5.0×, or 5.5×, or 6.0×, or 6.5×, or 7.0×, or 7.5×, or 8.0×, or 8.5×, or 9.0×, or 9.5×, or 10×, or greater than about 10×.

In other embodiments of this aspect of the invention, the combined treatment has a longer or improved therapeutic effect in the subject than is attained by administering the SV2A inhibitor or a pharmaceutically acceptable salt, hydrate, solvate, polymorph or prodrug thereof in the absence of valproate or a derivative or an analog or a pharmaceutically acceptable salt, hydrate, solvate, polymorph or prodrug thereof by at least about 1.5×, or 2.0×, or 2.5×, or 3.0×, or 3.5×, or 4.0×, or 4.5×, or 5.0×, or 5.5×, or 6.0×, or 6.5×, or 7.0×, or 7.5×, or 8.0×, or 8.5×, or 9.0×, or 9.5×, or 10×, or greater than about 10×.

In accordance with another aspect of the present invention, there is provided a method of increasing the therapeutic index of valproate or a derivative or an analog or a pharmaceutically acceptable salt, hydrate, solvate, polymorph or prodrug thereof in a method of treating cognitive impairment associated with a central nervous system (CNS) disorder in a subject in need or at risk thereof, comprising administering an SV2A inhibitor or a pharmaceutically acceptable salt, hydrate, solvate, polymorph or prodrug thereof in combination with valproate or a derivative or an analog or a pharmaceutically acceptable salt, hydrate, solvate, polymorph or prodrug thereof to said subject.

In some embodiments of this aspect of the invention, the increase in the therapeutic index of valproate or a derivative or an analog or a pharmaceutically acceptable salt, hydrate, solvate, polymorph or prodrug thereof is greater than the therapeutic index of valproate or a derivative or an analog or a pharmaceutically acceptable salt, hydrate, solvate, polymorph or prodrug thereof when administered in the absence of the SV2A inhibitor or a pharmaceutically acceptable salt, hydrate, solvate, polymorph or prodrug thereof by at least about 1.5×, or 2.0×, or 2.5×, or 3.0×, or 3.5×, or 4.0×, or 4.5×, or 5.0×, or 5.5×, or 6.0×, or 6.5×, or 7.0×, or 7.5×, or 8.0×, or 8.5×, or 9.0×, or 9.5×, or 10×, or greater than about 10×.

In accordance with another aspect of the present invention, there is provided a method of increasing the therapeutic index of an SV2A inhibitor or a pharmaceutically acceptable salt, hydrate, solvate, polymorph or prodrug thereof in a method of treating a cognitive impairment associated with central nervous system (CNS) disorder in a subject in need or at risk thereof, comprising administering an SV2A inhibitor or a pharmaceutically acceptable salt, hydrate, solvate, polymorph or prodrug thereof in combination with valproate or a derivative or an analog or a pharmaceutically acceptable salt, hydrate, solvate, polymorph or prodrug thereof to said subject.

In some embodiments of this aspect of the invention, the increase in the therapeutic index of the SV2A inhibitor or a pharmaceutically acceptable salt, hydrate, solvate, polymorph or prodrug thereof is greater than the therapeutic index of the SV2A inhibitor or a pharmaceutically acceptable salt, hydrate, solvate, polymorph or prodrug thereof when administered in the absence of valproate or a derivative or an analog or a pharmaceutically acceptable salt, hydrate, solvate, polymorph or prodrug thereof by at least about 1.5×, or 2.0×, or 2.5×, or 3.0×, or 3.5×, or 4.0×, or 4.5×, or 5.0×, or 5.5×, or 6.0×, or 6.5×, or 7.0×, or 7.5×, or 8.0×, or 8.5×, or 9.0×, or 9.5×, or 10×, or greater than about 10×.

In accordance with another aspect of the present invention, there is provided a pharmaceutical composition comprising an SV2A inhibitor or a pharmaceutically acceptable salt, hydrate, solvate, polymorph or prodrug thereof. In certain embodiments of this aspect of the invention, the SV2A inhibitor or the pharmaceutically acceptable salt, hydrate, solvate, polymorph or prodrug thereof is present in an amount of 0.07-60 mg, 0.07-350 mg, 25-60 mg, 25-125 mg, 50-250 mg, 5-140 mg, 0.7-180 mg, 125-240 mg, 3-50 mg, or 3-60 mg. In other embodiments of this aspect of the invention, the SV2A inhibitor or the pharmaceutically acceptable salt, hydrate, solvate, polymorph or prodrug thereof is present in an amount of 0.05-35 mg, 0.1-500 mg, 0.1-350 mg, 0.7-350 mg, 3-300 mg, 3-150 mg, 3-110 mg, 7-70 mg, 70-350 mg, 100-300 mg, or 125-250 mg.

In accordance with another aspect of this invention, there is provided a pharmaceutical composition comprising an SV2A inhibitor or a pharmaceutically acceptable salt, hydrate, solvate, polymorph or prodrug thereof in combination with valproate or an analog, derivative, pharmaceutically acceptable salt, hydrate, solvate, polymorph, or prodrug thereof. In some embodiments of this aspect of the invention, the SV2A inhibitor or the pharmaceutically acceptable salt thereof is present in an amount of 0.05-35 mg, 0.07-60 mg, 0.07-350 mg, 25-60 mg, 25-125 mg, 50-250 mg, 5-15 mg, 5-30 mg, 5-140 mg, 0.7-180 mg, 125-240 mg, 3-50 mg, or 0.07-50 mg, 3-60 mg, or about 0.1-500 mg, 0.1-350 mg, 0.7-350 mg, 3-300 mg, 3-150 mg, 3-110 mg, 7-70 mg, 70-350 mg, 100-300 mg, or 125-250 mg. In other embodiments, the amount of the SV2A inhibitor or the pharmaceutically acceptable salt, hydrate, solvate, polymorph, or prodrug thereof is less than 500 mg, less than 350 mg, less than 300 mg, less than 250 mg, less than 200 mg, less than 150 mg, less than 110 mg, less than 100 mg, less than 70 mg, less than 50 mg, less than 35 mg, less than 10 mg, less than 7 mg, less than 5 mg, less than 3 mg, less than 1 mg, less than 0.7 mg, less than 0.5 mg, less than 0.1 mg, less than 0.07 mg, or less than 0.05 mg.

In certain embodiments of the composition provided in the invention, the composition is in a solid form. In some embodiments, the composition is in a liquid form. In some embodiments, the composition is in an aqueous solution. In some embodiments, the composition is in a suspension form. In some embodiments, the composition is in an extended release form, a controlled release form, a prolonged release form, a sustained release form, a delayed release form, or a slow release form. In some embodiments, the SV2A inhibitor or the pharmaceutically acceptable salt, hydrate, solvate, polymorph, or prodrug thereof is in an extended release form, a controlled release form, a prolonged release form, a sustained release form, a delayed release form, or a slow release form. In some embodiments, the SV2A inhibitor or the pharmaceutically acceptable salt, hydrate, solvate, polymorph, or prodrug thereof in an extended release form (or a controlled release form, a prolonged release form, a sustained release form, a delayed release form, or a slow release form) is formulated together with valproate or an analog, derivative, pharmaceutically acceptable salt, hydrate, solvate, polymorph, or prodrug thereof in a single formulation. In some embodiments, the SV2A inhibitor or the pharmaceutically acceptable salt, hydrate, solvate, polymorph, or prodrug thereof in an extended release form (or a controlled release form, a prolonged release form, a sustained release form, a delayed release form, or a slow release form) is formulated together with valproate or an analog, derivative, pharmaceutically acceptable salt, hydrate, solvate, polymorph, or prodrug thereof are formulated in separate formulations, which may be packaged together. In some of the above composition embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), valproate or an analog, derivative, pharmaceutically acceptable salt, hydrate, solvate, polymorph, or prodrug thereof is also in an extended release form (or a controlled release form, a prolonged release form, a sustained release form, a delayed release form, or a slow release form). In some of the above composition embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), valproate or an analog, derivative, pharmaceutically acceptable salt, hydrate, solvate, polymorph, or prodrug thereof is not in an extended release form (or a controlled release form, a prolonged release form, a sustained release form, a delayed release form, or a slow release form). In some embodiments of the composition of the present invention, valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form). In some embodiments, valproate or an analog, derivative, pharmaceutically acceptable salt, hydrate, solvate, polymorph, or prodrug thereof in an extended release form (or a controlled release form, a prolonged release form, a sustained release form, a delayed release form, or a slow release form) is formulated together with the SV2A inhibitor or the pharmaceutically acceptable salt, hydrate, solvate, polymorph, or prodrug thereof in a single formulation. In some embodiments, valproate or an analog, derivative, pharmaceutically acceptable salt, hydrate, solvate, polymorph, or prodrug thereof in an extended release form (or a controlled release form, a prolonged release form, a sustained release form, a delayed release form, or a slow release form) and the SV2A inhibitor or the pharmaceutically acceptable salt, hydrate, solvate, polymorph, or prodrug thereof are formulated in separate formulations, which may be packaged together. In some of the above composition embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof is also in an extended release form (or a controlled release form, a prolonged release form, a sustained release form, a delayed release form, or a slow release form). In some of the above embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof is not in an extended release form (or a controlled release form, a prolonged release form, a sustained release form, a delayed release form, or a slow release form). In some embodiments, the composition is in a unit dosage form. In some embodiments, the composition is in a capsule or tablet form. In some embodiments, the composition is for oral administration. In other embodiments, the two components of the compositions are in separate delivery forms packaged together.

In accordance with another aspect of the present invention, there is provided a method for treating cognitive impairment or improving cognitive function, delaying or slowing the progression of cognitive impairment, or reducing the rate of decline of cognitive function, in a subject suffering from cognitive impairment associated with a central nervous system (CNS) disorder, or at risk thereof, the method comprising the step of administering to said subject a therapeutically effective amount of levetiracetam or a pharmaceutically acceptable salt, hydrate, solvate, polymorph, or prodrug thereof. In some embodiments of this aspect of the invention, the methods improve or treat cognitive function in said subject. In some embodiments of this aspect of the invention, the methods delay or slow the progression of cognitive impairment in said subject. In some embodiments of this aspect of the invention, the methods reduce the rate of decline of cognitive function in said subject. In some embodiments of this aspect of the invention, the methods prevent or slow the progression of the cognitive impairment associated with said CNS disorder in said subject. In other embodiments of this aspect of invention, the methods alleviate, ameliorate, or slow the progression, of one or more symptoms associated with the cognitive impairment aspects of said CNS disorder in said subject.

In some embodiments of this aspect of the invention, the cognitive impairment is associated with age-related cognitive impairment, such as Mild Cognitive Impairment (MCI), Age-Associated Memory Impairment (AAMI), Age Related Cognitive Decline (ARCD). In one embodiment of this aspect of the invention, the MCI is amnestic MCI. In some embodiments of this aspect of the invention, the cognitive impairment is associated with dementia, Alzheimer's Disease (AD), prodromal AD, post traumatic stress disorder (PTSD), schizophrenia, bipolar disorder, amyotrophic lateral sclerosis, cancer-therapy-related cognitive impairment, mental retardation, Parkinson's disease, autism, compulsive behavior, or substance addiction. In one embodiment, the subject that suffers such cognitive impairment is a human patient.

In certain embodiments of this aspect of the invention, the levetiracetam or a pharmaceutically acceptable salt, hydrate, solvate, polymorph, or prodrug thereof is administered at a daily dose of about 1 to 2 mg/kg, or about 0.1 to 2.5 mg/kg, or about 0.4 to 2.5 mg/kg, or about 0.6 to 1.8 mg/kg, or about 2.0 to 3.0 mg/kg, or about 3.0 to 4.0 mg/kg, or about 2.0 to 4.0 mg/kg, or about 0.1-5 mg/kg, or about 70 to 140 mg, or about 7 to 180 mg, or about 25-180 mg, or about 40 to 130 mg, or about 140 to 300 mg, or about 200 to 300 mg, or about 140 to 200 mg, or about 7-350 mg, 70-350 mg, 100-300 mg, or 125-250 mg, or about 0.1-5 mg/kg, 1-5 mg/kg, 1.5-4 mg/kg, or 1.8-3.6 mg/kg.

In certain embodiments of this aspect of the invention, the levetiracetam or a pharmaceutically acceptable salt, hydrate, solvate, polymorph, or prodrug thereof is administered at a daily dose according to one of the daily dose ranges indicated as "+" listed in Table 1 or Table 2. In some embodiments, the levetiracetam or a pharmaceutically acceptable salt, hydrate, solvate, polymorph, or prodrug thereof administered is in an extended release form, a controlled release form, a prolonged release form, a sustained release form, a delayed release form, or a slow release form. In some embodiments, the levetiracetam or a pharmaceutically acceptable salt, hydrate, solvate, polymorph, or prodrug thereof administered is administered once or twice daily.

In accordance with another aspect of the present invention, there is provided a method for treating cognitive impairment or improving cognitive function, delaying or slowing the progression of cognitive impairment, or reducing the rate of decline of cognitive function, in a subject suffering from cognitive impairment associated with a central nervous system (CNS) disorder, or at risk thereof, the method comprising the step of administering to said subject a therapeutically effective amount of brivaracetam or a pharmaceutically acceptable salt, hydrate, solvate, polymorph, or prodrug thereof. In some embodiments of this aspect of the invention, the methods improve or treat cognitive function in said subject. In some embodiments of this aspect of the invention, the methods delay or slow the progression of cognitive impairment in said subject. In some embodiments of this aspect of the invention, the methods reduce the rate of decline of cognitive function in said subject. In some embodiments of this aspect of the invention, the methods prevent or slow the progression of the cognitive impairment associated with said CNS disorder in said subject. In other embodiments of this aspect of invention, the methods alleviate, ameliorate, or slow the progression, of one or more symptoms associated with the cognitive impairment aspects of said CNS disorder in said subject.

In some embodiments of this aspect of the invention, the cognitive impairment is associated with age-related cognitive impairment, such as Mild Cognitive Impairment (MCI), Age-Associated Memory Impairment (AAMI), Age Related Cognitive Decline (ARCD). In one embodiment of this aspect of the invention, the MCI is amnestic MCI. In some embodiments of this aspect of the invention, the cognitive impairment is associated with dementia, Alzheimer's Disease (AD), prodromal AD, post traumatic stress disorder (PTSD), schizophrenia, bipolar disorder, amyotrophic lateral sclerosis, cancer-therapy-related cognitive impairment, mental retardation, Parkinson's disease, autism, compulsive behavior, or substance addiction. In one embodiment, the subject that suffers such cognitive impairment is a human patient.

In certain embodiments of this aspect of the invention, the brivaracetam or the pharmaceutically acceptable salt, hydrate, solvate, polymorph, or prodrug thereof is administered at a daily dose of about 0.1 to 0.2 mg/kg, or about 0.01 to 2.5 mg/kg, or about 0.04 to 2.5 mg/kg, or about 0.06 to 1.8 mg/kg, or about 0.2 to 0.4 mg/kg, or about 7 to 15 mg, or about 0.7 to 180 mg, or about 2.5 to 180 mg, or about 4.0 to 130 mg, or about 14 to 30 mg. In other embodiments, the brivaracetam or the pharmaceutically acceptable salt, hydrate, solvate, polymorph, or prodrug thereof is administered at a daily dose of about 0.1-350 mg, 0.7-350 mg, 3-300 mg, 3-150 mg, 3-110 mg, or 7-70 mg; or 0.0015-5 mg/kg, 0.01-5 mg/kg, 0.05-4.0 mg/kg, 0.05-2 mg/kg, 0.05-1.5 mg/kg, or 0.1-1 mg/kg.

In certain embodiments of this aspect of the invention, the brivaracetam or the pharmaceutically acceptable salt, hydrate, solvate, polymorph, or prodrug thereof is administered at a daily dose of at least 0.1 mg, 0.5 mg, 0.75 mg, 1.0 mg, 1.5 mg, or 2.0 mg; but no more than a daily dose of 2.5 mg, 5 mg, 10 mg, 15 mg, 20 mg, 25 mg, 30 mg, or 35 mg. In other embodiments, the brivaracetam or the pharmaceutically acceptable salt, hydrate, solvate, polymorph, or prodrug thereof is administered at a daily dose of at least 0.0015 mg/kg, 0.0075 mg/kg, 0.01 mg/kg, 0.015 mg/kg, 0.02 mg/kg, or 0.03 mg/kg; but no more than a daily dose of 0.5 mg/kg, 0.4 mg/kg, 0.3 mg/kg, 0.2 mg/kg, 0.15 mg/kg, 0.1 mg/kg, 0.05 mg/kg, or 0.04 mg/kg.

In certain embodiments of this aspect of the invention, the brivaracetam or the pharmaceutically acceptable salt, hydrate, solvate, polymorph, or prodrug thereof is administered at a daily dose according to one of the daily dose ranges indicated as "+" listed in Tables 3-6. For example, the brivaracetam or the pharmaceutically acceptable salt, hydrate, solvate, polymorph, or prodrug thereof may be administered at a daily dose of 0.1-35 mg, 0.5-35 mg, 0.75-35 mg, 1.0-35 mg, 1.5-35 mg, 2.0-35 mg, 0.1-30 mg, 0.1-25 mg, 0.1-20 mg, 0.1-15 mg, 0.1-10 mg, 0.1-5 mg, 0.1-2.5 mg, 0.0015-0.5 mg/kg, 0.0075-0.5 mg/kg, 0.01-0.5 mg/kg, 0.015-0.5 mg/kg, 0.02-0.5 mg/kg, 0.03-0.5 mg/kg, 0.0015-0.4 mg/kg, 0.0015-0.3 mg/kg, 0.0015-0.2 mg/kg, 0.0015-0.15 mg/kg, 0.0015-0.1 mg/kg, 0.0015-0.05 mg/kg, or 0.0015-0.04 mg/kg. In some embodiments, the brivaracetam or the pharmaceutically acceptable salt, hydrate, solvate, polymorph, or prodrug thereof administered is in an extended release form, a controlled release form, a prolonged release form, a sustained release form, a delayed release form, or a slow release form. In some embodiments, the brivaracetam or the pharmaceutically acceptable salt, hydrate, solvate, polymorph, or prodrug thereof administered is administered once or twice daily.

In accordance with another aspect of the present invention, there is provided a method for treating cognitive impairment or improving cognitive function, delaying or slowing the progression of cognitive impairment, or reducing the rate of decline of cognitive function, in a subject suffering from cognitive impairment associated with a central nervous system (CNS) disorder, or at risk thereof, the method comprising the step of administering to said subject a therapeutically effective amount of seletracetam or a pharmaceutically acceptable salt thereof. In some embodiments of this aspect of the invention, the methods improve or treat cognitive function in said subject. In some embodiments of this aspect of the invention, the methods delay or slow the progression of cognitive impairment in said subject. In some embodiments of this aspect of the invention, the methods reduce the rate of decline of cognitive function in said subject. In some embodiments of this aspect of the invention, the methods prevent or slow the progression of the cognitive impairment associated with said CNS disorder in said subject. In other embodiments of this aspect of invention, the methods alleviate, ameliorate, or slow the progression, of one or more symptoms associated with the cognitive impairment aspects of said CNS disorder in said subject.

In some embodiments of this aspect of the invention, the cognitive impairment is associated with age-related cognitive impairment, such as Mild Cognitive Impairment (MCI), Age-Associated Memory Impairment (AAMI), Age Related Cognitive Decline (ARCD). In one embodiment of this aspect of the invention, the MCI is amnestic MCI. In some embodiments of this aspect of the invention, the cognitive impairment is associated with dementia, Alzheimer's Disease (AD), prodromal AD, post traumatic stress disorder (PTSD), schizophrenia, bipolar disorder, amyotrophic lateral sclerosis, cancer-therapy-related cognitive impairment, mental retardation, Parkinson's disease, autism, compulsive behavior, or substance addiction. In one embodiment, the subject that suffers such cognitive impairment is a human patient.

In certain embodiments of this aspect of the invention, the seletracetam or a pharmaceutically acceptable salt, hydrate, solvate, polymorph, or prodrug thereof is administered at a daily dose of at least 0.1 mg, 0.5 mg, 0.75 mg, 1.0 mg, 1.5 mg, or 2.0 mg; but no more than a daily dose of 2.5 mg, 5 mg, 10 mg, 15 mg, 20 mg, 25 mg, 30 mg, or 35 mg. In other embodiments, the seletracetam or a pharmaceutically acceptable salt, hydrate, solvate, polymorph, or prodrug thereof is administered at a daily dose of at least 0.0015 mg/kg, 0.0075 mg/kg, 0.01 mg/kg, 0.015 mg/kg, 0.02 mg/kg, or 0.03 mg/kg; but no more than a daily dose of 0.5 mg/kg, 0.4 mg/kg, 0.3 mg/kg, 0.2 mg/kg, 0.15 mg/kg, 0.1 mg/kg, 0.05 mg/kg, or 0.04 mg/kg. In other embodiments, the seletracetam or the pharmaceutically acceptable salt, hydrate, solvate, polymorph, or prodrug thereof is administered at a daily dose of about 0.1-350 mg, 0.7-350 mg, 3-300 mg, 3-150 mg, 3-110 mg, or 7-70 mg; or 0.0015-5 mg/kg, 0.01-5 mg/kg, 0.05-4.0 mg/kg, 0.05-2 mg/kg, 0.05-1.5 mg/kg, or 0.1-1 mg/kg.

In certain embodiments of this aspect of the invention, the seletracetam or a pharmaceutically acceptable salt, hydrate, solvate, polymorph, or prodrug thereof is administered at a daily dose according to one of the daily dose ranges indicated as "+" listed in Tables 7-10. For example, the seletracetam or a pharmaceutically acceptable salt, hydrate, solvate, polymorph, or prodrug thereof may be administered at a daily dose of 0.1-35 mg, 0.5-35 mg, 0.75-35 mg, 1.0-35 mg, 1.5-35 mg, 2.0-35 mg, 0.1-30 mg, 0.1-25 mg, 0.1-20 mg, 0.1-15 mg, 0.1-10 mg, 0.1-5 mg, 0.1-2.5 mg, 0.0015-0.5 mg/kg, 0.0075-0.5 mg/kg, 0.01-0.5 mg/kg, 0.015-0.5 mg/kg, 0.02-0.5 mg/kg, 0.03-0.5 mg/kg, 0.0015-0.4 mg/kg, 0.0015-0.3 mg/kg, 0.0015-0.2 mg/kg, 0.0015-0.15 mg/kg, 0.0015-0.1 mg/kg, 0.0015-0.05 mg/kg, or 0.0015-0.04 mg/kg. In some embodiments, the seletracetam or a pharmaceutically acceptable salt, hydrate, solvate, polymorph, or prodrug thereof administered is in an extended release form, a controlled release form, a prolonged release form, a sustained release form, a delayed release form, or a slow release form. In some embodiments, the seletracetam or the pharmaceutically acceptable salt, hydrate, solvate, polymorph, or prodrug thereof administered is administered once or twice daily.

In certain embodiments of the various aspect of the invention, the SV2A inhibitor (e.g., levetiracetam, brivaracetam, or seletracetam) or a pharmaceutically acceptable salt, hydrate, solvate, polymorph, or prodrug thereof is administered in an extended release form, a controlled release form, a prolonged release form, a sustained release form, a delayed release form, or a slow release form. In some embodiments, the SV2A inhibitor or the pharmaceutically acceptable salt, hydrate, solvate, polymorph, or prodrug thereof in an extended release form (or a controlled release form, a prolonged release form, a sustained release form, a delayed release form, or a slow release form) is administered together with valproate or an analog, derivative, pharmaceutically acceptable salt, hydrate, solvate, polymorph, or prodrug thereof. In some embodiments, the SV2A inhibitor or the pharmaceutically acceptable salt, hydrate, solvate, polymorph, or prodrug thereof in an extended release form (or a controlled release form, a prolonged release form, a sustained release form, a delayed release form, or a slow release form) and valproate or an analog, derivative, pharmaceutically acceptable salt, hydrate, solvate, polymorph, or prodrug thereof are administered separately. In some of the above embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), valproate or an analog, derivative, pharmaceutically acceptable salt, hydrate, solvate, polymorph, or prodrug thereof is also in an extended release form (or a controlled release form, a prolonged release form, a sustained release form, a delayed release form, or a slow release form). In some of the above embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), valproate or an analog, derivative, pharmaceutically acceptable salt, hydrate, solvate, polymorph, or prodrug thereof is not in an extended release form (or a controlled release form, a prolonged release form, a sustained release form, a delayed release form, or a slow release form). In some embodiments of the invention, valproate or an analog, derivative, pharmaceutically acceptable salt, hydrate, solvate, polymorph, or prodrug thereof is administered in an extended release form (or a controlled release form, a prolonged release form, a sustained release form, a delayed release form, or a slow release form). In some embodiments, valproate or an analog, derivative, pharmaceutically acceptable salt, hydrate, solvate, polymorph, or prodrug thereof in an extended release form (or a controlled release form, a prolonged release form, a sustained release form, a delayed release form, or a slow release form) is administered together with the SV2A inhibitor or the pharmaceutically acceptable salt, hydrate, solvate, polymorph, or prodrug thereof. In some embodiments, valproate or an analog, derivative, pharmaceutically acceptable salt, hydrate, solvate, polymorph, or prodrug thereof in an extended release form (or a controlled release form, a prolonged release form, a sustained release form, a delayed release form, or a slow release form) and the SV2A inhibitor or the pharmaceutically acceptable salt, hydrate, solvate, polymorph, or prodrug thereof are administered separately.

In some of the above embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof is also in an extended release form (or a controlled release form, a prolonged release form, a sustained release form, a delayed release form, or a slow release form). In some of the above embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof is not in an extended release form (or a controlled release form, a prolonged release form, a sustained release form, a delayed release form, or a slow release form).

In some of the above embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof are administered once daily. In some of the above embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the valproate or the analog, derivative or pharmaceutically acceptable salt thereof are administered once daily.

In some of the above embodiments, the SV2A inhibitor or the pharmaceutically acceptable salt, hydrate, solvate, polymorph, or prodrug thereof is levetiracetam, brivaracetam, or seletracetam. In some of the above embodiments, levetiracetam, brivaracetam, or seletracetam or a pharmaceutically acceptable salt, hydrate, solvate, polymorph, or prodrug thereof is in an extended release form (or a controlled release form, a prolonged release form, a sustained release form, a delayed release form, or a slow release form). In some of the above embodiments where levetiracetam, brivaracetam, or seletracetam or a pharmaceutically acceptable salt, hydrate, solvate, polymorph, or prodrug thereof is in an extended release form (or a controlled release form, a prolonged release form, a sustained release form, a delayed release form, or a slow release form), the levetiracetam, brivaracetam, or seletracetam or the pharmaceutically acceptable salt, hydrate, solvate, polymorph, or prodrug thereof is administered daily.

In some of the above embodiments, the effect of the treatment, the progression of cognitive impairment, or the rate of decline of cognitive function is measured by detecting the difference between the levels of reelin in the subject prior to and after the administration step.

In some of the above embodiments, the effect of the treatment, the progression of cognitive impairment, or the rate of decline of cognitive function is measured by detecting the difference between the levels of somatostatin in the subject prior to and after the administration step.

BRIEF DESCRIPTION OF THE DRAWINGS

FIG. 8C is a table of the data represented in FIGS. 8A and 8B.

FIG. 9A depicts the average activity in the left entorhinal cortex of age-matched control subjects with placebo treatment and aMCI subjects with placebo treatment during the presentation of lure stimuli that the subject correctly identified as "similar."

FIG. 9B depicts the average activity in the left entorhinal cortex of the same aMCI subjects with placebo treatment or levetiracetam treatment (125 mg twice a day for two weeks) during the presentation of lure stimuli that the subject correctly identified as "similar."

FIG. 9C is a table of the data represented in FIGS. 9A and 9B.

FIG. 13 is a table of the data represented in FIGS. 11 and 12.

FIG. 14A shows the difference between the age-matched control (placebo) subjects and the aMCI subjects treated with placebo or with levetiracetam (125 mg twice a day for two weeks) in their performance of the Bushke Selective reminding Test—Delayed Recall.

FIG. 14B is a table of the data represented in FIG. 14A.

FIG. 18A is a table showing the subject selection process for the human levetiracetam trial described in Example 2.

FIG. 18B is a table showing the characteristics of the subjects selected for the human levetiracetam trial described in Example 2.

FIG. 24A and FIG. 24B show the difference between the same aMCI subjects with placebo treatment or with levetiracetam treatment (62.5 mg BID and 250 mg BID) in their performance of the explicit 3-alternative forced choice task described in Example 4. Each bar represents the proportion of the subjects responses (old, similar, or new) when presented with a lure image.

DETAILED DESCRIPTION OF THE INVENTION

Figure 1:
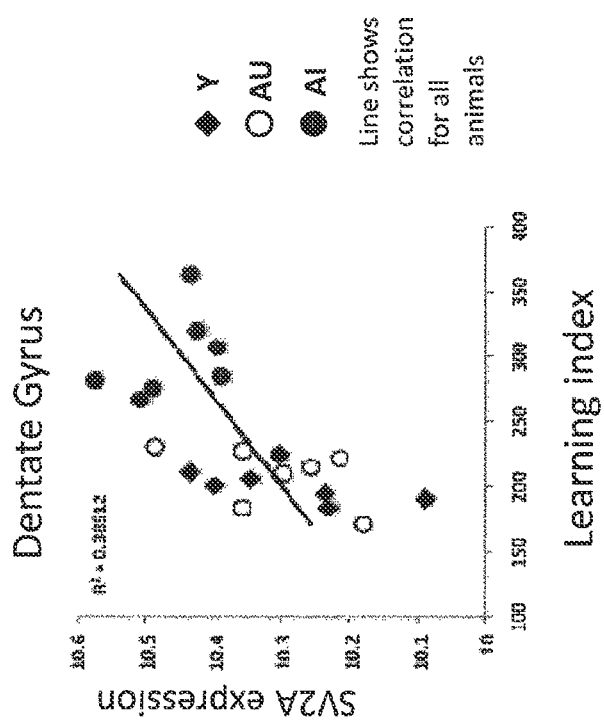
FIG. 1 depicts increased mRNA expression of the gene encoding SV2A in the dentate gyms of the hippocampus of aged-impaired rats (AI) as compared to young rats (Y) and aged-unimpaired rats (AU). Normalized Affymetrix GeneChip probe set signal values (Y-axis), as a measure of mRNA expression, are plotted against learning indices of different rats, as a measure of cognitive impairment.

Unless otherwise defined herein, scientific and technical terms used in this application shall have the meanings that are commonly understood by those of ordinary skill in the art. Generally, nomenclature used in connection with, and techniques of, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); Gilbert et al., "Developmental Biology, 6th ed.", Sinauer Associates, Inc., Sunderland, Mass. (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents which are known with respect to structure, and those which are not known with respect to structure. The SV2A inhibitory activity of such agents may render them suitable as "therapeutic agents" in the methods and compositions of this invention.

A "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care, speed of processing, reasoning and problem solving and social cognition.

In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test; or the explicit 3-alternative forced choice task, or MATRICS consensus neuropsychological test battery. See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011), The FDA-NIMH-MATRICS guidelines for clinical trial design of cognitive-enhancing drugs: what do we know 5 years later? Schizophr. Bull. 37, 1209-1217.

In animal model systems, cognitive function may be measured in various conventional ways known in the art, including using a Morris Water Maze (MWM), Barnes circular maze, elevated radial arm maze, T maze or any other mazes in which the animals use spatial information. Cognitive function can be assessed by reversal learning, extradimensional set shifting, conditional discrimination learning and assessments of reward expectancy. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

"Promoting" cognitive function refers to affecting impaired cognitive function so that it more closely resembles the function of a normal, unimpaired subject. Cognitive function may be promoted to any detectable degree, but in humans preferably is promoted sufficiently to allow an impaired subject to carry out daily activities of normal life a level of proficiency as close as possible to a normal, unimpaired subject or an age-matched normal, unimpaired subject.

In some cases, "promoting" cognitive function in a subject affected by age-related cognitive refers to affecting impaired cognitive function so that it more closely resembles the function of an aged-matched normal, unimpaired subject, or the function of a young adult subject. Cognitive function of that subject may be promoted to any detectable degree, but in humans preferably is promoted sufficiently to allow an impaired subject to carry out daily activities of normal life at a level of proficiency as close as possible to a normal, unimpaired subject or a young adult subject or an age-matched normal, unimpaired subject.

"Preserving" cognitive function refers to affecting normal or impaired cognitive function such that it does not decline or does not fall below that observed in the subject upon first presentation or diagnosis, or delays such decline.

"Improving" cognitive function includes promoting cognitive function and/or preserving cognitive function in a subject.

"Cognitive impairment" refers to cognitive function in subjects that is not as robust as that expected in a normal, unimpaired subject. In some cases, cognitive function is reduced by about 5%, about 10%, about 30%, or more, compared to cognitive function expected in a normal, unimpaired subject. In some cases, "cognitive impairment" in subjects affected by aged-related cognitive impairment refers to cognitive function in subjects that is not as robust as that expected in an aged-matched normal, unimpaired subject, or the function of a young adult subject (i.e. subjects with mean scores for a given age in a cognitive test).

"Age-related cognitive impairment" refers to cognitive impairment in aged subjects, wherein their cognitive function is not as robust as that expected in an age-matched normal subject or as that expected in young adult subjects. In some cases, cognitive function is reduced by about 5%, about 10%, about 30%, or more, compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with Mild Cognitive Impairment (MCI) (including amnestic MCI and non-amnestic MCI), Age-Associated Memory Impairment (AAMI), and Age-related Cognitive Decline (ARCD).

"Cognitive impairment" associated with AD or related to AD or in AD refers to cognitive function in subjects that is not as robust as that expected in subjects who have not been diagnosed AD using conventional methodologies and standards.

"Mild Cognitive Impairment" or "MCI" refers to a condition characterized by isolated memory impairment unaccompanied other cognitive abnormalities and relatively normal functional abilities. One set of criteria for a clinical characterization of MCI specifies the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV guidelines). Petersen et al., *Srch. Neurol.* 56: 303-308 (1999); Petersen, "Mild cognitive impairment: Aging to Alzheimer's Disease." Oxford University Press, N.Y. (2003).

Diagnosis of MCI usually entails an objective assessment of cognitive impairment, which can be garnered through the use of well-established neuropsychological tests, including the Mini Mental State Examination (MMSE), the Cambridge Neuropsychological Test Automated Battery (CANTAB) and individual tests such as Rey Auditory Verbal Learning Test (AVLT), Logical Memory Subtest of the revised Wechsler Memory Scale (WMS-R) and the New York University (NYU) Paragraph Recall Test. See Folstein et al., *J Psychiatric Res* 12: 189-98 (1975); Robbins et al., Dementia 5: 266-81 (1994); Kluger et al., *J Geriatric Psychiatry Neurol* 12:168-79 (1999).

"Age-Associate Memory Impairment (AAMI)" refers to a decline in memory due to aging. A patient may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans (e.g., Craik & Salthouse, 1992). This is also true in virtually all mammalian species. Age-Associated Memory Impairment refers to older persons with objective memory declines relative to their younger years, but cognitive functioning that is normal relative to their age peers (Crook et al., 1986). Age-Consistent Memory Decline, is a less pejorative label which emphasizes that these are normal developmental changes (Crook, 1993; Larrabee, 1996), are not pathophysiological (Smith et al., 1991), and rarely progress to overt dementia (Youngjohn & Crook, 1993). The DSM-IV (1994) has codified the diagnostic classification of ARCD.

Alzheimer's disease (AD) is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau.

Vascular dementia is caused by strokes. Symptoms overlap with those of AD, but without the focus on memory impairment.

Dementia with Lewy bodies is characterized by abnormal deposits of alpha-synuclein that form inside neurons in the brain. Cognitive impairment may be similar to AD, including impairments in memory and judgment and behavior changes.

Frontotemporal dementia is characterized by gliosis, neuronal loss, superficial spongiform degeneration in the frontal cortex and/or anterior temporal lobes, and Picks' bodies. Symptoms include changes in personality and behavior, including a decline in social skills and language expression/comprehension.

"Post traumatic stress disorder (PTSD)" refers to an anxiety disorder characterized by an immediate or delayed response to a catastrophic event, characterized by re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Such responses produce anxiety and can have significant impact, both chronic and acute, on a patient's quality of life and physical and emotional health. PTSD is also associated with impaired cognitive performance, and older individuals with PTSD have greater decline in cognitive performance relative to control patients.

"Schizophrenia" refers to a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. While abnormalities in the brain are proposed to underlie the full spectrum of psychopathology in schizophrenia, currently available antipsychotics are largely ineffective in treating cognitive impairments in patients.

"Bipolar disorder" or "BP" or "manic depressive disorder" or "manic depressive illness" refers to a chronic psychological/mood disorder which can be characterized by significant mood changes including periods of depression and euphoric manic periods. BP may be diagnosed by a skilled physician based on personal and medical history, interview consultation and physical examinations. The term "mania" or "manic periods" or other variants refers to periods where an individual exhibits some or all of the following characteristics: racing thoughts, rapid speech, elevated levels of activity and agitation as well as an inflated sense of self-esteem, euphoria, poor judgment, insomnia, impaired concentration and aggression.

"Amyotrophic lateral sclerosis," also known as ALS, refers to a progressive, fatal, neurodegenerative disease characterized by a degeneration of motor neurons, the nerve cells in the central nervous system that control voluntary muscle movement. ALS is also characterized by neuronal degeneration in the entorhinal cortex and hippocampus, memory deficits, and neuronal hyperexcitability in different brain areas such as the cortex.

"Cancer therapy-related cognitive impairment" refers to cognitive impairment that develops in subjects that are treated with cancer therapies such as chemotherapy and radiation. Cytotoxicity and other adverse side-effects on the brain of cancer therapies result in cognitive impairment in such functions as memory, learning and attention.

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

"Autism", as used herein, refers to an autism spectrum disorder characterized by a neural development disorder leading to impaired social interaction and communication by restricted and repetitive behavior. "Autism Spectrum Disorder" refers to a group of developmental disabilities that includes: autism; Asperger syndrome; pervasive developmental disorder not otherwise specified (PDD-NOS or atypical autism); Rett syndrome; and childhood disintegrative disorder.

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental redardation (Myrrhe van Spronsen and Casper C. Hoogenraad, Curr. Neurol. Neurosci. Rep. 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, 4th edition text revision (DSM-IV-TR) (2000) diagnostic criteria that include characteristics of obsessions and compulsions.

Substance addiction (e.g., drug addiction, alcohol addiction) is a mental disorder. The addiction is not triggered instantaneously upon exposure to substnace of abuse. Rather, it involves multiple, complex neural adaptations that develop with different time courses ranging from hours to days to months (Kauer J. A. Nat. Rev. Neurosci. 2007, 8, 844-858). The path to addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize addictions to other controlled substances. The craving for alcohol, as well as other controlled substances, often is as strong as the need for food or water. Thus, an alcoholic may continue to drink despite serious family, health and/or legal ramifications.

"Treating" a condition or patient refers to taking steps to obtain beneficial or desired results, including clinical results. Beneficial or desired clinical results include, but are not limited to, improving cognitive function, delaying or slowing the progression of cognitive impairment, reducing the rate of decline of cognitive function, preventing or slowing the progression of the disease or disorder, or alleviation, amelioration, or slowing the progression, of one or more symptoms associated of cognitive impairment associated with CNS disorders, such as age-related cognitive impairment, Mild Cognitive Impairment (MCI), amnestic MCI, dementia, Alzheimer's Disease (AD), prodromal AD, PTSD, schizophrenia or bipolar disorder (in particular, mania), amyotrophic lateral sclerosis (ALS) or cancer therapy-related cognitive impairment. Treating age-related cognitive impairment further comprises slowing the conversion of age-related cognitive impairment (including, but not limited to MCI, ARCD and AAMI) into dementia (e.g., AD).

"Treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal, unimpaired subject. Treatment of cognitive impairment in humans may improve cognitive function to any detectable degree, but is preferably improved sufficiently to allow the impaired subject to carry out daily activities of normal life at the same level of proficiency as a normal, unimpaired subject. In some cases, "treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal, unimpaired subject. In some cases, "treating cognitive impairment" in a subject affecting by age-related cognitive impairment refers to takings steps to improve cognitive function in the subject so that the subject's cognitive function, after treatment of cognitive impairment, more closely resembles the function of an age-matched normal, unimpaired subject, or the function of a young adult subject. In some cases, "treating cognitive impairment" in a subject refers to taking steps to delay or slow the progression of cognitive impairment in a subject with cognitive impairment. In some cases, "treating cognitive impairment" in a subject refers to taking steps to reduce the rate of decline of cognitive function in a subject with cognitive impairment.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneaty, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity). In some embodiments, a compound or an agent is administered orally, e.g., to a subject by ingestion, or intravenously, e.g., to a subject by injection. In some embodiments, the orally administered compound or agent is in an extended release or slow release formulation, or administered using a device for such slow or extended release.

As used herein, administration of an SV2A inhibitor or a pharmaceutically acceptable salt, hydrate, solvate, polymorph, or prodrug thereof and valproate or an analog, derivative, pharmaceutically acceptable salt, hydrate, solvate, polymorph, or prodrug thereof "in combination" or "together" includes simultaneous administration and/or administration at different times, such as sequential administration. It also includes administration in a single formulation or in separate formulation packaged together. For example, the SV2A inhibitor or a pharmaceutically acceptable salt, hydrate, solvate, polymorph, or prodrug thereof may be formulated/administered in an extended release form, which may be administered together or separately with valproate or an analog, derivative, pharmaceutically acceptable salt, hydrate, solvate, polymorph, or prodrug thereof, wherein valproate or an analog, derivative, pharmaceutically acceptable salt, hydrate, solvate, polymorph, or prodrug thereof may or may not be in an extended release form itself. In some embodiments, valproate or an analog, derivative, pharmaceutically acceptable salt, hydrate, solvate, polymorph, or prodrug thereof may be formulated/administered in an extended release form, which may be administered together or separately with an SV2A inhibitor or a pharmaceutically acceptable salt, hydrate, solvate, polymorph, or prodrug thereof, wherein the SV2A inhibitor or a pharmaceutically acceptable salt, hydrate, solvate, polymorph, or prodrug thereof may or may not be in an extended release form itself.

The term "simultaneous administration," as used herein, means that the SV2A inhibitor or its pharmaceutically acceptable salt, hydrate, solvate, polymorph, or prodrug and valproate or its analog, derivative or pharmaceutically acceptable salt, are administered with a time separation of no more than about 15 minutes, and in some embodiments no more than about 10 minutes. When the drugs are administered simultaneously, the SV2A inhibitor or its pharmaceutically acceptable salt, hydrate, solvate, polymorph, or prodrug and valproate or its analog, derivative or pharmaceutically acceptable salt, may be contained in the same dosage (e.g., a unit dosage form comprising both the SV2A inhibitor and the valproate) or in discrete dosages (e.g., the SV2A inhibitor or its pharmaceutically acceptable salt, hydrate, solvate, polymorph, or prodrug, is contained in one dosage form and the valproate or its analog, derivative, pharmaceutically acceptable salt, hydrate, solvate, polymorph or prodrug, is contained in another dosage form).

The term "sequential administration" as used herein means that the SV2A inhibitor or its pharmaceutically acceptable salt, hydrate, solvate, polymorph, or prodrug are valproate or its analog, derivative or pharmaceutically acceptable salt, are administered with a time separation of more than about 15 minutes, and in some embodiments more than about one hour, or up to 12 hours. Either the SV2A inhibitor the valproate may be administered first. For sequential administration, he SV2A inhibitor its pharmaceutically acceptable salt, hydrate, solvate, polymorph, or prodrug, and valproate or its analog, derivative or pharmaceutically acceptable salt, may be contained in discrete dosage forms, optionally contained in the same container or package.

A "therapeutically effective amount" of a drug or agent is an amount of a drug or an agent that, when administered to a subject will have the intended therapeutic effect, e.g. improving cognitive function, or delaying or slowing the progression of cognitive impairment, or reducing the rate of decline of cognitive function in a subject, e.g., a patient having cognitive impairment associated with a CNS disorder with. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. The skilled worker can readily determine the effective amount for a given situation by routine experimentation.

"Subtherapeutic amount" refers to an amount administered of an agent or compound of the invention that is less than the therapeutic amount, that is, less than the amount normally used when said agent or compound is administered alone (i.e., individually and in the absence of other therapeutic agents or compounds) to treat disorders involving cognitive dysfunction.

"Analog" is used herein to refer to a compound which functionally resembles another chemical entity, but does not share the identical chemical structure. For example, an analog is sufficiently similar to a base or parent compound such that it can substitute for the base compound in therapeutic applications, despite minor structural differences.

"Derivative" is used herein to refer to the chemical modification of a compound. Chemical modifications of a compound can include, for example, replacement of hydrogen by an alkyl, acyl, or amino group. Many other modifications are also possible.

The term "prodrug" is art-recognized and is intended to encompass compounds or agents which, under physiological conditions, are converted into an SV2A inhibitor valproate. A common method for making a prodrug is to select moieties which are hydrolyzed or metabolized under physiological conditions to provide the desired compound or agent. In other embodiments, the prodrug is converted by an enzymatic activity of the host animal to an inhibitor of SV2A or valproate.

"Pharmaceutically acceptable salts" is used herein to refer to an agent or a compound according to the invention that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726.

Description of Methods of the Invention

The methods of this invention comprise administration of an SV2A inhibitor or a pharmaceutically acceptable salt, hydrate, solvate, polymorph or prodrug thereof. The methods of this invention further comprise administration of an SV2A inhibitor or a pharmaceutically acceptable salt, hydrate, solvate, polymorph or prodrug thereof in combination with administration of valproate or a pharmaceutically acceptable salt thereof. The agents or compounds of the SV2A inhibitor the valproate and their pharmaceutically acceptable salts also include hydrates, solvates, polymorphs, and prodrugs of those agents, compounds, and salts.

Methods of Assessing Cognitive Impairment

Animal models serve as an important resource for developing and evaluating treatments for cognitive impairment associated with CNS disorders. Features that characterize cognitive impairment in animal models typically extend to cognitive impairment in humans. Efficacy in such animal models is, thus, expected to be predictive of efficacy in humans. The extent of cognitive impairment in an animal model for a CNS disorder, and the efficacy of a method of treatment for said CNS disorder may be tested and confirmed with the use of a variety of cognitive tests.

A Radial Arm Maze (RAM) behavioral task is one example of a cognitive test, specifically testing spacial memory (Chappell et al. *Neuropharmacology* 37: 481-487, 1998). The RAM apparatus consists of, e.g., eight equidistantly spaced arms. A maze arm projects from each facet of a center platform. A food well is located at the distal end of each arm. Food is used as a reward. Blocks can be positioned to prevent entry to any arm. Numerous extra maze cues surrounding the apparatus may also be provided. After habituation and training phases, spatial memory of the subjects may be tested in the RAM under control or test compound-treated conditions. As a part of the test, subjects are pretreated before trials with a vehicle control or one of a range of dosages of the test compound. At the beginning of each trial, a subset of the arms of the eight-arm maze is blocked. Subjects are allowed to obtain food on the unblocked arms to which access is permitted during this initial "information phase" of the trial. Subjects are then removed from the maze for a delay period, e.g., a 60 second delay, a 15 minute delay, a one-hour delay, a two-hour delay, a six hour delay, a 24 hour delay, or longer) between the information phase and the subsequent "retention test," during which the barriers on the maze are removed, thus allowing access to all eight arms. After the delay period, subjects are placed back onto the center platform (with the barriers to the previously blocked arms removed) and allowed to obtain the remaining food rewards during this retention test phase of the trial. The identity and configuration of the blocked arms vary across trials. The number of "errors" the subjects make during the retention test phase is tracked. An error occurs in the trial if the subjects entered an arm from which food had already been retrieved in the pre-delay component of the trial, or if it re-visits an arm in the post-delay session that had already been visited. A fewer number of errors would indicate better spatial memory. The number of errors made by the test subject, under various test compound treatment regimes, can then be compared for efficacy of the test compound in treating cognitive impairment associated with CNS disorders.

Another cognitive test that may be used to assess the effects of a test compound on the cognitive impairment of a CNS disorder model animal is the Morris water maze. A water maze is a pool surrounded with a novel set of patterns relative to the maze. The training protocol for the water maze may be based on a modified water maze task that has been shown to be hippocampal-dependent (de Hoz et al., *Eur. J. Neurosci.*, 22:745-54, 2005; Steele and Morris, *Hippocampus* 9:118-36, 1999). The subject is trained to locate a submerged escape platform hidden underneath the surface of the pool. During the training trial, a subject is released in the maze (pool) from random starting positions around the perimeter of the pool. The starting position varies from trial to trial. If the subject does not locate the escape platform within a set time, the experimenter guides and places the subject on the platform to "teach" the location of the platform. After a delay period following the last training trial, a retention test in the absence of the escape platform is given to assess spatial memory. The subject's level of preference for the location of the (now absent) escape platform, as measured by, e.g., the time spent in that location or the number of crossings of that location made by the mouse, indicates better spatial memory, i.e., treatment of cognitive impairment. The preference for the location of the escape platform under different treatment conditions, can then be compared for efficacy of the test compound in treating cognitive impairment associated with CNS disorders.

There are various tests known in the art for assessing cognitive function in humans, for example and without limitation, the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or MATRICS consensus neuropsychological test battery which includes tests of working memory, speed of processing, attention, verbal learning, visual learning, reasoning and problem solving and social cognition. See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry Neurol* 12:168-79, (1999); Marquis et al., 2002 and Masur et al., 1994, or MATRICS consensus neuropsychological test battery which includes tests of working memory, speed of processing, attention, verbal learning, visual learning, reasoning and problem solving and social cognition. Another example of a cognitive test in humans is the explicit 3-alternative forced choice task. In this test, subjects are presented with color photographs of common objects consisting of a mix of three types of image pairs: similar pairs, identical pairs and unrelated foils. The second of the pair of similar objects is referred to as the "lure". These image pairs are fully randomized and presented individually as a series of images. Subjects are instructed to make a judgment as to whether the objects seen are new, old or similar. A "similar" response to the presentation of a lure stimulus indicates successful memory retrieval by the subject. By contrast, calling the lure stimulus "old" or "new" indicates that correct memory retrieval did not occur.

In addition to assessing cognitive performance, the progression of age-related cognitive impairment and dementia, as well as the conversion of age-related cognitive impairment into dementia, may be monitored by assessing surrogate changes in the brain of the subject. Surrogate changes include, without limitation, changes in regional brain volumes, perforant path degradation, and changes seen in brain function through resting state fMRI (R-fMRI) and fluorodeoxyglucose positron emission tomography (FDG-PET). Examples of regional brain volumes useful in monitoring the progression of age-related cognitive impairment and dementia include reduction of hippocampal volume and reduction in volume or thickness of entorhinal cortex. These volumes may be measured in a subject by, for example, MRI. Aisen et al., Alzheimer's & Dementia 6:239-246 (2010). Perforant path degradation has been shown to be linked to age, as well as reduced cognitive function. For example, older adults with more perforant path degradation tend to perform worse in hippocampus-dependent memory tests. Perforant path degradation may be monitored in subjects through ultrahigh-resolution diffusion tensor imaging (DTI). Yassa et al., PNAS 107:12687-12691 (2010). Resting-state fMRI (R-fMRI) involves imaging the brain during rest, and recording large-amplitude spontaneous low-frequency (<0.1 Hz) fluctuations in the fMRI signal that are temporally correlated across functionally related areas. Seed-based functional connectivity, independent component analyses, and/or frequency-domain analyses of the signals are used to reveal functional connectivity between brain areas, particularly those areas whose connectivity increase or decrease with age, as well as the extent of cognitive impairment and/or dementia. FDG-PET uses the uptake of FDG as a measure of regional metabolic activity in the brain. Decline of FDG uptake in regions such as the posterior cingulated cortex, temporoparietal cortex, and prefrontal association cortex has been shown to relate to the extent of cognitive decline and dementia. Aisen et al., Alzheimer's & Dementia 6:239-246 (2010), Herholz et al., Neurolmage 17:302-316 (2002).

Age-Related Cognitive Impairment

This invention provides methods and compositions for treating age-related cognitive impairment or the risk thereof using an SV2A inhibitor or a pharmaceutically acceptable salt, hydrate, solvate, polymorph, or prodrug thereof, alone or in combination with valproate or an analog, derivative or pharmaceutically acceptable salt, hydrate, solvate, polymorph, or prodrug thereof. In certain embodiments, treatment comprises improving cognitive function in patients with age-related cognitive impairment. In certain embodiments, treatment comprises slowing or delaying the progression of age-related cognitive impairment. In certain embodiments, treatment comprises reducing the rate of decline of cognitive function associated with age-related cognitive impairment. In certain embodiments, treatment comprises preventing or slowing the progression, of age-related cognitive impairment. In certain embodiments, treatment comprises alleviation, amelioration or slowing the progression, of one or more symptoms associated with age-related cognitive impairment. In certain embodiments, treatment of age-related cognitive impairment comprises slowing the conversion of age-related cognitive impairment (including, but not limited to MCI, ARCD and AAMI) into dementia (e.g., AD). The methods and compositions may be used for human patients in clinical applications in the treating age-related cognitive impairment in conditions such as MCI, ARCD and AAMI or for the risk thereof. The dose of the composition and dosage interval for the method is, as described herein, one that is safe and efficacious in those applications.

In some embodiments, a subject to be treated by the methods and compositions of this invention exhibits age-related cognitive impairment or is at risk of such impairment. In some embodiments, the age-related cognitive impairment includes, without limitation, Age-Associated Memory Impairment (AAMI), Mild Cognitive Impairment (MCI) and Age-related Cognitive Decline (ARCD).

Animal models serve as an important resource for developing and evaluating treatments for such age-related cognitive impairments. Features that characterize age-related cognitive impairment in animal models typically extend to age-related cognitive impairment in humans. Efficacy in such animal models is, thus, expected to be predictive of efficacy in humans.

Various animal models of age-related cognitive impairment are known in the art. For example, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Gallagher et al. *Behav. Neurosci.* 107:618-626, (1993); Rapp and Gallagher, *Proc. Natl. Acad. Sci.* 93: 9926-9930, (1996); Nicolle et al., *Neuroscience* 74: 741-756, (1996); Nicolle et al., *J. Neurosci.* 19: 9604-9610, (1999); International Patent Publication WO2007/019312 and International Patent Publication WO 2004/048551. Such an animal model of age-related cognitive impairment may be used to assay the effectiveness of the methods and compositions this invention in treating age-related cognitive impairment.

The efficacy of the methods and compositions of this invention in treating age-related cognitive impairment may be assessed using a variety of cognitive tests, including the Morris water maze and the radial arm maze, as discussed above.

Dementia

This invention also provides methods and compositions for treating dementia using an SV2A inhibitor or a pharmaceutically acceptable salt, hydrate, solvate, polymorph, or prodrug thereof, alone or in combination with valproate or an analog, derivative or pharmaceutically acceptable salt, hydrate, solvate, polymorph, or prodrug thereof. In certain embodiments, treatment comprises improving cognitive function in patients with dementia. In certain embodiments, treatment comprises slowing or delaying the progression of dementia. In certain embodiments, treatment comprises reducing the rate of decline of cognitive function associated with dementia. In certain embodiments, treatment comprises preventing or slowing the progression, of dementia. In certain embodiments, treatment comprises alleviation, amelioration, or slowing the progression of one or more symptoms associated with dementia. In certain embodiments, the symptom to be treated is cognitive impairment. In certain embodiments, the dementia is Alzheimer's disease (AD), vascular dementia, dementia with Lewy bodies, or fronto-temporal dementia. The methods and compositions may be used for human patients in clinical applications in treating dementia. The dose of the composition and dosage interval for the method is, as described herein, one that is safe and efficacious in those applications.

Animal models serve as an important resource for developing and evaluating treatments for dementia. Features that characterize dementia in animal models typically extend to dementia in humans. Thus, efficacy in such animal models is expected to be predictive of efficacy in humans. Various animal models of dementia are known in the art, such as the PDAPP, Tg2576, APP23, TgCRND8, J20, hPS2 Tg, and APP+PS1 transgenic mice. Sankaranarayanan, *Curr. Top. Medicinal Chem.* 6: 609-627, 2006; Kobayashi et al. *Genes Brain Behav.* 4: 173-196. 2005; Ashe and Zahns, Neuron. 66: 631-45, 2010. Such animal models of dementia may be used to assay the effectiveness of the methods and compositions of this invention of the invention in treating dementia.

The efficacy of the methods and compositions of this invention in treating dementia, or cognitive impairment associated with dementia, may be assessed in animals models of dementia, as well as human subjects with dementia, using a variety of cognitive tests known in the art, as discussed above.

Post Traumatic Stress Disorder

This invention also provides methods and compositions for treating post traumatic stress disorder (PTSD) using an SV2A inhibitor or a pharmaceutically acceptable salt, hydrate, solvate, polymorph, or prodrug thereof, alone or in combination with valproate or an analog, derivative or pharmaceutically acceptable salt, hydrate, solvate, polymorph, or prodrug thereof. In certain embodiments, treatment comprises improving cognitive function in patients with PTSD. In certain embodiments, treatment comprises slowing or delaying the progression of PTSD. In certain embodiments, treatment comprises reducing the rate of decline of cognitive function associated with PTSD. In certain embodiments, treatment comprises preventing or slowing the progression, of PTSD. In certain embodiments, treatment comprises alleviation, amelioration, or slowing the progression of one or more symptoms associated with PTSD. In certain embodiments, the symptom to be treated is cognitive impairment. The methods and compositions may be used for human patients in clinical applications in treating PTSD. The dose of the composition and dosage interval for the method is, as described herein, one that is safe and efficacious in those applications.

Patients with PTSD (and, to a lesser degree trauma-exposed patients without PTSD) have smaller hippocampal volumes (Woon et al., *Prog. Neuro-Psychopharm. & Biological Psych.* 34, 1181-1188; Wang et al., *Arch. Gen. Psychiatry* 67:296-303, 2010). PTSD is also associated with impaired cognitive performance. Older individuals with PTSD have greater declines in cognitive performance relative to control patients (Yehuda et al., *Bio. Psych.* 60: 714-721, 2006) and have a greater likelihood of developing dementia (Yaffe et al., *Arch. Gen. Psych.* 678: 608-613, 2010).

Animal models serve as an important resource for developing and evaluating treatments for PTSD. Features that characterize PTSD in animal models typically extend to PTSD in humans. Thus, efficacy in such animal models is expected to be predictive of efficacy in humans. Various animal models of PTSD are known in the art.

One rat model of PTSD is Time-dependent sensitization (TDS). TDS involves exposure of the animal to a severely stressful event followed by a situational reminder of the prior stress. The following is an example of TDS. Rats are placed in a restrainer, then placed in a swim tank and made to swim for a period of time, e.g., 20 min. Following this, each rat is then immediately exposed to a gaseous anesthetic until loss of consciousness, and finally dried. The animals are left undisturbed for a number of days, e.g., one week. The rats are then exposed to a "restress" session consisting of an initial stressor, e.g., a swimming session in the swim tank (Liberzon et al., *Psychoneuroendocrinology* 22: 443-453, 1997; Harvery et al., *Psychopharmacology* 175:494-502, 2004). TDS results in an enhancement of the acoustic startle response (ASR) in the rat, which is comparable to the exaggerated acoustic startle that is a prominent symptom of PTSD (Khan and Liberzon, Psychopharmacology 172: 225-229, 2004). Such animal models of PTSD may be used to assay the effectiveness of the methods and compositions of this invention of the invention in treating PTSD.

The efficacy of the methods and compositions of this invention in treating PTSD, or cognitive impairment associated with PTSD, may also be assessed in animals models of PTSD, as well as human subjects with PTSD, using a variety of cognitive tests known in the art, as discussed above.

Schizophrenia

This invention provides methods and compositions for treating schizophrenia or bipolar disorder (in particular, mania) using an SV2A inhibitor or a pharmaceutically acceptable salt, hydrate, solvate, polymorph, or prodrug thereof, alone or in combination with valproate or an analog, derivative or pharmaceutically acceptable salt, hydrate, solvate, polymorph, or prodrug thereof. In certain embodiments, treatment comprises improving cognitive function in patients with schizophrenia. In certain embodiments, treatment comprises slowing or delaying the progression of schizophrenia. In certain embodiments, treatment comprises reducing the rate of decline of cognitive function associated with schizophrenia. In certain embodiments, treatment comprises preventing or slowing the progression of schizophrenia or bipolar disorder (in particular, mania). Schizophrenia is characterized by a wide spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. In certain embodiments, treatment comprises alleviation, amelioration or slowing the progression of one or more positive and/or negative symptoms, as well as cognitive impairment, associated with schizophrenia. Further, there are a number of other psychiatric diseases such as schizotypical and schizoaffective disorder, other acute- and chronic psychoses and bipolar disorder (in particular, mania), which have an overlapping symptomatology with schizophrenia. In some embodiments, treatment comprises alleviation, amelioration or slowing the progression of one or more symptoms, as well as cognitive impairment, associated with bipolar disorder (in particular, mania). The methods and compositions may be used for human patients in clinical applications in treating schizophrenia or bipolar disorder (in particular, mania). The dose of the composition and dosage interval for the method is, as described herein, one that is safe and efficacious in those applications.

Cognitive impairments are associated with schizophrenia. They precede the onset of psychosis and are present in non-affected relatives. The cognitive impairments associated with schizophrenia constitute a good predictor for functional outcome and are a core feature of the disorder. Cognitive features in schizophrenia reflect dysfunction in frontal cortical and hippocampal circuits. Patients with schizophrenia also present hippocampal pathologies such as reductions in hippocampal volume, reductions in neuronal size and dysfunctional hyperactivity. An imbalance in excitation and inhibition in these brain regions has also been documented in schizophrenic patients suggesting that drugs targeting inhibitory mechanisms could be therapeutic. See, e.g., Guidotti et al., *Psychopharmacology* 180: 191-205, 2005; Zierhut, *Psych. Res. Neuroimag.* 183:187-194, 2010; Wood et al., *NeuroImage* 52:62-63, 2010; Vinkers et al., *Expert Opin. Investig. Drugs* 19:1217-1233, 2009; Young et al., *Pharmacol. Ther.* 122:150-202, 2009.

Animal models serve as an important resource for developing and evaluating treatments for schizophrenia. Features that characterize schizophrenia in animal models typically extend to schizophrenia in humans. Thus, efficacy in such animal models is expected to be predictive of efficacy in humans. Various animal models of schizophrenia are known in the art.

One animal model of schizophrenia is protracted treatment with methionine. Methionine-treated mice exhibit deficient expression of GAD67 in frontal cortex and hippocampus, similar to those reported in the brain of postmortem schizophrenia patients. They also exhibit prepulse inhibition of startle and social interaction deficits (Tremonlizzo et al., *PNAS*, 99: 17095-17100, 2002). Another animal model of schizophrenia is methylaoxymethanol acetate (MAM)-treatment in rats. Pregnant female rats are administered MAM (20 mg/kg, intraperitoneal) on gestational day 17. MAM-treatment recapitulate a pathodevelopmental process to schizophrenia-like phenotypes in the offspring, including anatomical changes, behavioral deficits and altered neuronal information processing. More specifically, MAM-treated rats display a decreased density of parvalbumin-positive GABAergic interneurons in portions of the prefrontal cortex and hippocampus. In behavioral tests, MAM-treated rats display reduced latent inhibition. Latent inhibition is a behavioral phenomenon where there is reduced learning about a stimulus to which there has been prior exposure with any consequence. This tendency to disregard previously benign stimuli, and reduce the formation of association with such stimuli is believed to prevent sensory overload. Low latent inhibition is indicative of psychosis. Latent inhibition may be tested in rats in the following manner. Rats are divided into two groups. One group is pre-exposed to a tone over multiple trials. The other group has no tone presentation. Both groups are then exposed to an auditory fear conditioning procedure, in which the same tone is presented concurrently with a noxious stimulus, e.g. an electric shock to the foot. Subsequently, both groups are presented with the tone, and the rats' change in locomotor activity during tone presentation is monitored. After the fear conditioning the rats respond to the tone presentation by strongly reducing locomotor activity. However, the group that has been exposed to the tone before the conditioning period displays robust latent inhibition: the suppression of locomotor activity in response to tone presentation is reduced. MAM-treated rats, by contrast show impaired latent inhibition. That is, exposure to the tone previous to the fear conditioning procedure has no significant effect in suppressing the fear conditioning. (see Lodge et al., J. Neurosci., 29:2344-2354, 2009) Such animal models of schizophrenia may be used to assay the effectiveness of the methods and compositions of the invention in treating schizophrenia or bipolar disorder (in particular, mania).

MAM-treated rats display a significantly enhanced locomotor response (or aberrant locomotor activity) to low dose D-amphetamine administration. The MAM-treated rats also display a significantly greater number of spontaneously firing ventral tegmental dopamine (DA) neurons. These results are believed to be a consequence of excessive hippocampal activity because in MAM-treated rats, the ventral hippocampus (vHipp) inactivation (e.g., by intra-vHipp administration of a sodium channel blocker, tetrodotoxin (TTX), to MAM rats) completely reversed the elevated DA neuron population activity and also normalized the augmented amphetamine-induced locomotor behavior. The correlation of hippocampal dysfunction and the hyper-responsivity of the DA system is believed to underlie the augmented response to amphetamine in MAM-treated animals and psychosis in schizophrenia patients. See Lodge D. J. et al. *Neurobiology of Disease* (2007), 27(42), 11424-11430. The use of MAM-treated rats in the above study may be suitable for use to assay the effectiveness of the methods and compositions of the present invention in treating schizophrenia or bipolar disorder (in particular, mania). For example, the methods and compositions of this invention may be evaluated, using MAM-treated animals, for their effects on the central hippocampus (vHipp) regulation, on the elevated DA neuron population activity and on the hyperactive locomotor response to amphetamine in the MAM-treated animals.

In MAM-treated rats, hippocampal (HPC) dysfunction leads to dopamine system hyperactivity. A benzodiazepine-positive allosteric modulator (PAM), selective for the α5 subunit of the $GABA_A$ receptor, SH-053-2′F—R—$CH_3$, is tested for its effects on the output of the hippocampal (HPC). The effect of SH-053-2′F—R—$CH_3$ on the hyperactive locomotor response to amphetamine in MAM-treated animals is also examined. The α5GABAAR PAM reduces the number of spontaneously active DA neurons in the ventral tegmental area (VTA) of MAM rats to levels observed in saline-treated rats (control group), both when administered systemically and when directly infused into the ventral HPC. Moreover, HPC neurons in both saline-treated and MAM-treated animals show diminished cortical-evoked responses following the α5GABAAR PAM treatment. In addition, the increased locomotor response to amphetamine observed in MAM-treated rats is reduced following the α5$GABA_A$R PAM treatment. See Gill K. M et al. *Neuropsychopharmacology* (2011), 1-9. The use of MAM-treated rats in the above study may be suitable for use in the present invention to assay the effectiveness of the methods and compositions of the invention in treating schizophrenia or bipolar disorder (in particular, mania). For example, the methods and compositions of this invention maybe evaluated, using MAM-treated animals, for their effects on the output of the hippocampal (HPC) and on the hyperactive locomotor response to amphetamine in the MAM-treated animals.

Administration of MAM to pregnant rats on embryonic day 15 (E15) severely impairs spatial memory or the ability to learn the spatial location of four items on an eight-arm radial maze in the offspring. In addition, embryonic day 17 (E17) MAM-treated rats are able to reach the level of performance of control rats at the initial stages of training, but are unable to process and retrieve spatial information when a 30-min delay is interposed, indicating a significant impairment in working memory. See Gourevitch R. et al. (2004). *Behav. Pharmacol*, 15, 287-292. Such animal models of schizophrenia may be used to assay the effectiveness of the methods and compositions of the invention in treating schizophrenia or bipolar disorder (in particular, mania).

Apomorphine-induced climbing (AIC) and stereotype (AIS) in mice is another animal model useful in this invention. Agents are administered to mice at a desired dose level (e.g., via intraperitoneal administration). Subsequently, e.g., thirty minutes later, experimental mice are challenges with apomorphine (e.g., with 1 mg/kg sc). Five minutes after the apomorphine injection, the sniffing-licking-gnawing syndrome (stereotyped behavior) and climbing behavior induced by apomorphine are scored and recorded for each animal. Readings can be repeated every 5 min during a 30-min test session. Scores for each animal are totaled over the 30-min test session for each syndrome (stereotyped behavior and climbing). If an effect reached at least of 50% inhibition, and $ID_{50}$ value (95% confidence interval) is calculated using a nonlinear least squares calculation with inverse prediction. Mean climbing and stereotype scores can be expressed as a percent of control values observed in vehible treated (e.g., saline-treated) mice that receive apomorphine. See Grauer S. M. et al. *Psychopharmacology* (2009) 204, 37-48. This mice model may be used to assay the effectiveness of the methods and compositions of the invention in treating schizophrenia or bipolar disorder (in particular, mania).

The efficacy of the methods and compositions of this invention in treating schizophrenia may also be assessed in animal models of schizophrenia or bipolar disorder (in particular, mania), as well as human subjects with schizophrenia, using a variety of cognitive tests known in the art, as discussed above.

Amyotrophic Lateral Sclerosis (ALS)

This invention additionally provides methods and compositions for treating ALS using an SV2A inhibitor or a pharmaceutically acceptable salt, hydrate, solvate, polymorph, or prodrug thereof, alone or in combination with valproate or an analog, derivative or pharmaceutically acceptable salt, hydrate, solvate, polymorph, or prodrug thereof. In certain embodiments, treatment comprises improving cognitive function in patients with ALS. In certain embodiments, treatment comprises slowing or delaying the progression of ALS. In certain embodiments, treatment comprises reducing the rate of decline of cognitive function associated with ALS. In certain embodiments, treatment comprises preventing or slowing the progression, of ALS. In certain embodiments, treatment comprises alleviation, amelioration or slowing the progression, of one or more symptoms associated with ALS. In certain embodiments, the symptom to be treated is cognitive impairment. The methods and compositions may be used for human patients in clinical applications in treating ALS. The dose of the composition and dosage interval for the method is, as described herein, one that is safe and efficacious in those applications.

In addition to the degeneration of motor neurons, ALS is characterized by neuronal degeneration in the entorhinal cortex and hippocampus, memory deficits, and neuronal hyperexcitability in different brain areas such as the cortex.

The efficacy of the methods and compositions of this invention in treating ALS, or cognitive impairment associated with ALS, may also be assessed in animal models of ALS, as well as human subjects with ALS, using a variety of cognitive tests known in the art, as discussed above.

Cancer Therapy-Related Cognitive Impairment

This invention additionally provides methods and compositions for treating cancer therapy-related cognitive impairment using an SV2A inhibitor or a pharmaceutically acceptable salt, hydrate, solvate, polymorph, or prodrug thereof, alone or in combination with valproate or an analog, derivative or pharmaceutically acceptable salt, hydrate, solvate, polymorph, or prodrug thereof. In certain embodiments, treatment comprises improving cognitive function in patients with cancer therapy-related cognitive impairment. In certain embodiments, treatment comprises slowing or delaying the progression of cancer therapy-related cognitive impairment. In certain embodiments, treatment comprises reducing the rate of decline of cognitive function associated with cancer therapy-related cognitive impairment. In certain embodiments, treatment comprises preventing or slowing the progression, of cancer therapy-related cognitive impairment. In certain embodiments, treatment comprises alleviation, amelioration or slowing the progression, of one or more symptoms associated with cancer therapy-related cognitive impairment. The methods and compositions may be used for human patients in clinical applications in treating cancer therapy-related cognitive impairment. The dose of the composition and dosage interval for the method is, as described herein, one that is safe and efficacious in those applications.

Therapies that are used in cancer treatment, including chemotherapy, radiation, or combinations thereof, can cause cognitive impairment in patients, in such functions as memory, learning and attention. Cytotoxicity and other adverse side-effects on the brain of cancer therapies are the basis for this form of cognitive impairment, which can persist for decades. (Dietrich et al., Oncologist 13:1285-95, 2008; Soussain et al., Lancet 374:1639-51, 2009).

Cognitive impairment following cancer therapies reflects dysfunction in frontal cortical and hippocampal circuits that are essential for normal cognition. In animal models, exposure to either chemotherapy or radiation adversely affects performance on tests of cognition specifically dependent on these brain systems, especially the hippocampus (Kim et al., J. Radiat. Res. 49:517-526, 2008; Yang et al., Neurobiol. Learning and Mem. 93:487-494, 2010). Thus, drugs targeting these cortical and hippocampal systems could be neuroprotective in patients receiving cancer therapies and efficacious in treating symptoms of cognitive impairment that may last beyond the interventions used as cancer therapies.

Animal models serve as an important resource for developing and evaluating treatments for cancer therapy-related cognitive impairment. Features that characterize cancer therapy-related cognitive impairment in animal models typically extend to cancer therapy-related cognitive impairment in humans. Thus, efficacy in such animal models is expected to be predictive of efficacy in humans. Various animal models of cancer therapy-related cognitive impairment are known in the art.

Examples of animal models of cancer therapy-related cognitive impairment include treating animals with antineoplastic agents such as cyclophosphamide (CYP) or with radiation, e.g., $^{60}$Co gamma-rays. (Kim et al., J. Radiat. Res. 49:517-526, 2008; Yang et al., Neurobiol. Learning and Mem. 93:487-494, 2010). The cognitive function of animal models of cancer therapy-related cognitive impairment may then be tested with cognitive tests to assay the effectiveness of the methods and compositions of the invention in treating cancer therapy-related cognitive impairment. The efficacy of the methods and compositions of this invention in treating cancer therapy-related cognitive impairment, as well as human subjects with cancer therapy-related cognitive impairment, using a variety of cognitive tests known in the art, as discussed above.

Parkinson's Disease (PD)

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

Parkinson's disease, the etiology of which is unknown, belongs to a group of the most common movement disorders named parkinsonism, which affects approximately one person per one thousand. These other disorders grouped under the name of parkinsonism may result from viral infection, syphilis, arteriosclerosis and trauma and exposure to toxic chemicals and narcotics. Nonetheless, it is believed that the inappropriate loss of synaptic stability may lead to the disruption of neuronal circuits and to brain diseases. Whether as the result of genetics, drug use, the aging process, viral infections, or other various causes, dysfunction in neuronal communication is considered the underlying cause for many neurologic diseases, such as PD (Myrrhe van Spronsen and Casper C. Hoogenraad, Curr. Neurol. Neurosci. Rep. 2010 10, 207-214).

Regardless of the cause of the disease, the main pathologic feature is degeneration of dopaminergic cells in basal ganglia, especially in substantia nigra. Due to premature death of the dopamine containing neurons in substantia nigra, the largest structure of the basal ganglia, the striatum, will have reduced input from substantia nigra resulting in decreased dopamine release. The understanding of the underlying pathology led to the introduction of the first successful treatment which can alleviate Parkinson's disease. Virtually all approaches to the therapy of the disease are based on dopamine replacement. Drugs currently used in the treatment can be converted into dopamine after crossing the blood brain barrier, or they can boost the synthesis of dopamine and reduce its breakdown. Unfortunately, the main pathologic event, degeneration of the cells in substantia nigra, is not helped. The disease continues to progress and frequently after a certain length of time, dopamine replacement treatment will lose its effectiveness.

This invention provides methods and compositions for treating PD using an SV2A inhibitor or a pharmaceutically acceptable salt, hydrate, solvate, polymorph, or prodrug thereof, alone or in combination with valproate or a derivative or an analog or a pharmaceutically acceptable salt thereof. In certain embodiments, treatment comprises preventing or slowing the progression of PD. In certain embodiments, treatment comprises alleviation, amelioration, or slowing the progression of one or more symptoms associated with PD. In certain embodiments, the symptom to be treated is cognitive impairment. For example, methods and compositions of the disclosure can be used to improve the motor/cognitive impairments symptomatic of Parkinson's disease. Moreover, methods and compositions of the disclosure may be useful for treating the memory impairment symptomatic of Parkinson's disease.

There are a number of animal models for PD. Exemplary animal models for PD include the reserpine model, the methamphetamine model, the 6-hydroxydopamine (6-OHDA) model, the 1-methyl-4-phenyl-1,2,3,6-tetrahydropyridine (MPTP) model, the paraquat (PQ)-Maneb model, the rotenone model, the 3-nitrotyrosine model and genetic models using transgenic mice. Transgenic models include mice that over express α-synuclein, express human mutant forms of α-synuclein, or mice that express LRKK2 mutations. See review of these models by Ranjita B. et al. (Ranjita B. et al. *BioEssays* 2002, 24, 308-318). Additional information regarding these animal models is readily available from Jackson Laboratories (see also http://research.jax.org/grs/parkinsons.html), as well as in numerous publications disclosing the use of these validated models.

The efficacy of the methods and compositions of this invention in treating PD, or cognitive impairment associated with PD, may be assessed in any of the above animal models of PD, as well as human subjects with PD, using a variety of cognitive tests known in the art, as discussed above.

Autism

"Autism", as used herein, refers to an autism spectrum disorder characterized by a neural development disorder leading to impaired social interaction and communication by restricted and repetitive behavior. "Autism Spectrum Disorder" refers to a group of developmental disabilities that includes: autism; Asperger syndrome; pervasive developmental disorder not otherwise specified (PDD-NOS or atypical autism); Rett syndrome; and childhood disintegrative disorder.

Autism is a neurodevelopmental disorder characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities. Autism is a disabling neurological disorder that affects thousands of Americans and encompasses a number of subtypes, with various putative causes and few documented ameliorative treatments. The disorders of the autistic spectrum may be present at birth, or may have later onset, for example, at ages two or three. There are no clear cut biological markers for autism. Diagnosis of the disorder is made by considering the degree to which the child matches the behavioral syndrome, which is characterized by poor communicative abilities, peculiarities in social and cognitive capacities, and maladaptive behavioral patterns. The dysfunction in neuronal communication is considered one of the underlying causes for autism (Myrrhe van Spronsen and Casper C. Hoogenraad, *Curr. Neurol. Neurosci. Rep.* 2010, 10, 207-214).

This invention provides methods and compositions for treating autism using an SV2A inhibitor or a pharmaceutically acceptable salt, hydrate, solvate, polymorph, or prodrug thereof, alone or in combination with valproate or a derivative or an analog or a pharmaceutically acceptable salt thereof. In certain embodiments, treatment comprises preventing or slowing the progression of autism. In certain embodiments, treatment comprises alleviation, amelioration, or slowing the progression of one or more symptoms associated with autism. In certain embodiments, the symptom to be treated is cognitive deficit. For example, methods and compositions of the disclosure can be used to improve the motor/cognitive deficits symptomatic of autism.

The valproic acid (VPA) rat model of autism using in vitro electrophysiological techniques, established by Rodier et al. (Rodier, P. M. et al. *Reprod. Toxicol.* 1997, 11, 417-422) is one of the most exhaustively established insult-based animal models of autism and is based on the observation that pregnant women treated with VPA in the 1960s, during a circumscribed time window of embryogenesis, had a much higher risk of giving birth to an autistic child than the normal population. Offspring of VPA-exposed pregnant rats show several anatomical and behavioral symptoms typical of autism, such as diminished number of cerebellar Purkinje neurons, impaired social interaction, repetitive behaviors as well as other symptoms of autism, including enhanced fear memory processing. See, Rinaldi T. et al. *Frontiers in Neural Circuits,* 2008, 2, 1-7. The efficacy of the methods and compositions of this invention in treating autism, or cognitive deficits associated with autism, may be assessed in the VPA-treated rat model of autism, as well as human subjects with autism, using a variety of cognitive tests known in the art, as discussed above.

Mental Retardation

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, *Curr. Neurol. Neurosci. Rep.* 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

The present invention contemplates the treatment of mild mental retardation, moderate mental retardation, severe mental retardation, profound mental retardation, and mental retardation severity unspecified. Such mental retardation may be, but is not required to be, associated with chromosomal changes, (for example Down Syndrome due to trisomy 21), heredity, pregnancy and perinatal problems, and other severe mental disorders. This invention provides methods and compositions for treating mental retardation an SV2A inhibitor or a pharmaceutically acceptable salt, hydrate, solvate, polymorph, or prodrug thereof, alone or in combination with valproate or a derivative or an analog or a pharmaceutically acceptable salt thereof. In certain embodiments, treatment comprises preventing or slowing the progression of mental retardation. In certain embodiments, treatment comprises alleviation, amelioration, or slowing the progression of one or more symptoms associated with mental retardation. In certain embodiments, the symptom to be treated is cognitive deficit/impairment. For example, methods and compositions of the disclosure can be used to improve the motor/cognitive impairments symptomatic of mental retardation.

Several animal models have been developed for mental retardation. For example, a knockout mouse model has been developed for Fragile X syndrome. Fragile X syndrome is a common form of mental retardation caused by the absence of the FMR1 protein, FMRP. Two homologs of FMRP have been identified, FXR1P and FXR2P. FXR2P shows high expression in brain and testis, like FMRP. Both Fxr2 and Fmr1 knockout mice, and Fmr1/Fxr2 double knockout mice are believed to be useful models for mental retardation such as Fragile X syndrome. See, Bontekoe C. J. M. et al. *Hum. Mol. Genet.* 2002, 11 (5): 487-498. The efficacy of the methods and compositions of this invention in treating mental retardation, or cognitive deficit/impairment associated with mental retardation, may be assessed in the these mouse models and other animal models developed for mental retardation, as well as human subjects with mental retardation, using a variety of cognitive tests known in the art, as discussed above.

Compulsive Behavior (Obsessive Compulsive Disorder)

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, 4th edition text revision (DSM-IV-TR) (2000) diagnostic criteria that include characteristics of obsessions and compulsions. Characteristics of obsession include: (1) recurrent and persistent thoughts, impulses, or images that are experienced as intrusive and that cause marked anxiety or distress; (2) the thoughts, impulses, or images are not simply excessive worries about real-life problems; and (3) the person attempts to ignore or suppress such thoughts, impulses, or images, or to neutralize them with some other thought or action. The person recognizes that the obsessional thoughts, impulses, or images are a product of his or her own mind, and are not based in reality. Characteristics of compulsion include: (1) repetitive behaviors or mental acts that the person feels driven to perform in response to an obsession, or according to rules that must be applied rigidly; (2) the behaviors or mental acts are aimed at preventing or reducing distress or preventing some dreaded event or situation; however, these behaviors or mental acts are not actually connected to the issue, or they are excessive.

Individuals with OCD typically perform tasks (or compulsion) to seek relief from obsession-related anxiety. Repetitive behaviors such as handwashing, counting, checking, or cleaning are often performed with the hope of preventing obsessive thoughts or making them go away. Performing these "rituals," however, only provides temporary relief. People with OCD may also be diagnosed with a spectrum of other mental disorders, such as generalized anxiety disorder, anorexia nervosa, panic attack, or schizophrenia.

The dysfunction in neuronal communication is considered one of the underlying causes for obsession disorder (Myrrhe van Spronsen and Casper C. Hoogenraad, *Curr. Neural. Neurosci. Rep.* 2010, 10, 207-214). Studies suggest that OCD may be related to abnormal levels of a neurotransmitter called serotonin. The first-line treatment of OCD consists of behavioral therapy, cognitive therapy, and medications. Medications for treatment include serotonin reuptake inhibitors (SRIs) such as paroxetine (Seroxat™, Xetanor™, Paro-Merck™, Rexetin™), sertraline (Zoloft®, Stimuloton™), fluoxetine (Prozac®, Bioxetin™), escitalopram (Lexapro®), and fluvoxamine (Luvox®) as well as the tricyclic antidepressants, in particular clomipramine (Anafranil®). Benzodiazepines are also used in treatment. As much as 40 to 60% of the patients, however, fail to adequately respond to the SRI therapy and an even greater proportion of patients fail to experience complete remission of their symptoms.

This invention provides methods and compositions for treating OCD using an SV2A inhibitor or a pharmaceutically acceptable salt, hydrate, solvate, polymorph, or prodrug thereof, alone or in combination with valproate or a derivative or an analog or a pharmaceutically acceptable salt thereof. In certain embodiments, treatment comprises preventing or slowing the progression of OCD. In certain embodiments, treatment comprises alleviation, amelioration, or slowing the progression of one or more symptoms associated with OCD. In certain embodiments, the symptom to be treated is cognitive deficit. For example, methods and compositions of the disclosure can be used to treat the cognitive deficits in OCD, and/or to improve cognitive function in patients with OCD. A quinpirole-sensitized rat model has been developed for OCD. The compulsive checking behavior of the quinpirole-sensitized rats is subject to interruption, which is an attribute characteristic of OCD compulsions. The efficacy of the methods and compositions of this invention in treating OCD, or cognitive deficits associated with OCD, may be assessed in this rat model and other animal models developed for OCD, as well as human subjects with OCD, using a variety of cognitive tests known in the art, as discussed above.

Substance Addiction

Substance addiction (e.g., drug substance addiction, alcohol substance addiction) is a mental disorder. The substance addiction is not triggered instantaneously upon exposure to substnace of abuse. Rather, it involves multiple, complex neural adaptations that develop with different time courses ranging from hours to days to months (Kauer J. A. *Nat Rev. Neurosci*, 2007, 8, 844-858). The path to substance addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize substance addictions to other controlled substances. The craving for alcohol, as well as other controlled substances, often is as strong as the need for food or water. Thus, an alcoholic may continue to drink despite serious family, health and/or legal ramifications.

Recent work exploring the effects of abusing alcohol, central stimulants, and opiates on the central nervous system (CNS) have demonstrated a variety of adverse effects related to mental health, including substance-induced impairments in cognition. See, Nyberg F. *Cognitive Impairments in Drug Addicts*, Chapter 9. In several laboratories and clinics substantial damages of brain function are seen to result from these drugs. Among the harmful effects of the abusing drugs on brain are those contributing to accelerated obsolescence. An observation that has received special attention during recent years is that chronic drug users display pronounced impairment in brain areas associated with executive and memory function. A remarked neuroadaptation caused by addictive drugs, such as alcohol, central stimulants and opiates involves diminished neurogenesis in the subgranular zone (SGZ) of the hippocampus. Indeed, it has been proposed that decreased adult neurogenesis in the SGZ could modify the hippocampal function in such a way that it contributes to relapse and a maintained addictive behavior. It also raises the possibility that decreased neurogenesis may contribute to cognitive deficits elicited by these abusing drugs.

This invention provides methods and compositions for treating substance addiction an SV2A inhibitor or a pharmaceutically acceptable salt, hydrate, solvate, polymorph, or prodrug thereof, alone or in combination with valproate or a derivative or an analog or a pharmaceutically acceptable salt thereof. In certain embodiments, treatment comprises preventing or slowing the progression of substance addiction. In certain embodiments, treatment comprises alleviation, amelioration, or slowing the progression of one or more symptoms associated with substance addiction. In certain embodiments, the symptom to be treated is cognitive impairment. For example, methods and compositions of the disclosure can be used to treat the cognitive impairment and/or to improve cognitive function in patients with substance addiction.

Several animal models have been developed to study substance addiction. For example, a genetically selected Marchigian Sardinian alcohol-preferring (msP) rat models was developed to study the neurobiology of alcoholism. See, Ciccocioppo R. et al. *Substance addiction Biology* 2006, 11, 339-355. The efficacy of the methods and compositions of this invention in treating substance addiction, or cognitive impairment associated with substance addiction, may also be assessed in animal models of substance addiction, as well as human subjects with substance addiction, using a variety of cognitive tests known in the art, as discussed above.

SV2A Inhibitor

"Synaptic vesicle protein-2 (SV2)" is a family of synaptic vesicle proteins, which consists of three members, designated SV2A, SV2B, and SV2C. SV2A is the most widely distributed family member, being expressed ubiquitously in the brain. The proteins are integral membrane proteins and have a low-level homology (20-30%) to the twelve transmembrane family of bacterial and fungal transporter proteins that transport sugar, citrate, and xenobiotics (Bajjalieh et al., Science. 257: 1271-1273. (1992)). SV2 family proteins are present in the brain and endocrine cells, and further are present in all synaptic and endocrine vesicles. SV2 proteins are reported to play a role in normal synaptic function, and functions in a maturation step of primed vesicles that converts the vesicles into a $Ca^{(2+)}$— and synaptotagmin-responsive state (Sudhof et al., 2009). Functionally, SV2 proteins are reported to enhance synaptic currents and increase the probability of transmitter release by maintaining the size of the readily releasable pool of vesicles (Custer et al., 2006).

"SV2A inhibitor" refers to any agent, substance or compound that binds to SV2A and reduces synaptic function by reducing pre-synaptic vesicle release (See, e.g., Noyer et al. 1995; Fuks et al. 2003; Lynch et al. 2004; Gillard et al. 2006; Custer et al., 2006; Smedt et al., 2007; Yang et al., 2007; Meehan, "Levetiracetam has an activity-dependent effect on inhibitory transmission," *Epilepsia*, 2012 Jan. 31; and Example 8 of WO 2001/62726, all of which are specifically incorporated herein by reference.) A substance, or a compound or an agent is an SV2A inhibitor even if it does not itself bind to SV2A, as long as it causes, or affects the ability of, another compound or agent to bind SV2A or reduce synaptic function by reducing pre-synaptic vesicle release. SV2A inhibitors, suitable for use in the present invention, include the SV2A inhibitor formulas and specific SV2A inhibitors described herein, and their derivatives, analogs, hydrates, polymorphs, prodrugs, salts (e.g., pharmaceutically acceptable salts), and solvates.

Among the SV2A inhibitors or pharmaceutically acceptable salts, hydrates, solvates, polymorphs, and thereof that are useful in the methods and compositions of this invention are those disclosed, for example, U.S. patent application Ser. No. 12/580,464, International Patent Application PCT/US2009/005647, U.S. Patent Application 61/105,847, U.S. Patent Application 61/152,631, and U.S. Patent Application 61/175,536. However, any SV2A inhibitor or a pharmaceutically acceptable salt, hydrate, solvate, polymorph, or prodrug thereof may be used in the methods and compositions of the invention. In some embodiments, the SV2A inhibitor is selected from the group of SV2A inhibitors referred to in International Patent Applications WO2010/144712; WO2010/002869; WO2008/132139; WO2007/065595; WO2006/128693; WO2006/128692; WO2005/054188; WO2004/087658; WO2002/094787; WO2001/062726; U.S. Pat. Nos. 7,465,549; 7,244,747; 5,334,720; 4,696,943; 4,696,942; U.S. Patent Application Publication Numbers 20090312333; 20090018148; 20080081832; 2006258704; and UK Patent Numbers 1,039,113; and 1,309,692 or their pharmaceutically acceptable salts, hydrates, solvates, polymorphs or prodrugs. Other SV2A inhibitors may also be used in this invention. Applicants also refer to methods of preparing these compounds found in the documents cited above. Other synthetic methods may also be used. These methods are well known to those skilled in the art.

In some embodiments of this invention, the SV2A inhibitor is selected from the group consisting of levetiracetam, brivaracetam, and seletracetam or derivatives or analogs or pharmaceutically acceptable salts, solvates, hydrates, polymorphs, or prodrugs thereof.

In some embodiments of this invention, the SV2A inhibitor is levetiracetam or salts, solvates, hydrates, polymorphs or prodrugs thereof. Levetiracetam refers to the International Union of Pure and Applied Chemistry (IUPAC) name of the compound (2S)-2-(2-oxopyrrolidin-1-yl)butanamide). Levetiracetam is a widely used antiepileptic drug. Levetiracetam binds to a specific site in the CNS: the synaptic vesicle protein 2A (SV2A) (See. e.g., Noyer et al. 1995;

Fuks et al. 2003; Lynch et al. 2004; Gillard et al. 2006) and has further been shown to directly inhibit synaptic activity and neurotransmission by inhibiting presynaptic neurotransmitter release (Yang et al., 2007).

Among the SV2A inhibitors useful for the methods and compositions of this invention are the following:

i) International Patent Application WO 2001/062726:

A compound having the formula I or a pharmaceutically acceptable salt thereof,

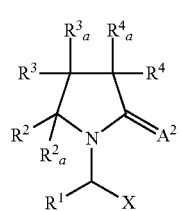

(I)

wherein X is —$CA^1NR^5R^6$ or —$CA^1OR^7$ or —$CA^1$-$R^8$ or CN;

$A^1$ and $A^2$ are independently oxygen, sulfur or —$NR^9$;

$R^1$ is hydrogen, alkyl, aryl or —$CH_2$—$R^{1a}$ wherein $R^{1a}$ is aryl, heterocycle, halogen, hydroxy, amino, nitro or cyano;

$R^2$, $R^3$ and $R^4$ are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative;

$R^{2a}$, $R^{3a}$ and $R^{4a}$ are the same or different and each is independently hydrogen, halogen, alkyl, alkenyl, alkynyl or aryl;

$R^5$, $R^6$, $R^7$ and $R^9$ are the same or different and each is independently hydrogen, hydroxy, alkyl, aryl, heterocycle or an oxy derivative; and $R^8$ is hydrogen, hydroxy, thiol, halogen, alkyl, aryl, heterocycle or a thio derivative;

with the provisos that at least one of as $R^2$, $R^3$, $R^4$, $R^{2a}$, $R^{3a}$ and $R^{4a}$ is other than hydrogen; and that when the compound is a mixture of all possible isomers, X is —$CONR^5R^6$, $A^2$ is oxygen and $R^1$ is hydrogen, methyl, ethyl or propyl then substitution on the pyrollidine ring is other than mono-, di-, or tri-methyl or mono-ethyl; and that when $R^1$, $R^2$, $R^4$, $R^{2a}$, $R^{3a}$ and $R^{4a}$ are each hydrogen, $A^2$ is oxygen and X is $CONR^5R^6$ then $R^3$ is different from carboxy, ester, amido, substituted oxo-pyrrolidine, hydroxy, oxy derivative, amino, amino derivatives, methyl, naphthyl, phenyl optionally substituted by oxy derivatives or in the para position by an halogen atom.

In the definitions set forth below, unless otherwise stated, $R^{11}$ and $R^{12}$ are the same or different and each is independently amido, alkyl, alkenyl, alkynyl, acyl, ester, ether, aryl, aralkyl, heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein is defined as including —O—$R^{11}$ groups wherein $R^{11}$ is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative" as used herein, is defined as including —S—$R^{11}$ groups wherein $R^{11}$ is as defined above except for "thio derivative". Non-limiting examples are alkylthio, alkenylthio, alkynylthio and arylthio.

The term "amino derivative" as used herein, is defined as including —$NHR^{11}$ or —$NR^{11}R^{12}$ groups wherein $R^{11}$ and $R^{12}$ are as defined above. Non-limiting examples are mono- or di-alkyl-, alkenyl-, alkynyl- and arylamino or mixed amino.

The term "acyl derivative" as used herein, represents a radical derived from carboxylic acid and thus is defined as including groups of the formula $R^{11}$—CO—, wherein $R^{11}$ is as defined above and may also be hydrogen. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative" as used herein, is defined as including a group of the formula —$SO_2$—$R^{11}$, wherein $R^{11}$ is as defined above except for "sulfonyl derivative". Non-limiting examples are alkylsulfonyl, alkenylsulfonyl, alkynylsulfonyl and arylsulfonyl.

The term "sulfinyl derivative" as used herein, is defined as including a group of the formula —SO—$R^{11}$, wherein $R^{11}$ is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and containing 1-20 carbon atoms, preferably 1-6 carbon atoms for non-cyclic alkyl and 3-6 carbon atoms for cycloalkyl (in these two preferred cases, unless otherwise specified, "lower alkyl"). Alkyl moieties may optionally be substituted by 1 to 5 substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, oxyester, oxyamido, heterocycle, vinyl, C1-5-alkoxy, C6-10-aryloxy and C6-10-aryl.

Preferred alkyl groups are methyl, ethyl, propyl, isopropyl, butyl, iso or ter-butyl, and 2,2,2-trimethylethyl each optionally substituted by at least one substituent selected from the group consisting of halogen, hydroxy, thiol, amino, nitro and cyano, such as trifluoromethyl, trichloromethyl, 2,2,2-trichloroethyl, 1,1-dimethyl-2,2-dibromoethyl, 1,1-dimethyl-2,2,2-trichloroethyl.

The term "alkenyl" as used herein, is defined as including both branched and unbranched, unsaturated hydrocarbon radicals having at least one double bond such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like and being optionally substituted by at least one substituent selected from the group consisting of halogen, hydroxy, thiol, amino, nitro, cyano, aryl and heterocycle such as mono- and di-halo vinyl where halo is fluoro, chloro or bromo.

The term "alkynyl" as used herein, is defined as including a monovalent branched or unbranched hydrocarbon radical containing at least one carbon-carbon triple bond, for example ethynyl, 2-propynyl (=propargyl), and the like and being optionally substituted by at least one substituent selected from the group consisting of halogen, hydroxy, thiol, amino, nitro, cyano, aryl and heterocycle, such as haloethynyl.

When present as bridging groups, alkyl, alkenyl and alkynyl represent straight- or branched chains, C1-12, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g., "n-propyl", "sec-butyl") are in the n-form unless otherwise stated.

The term "aryl" as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, alkylthio, oxyester, oxyamido, aryl, C1-6-alkoxy, C6-10-aryloxy, C1-6-alkyl, C1-6-haloalkyl. Aryl radicals are preferably monocyclic containing 6-10 carbon atoms. Preferred aryl groups are phenyl and naphthyl each optionally substituted by 1 to 5 substituents independently selected from halogen, nitro, amino, azido, C1-6-alkoxy, C1-6-alkylthio, C1-6-alkyl, C1-6-haloalkyl and phenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "nitrooxy", as used herein, represents a group of the formula —$ONO_2$.

The term "amino", as used herein, represents a group of the formula —$NH_2$.

The term "azido", as used herein, represents a group of the formula —$N_3$.

The term "carboxy", as used herein, represents a group of the formula —COOH. The term "sulfonic acid", as used herein, represents a group of the formula —$SO_3H$.

The term "sulfonamide", as used herein, represents a group of the formula —$SO_2NH_2$.

The term "ester", as used herein is defined as including a group of formula —COO—$R^{11}$ wherein $R^{11}$ is as defined above except oxy derivative, thio derivative or amino derivative.

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —$CONH_2$ or —$CONHR^{11}$ or —$CONR^{11}R^{12}$ wherein $R^{11}$ and $R^{12}$ are as defined above.

The term "heterocycle", as used herein is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl. Non-limiting examples of aromatic heterocycles are pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno (2,3-b) furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5) dec-2-yl, pyrrolidinyl, 2-oxo-pyrrolidinyl, sugar moieties (i.e. glucose, pentose, hexose, ribose, fructose, which may also be substituted) or the same which can optionally be substituted with any suitable group, including but not limited to one or more moieties selected from lower alkyl, or other groups as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1) heptanyl, 8-azabicyclo(3.2.1)octanyl.

In the above definitions it is to be understood that when a substituent such as $R^2$, $R^3$, $R^4$, $R^{2a}$, $R^{3a}$, $R^{4a}$, $R^5$, $R^6$, $R^7$, $R^8$ is attached to the rest of the molecule via a heteroatom or a carbonyl, a straight- or branched chain, C1-12-, preferably C1-4-alkylene or C2-12, preferably C2-4-alkenylene or -alkynylene bridge may optionally be interposed between the heteroatom or the carbonyl and the point of attachment to the rest of the molecule.

Preferred examples of X are —$COOR^7$ or —$CONR^5R^6$, wherein $R^5$, $R^6$ and $R^7$ are preferably hydrogen, C1-4-alkyl, phenyl or alkylphenyl.

Preferably X is carboxy or —$CONR^5R^6$, wherein $R^5$ and $R^6$ are preferably hydrogen, C1-4-alkyl, phenyl or alkylphenyl, especially —$CONH_2$.

Preferably $A^1$ and $A^2$ are each oxygen.

Preferably $R^1$ is hydrogen, alkyl, especially C1-12 alkyl, particularly lower alkyl or aryl especially phenyl.

Examples of preferred $R^1$ groups are methyl, ethyl, propyl, isopropyl, butyl, iso- or ter-butyl, 2,2,2-trimethylethyl each optionally attached via a methylene bridge or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

$R^1$ as ethyl is especially preferred.

Preferably $R^2$ and $R^{2a}$ are independently hydrogen, halogen or alkyl, especially lower alkyl.

Examples of preferred $R^2$ and $R^{2a}$ groups are independently hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

Especially at least one and most preferably both of $R^2$ and $R^{2a}$ are hydrogen.

Preferably $R^{3a}$, $R^4$ and $R^{4a}$ are independently hydrogen, alkyl, especially methyl or ethyl or aryl especially phenyl or aralkyl, especially benzyl.

Examples of preferred $R^{3a}$, $R^4$ and $R^{4a}$ groups are independently hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

Especially at least one and most preferably both of $R^4$ and $R^{4a}$ are hydrogen.

$R^{3a}$ is particularly hydrogen or alkyl, especially lower alkyl and is most preferably hydrogen.

Preferably $R^3$ is hydrogen, C1-12-alkyl, especially C1-6-alkyl, each optionally substituted by one or more substituents selected from hydroxy, halogen, cyano, thiocyanato or alkoxy and attached to the ring either directly or via a thio, sulfinyl, sulfonyl, carbonyl or oxycarbonyl group and optionally, a C1-4-alkylene bridge, particularly methylene; C2-6-alkenyl or -alkynyl, especially C2-3-alkenyl or -alkynyl each optionally substituted by one or more halogens; azido; cyano; amido; carboxy; triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl or piperazinyl each optionally substituted by one or more substituents selected from halogen, C1-6-alkyl and phenyl and attached to the ring either directly or via a carbonyl group or a C1-4-alkylene bridge, particularly methylene; naphthyl; or phenyl, phenylalkyl or phenylalkenyl each optionally substituted by one or more substituents selected from halogen, C1-6-alkyl, C1-6 haloalkyl, C1-6-alkoxy, C1-6-alkylthio, amino, azido, phenyl and nitro and each attached to the ring either directly or via an oxy, sulfonyl, sulfonyloxy, carbonyl or carbonyloxy group and optionally additionally a C1-4-alkylene bridge, particularly methylene.

Also, preferably, $R^3$ is C1-6-alkyl optionally substituted by one or more substituents selected from halogen, thiocyanato, azido, alkoxy, alkylthio, phenylsulfonyl; nitrooxy; C2-3-alkenyl or -alkynyl each optionally substituted by one or more halogens or by acetyl; tetrazolyl, pyridyl, furyl, pyrrolyl, thiazolyl or thienyl; or phenyl or phenylalkyl each optionally substituted by one or more substituents selected from halogen, C1-6-alkyl, C1-6 haloalkyl, C1-6-alkoxy, amino, azido, phenyl and nitro and each attached to the ring either directly or via a sulfonyloxy and optionally additionally a C1-4-alkylene bridge, particularly methylene.

Other examples of preferred $R^3$ groups are hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

$R^3$ is especially C1-4-alkyl optionally substituted by one or more substituents selected from halogen, thiocyanato or azido; C2-5-alkenyl or -alkynyl, each optionally substituted by one or more halogens; thienyl; or phenyl optionally substituted by one or more substituents selected from halogen, C1-6-alkyl, C1-6 haloalkyl or azido.

Further examples of preferred $R^3$ groups are C1-6 alkyl and C2-6 haloalkenyl.

Preferably $R^5$ and $R^6$ are independently hydrogen, methyl, ethyl, propyl, isopropyl, butyl, iso or ter-butyl, 2,2,2-trimethylethyl, especially hydrogen or methyl.

Especially at least one and most preferably both of $R^5$ and $R^6$ are hydrogen.

Preferably $R^7$ is hydrogen, methyl, ethyl, propyl, isopropyl, butyl, iso or tert-butyl, 2,2,2-trimethylethyl, methoxy, ethoxy, phenyl, benzyl or the same substituted by at least one halogen atom such as trifluoromethyl, chlorophenyl.

Preferably $R^7$ is hydrogen, methyl or ethyl especially hydrogen.

Preferably $R^8$ is hydrogen, methyl, ethyl, propyl, isopropyl, butyl, iso or ter-butyl, 2,2,2-trimethylethyl, phenyl, benzyl or the same substituted by at least one halogen atom such as trifluoromethyl, chlorobenzyl.

Preferably $R^8$ is hydrogen or methyl.

Combinations of one or more of these preferred compound groups are especially preferred.

A particular group of compounds of formula I (Compounds 1A) comprises those wherein, $A^2$ is oxygen;

X is —$CONR^5R^6$ or —$COOR^7$ or —CO—$R^8$ or CN;

$R^1$ is hydrogen or alkyl, aryl, halogen, hydroxy, amino, nitro, cyano;

$R^2$, $R^3$, $R^4$, are the same or different and each is independently hydrogen or halogen, hydroxy, amino, nitro, cyano, acyl, acyloxy, a sulfonyl derivative, a sulfinyl derivative, an amino derivative, carboxy, ester, ether, amido, sulfonic acid, sulfonamide, alkoxycarbonyl, a thio derivative, alkyl, alkoxy, oxyester, oxyamido, aryl, an oxy derivative, heterocycle, vinyl and $R^3$ may additionally represent C2-5 alkenyl, C2-5 alkynyl or azido each optionally substituted by one or more halogen, cyano, thiocyano, azido, cyclopropyl, acyl and/or phenyl; or phenylsulfonyloxy whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

$R^{2a}$, $R^{3a}$ and $R^{4a}$ are hydrogen;

$R^5$, $R^6$, $R^7$ are the same or different and each is independently hydrogen, hydroxy, alkyl, aryl, heterocycle or oxy derivative; and $R^8$ is hydrogen, hydroxy, thiol, halogen, alkyl, aryl, heterocycle, alkylthio or thio derivative.

Within these Compounds 1A, $R^1$ is preferably methyl, ethyl, propyl, isopropyl, butyl, or isobutyl; most preferably methyl, ethyl or n-propyl.

$R^2$ and $R^4$ are preferably independently hydrogen or halogen or methyl, ethyl, propyl, isopropyl, butyl, isobutyl; and, most preferably, are each hydrogen.

$R^3$ is preferably C1-5 alkyl, C2-5 alkenyl, C2-C5 alkynyl, cyclopropyl, azido, each optionally substituted by one or more halogen, cyano, thiocyano, azido, alkylthio, cyclopropyl, acyl and/or phenyl; phenyl; phenylsulfonyl; phenylsulfonyloxy, tetrazole, thiazole, thienyl, furyl, pyrrole, pyridine, whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

X is preferably —COOH or —COOMe or —COOEt or —$CONH_2$; most preferably —$CONH_2$.

A further particular group of compounds of formula I (Compounds 1B) comprises those wherein, X is —$CA^1NH_2$, —$CA^1NHCH_3$ or —$CA^1N(CH_3)_2$;

$R^1$ is alkyl or phenyl;

$R^3$ is alkyl, alkenyl, alkynyl, cyano, isothiocyanato, ether, carboxyl, amido, aryl, heterocycle; or $R^3$ is $CH_2R^{10}$ wherein $R^{10}$ is hydrogen, cycloalkyl, oxyester, oxyalkylsulfonyl, oxyarylsufonyl, aminoalkylsulfonyl, aminoarylsulfonyl, nitrooxy, cyano, isothiocyanato, azido, alkylthio, arylthio, alkylsulfinyl, alkylsulfonyl, heterocycle, aryloxy, alkoxy or trifluoroethyl;

49

$R^{3a}$ is hydrogen, alkyl or aryl (especially with the proviso that when $R^{3'}$ is hydrogen, $R^3$ other than methyl);
or $R^3 R^{3a}$ form a cycloalkyl;
and $R^2$, $R^{2a}$, $R^4$ and $R^{4a}$ are each hydrogen.

Within the compounds of formula I,
$R^1$ is preferably alkyl especially C1-12-more particularly C1-6-alkyl and is most preferably ethyl;
$R^2$, $R^{2a}$, $R^{3a}$ and $R^{4a}$ are preferably hydrogen;
$R^3$ is preferably selected from hydrogen; C1-12-alkyl, especially C1-6-alkyl, each optionally substituted by one or more substituents selected from hydroxy, halogen, cyano, thiocyanato or alkoxy and attached to the ring either directly or via a thio, sulfinyl, sulfonyl, carbonyl or oxycarbonyl group and optionally additionally a C1-4-alkylene bridge, particularly methylene; C2-6-alkenyl or -alkynyl, especially C2-3-alkenyl or -alkynyl, each optionally substituted by one or more halogens; azido; cyano; amido; carboxy; triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl or piperazinyl each optionally substituted by one or more substituents selected from halogen, C1-6-alkyl and phenyl and attached to the ring either directly or via a carbonyl group or a C1-4-alkylene bridge, particularly methylene; naphthyl; or phenyl, phenylalkyl or phenylalkenyl each optionally substituted by one or more substituents selected from halogen, C1-6-alkyl, C1-6 haloalkyl, C1-6-alkoxy, C1-6-alkylthio, amino, azido, phenyl and nitro and each attached to the ring either directly or via an oxy, sulfonyl, sulfonyloxy, carbonyl or carbonyloxy group and optionally additionally a C1-4-alkylene bridge, particularly methylene;

$R^{3a}$ is preferably hydrogen or C1-4-alkyl;
$R^4$ and $R^{4a}$ are preferably, independently, hydrogen, C1-4-alkyl, phenyl or benzyl.

A further group of compounds of formula I (Compounds 1C) comprises those in racemic form wherein, when X is —CONR$^5$R$^6$ and $R^1$ is hydrogen, methyl, ethyl or propyl, then substitution on the pyrrolidine ring is other than mono-, di-, or tri-methyl or mono-ethyl.

A further group of compound of formula I (Compounds 1D) comprises those in racemic form wherein, when X is —CONR$^5$R$^6$ and $R^1$ is hydrogen or C1-6-alkyl, C2-6-alkenyl or -alkynyl or cycloalkyl, each unsubstituted, then substitution in the ring is other than by alkyl, alkenyl or alkynyl, each unsubstituted.

A further particular group of compounds of formula I (Compounds IE) comprises those wherein,
X is —CA$^1$NH$_2$;
$R^1$ is H;
$R^3$ is azidomethyl, iodomethyl, ethyl optionally substituted by 1 to 5 halogen atoms, n-propyl optionally substituted by 1 to 5 halogen atoms, vinyl optionally substituted by one or two methyl, and/or 1 to 3 halogen atoms, acetylene optionally substituted by C1-4-alkyl, phenyl or halogen;
$R^{3a}$ is hydrogen or halogen, preferably fluorine;
and $R^2$, $R^{2a}$, $R^4$ and $R^{4a}$ are each hydrogen;
as their racemates or in enantiomerically enriched form, preferably the pure enantiomers.

A further particular group of compounds of formula I (Compounds 1F) comprises those wherein,
X is —CA$^1$NH$_2$;
$R^1$ is H;
$R^3$ is C1-6-alkyl, C2-6-alkenyl or C2-6-alkynyl optionally substituted by azido, oxynitro, 1 to 6 halogen atoms;
$R^{3a}$ is hydrogen or halogen, preferably fluorine;

50 and $R^2$, $R^{2a}$, $R^4$ and $R^{4a}$ are each hydrogen; as their racemates or in enantiomerically enriched form, preferably the pure enantiomers.

In all the above mentioned scopes when the carbon atom to which $R^1$ is attached is asymmetric it is preferably in the "S"-configuration.

In some embodiments, compounds useful in the methods and compositions of this invention are selected from the group consisting of:
(2S)-2-[4-(bromomethyl)-2-oxo-1-pyrrolidinyl]butanamide;
(2S)-2-[(4R)-4-(iodomethyl)-2-oxopyrrolidinyl]butanamide;
(2S)-2-(2-oxo-4-phenyl-1-pyrrplidinyl)butanamide;
(2S)-2-[4-(iodomethyl)-2-oxo-1-pyrrolidinyl]butanamide;
(2S)-2-[4-(chloromethyl)-2-oxo-1-pyrrolidinyl]butanamide;
{1-[(1S)-1-(aminocarbonyl)propyl]-5-oxo-3-pyrrolidinyl}methyl 4-methylbenzenesulfonate;
(2S)-2-[(4R)-4-(azidomethyl)-2-oxopyrrolidinyl]butanamide;
2-[4-(2,2-dibromovinyl)-2-oxo-1-pyrrolidinyl]butanamide;
{1-[(1S)-1-(aminocarbonyl)propyl]-5-oxo-3-pyrrolidinyl}methyl nitrate;
(2S)-2-[2-oxo-4-(1H-tetraazol-1-ylmethyl)-1-pyrrolidinyl]butanamide;
2-(2-oxo-4-vinyl-1-pyrrolidinyl)butanamide;
2-{2-oxo-4-[(phenylsulfonyl)methyl]-1-pyrrolidinyl]butanamide;
(2S)-2-[(4R)-4-(2,2-dibromovinyl)-2-oxopyrrolidinyl]butanamide;
(2S)-2-[(4S)-4-(2,2-dibromovinyl)-2-oxopyrrolidinyl]butanamide;
(2S)-2-[4-(isothiocyanatomethyl)-2-oxo-1-pyrrolidinyl]butanamide;
2-[2-oxo-4-(1,3-thiazol-2-yl)-1-pyrrolidinyl]butanamide;
(2S)-2-[2-oxo-4-(2-thienyl)-1-pyrrolidinyl]butanamide;
(2S)-2-[4-(2-methoxyphenyl)-2-oxo-1-pyrrolidinyl]butanamide;
(2S)-2-[4-(3-methoxyphenyl)-2-oxo-1-pyrrolidinyl]butanamide;
(2S)-2-[4-(4-azidophenyl)-2-oxo-1-pyrrolidinyl]butanamide;
(2S)-2-[2-oxo-4-(3-thienyl)-1-pyrrolidinyl]butanamide;
(2S)-2-[4-(3-azidophenyl)-2-oxo-1-pyrrolidinyl]butanamide;
(2S)-2-[2-oxo-4-(3-thienyl)-1-pyrrolidinyl]butanamide;
(2S)-2-[(4S)-2-oxo-4-vinylpyrrolidinyl]butanamide;
(2S)-2-[(4R)-2-oxo-4-vinylpyrrolidinyl]butanamide;
2-[4-(2-bromophenyl)-2-oxo-1-pyrrolidinyl]butanamide;
2-[2-oxo-4-(3-pyridinyl)-1-pyrrolidinyl]butanamide;
(2S)-2-(4-[1,1'-biphenyl]-4-yl-2-oxo-1-pyrrolidinyl)butanamide;
(2S)-2-{4-[(methylsulfanyl)methyl]-2-oxo-1-pyrrolidinyl}butanamide;
2-[4-(iodomethyl)-2-oxo-1-pyrrolidinyl]butanamide;
(2S)-2-[(4R)-4-(iodomethyl)-2-oxo-1-pyrrolidinyl]pentanamide;
(2S)-2-[(4R)-4-(iodomethyl)-2-oxopyrrolidinyl]propanamide;
2-(2-oxo-4-propyl-1-pyrrolidinyl)propanamide;
2-(2-oxo-4-propyl-1-pyrrolidinyl)butanamide;
2-(2-oxo-4-pentyl-1-pyrrolidinyl)butanamide;
(2S)-2-[(4R)-4-(iodomethyl)-2-oxopyrrolidinyl]-N-methylbutanamide;
(2S)-2-(4-neopentyl-2-oxo-1-pyrrolidinyl)butanamide;
(2S)-2-(4-ethyl-2-oxo-1-pyrrolidinyl)butanamide;
2-[4-(2,2-difluorovinyl)-2-oxo-1-pyrrolidinyl]butanamide;
2-[4-(2,2-difluoroethyl)-2-oxo-1-pyrrolidinyl]butanamide;

(2S)-2-[(4S)-2-oxo-4-propylpyrrolidinyl]butanamide;
(2S)-2-[(4R)-2-oxo-4-propylpyrrolidinyl]butanamide;
2-{4-[(Z)-2-fluoroethenyl]-2-oxo-1-pyrrolidinyl}butanamide;
2-[4-(2-methyl-1-propenyl)-2-oxo-1-pyrrolidinyl]butanamide;
2-(4-butyl-2-oxo-1-pyrrolidinyl)butanamide;
2-[4-(cyclopropylmethyl)-2-oxo-1-pyrrolidinyl]butanamide;
2-(4-isobutyl-2-oxo-1-pyrrolidinyl)butanamide;
2-[4-(4-chlorophenyl)-2-oxo-1-pyrrolidinyl]butanamide;
2-[4-(3-chlorophenyl)-2-oxo-1-pyrrolidinyl]butanamide;
2-{2-oxo-4-[2-(trifluoromethyl)phenyl]-1-pyrrolidinyl}butanamide;
2-[4-(2-fluorophenyl)-2-oxo-1-pyrrolidinyl]butanamide;
2-[4-(3-methylphenyl)-2-oxo-1-pyrrolidinyl]butanamide;
(2S)-2-[2-oxo-4-(2-phenylethyl)-1-pyrrolidinyl]butanamide;
(2S)-2-[4-(3-bromophenyl)-2-oxo-1-pyrrolidinyl]butanamide;
2-{4-[3,5-bis(trifluoromethyl)phenyl]-2-oxo-1-pyrrolidinyl}butanamide;
2-[4-(3,4-dichlorophenyl)-2-oxo-1-pyrrolidinyl]butanamide;
2-[4-(2,4-dichlorophenyl)-2-oxo-1-pyrrolidinyl]butanamide;
2-[4-(2-furyl)-2-oxo-1-pyrrolidinyl]butanamide;
(2S)-2-[2-oxo-4-(3-phenylpropyl)-1-pyrrolidinyl]butanamide;
(2S)-2-[4-(3,5-dibromophenyl)-2-oxo-1-pyrrolidinyl]butanamide;
2-[4-(3,4-dichlorophenyl)-2-oxo-1-pyrrolidinyl]butanamide;
2-(2-oxo-4-propyl-1-pyrrolidinyl)butanamide;
2-[4-(3-chlorophenyl)-2-oxo-1-pyrrolidinyl]butanamide;
2-(4-ethynyl-2-oxo-1-pyrrolidinyl) butanamide;
2-[4-(2-fluorophenyl)-2-oxo-1-pyrrolidinyl]butanamide;
(2S)-2-[4-(cyclopropylmethyl)-2-oxo-1-pyrrolidinyl]butanamide;
(2S)-2-[(4S)-4-(2,2-difluorovinyl)-2-oxopyrrolidinyl]butanamide;
(2S)-2-[2-oxo-4-(3,3,3-trifluoropropyl)-1-pyrrolidinyl]butanamide;
2-[4-(3-methylphenyl)-2-oxo-1-pyrrolidinyl]butanamide;
(2S)-2-[4-(cyclopropylmethyl)-2-oxo-1-pyrrolidinyl]butanamide;
(2S)-2-[(4R)-4-(2,2-difluorovinyl)-2-oxopyrrolidinyl]butanamide;
(2S)-2-[2-oxo-4-(1H-pyrrol-1-yl)-1-pyrrolidinyl]butanamide;
(2S)-2-(4-allyl-2-oxo-1-pyrrolidinyl)butanamide;
(2S)-2-[4-(2-iodopropyl)-2-oxo-1-pyrrolidinyl]butanamide;
(2S)-2-(4-allyl-2-oxo-1-pyrrolidinyl)butanamide;
(2S)-2-[2-oxo-4-(2-oxopropyl)-1-pyrrolidinyl]butanamide;
(2S)-2-[4-(2-bromo-1H-pyrrol-1-yl)-2-oxo-1-pyrrolidinyl]butanamide;
(2S)-2-(4-methyl-2-oxo-4-propyl-1-pyrrolidinyl)butanamide;
(2R)-2-[4-(2,2-dichlorovinyl)-2-oxo-1-pyrrolidinyl]butanamide;
2-[4-(bromoethynyl)-2-oxo-1-pyrrolidinyl]butanamide;
2-[(4S)-4-(2,2-difluoropropyl)-2-oxopyrrolidinyl]butanamide;
(2S)-2-[4-(bromoethynyl)-2-oxo-1-pyrrolidinyl]butanamide;
2-(2-oxo-4-propyl-1-pyrrolidinyl)pentanamide;
3-cyclopropyl-2-(2-oxo-4-propyl-1-pyrrolidinyl)propanamide;
2-(2-oxo-4-propyl-1-pyrrolidinyl)-3-(1,3-thiazol-4-yl)propanamide;
2-(2-oxo-4-propyl-1-pyrrolidinyl)-4-pentenamide;
(2S)-2-[(4R)-2-oxo-4-vinylpyrrolidinyl]butanamide;
including all isomeric forms and mixtures thereof or a pharmaceutically acceptable salt thereof.

In some embodiments, compounds useful in the methods and compositions of this invention are selected from the group consisting of:
(2S)-2-[(4S)-4-(2,2-difluorovinyl)-2-oxopyrrolidinyl]butanamide;
(2S)-2-[(4S)-2-oxo-4-propylpyrrolidinyl]butanamide;
(2S)-2-[(4R)-2-oxo-4-propylpyrrolidinyl]butanamide.

ii) International Patent Application WO 2002/094787:
Compounds of the formula I

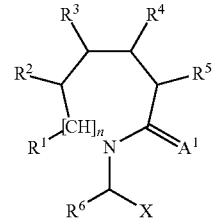

wherein n represents 0 or 1 whereby $R^1$ is not existent when n=0 and $R^1$ is existent when n=1;
$A^1$ represents an oxygen or a sulfur atom;
X is —$CONR^7R^8$, —$COOR^9$, —CO—$R^{10}$ or CN;
$R^1$ when existent, $R^2$, $R^3$, $R^4$ and $R^5$ are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative,
provided that at least one of the substituents R chosen from $R^1$ when existent, $R^2$, $R^3$, $R^4$ or $R^5$ is not hydrogen;
$R^6$ is hydrogen, alkyl, aryl or —$CH_2$—$R^{6a}$ wherein $R^{6a}$ is aryl, heterocycle, halogen, hydroxy, amino, nitro or cyano;
$R^7$, $R^8$ and $R^9$ are the same or different and each is independently hydrogen, hydroxy, alkyl, aryl, heterocycle or an oxy derivative; and
$R^{10}$ is hydrogen, hydroxy, thiol, halogen, alkyl, aryl, heterocycle or a thio derivative;
their pharmaceutically acceptable salts, geometrical isomers (including cis and trans, Z and E isomers), enantiomers, diastereoisomers and mixtures thereof (including all possible mixtures of stereoisomers).

In the above formula, at least one substituent $R^1$ to $R^5$ is different from hydrogen. Some non-substituted compounds are referred to in U.S. Pat. Nos. 5,468,733 and 5,516,759. U.S. Pat. No. 5,468,733 refers to non-ring substituted 2-oxo-1-pyrrolidinyl and 2-oxo-1-piperidinyl derivatives as inhibitors of the oncogene Ras protein. In particular, these compounds block the ability of Ras to transform normal cells to cancer cells, and therefore can be included in several chemotherapeutic compositions for treating cancer.

U.S. Pat. No. 5,516,759 refers to non-ring substituted 2-oxo-1-pyrrolidinyl, 2-oxo-1-piperidinyl and azepanyl derivatives present at the N-terminus of dodecapeptides possessing LHRH (luteinizing hormone-releasing hormone)

antagonistic activity. Such LHRH antagonists are useful in the treatment of a variety of conditions in which suppression of sex steroids plays a key role including contraception, delay of puberty, treatment of benign prostatic hyperplasia a. o.

In the definitions set forth below, unless otherwise stated, $R^{11}$ and $R^{12}$ are the same or different and each is independently amido, alkyl, alkenyl, alkynyl, acyl, ester, ether, aryl, aralkyl. heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein, is defined as including —O—$R^{11}$ groups wherein $R^{11}$ is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative", as used herein, is defined as including —S—$R^{11}$ groups wherein $R^{11}$ is as defined above except for "thio derivative". Non-limiting examples are alkylthio, alkenylthio, alkynylthio and arylthio.

The term "amino derivative", as used herein, is defined as including -NH$R^{11}$ or —N$R^{11}R^{12}$ groups wherein $R^{11}$ and $R^{12}$ are as defined above. Non-limiting examples are mono- or di-alkyl-, alkenyl-, alkynyl- and arylamino or mixed amino.

The term "acyl derivative", as used herein, represents a radical derived from carboxylic acid and thus is defined as including groups of the formula $R^{11}$—CO—, wherein $R^{11}$ is as defined above and may also be hydrogen. Preferred are acyl derivatives of formula —CO$R^{11}$ wherein $R^{11}$ is selected from hydrogen, C1-12 alkyl, C2-12 alkenyl, C2-12 alkenyl, heterocyle and aryl. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative", as used herein, is defined as including a group of the formula —SO$_2$—$R^{11}$, wherein $R^{11}$ is as defined above except for "sulfonyl derivative". Non-limiting examples are alkylsulfonyl, alkenylsulfonyl, alkynylsulfonyl and arylsulfonyl.

The term "sulfinyl derivative", as used herein, is defined as including a group of the formula —SO—$R^{11}$, wherein $R^{11}$ is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and generally containing 1-20 carbon atoms, most often 1 to 12 carbon atoms, preferably 1-7 carbon atoms for non-cyclic alkyl and 3-7 carbon atoms for cycloalkyl (in these two preferred cases, unless otherwise specified, "lower alkyl"), each optionally substituted by, preferably 1 to 5, substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, alkylthio, oxyester, oxyamido, heterocycle, vinyl, alkoxy (preferably C1-5), aryloxy (preferably C6-10) and aryl (preferably C6-10).

Preferred are alkyl groups containing 1 to 7 carbon atoms, each optionally substituted by one or more substituents selected from hydroxy, halogen, cyano, thiocyanato, alkoxy, azido, alkylthio, cyclopropyl, acyl and phenyl. Most preferred are C1-4 alkyl and C3-7 cycloalkyl, each optionally substituted by one or more hydroxy, halogen, lower alkyl or/and azido.

Most preferred alkyl groups are hydroxymethyl, propyl, butyl, 2,2,2-trifluoroethyl, 2-bromo-2,2-difluoroethyl, 2-chloro-2,2-difluoroethyl, 3,3,3-trifluoropropyl, cyclopropylmethyl, iodomethyl, azidomethyl, 2,2-difluoropropyl, 2-iodo-2,2-difluoroethyl.

The term "lower alkyl", as used herein, and unless otherwise specified, refers to $C_1$ to $C_7$ saturated straight, branched or cyclic hydrocarbon. Non limiting examples are methyl, ethyl, propyl, isopropyl, butyl, tertiobutyl, pentyl, cyclopropyl, cyclopentyl, isopentyl, neopentyl, hexyl, isohexyl, cyclohexyl, 3-methypentyl, 2,2-dimethylbutyl, optionally substituted with any suitable group, including but not limited to one or more moieties selected from groups as described above for the alkyl groups. Preferably, lower alkyl is methyl.

The term "alkenyl", as used herein, is defined as including both branched and unbranched, unsaturated hydrocarbon radicals having at least one double bond, and being optionally substituted by at least one substituent selected from the group consisting of halogen, hydroxy, thiol, amino, thiocyanato, azido, alkylthio, cycloalkyl, acyl, nitro, cyano, aryl and heterocycle.

Preferred alkenyl groups are C2-C12 alkenyls, especially C2-6 alkenyls, such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl and the like, optionally being substituted by one or more substituents selected from halogen, cyano, thiocyanato, azido, alkylthio, cycloalkyl, phenyl and acyl. Most preferred is vinyl, optionally substituted by one or more halogen or/and lower alkyl, and especially 2,2-difluorovinyl, 2,2-dibromovinyl and 2,2-dichlorovinyl.

The term "alkynyl" as used herein, is defined as including a monovalent branched or unbranched hydrocarbon radical containing at least one carbon-carbon triple bond, for example ethynyl, 2-propynyl (=propargyl), and the like, and being optionally substituted by at least one substituent selected from the group consisting of halogen, hydroxy, thiol, amino, nitro, cyano, aryl, heterocycle, thiocyanato, azido, alkylthio, alkyl and acyl.

Preferred alkynyl groups are C2-12 alkynyl, especially C2-6 alkynyl, optionally being substituted by one or more substituents selected from halogen, cyano, thiocyanato, azido, alkylthio, acyl, aryl such as phenyl and alkyl, preferably cycloalkyl.

Most preferred are ethynyl, propynyl and butynyl, optionally substituted by lower alkyl or/and halogen, and especially 1-propynyl, cyclopropylethynyl, 3-methyl-1-butynyl and 3,3,3-trifluoro-1-propynyl.

When present as bridging groups, alkyl, alkenyl and alkynyl represent straight- or branched chains, C1-12, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl", as used herein, is defined as including an organic radical derived from an aromatic hydrocarbon consisting of at least one ring, most often 1 to 3 rings and generally containing 6-30 carbon atoms by removal of one hydrogen, such as phenyl and naphthyl, each optionally substituted by one or more substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, C1-6-alkylthio, oxyester, oxyamido, aryl, C1-6-alkoxy, C6-10-aryloxy, C1-6-alkyl, C1-6-haloalkyl. Aryl radicals are preferably monocyclic or bicyclic containing 6-10 carbon atoms. Preferred aryl groups are phenyl and naphthyl each optionally substituted by one or more substituents independently selected from halogen, nitro, amino, azido, C1-6-alkoxy, C1-6-alkyl, C1-6-haloalkyl, sulfonyl and phenyl.

Preferred aryl is phenyl, optionally substituted by one or more halogen, lower alkyl, azido or nitro, such as 3-chlorophenyl and 3-azidophenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "nitrooxy", as used herein, represents a group of the formula —$ONO_2$.

The term "amino", as used herein, represents a group of the formula —$NH_2$.

The term "azido", as used herein, represents a group of the formula —$N_3$.

The term "carboxy", as used herein, represents a group of the formula —COOH.

The term "sulfonic acid", as used herein, represents a group of the formula —$SO_3H$.

The term "sulfonamide", as used herein, represents a group of the formula —$SO_2NH_2$.

The term "ester", as used herein, is defined as including a group of formula —COO—$R^{11}$ wherein $R^{11}$ is as defined above except oxy derivative, thio derivative or amino derivative. Preferred are esters of formula —$COOR^{11}$ wherein $R^{11}$ is selected from C1-12 alkyl, C2-12 alkenyl, C2-12 alkynyl and aryl. Most preferred are esters where $R^{11}$ is a lower alkyl, especially methyl.

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —$CONH_2$ or —$CONHR^{11}$ or —$CONR^{11}R^{12}$ wherein $R^{11}$ and $R^{12}$ are as defined above.

The term "heterocycle", as used herein, is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl, and optionally being substituted with any suitable group, including but not limited to one or more moieties selected from lower alkyl, or other groups as described above for the alkyl groups. Non-limiting examples of heterocycles are pyridyl, furyl, pyrrolyl, thienyl, isothiazolyl, triazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thiomorpholinyl, thieno (2,3-b) furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, 1-oxidopyridyl, phenanthridinyl, acridinyl, perimidinyl, phenanthrolinyl, phenothiazinyl, furazanyl, benzodioxolyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, tetrahydrofuranyl, tetrahydropyranyl, piperidinyl, piperidyl, piperazinyl, imidazolidinyl, morpholino, morpholinyl, 1-oxaspiro(4.5) dec-2-yl, pyrrolidinyl, 2-oxo-pyrrolidinyl, sugar moieties (i.e. glucose, pentose, hexose, ribose, fructose, which may also be substituted) optionally substituted by alkyl or as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1) heptanyl, 7-oxabicyclo(2.2.1)heptanyl, 8-azabicyclo(3.2.1) octanyl.

The heterocycle is preferably selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl.

More preferably the heterocycle is selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl, and especially from 2- and 3-thienyl, optionally substituted by one or more halogen, acyl such as formyl, cyano and/or lower alkyl, such as methyl.

In the above definitions it is to be understood that when a substituent such as $R^1$, $R^2$, $R^3$, $R^4$, $R^5$, $R^7$, $R^8$, $R^9$, $R^{10}$ is attached to the rest of the molecule via a heteroatom or a carbonyl, a straight- or branched chain, C1-12-, preferably C1-4-alkylene or C2-12, preferably C2-4-alkenylene or -alkynylene bridge may optionally be interposed between the heteroatom or the carbonyl and the point of attachment to the rest of the molecule.

The term "R substituent" refers to $R^1$, $R^2$, $R^3$, $R^4$ or $R^5$, independently.

According to a preferred embodiment, a compound of formula I is as defined above wherein n represents 0. The compound is a 6-ring structure (2-thioxo- or 2-oxo-piperidinyl derivative) wherein $R^1$ is not existent since n=0, and is depicted by the formula (I-A).

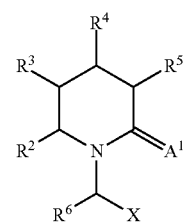

[I-A]

According to a following embodiment, the compound of formula I is as defined above wherein n represents 1. The compound is a 7-ring structure (2-thioxo- or 2-oxo-azepanyl derivative) wherein $R^1$ is existent since n=1 and depicted by the formula (I-B).

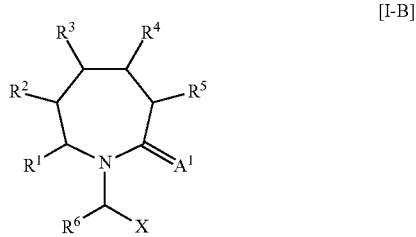

According to a more preferred embodiment, said compound is as defined above wherein n=0, $R^3$ and/or $R^4$ are different from hydrogen and $R^2$ and $R^5$ represent hydrogen.

According to another more preferred embodiment, said compound is as defined above wherein n=1, $R^2$, $R^3$ and/or $R^4$ are different from hydrogen and wherein $R^1$ and $R^5$ represent hydrogen.

According to a yet more preferred embodiment, said compound is as defined above wherein only one R substituent chosen from $R^3$ or $R^4$ when n=0 or from $R^2$, $R^3$ or $R^4$ when n=1, is different from hydrogen and the remaining R substituent(s) is/are hydrogen. We hereby refer to a monosubstituted 2-thioxo- or 2-oxo-piperidinyl or 2-thioxo- or 2-oxo-azepanyl derivatives.

According to another preferred embodiment, compounds of formula I are as defined above wherein $A^1$ represents an oxygen atom. We hereby refer to 2-oxo-piperidinyl or 2-oxo-azepanyl derivatives.

According to another preferred embodiment, compounds of formula I are as defined above wherein X is $CONR^7R^8$, especially $CONH_2$. We hereby refer to amido derivatives of 2-oxo (or thioxo)-piperidinyl or 2-oxo (or thioxo)-azepanyl.

According to another preferred embodiment, compounds of formula I are as defined above wherein $R^6$ represents hydrogen, C1-4 alkyl, or a $CH_2$—$R^{6a}$ group wherein $R^{6a}$ represents a heterocycle. Most preferably $R^6$ is a C1-4 alkyl, especially ethyl. When $R^6$ is ethyl we refer to 2-(2-oxo (or thioxo)-1-piperidinyl) butanamide or 2-(2-oxo (or thioxo)-1-azepanyl) butanamide derivatives.

According to another preferred embodiment, compounds of formula I are as defined above wherein the carbon atom to which $R^6$ is attached is of the S configuration. In case where $R^6$ is ethyl, A is oxygen and X is $CONR^7R^8$ we refer then to (2S)-2-(2-oxo-1-piperidinyl) butanamide or (2S)-2-(2-oxo-1-azepanyl) butanamide derivatives.

According to a preferred embodiment, the compound is as defined above wherein $R^2$ when n=1, $R^3$ and $R^4$ are the same or different and each is independently hydrogen, halogen, nitro, nitrooxy, cyano, carboxy, amido, sulfonic acid, sulfonamide, alkyl, alkenyl, alkynyl, ester, ether, aryl, heterocycle, acyl derivative, sulfonyl derivative or sulfinyl derivative;

$R^1$ when existent, $R^2$ when n=0 and $R^5$ are hydrogen;

$R^6$ is hydrogen, alkyl, aryl or —$CH_2$—$R^{6a}$ wherein $R^{6a}$ is aryl, heterocycle, halogen, hydroxy, amino, nitro or cyano;

According to this preferred embodiment, generally such that when $R^6$ is benzyl, X is —$COOCH_3$ and n=1, $R^2$ is different from methyl when $R^3$ and $R^4$ are both hydrogen and $R^4$ is different from methyl when $R^2$ and $R^3$ are both hydrogen.

According to another preferred embodiment, the compound is as defined above wherein $R^2$ when n=1, $R^3$ and $R^4$ are the same or different and each is independently hydrogen; cyano; carboxy; amido;

C1-12 alkyl, each optionally substituted by one or more substituents selected from hydroxy, halogen, cyano, thiocyanato, alkoxy, azido, alkyltio, cycloalkyl, acyl, aryl and heterocycle;

C2-12 alkenyl, each optionally substituted by one or more substituents selected from halogen, cyano, thiocyanato, azido, alkylthio, alkyl, aryl and acyl;

C2-12 alkynyl, each optionally substituted by one or more substituents selected from halogen, cyano, thiocyanato, azido, alkylthio, alkyl, aryl and acyl; acyl derivative of formula —CO—$R^{11}$, wherein $R^{11}$ is selected from C1-12 alkyl, C2-12 alkenyl, C2-12 alkynyl, heterocycle and aryl;

ester of formula —CO—O—$R^{11}$ wherein $R^{11}$ is selected from C1-12 alkyl, C2-12 alkenyl, C2-12 alkynyl and aryl;

heterocycle selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl;

aryl, each optionally substituted by one or more substituents selected from C1-6 alkyl, C1-6 haloalkyl, C1-6 alkoxy, C1-6 alkylthio, amino, azido, sulfonyl, aryl and nitro.

According to another preferred embodiment, the compound is as defined above, wherein $R^2$ when n=1, $R^3$ and $R^4$ are the same or different and each is independently hydrogen;

C1-7 alkyl, each optionally substituted by one or more substituents selected from hydroxy, halogen, cyano, thiocyanato, alkoxy, azido, alkyltio, cyclopropyl, acyl and phenyl;

C2-6 alkenyl, each optionally substituted by one or more substituents selected from halogen, cyano, thiocyanato, azido, alkylthio, cycloalkyl, phenyl and acyl;

C2-6 alkynyl, each optionally substituted by one or more substituents selected from halogen, cyano, thiocyanato, azido, alkylthio, cycloalkyl, phenyl and acyl; heterocycle selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl;

phenyl, each optionally substituted by one or more substituents selected from C1-6 alkyl, halogen substituted alkyl, halogen, alkoxy, amino, azido, sulfonyl, phenyl and nitro.

According to another preferred embodiment, the compound is as defined above wherein at least one of the R substituents chosen from the group $R^2$, $R^3$ and $R^4$ when n=1 or from the group $R^3$ and $R^4$ when n=0, represents independently C1-4-alkyl or C3-7-cycloalkyl, optionally substituted by one or more halogen, hydroxy, lower alkyl and/or azido.

According to another preferred embodiment, the compound is as defined above wherein at least one of the R substituents chosen from the group $R^2$, $R^3$ and $R^4$ when n=1 or from the group $R^3$ and $R^4$ when n=0, represents independently vinyl, optionally substituted by one or more halogen or/and lower alkyl.

According to another preferred embodiment, the compound is as defined above wherein at least one of the R substituents chosen from the group $R^2$, $R^3$ and $R^4$ when n=1 or from the group $R^3$ and $R^4$ when n=0, represents independently ethynyl, propynyl or butynyl, optionally substituted by one or more halogen and/or lower alkyl.

According to another preferred embodiment, the compound is as defined above wherein at least one of the R substituents chosen from the group $R^2$, $R^3$ and $R^4$ when n=1 or from the group $R^3$ and $R^4$ when n=0, represents independently phenyl, optionally substituted by one or more halogen, lower alkyl, azido and/or nitro.

According to another preferred embodiment, the compound is as defined above wherein at least one of the R substituents chosen from the group $R^2$, $R^3$ and $R^4$ when n=1 or from the group $R^3$ and $R^4$ when n=0, represents independently 2- or 3-thienyl, optionally substituted by one or more halogen, acyl, cyano or/and lower alkyl.

According to a particular preferred embodiment, the compound is as defined above wherein at least one of the R substituents chosen from the group $R^3$, $R^4$ and $R^2$ when n=1 or from the group $R^3$ and $R^4$ when n=0, is hydroxymethyl, propyl, butyl, 3,3,3-trifluoropropyl, 2,2,2-trifluoroethyl, cyclopropylmethyl, iodomethyl, azidomethyl, 2-thienyl, 3-thienyl, phenyl, 3-chlorophenyl, 3-azidophenyl, 2,2-difluorovinyl, 2,2-dibromovinyl, 2,2-dichlorovinyl, 2-ethynyl, 5-methyl-2-thienyl, 5-formyl-2-ethynyl, 5-cyano-2-thienyl, 3-bromo-2-thienyl, 4-methyl-2-thienyl, 3,3,3-trifluoro-1-propynyl, 1-propynyl, cyclopropylethynyl, 3-methyl-1-butynyl, 1-butynyl, 2,2-difluoropropyl, 2-chloro-2,2-difluoroethyl, 2-bromo-2,2-difluoroethyl and 2-iodo-2,2-difluoroethyl.

According to yet another preferred embodiment, the compound is as defined above wherein $R^1$, $R^2$, $R^4$ and $R^5$ are hydrogen.

According to even another preferred embodiment, the compound is as defined above wherein $R^1$, $R^2$, $R^3$ and $R^5$ are hydrogen.

According to even another preferred embodiment, the compound is as defined above wherein n=1 and R', $R^3$, $R^4$ and $R^5$ are hydrogen.

In all the above-mentioned scopes when the carbon atom to which $R^6$ is attached is asymmetric it is preferably in the"S"-configuration.

Representative compounds useful in the methods and compositions of this invention as defined above are selected from the group consisting of
2-[5-(hydroxymethyl)-2-oxo-1-piperidinyl]butanamide,
2-(2-oxo-5-propyl-1-piperidinyl)butanamide,
2-[2-oxo-5-(3,3,3-trifluoropropyl)-1-piperidinyl]butanamide,
2-[5-(cyclopropylmethyl)-2-oxo-1-piperidinyl]butanamide,
2-[5-(iodomethyl)-2-oxo-1-piperidinyl]butanamide,
2-[5-(azidomethyl)-2-oxo-1-piperidinyl]butanamide,
2-(2-oxo-5-phenyl-1-piperidinyl)butanamide,
2-[2-oxo-5-(2-thienyl)-1-piperidinyl]butanamide,
2-[2-oxo-5-(3-thienyl)-1-piperidinyl]butanamide,
2-[5-(3-chlorophenyl)-2-oxo-1-piperidinyl]butanamide,
2-[5-(3-azidophenyl)-2-oxo-1-piperidinyl]butanamide,
2-[5-(2,2-difluorovinyl)-2-oxo-1-piperidinyl]butanamide,
2-[5-(2,2-dibromovinyl)-2-oxo-1-piperidinyl]butanamide,
2-[5-(2,2-dichlorovinyl)-2-oxo-1-piperidinyl]butanamide,
2-(5-ethynyl-2-oxo-1-piperidinyl)butanamide,
2[5-(5-methyl-2-thienyl)-2-oxo-1-piperidinyl]butanamide,
2-[5-(5-formyl-2-thienyl)-2-oxo-1-piperidinyl]butanamide,
2-[5-(5-cyano-2-thienyl)-2-oxo-1-piperidinyl]butanamide,
2-[5-(3-bromo-2-thienyl)-2-oxo-1-piperidinyl]butanamide,
2-[5-(4-methyl-2-thienyl)-2-oxo-1-piperidinyl]butanamide,
2-[2-oxo-5-(3,3,3-trifluoro-1-propynyl)-1-piperidinyl]butanamide,
2-[2-oxo-5-(1-propynyl)-1-piperidinyl]butanamide,
2-[5-(cyclopropylethynyl)-2-oxo-1-piperidinyl]butanamide,
2-[5-(3-methyl-1-butynyl)-2-oxo-1-piperidinyl]butanamide,
2-[5-(1-butynyl)-2-oxo-1-piperidinyl]butanamide,
2-[5-(2,2-difluoropropyl)-2-oxo-1-piperidinyl]butanamide,
2-[5-(2-chloro-2,2-difluoroethyl)-2-oxo-1-piperidinyl]butanamide,
2-[5-(2-bromo-2,2-difluoroethyl)-2-oxo-1-piperidinyl]butanamide,
2-[4-(hydroxymethyl)-2-oxo-1-piperidinyl]butanamide,
2-(2-oxo-4-propyl-1-piperidinyl)butanamide,
2-[2-oxo-4-(3,3,3trifluoropropyl)-1-piperidinyl]butanamide,
2-[4-(cyclopropylmethyl)-2-oxo-1-piperidinyl]butanamide,
2-[4-(iodomethyl)-2-oxo-1-piperidinyl]butanamide,
2-[4-(azidomethyl)-2-oxo-1-piperidinyl]butanamide,
2-(2-oxo-4-phenyl-1-piperidinyl)butanamide,
2[2-oxo-4-(2-thienyl)-1-piperidinyl]butanamide,
2-[2-oxo-4-(3-thienyl)-1-piperidinyl]butanamide,
2-[4-(3-chlorophenyl)-2-oxo-1-piperidinyl]butanamide,
2-[4-(3-azidophenyl)-2-oxo-1-piperidinyl]butanamide,
2-[4-(2,2-difluorovinyl)-2-oxo-1-piperidinyl]butanamide,
2-[4-(2,2-dibromovinyl)-2-oxo-1-piperidinyl]butanamide,
2-[4-(2,2-dichlorovinyl)-2-oxo-1-piperidinyl]butanamide,
2-(4-ethynyl-2-oxo-1-piperidinyl)butanamide,
2-[4-(5-methyl-2-thienyl)-2-oxo-1-piperidinyl]butanamide,
2-[4-(5-formyl-2-thienyl)-2-oxo-1-piperidinyl]butanamide,
2-[4-(5-cyano-2-thienyl)-2-oxo-1-piperidinyl]butanamide,
2-[4-(3-bromo-2-thienyl)-2-oxo-1-piperidinyl]butanamide,
2-[4-(4-methyl-2-thienyl)-2-oxo-1-piperidinyl]butanamide,
2-[2-oxo-4-(3,3,3-trifluoro-1-propynyl)-1-piperidinyl]butanamide,
2-[2-oxo-4-(1-propynyl)-1-piperidinyl]butanamide,
2-[4-(cyclopropylethynyl)-2-oxo-1-piperidinyl]butanamide,
2-[4-(3-methyl-1-butynyl)-2-oxo-1-piperidinyl]butanamide,
2-[4-(1-butynyl)-2-oxo-1-piperidinyl]butanamide,
2-[4-(2,2-difluoropropyl)-2-oxo-1-piperidinyl]butanamide,
2-[4-(2-chloro-2,2-difluoroethyl)-2-oxo-1-piperidinyl]butanamide,
2-[4-(2-bromo-2,2-difluoroethyl)-2-oxo-1-piperidinyl]butanamide,
2[4-(2,2,2-trifluoroethyl)-2-oxo-1-piperidinyl]butanamide,
2-[5-(hydroxymethyl)-2-oxo-1-azepanyl]butanamide,
2-(2-oxo-5-propyl-1-azepanyl)butanamide,
2-[2-oxo-5-(3,3,3-trifluoropropyl)-1-azepanyl]butanamide,
2-[5-(cyclopropylmethyl)-2-oxo-1-azepanyl]butanamide,
2-[5-(iodomethyl)-2-oxo-1-azepanyl]butanamide,
2-[5-(azidomethyl)-2-oxo-1-azepanyl]butanamide,
2-(2-oxo-5-phenyl-1-azepanyl)butanamide,
2-[2-oxo-5-(2-thienyl)-1-azepanyl]butanamide,
2-[2-oxo-5-(3-thienyl)-1-azepanyl]butanamide,
2-[5-(3-chlorophenyl)-2-oxo-1-azepanyl]butanamide,
2-[5-(3-azidophenyl)-2-oxo-1-azepanyl]butanamide,
2-[5-(2,2-difluorovinyl)-2-oxo-1-azepanyl]butanamide,
2-[5-(2,2-dibromovinyl)-2-oxo-1-azepanyl]butanamide,
2-[5-(2,2-dichlorovinyl)-2-oxo-1-azepanyl]butanamide,
2-(5-ethynyl-2-oxo-1-azepanyl)butanamide,
2-[5-(5-methyl-2-thienyl)-2-oxo-1-azepanyl]butanamide,
2-[5-(5-formyl-2-thienyl)-2-oxo-1-azepanyl]butanamide,
2-[5-(5-cyano-2-thienyl)-2-oxo-1-azepanyl]butanamide,
2-[5-(3-bromo-2-thienyl)-2-oxo-1-azepanyl]butanamide,
2-[5-(4-methyl-2-thienyl)-2-oxo-1-azepanyl]butanamide,
2-[2-oxo-5-(3,3,3-trifluoro-1-propynyl)-1-azepanyl]butanamide,
2-[2-oxo-5-(1-propynyl)-1-azepanyl]butanamide,
2-[5-(cyclopropylethynyl)-2-oxo-1-azepanyl]butanamide,
2-[5-(3-methyl-1-butynyl)-2-oxo-1-azepanyl]butanamide,
2-[5-(1-butynyl)-2-oxo-1-azepanyl]butanamide,
2-[5-(2,2-difluoropropyl)-2-oxo-1-azepanyl]butanamide, 2-[5-(2-chloro-2,2-difluoroethyl)-2-oxo-1-azepanyl]butanamide,
2-[5-(2-bromo-2,2-difluoroethyl)-2-oxo-1-azepanyl]butanamide,
2-[5-(2,2,2-trifluoroethyl)-2-oxo-1-azepanyl]butanamide,
2-[6-(hydroxymethyl)-2-oxo-1-azepanyl]butanamide,
2-(2-oxo-6-propyl-1-azepanyl)butanamide,
2-[2-oxo-6-(3,3,3-trifluoropropyl)-1-azepanyl]butanamide,
2-[6-(cyclopropylmethyl)-2-oxo-1-azepanyl]butanamide,
2-[6-(iodomethyl)-2-oxo-1-azepanyl]butanamide,
2-[6-(azidomethyl)-2-oxo-1-azepanyl]butanamide,
2-(2-oxo-6-phenyl-1-azepanyl)butanamide,
2-[2-oxo-6-(2-thienyl)-1-azepanyl]butanamide,
2-[2-oxo-6-(3-thienyl)-1-azepanyl]butanamide,
2-[6-(3-chlorophenyl)-2-oxo-1-azepanyl]butanamide,
2-[6-(3-azidophenyl)-2-oxo-1-azepanyl]butanamide,
2-[6-(2,2-difluorovinyl)-2-oxo-1-azepanyl]butanamide,
2-[6-(2,2-dibromovinyl)-2-oxo-1-azepanyl]butanamide,
2-[6-(2,2-dichlorovinyl)-2-oxo-1-azepanyl]butanamide,
2-(6-ethynyl-2-oxo-1-azepanyl)butanamide,
2-[6-(5-methyl-2-thienyl)-2-oxo-1-azepanyl]butanamide,
2-[6-(5-formyl-2-thienyl)-2-oxo-1-azepanyl]butanamide,
2-[6-(5-cyano-2-thienyl)-2-oxo-1-azepanyl]butanamide,
2-[6-(3-bromo-2-thienyl)-2-oxo-1-azepanyl]butanamide,
2-[6-(4-methyl-2-thienyl)-2-oxo-1-azepanyl]butanamide,
2-[2-oxo-6-(3,3,3-trifluoro-1-propynyl)-1-azepanyl]butanamide,
2-[2-oxo-6-(1-propynyl)-1-azepanyl]butanamide,
2-[6-(cyclopropylethynyl)-2-oxo-1-azepanyl]butanamide,
2-[6-(3-methyl-1-butynyl)-2-oxo-1-azepanyl]butanamide,
2-[6-(1-butynyl)-2-oxo-1-azepanyl]butanamide,
2-[6-(2,2-difluoropropyl)-2-oxo-1-azepanyl]butanamide,
2-[6-(2-chloro-2,2-difluoroethyl)-2-oxo-1-azepanyl]butanamide,
2-[6-(2-bromo-2,2-difluoroethyl)-2-oxo-1-azepanyl]butanamide,
2-[6-(2,2,2-trifluoroethyl)-2-oxo-1-azepanyl]butanamide,
2-[4-(hydroxymethyl)-2-oxo-1-azepanyl]butanamide,
2-(2-oxo-4-propyl-1-azepanyl)butanamide,
2-[2-oxo-4-(3,3,3-trifluoropropyl)-1-azepanyl]butanamide,
2-[4-(cyclopropylmethyl)-2-oxo-1-azepanyl]butanamide,
2-[4-(iodomethyl)-2-oxo-1-azepanyl]butanamide,
2-[4-(azidomethyl)-2-oxo-1-azepanyl]butanamide,
2-(2-oxo-4-phenyl-1-azepanyl)butanamide,
2-[2-oxo-4-(2-thienyl)-1-azepanyl]butanamide,
2-[2-oxo-4-(3-thienyl)-1-azepanyl]butanamide,
2-[4-(3-chlorophenyl)-2-oxo-1-azepanyl]butanamide,
2-[4-(3-azidophenyl)-2-oxo-1-azepanyl]butanamide,
2-[4-(2,2-difluorovinyl)-2-oxo-1-azepanyl]butanamide,
2-[4-(2,2-dibromovinyl)-2-oxo-1-azepanyl]butanamide,
2-[4-(2,2-dichlorovinyl)-2-oxo-1-azepanyl]butanamide,
2-(4-ethynyl-2-oxo-1-azepanyl)butanamide,
2-[4-(5-methyl-2-thienyl)-2-oxo-1-azepanyl]butanamide,
2-[4-(5-formyl-2-thienyl)-2-oxo-1-azepanyl]butanamide,
2-[4-(5-cyano-2-thienyl)-2-oxo-1-azepanyl]butanamide,
2-[4-(3-bromo-2-thienyl)-2-oxo-1-azepanyl]butanamide,
2-[4-(4-methyl-2-thienyl)-2-oxo-1-azepanyl]butanamide,
2-[2-oxo-4-(3,3,3-trifluoro-1-propynyl)-1-azepanyl]butanamide,
2-[2-oxo-4-(1-propynyl)-1-azepanyl]butanamide,
2-[4-(cyclopropylethynyl)-2-oxo-1-azepanyl]butanamide,
2-[4-(3-methyl-1-butynyl)-2-oxo-1-azepanyl]butanamide,
2-[4-(1-butynyl)-2-oxo-1-azepanyl]butanamide,
2-[4-(2,2-difluoropropyl)-2-oxo-1-azepanyl]butanamide,
2-[4-(2-chloro-2,2-difluoroethyl)-2-oxo-1-azepanyl]butanamide,
2-[4-(2-bromo-2,2-difluoroethyl)-2-oxo-1-azepanyl]butanamide,
2-[4-(2,2,2-tritluoroethyl)-2-oxo-1-azepanyl]butanamide.

In some embodiments, compounds useful in the methods and compositions of this invention are selected from the group consisting of:
(2S)-2-[5-(iodomethyl)-2-oxo-1-piperidinyl]butanamide,
(2S)-2-[5-(azidomethyl)-2-oxo-1-piperidinyl]butanamide,
2-(2-oxo-5-phenyl-1-piperidinyl]butanamide,
(2S)-2-[4-(iodomethyl)-2-oxo-1-piperidinyl]butanamide,
2-[5-(iodomethyl)-2-oxo-1-azepanyl]butanamide.

iii) International Patent Application WO 2004/087658:
A compound having the formula I or a pharmaceutically acceptable salt thereof or stereoisomeric forms thereof,

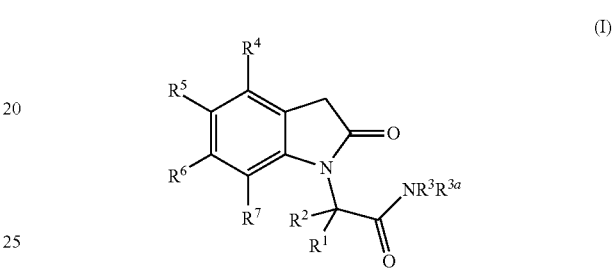

(I)

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$, $R^{3a}$ is hydrogen, C1-20-alkyl or a group of formula:

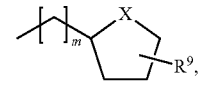

or $NR^3R^{3a}$ is a group of formula

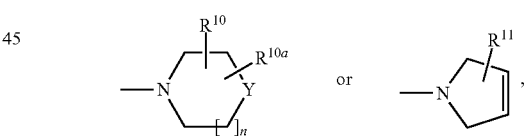

$R^4$ is hydrogen,
$R^5$ is hydrogen; nitro; halogen; azido; cyano; —S—C1-4-alkyl; —SO—C1-4-alkyl; —SO$_2$—C1-4-alkyl; —SONH$_2$; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —CR$^{12}$R$^{13}$—, —NR$^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl,
or $R^{10}$ and $R^{10a}$ together form a C3-6-alkylene,
$R^{12}$ is hydrogen, C1-4-alkyl, halogen or hydroxy, $R^{13}$ is hydrogen,
or $CR^{12}R^{13}$ is dioxolanyl,
$R^{14}$ is aryl, heterocycle or a group of formula —V—$R^{15}$,
V is $C_{1-12}$-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

In another aspect, the compound has the formula I or a pharmaceutically acceptable salt thereof or stereoisomeric forms thereof,

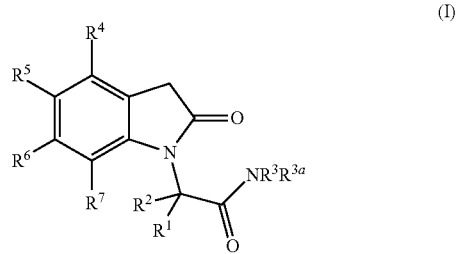

(I)

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$,
$R^{3a}$ is hydrogen, C1-20-alkyl or a group of formula:

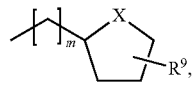

or $NR^3R^{3a}$ is a group of formula

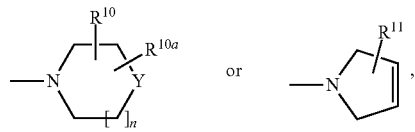

$R^4$ is hydrogen,
$R^5$ is hydrogen; nitro; halogen; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —$CR^{12}R^{13}$—, —$NR^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl,
or $R^{10}$ and $R^{10a}$ together form a C3-6-alkylene,
$R^{12}$ is hydrogen, C1-4-alkyl, halogen or hydroxy,
$R^{13}$ is hydrogen,
or $CR^{12}R^{13}$ is dioxolanyl,
$R^{14}$ is aryl, heterocycle or a group of formula —V—$R^{15}$,
V is C1-12-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

The term "alkyl", as used herein, is defined as including saturated, monovalent hydrocarbon radicals having straight, branched or cyclic moieties or combinations thereof and containing 1-20 carbon atoms, preferably 1-6 carbon atoms and more preferably 1-4 carbon atoms for non-cyclic alkyl and 3-8 carbon atoms for cycloalkyl. Alliyl moieties may optionally be substituted by 1 to 5 substituents independently selected from halogen, hydroxy, alkoxy, alkoxycarbonyl, ester or alkylamino. Preferred alkyl groups are methyl, ethyl, n-propyl, isopropyl, trifluoromethyl, n-butyl, 2-fluoroethyl, 3-hydroxypropyl, 3-hydroxy-2,2-dimethylpropyl, 1-(hydroxymethyl) propyl, 3,3,3-trifluoro-2-hydroxypropyl, 3-ethoxypropyl, 2-ethoxy-2-oxoethyl and 3-(dimethylamino) propyl.

The term "cycloalkyl", as used herein, refers to a monovalent group of 3 to 18 carbon atoms, preferably 4-8 carbon atoms, derived from a saturated cyclic or polycyclic hydrocarbon which may be substituted by any suitable group including but not limited to one or more moieties selected from groups as described above for the alkyl groups. Preferred cycloalkyl group is cycloheptyl.

The term "alkylene", as used herein, represents a divalent alkyl group, having straight or branched moieties, containing 1-12 carbon atoms, preferably 1-6 carbon atoms, and being optionally substituted with any suitable group, including but not limited to one or more moieties selected from groups as described above for the alkyl groups. Preferred alkylene groups are methylene, ethylene, hydroxyethylene, trimethylene or propylene.

The term "cycloalkenyl", as used herein, is defined as a cyclic unsaturated hydrocarbon radical having at least one double bond, containing 4-20 carbon atoms, preferably 5-8 carbon atoms, and being optionally substituted with any suitable group, including but not limited to one or more moieties selected from groups as described above for the alkyl groups. Preferred cycloalkenyl group is 6-(hydroxymethyl)cyclohex-3-en-1-yl.

The term "aryl", as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, nitro, C1-6-alkyl, C1-6-alkoxy, C1-6-alkylsulfonyl, trifluoromethylthio or pyridinylalkyl. Aryl radicals are preferably phenyl radicals. Preferred aryl groups are phenyl, 3-hydroxyphenyl, 3-fluorophenyl, 3-methylphenyl, 4-methylphenyl, 4-hydroxyphenyl, 4-hydroxy-3-methoxyphenyl, 3-(2-pyridin-2-ylethyl)phenyl, 3,4-dimethylphenyl, 4-tert-butylphenyl, 4-methylsulfonylphenyl, 2-nitrophenyl, 2-chloro-6-fluorophenyl, 2-[(trifluoromethyl)thio]phenyl, 2-chlorophenyl or 4-bromophenyl.

The term "halogen", as used herein, includes an atom of Cl, Br, F, I.

The term "nitro", as used herein, represents a group of the formula —$NO_2$.

The term "hydroxy", as used herein, represents a group of the formula —OH.

The term "alkoxy", as used herein, represents a group of formula —OR$^b$ wherein R$^b$ is an alkyl group, as defined above.

The term "ester", as used herein, represents a group of formula —COOR$^C$ wherein R$^c$ is an alkyl group or an aryl group, as defined above.

The term "alkoxycarbonyl", as used herein, represents a group of formula —COOR$^d$ wherein R$^d$ is an alkyl group, as defined above.

The term "amino", as used herein, represents a group of the formula —NH$_2$.

The term "alkylamino", as used herein, represents a group of formula —NHR$^e$ or —NR$^e$R$^f$ wherein R$^e$ and R$^f$ are alkyl group as defined above.

The term alkylsulfonyl, as used herein is defined as representing a group of formula —SO$_2$—R$^g$, wherein R$^g$ is C1-4-alkyl.

The term "heterocycle", as used herein is defined as including an aromatic or non aromatic cycloalkyl or cycloalkenyl moiety as defined above, having at least one O, S and/or N atom interrupting the carbocyclic ring structure and optionally, one of the carbon of the carbocyclic ring structure may be replaced by a carbonyl.

Non-limiting examples of aromatic heterocycles are pyrazolyl, furyl, imidazolyl, triazolyl, oxazolyl, pyridinyl, pyrrolyl, thienyl, isothiazolyl, benzimidazolyl, tetrazolyl, isooxazolyl, oxazolyl, thiazolyl, 1,2,4-thiadiazolyl, oxadiazole, pyridazinyl, pyrimidinyl, pyrazinyl, isoindolyl, triazolopyridinyl, imidazolopyridinyl, pyrrolopyrimidinyl, pyrazolopyrimidinyl, quinazolinyl, quinolizinyl, naphthyridinyl, quinolyl, isoquinolyl, isobenzofuranyl, benzothienyl, indolyl, indolizinyl, purinyl, carbazolyl, thieno (2,3-b) furanyl, thianthrenyl, benzothiazolyl, benzoxazolyl, cinnolinyl, quinoxalinyl, phenothiazinyl, isochromanyl and xanthenyl, optionally substituted by 1 to 5 substituents independently selected from halogen, hydroxy, thiol, amino, nitro, cyano, azido, C1-6-alkoxy, C1-6-alkylthio, C1-6-alkyl, C1-6-haloalkyl, formyl or ester. More preferred aromatic heterocycles are pyrazolyl, furyl, imidazolyl, triazolyl, oxazolyl and pyridinyl.

Non-limiting examples of non aromatic heterocycles are tetrahydrofuranyl, piperidinyl, piperidyl, piperazinyl, imidazolidinyl, morpholinyl, thiomorpholinyl, pyrrolidinyl, thiazolidinyl, indolinyl, tetrahydrobenzazocinyl, dihydroisochromenyl, tetrahydropyranyl, oxooctahydroquinolinyl, dioxolanyl, 1-oxaspiro(4.5) dec-2-yl, pyrrolidinyl, 2-oxopyrrolidinyl, 8-thiabicyclo[3.2.1]cyclooctanyl, 1,4-dithiepanyl, tetrahydro-2H-thiopyranyl, azepanyl and azocanyl, optionally substituted by 1 to 5 substituents independently selected from halogen, hydroxy, thiol, amino, nitro, cyano, azido, C1-6-alkoxy, C1-6-alkylthio, C1-6-alkyl, C1-6-haloalkyl, formyl or ester. More preferred non aromatic heterocycles are tetrahydrofuranyl, piperidinyl, piperidyl, piperazinyl, imidazolidinyl, morpholinyl, thiomorpholinyl, pyrrolidinyl, thiazolidinyl, indolinyl, tetrahydro-1-benzazocin-1 (2H)-yl, 3,4-dihydro-1H-isochromen-1-yl, tetrahydropyranyl, oxooctahydroquinolinyl and dioxolanyl. The term-"heterocycle" also includes bicyclic, tricyclic and tetracyclic, spiro groups in which any of the above heterocyclic rings is fused to one or two rings independently selected from an aryl ring, a cycloalkyl ring, a cycloalkenyl ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl and 8-azabicyclo(3.2.1)octanyl.

The term "pyridinylalkyl", as used herein, represents a group of formula —R$^h$-pyridinyl in which R$^h$ is C1-4-alkylene.

The term "azido" as used herein, represents a group of the formula —N$_3$.

The term "cyano" as used herein, represents a group of the formula —CN.

Generally, R$^2$ is hydrogen or C1-4-alkyl.

Preferably, R$^2$ is hydrogen, methyl or ethyl. More preferably, R$^2$ is hydrogen or methyl.

Generally, R$^3$ is hydrogen; C1-6-alkyl unsubstituted or substituted by 1 to 5 substituents selected from halogen, hydroxy, alkoxy, alkoxycarbonyl or alkylamino; C5-7-cycloalkyl; (hydroxymethyl) cyclohexenyl; phenyl unsubstituted or substituted by 1 to 5 substituents selected from halogen, C1-4-alkyl, hydroxy, methoxy, nitro, methylsulfonyl, trifluoromethylthio or pyridinylalkyl; pyridinyl unsubstituted or substituted by methoxy; triazolyl; C1-4-alkoxy; or a group of formula —W—R$^8$ wherein:

Generally, W is C1-4-alkylene unsubstituted or substituted by halogen, hydroxy, C1-4-alkyl or alkoxy; —NH—; or —NHC(=O)—; and R$^8$ is phenyl unsubstituted or substituted by 1 to 5 substituents selected from halogen, C1-4-alkyl, hydroxy, methoxy, nitro, methylsulfonyl or trifluoromethylthio; furyl unsubstituted or substituted by methyl; pyrazolyl; pyridinyl; morpholinyl; tetrahydrobenzazocinyl; piperidinyl unsubstituted or substituted by methyl; dihydroisochromenyl or dihydroimidazolyl.

Preferably, R$^3$ is hydrogen, n-butyl, cycloheptyl, 2-fluoroethyl, 3-hydroxypropyl, 3-hydroxy-2,2-dimethylpropyl, 1-(hydroxymethyl) propyl, 3,3,3-trifluoro-2-hydroxypropyl, 3-ethoxypropyl, 2-ethoxy-2-oxoethyl, 3-(dimethylamino) propyl, 6-(hydroxymethyl)cyclohex-3-en-1-yl, 3-hydroxyphenyl, 3-fluorophenyl, 3-(2-pyridin-2-ylethyl)phenyl, 3,4-dimethylphenyl, 4-tert-butylphenyl, benzyl, 4-hydroxy-3-methoxybenzyl, 4-methylsulfonylbenzyl, 2-nitrobenzyl, 2-chloro-6-fluorobenzyl, 2-[(trifluoromethyl)thio]benzyl, 2-hydroxy-2-phenylethyl, 2-(3,4-dimethoxyphenyl)ethyl, 2-(2-chlorophenyl)ethyl, 2-(4-methylphenyl)ethyl, (4-bromophenyl)amino, pyridin-3-yl, 6-methoxypyridin-3-yl, 4H-1,2,4-triazol-3-yl, pyridin-4-ylmethyl, (5-methyl-2-furyl)methyl, 3-(1H-pyrazol-1-yl)propyl, 2-morpholin-4-ylethyl, 2-((3,4,5,6-tetrahydro-1-benzazocin-1(2H)-yl) propyl, 2-(2-methylpiperidin-1-yl)ethyl, 3,4-dihydro-1H-isochromen-1-ylmethyl, methoxy, (4-pyridinylcarbonyl) amino or 4,5-dihydro-1H-imidazol-2-ylamino. More preferably, R$^3$ is hydrogen.

Generally, R$^{3a}$ is hydrogen, C1-4-alkyl or a group of formula

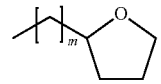

wherein m is 1 to 4.

Preferably, R$^{3a}$ is hydrogen, methyl or tetrahydrofuran-2-ylmethyl. More preferably, R$^{3a}$ is hydrogen.

In another embodiment, NR$^3$R$^{3a}$ is piperidinyl unsubstituted or substituted by hydroxy; thiomorpholinyl; thiazolidinyl unsubstituted or substituted by C1-4-alkoxycarbonyl; 2,5-dihydro-1H-pyrrol-1-yl; 1,4-dioxa-8-azaspiro[4.5]dec-8-yl; 4-oxooctahydro-1(2H)-quinolinyl; or a group of formula

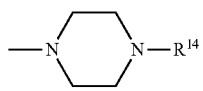

wherein R[14] is pyridinyl; phenyl unsubstituted or substituted by halogen, hydroxy, C1-4-alkyl; or a group of formula —V—R[15] wherein V is unsubstituted C1-4-alkylene and R[15] is phenyl or morpholinyl.

In a preferred embodiment, NR[3]R[3a] is 4-pyridin-2-ylpiperazin-1-yl, 4-(3-methylphenyl) piperazin-1-yl, 4-(4-hydroxyphenyl) piperazin-1-yl, 4-(2-phenylethyl) piperazin-1-yl, 4-(2-morpholin-4-ylethyl) piperazin-1-yl, 3-hydroxypiperidin-1-yl, thiomorpholin-4-yl, 4-methoxycarbonyl-1,3-thiazolidin-3-yl, 2,5-dihydro-1H-pyrrol-1-yl, 1,4-dioxa-8-azaspiro[4.5]dec-8-yl or 4-oxooctahydro-1(2H)-quinolinyl.

Generally, R[5] is hydrogen, nitro, halogen, C1-4-alkyl, unsubstituted or substituted by halogen, or C1-4-alkoxy unsubstituted or substituted by halogen.

Preferably, R[5] is hydrogen, methyl, ethyl, trifluoromethyl, trifluoromethoxy, n-propyl, isopropyl, nitro, or halogen. More preferably, R[5] is halogen or trifluoromethyl.

Generally, R[6] is hydrogen, C1-6-alkyl or halogen.

Preferably, R[6] is hydrogen, methyl or Cl. More preferably, R[6] is hydrogen.

Generally, R[7] is hydrogen, methyl or halogen.

Preferably, R[7] is hydrogen, methyl, Br, F or Cl. More preferably, R[7] is hydrogen, Br or F.

Combinations of one or more of these preferred compound groups are especially preferred.

In a preferred embodiment, the compound has the formula I or a pharmaceutically acceptable salt thereof or stereoisomeric forms thereof,

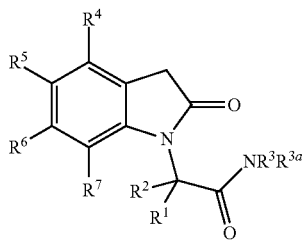

wherein R[1] is hydrogen,
R[2] is hydrogen or C1-4-alkyl,
R[3] is hydrogen; C1-6-alkyl unsubstituted or substituted by 1 to 5 substituents selected from halogen, hydroxy, alkoxy, alkoxycarbonyl or alkylamino; C5-7-cycloalkyl; (hydroxymethyl) cyclohexenyl; phenyl unsubstituted or substituted by 1 to 5 substituents selected from halogen, C1-4-alkyl, hydroxy, methoxy, nitro, methylsulfonyl, trifluoromethylthio or pyridinylalkyl; pyridinyl unsubstituted or substituted by methoxy; triazolyl; C1-4-alkoxy; or a group of formula —W—R[8],
R[3a] is hydrogen, C1-4-alkyl or a group of formula

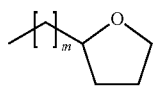

or NR[3]R[3a] is piperidinyl unsubstituted or substituted by hydroxy; thiomorpholinyl; thiazolidinyl unsubstituted or substituted by C1-4-alkoxycarbonyl; 2,5-dihydro-1H-pyrrol-1-yl; 1,4-dioxa-8-azaspiro[4.5]dec-8-yl; 4-oxooctahydro-1(2H)-quinolinyl; or a group of formula

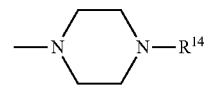

R[4] is hydrogen,
R[5] is hydrogen; nitro; halogen; C1-4-alkyl, unsubstituted or substituted by halogen; or C1-4-alkoxy unsubstituted or substituted by halogen,
R6 is hydrogen, C1-6-allyl or halogen,
R7 is hydrogen, methyl or halogen, W is C1-4-alkylene unsubstituted or substituted by halogen, hydroxy, C1-4-alkyl or alkoxy; —NH—; or —NHC(=O)—,
R8 is phenyl unsubstituted or substituted by 1 to 5 substituents selected from halogen, C1-4-alkyl, hydroxy, methoxy, nitro, methylsulfonyl or trifluoromethylthio; furyl unsubstituted or substituted by methyl; pyrazolyl; pyridinyl; morpholinyl; tetrahydrobenzazocinyl; piperidinyl unsubstituted or substituted by methyl; dihydroisochromenyl or dihydroimidazolyl,
R[14] is pyridinyl; phenyl unsubstituted or substituted by halogen, hydroxy, C1-4-alkyl; or a group of formula —V—R[15],
V is unsubstituted C1-4-alkylene,
R[15] is phenyl or morpholinyl,
m is 1 to 4,
and at least one of R[5], R[6] or R[7] is different from hydrogen when R[2] is hydrogen, R[3] is H or 2,6-diisopropylphenyl, and R[3a] is H.

In a more preferred embodiment, the compound has the formula I or a pharmaceutically acceptable salt thereof or stereoisomeric forms thereof,

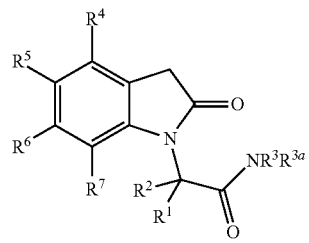

wherein
R[1] is hydrogen,
R[2] is hydrogen, methyl or ethyl,
R[3] is hydrogen, n-butyl, cycloheptyl, 2-fluoroethyl, 3-hydroxypropyl, 3-hydroxy-2,2-dimethylpropyl, 1-(hydroxymethyl) propyl, 3,3,3-trifluoro-2-hydroxypropyl, 3-ethoxypropyl, 2-ethoxy-2-oxoethyl, 3-(dimethylamino) propyl, 6-(hydroxymethyl)cyclohex-3-en-1-yl, 3-hydroxyphenyl, 3-fluorophenyl, 3-(2-pyridin-2-ylethyl)phenyl, 3,4-dimethylphenyl, 4-tert-butylphenyl, benzyl, 4-hydroxy-3-methoxybenzyl, 4-methylsulfonylbenzyl, 2-nitrobenzyl, 2-chloro-6-fluorobenzyl, 2-[(trifluoromethyl)thio]benzyl, 2-hydroxy-2-phenylethyl, 2-(3,4-dimethoxyphenyl)ethyl, 2-(2-chlorophenyl)ethyl, 2-(4-methylphenyl)ethyl, (4-bromophenyl)amino, pyridin-3-yl, 6-methoxypyridin-3- yl, 4H-1,2,4-triazol-3-yl, pyridin-4-ylmethyl, (5-methyl-2-furyl)methyl, 3-(1H-pyrazol-1-yl) propyl, 2-morpholin-4-ylethyl, 2-((3,4,5,6-tetrahydro-1-benzazocin-1(2H)-yl) propyl, 2-(2-methylpiperidin-1-yl)ethyl, 3,4-dihydro-1H-isochromen-1-ylmethyl, methoxy, (4-pyridinylcarbonyl) amino or 4,5-dihydro-1H-imidazol-2-ylamino, $R^{3a}$ is hydrogen, methyl or tetrahydrofuran-2-ylmethyl, or $NR^3R^{3a}$ 4-pyridin-2-ylpiperazin-1-yl, 4-(3-methylphenyl) piperazin-1-yl, 4-(4-hydroxyphenyl)piperazin-1-yl, 4-(2-phenylethyl)piperazin-1-yl, 4-(2-morpholin-4-ylethyl)piperazin-1-yl, 3-hydroxypiperidin-1-yl, thiomorpholin-4-yl, 4-methoxycarbonyl-1,3-thiazolidin-3-yl, 2,5-dihydro-1H-pyrrol-1-yl, 1,4-dioxa-8-azaspiro[4.5]dec-8-yl or 4-oxooctahydro-1(2H)-quinolinyl, $R^4$ is hydrogen, R5 is hydrogen, methyl, ethyl, trifluoromethyl, trifluoromethoxy, n-propyl, isopropyl, nitro or halogen, $R^6$ is hydrogen, methyl or Cl, $R^7$ is hydrogen, methyl, Br, F or Cl, and at least one of $R^5$, $R^6$ or $R^7$ is different from hydrogen when $R^2$ is hydrogen, $R^3$ is H or 2,6-diisopropylphenyl, and $R^{3a}$ is H.

More preferably, $R^2$ is hydrogen or methyl, $R^3$ is hydrogen, $R^{3a}$ is hydrogen, $R^5$ is halogen or trifluoromethyl, $R^6$ is hydrogen and $R^7$ is hydrogen, Br or F.

In all the above-mentioned scopes, when $R^2$ is C1-20-alkyl, the carbon atom to which $R^2$ is attached is preferably in the "S"-configuration.

In some embodiments, compounds useful in the methods and compositions of this invention are selected from the group consisting of: 2-(5-iodo-2-oxo-2,3-dihydro-1H-indol-1-yl)acetamide; 2-(5-chloro-2-oxo-2,3-dihydro-1H-indol-1-yl)acetamide; 2-(5,7-dibromo-2-oxo-2,3-dihydro-1H-indol-1-yl)acetamide; 2-(5-nitro-2-oxo-2,3-dihydro-1H-indol-1-yl)acetamide; 2-(5-methyl-2-oxo-2,3-dihydro-1H-indol-1-yl)acetamide; 2-(5-chloro-2-oxo-2,3-dihydro-1H-indol-1-yl) propanamide; (2R)-2-(5-chloro-2-oxo-2,3-dihydro-1H-indol-1-yl)propanamide; (2S)-2-(5-chloro-2-oxo-2,3-dihydro-1H-indol-1-yl)propanamide; 2-[2-oxo-5-(trifluoromethoxy)-2,3-dihydro-1H-indol-1-yl]acetamide; 2-(5-isopropyl-2-oxo-2,3-dihydro-1H-indol-1-yl)acetamide; 2-(5-ethyl-2-oxo-2,3-dihydro-1H-indol-1-yl)acetamide; 2-(5-fluoro-2-oxo-2,3-dihydro-1H-indol-1-yl)acetamide; 2-(5,7-dimethyl-2-oxo-2,3-dihydro-1H-indol-1-yl) acetamide; 2-(5-bromo-2-oxo-2,3-dihydro-1H-indol-1-yl) acetamide; 2-(2-oxo-5-propyl-2,3-dihydro-1H-indol-1-yl) acetamide; 2-[2-oxo-5-(trifluoromethyl)-2,3-dihydro-1H-indol-1-yl]acetamide; 2-(5,6-dimethyl-2-oxo-2,3-dihydro-1H-indol-1-yl)acetamide; 2-(7-chloro-2-oxo-2,3-dihydro-1H-indol-1-yl)acetamide; 2-(6-chloro-2-oxo-2,3-dihydro-1H-indol-1-yl)acetamide; 2-(5-chloro-2-oxo-2,3-dihydro-1H-indol-1-yl)butanamide; (+)-2-(5-chloro-2-oxo-2,3-dihydro-1H-indol-1-yl)butanamide; (−)-2-(5-chloro-2-oxo-2,3-dihydro-1H-indol-1-yl)butanamide; 2-(5-methyl-2-oxo-2,3-dihydro-1H-indol-1-yl)propanamide; (+)-2-(5-methyl-2-oxo-2,3-dihydro-1H-indol-1-yl)propanamide; (−)-2-(5-methyl-2-oxo-2,3-dihydro-1H-indol-1-yl)propanamide; 2-(5-bromo-2-oxo-2,3-dihydro-1H-indol-1-yl)propanamide; (−)-2-(5-bromo-2-oxo-2,3-dihydro-1H-indol-1-yl)propanamide; (+)-2-(5-bromo-2-oxo-2,3-dihydro-1H-indol-1-yl)propanamide; 2-(5-chloro-7-fluoro-2-oxo-2,3-dihydro-1H-indol-1-yl)acetamide; 2-(5-chloro-2-oxo-2,3-dihydro-1H-indol-1-yl)-N-(3-hydroxyphenyl)acetamide; 2-(5-chloro-2-oxo-2,3-dihydro-1H-indol-1-yl)-N-(3-fluorophenyl)acetamide; 2-(5-chloro-2-oxo-2,3-dihydro-1H-indol-1-yl)-N-[3-(2-pyridin-2-ylethyl) phenyl]acetarnide; 2-(5-chloro-2-oxo-2,3-dihydro-1H-indol-1-yl)-N-[6-(hydroxymethyl)cyclohex-3-en-1-yl]acetanuide; 5-chloro-1-[2-oxo-2-(4-pyridin-2-ylpiperazin-1-yl) ethyl3-1,3-dihydro-2H-indol-2-one; 5-chloro-1-{2-[4-(3-methylphenyl) piperazin-1-yl]-2-oxoethyl}-1,3-dihydro-2H-indol-2-one; 2-(5-chloro-2-oxo-2,3-dihydro-1H-indol-1-yl)-N-(4-hydroxy-3-methoxybenzyl)acetamide; 2-(5-chloro-2-oxo-2,3-dihydro-1H-indol-1-yl)-N-(pyridin-4-ylmethyl)-N-(tetrahydrofuran-2-ylmethyl)acetamide; 5-chloro-1-[2-(3-hydroxypiperidin-1-yl)-2-oxoethyl]-1,3-dihydro-2H-indol-2-one; 2-(5-chloro-2-oxo-2,3-dihydro-1H-indol-1-yl)-N'-isonicotinoylacetohydrazide; 5-chloro-1-(2-oxo-2-thiomorpholin-4-ylethyl)-1,3-dihydro-2H-indol-2-one; 2-(5-chloro-2-oxo-2,3-dihydro-1H-indol-1-yl)-N-(4H-1,2,4-triazol-3-yl)acetamide; 2-(5-chloro-2-oxo-2,3-dihydro-1H-indol-1-yl)-N-[4-(methylsulfonyl)benzyl] acetamide; 1-[(5-chloro-2-oxo-2,3-dihydro-1H-indol-1-yl) acetyl]octahydroquinolin-4(1H)-one; N'-(4-bromophenyl)-2-(5-chloro-2-oxo-2,3-dihydro-1H-indol-1-yl) acetohydrazide; 2-(5-chloro-2-oxo-2,3-dihydro-1H-indol-1-yl)-N-(6-methoxypyridin-3-yl)acetamide; N-butyl-2-(5-chloro-2-oxo-2,3-dihydro-1H-indol-1-yl)acetamide; 2-(5-chloro-2-oxo-2,3-dihydro-1H-indol-1-yl)-N-(3-hydroxypropyl) acetamide; 2-(5-chloro-2-oxo-2,3-dihydro-1H-indol-1-yl)-N-[3-(dimethylamino)propyl]acetamide; 5-chloro-1-{2-oxo-2-[4-(2-phenylethyl)pperazin-1-yl]ethyl}-1,3-dihydro-2H-indol-2-one; ethyl {[(5-chloro-2-oxo-2,3-dihydro-1H-indol-1-yl) acetyl]amino}acetate; 2-(5-chloro-2-oxo-2,3-dihydro-1H-indol-1-yl)-N-(3-ethoxypropyl)acetamide; 2-(5-chloro-2-oxo-2,3-dihydro-1H-indol-1-yl)-N-(2-fluoroethyl)acetamide; 2-(5-chloro-2-oxo-2,3-dihydro-1H-indol-1-yl)-N-methoxy-N-methylacetamide; 2-(5-chloro-2-oxo-2,3-dihydro-1H-indol-1-yl)-N-(3,4-dimethylphenyl) acetamide; N-(4-tert-butylphenyl)-2-(5-chloro-2-oxo-2,3-dihydro-1H-indol-1-yl)acetamide; 2-(5-chloro-2-oxo-2,3-dihydro-1H-indol-1-yl)-N-(3-hydroxy-2,2-dimethylpropyl) acetamide; 2-(5-chloro-2-oxo-2,3-dihydro-1H-indol-1-yl)-N-[1-(hydroxymethyl) propyl]acetamide; 2-(5-chloro-2-oxo-2,3-dihydro-1H-indol-1-yl)-N-(3,3,3-trifluoro-2-hydroxypropyl)acetamide; 2-(5-chloro-2-oxo-2,3-dihydro-1H-indol-1-yl)-N-(2-hydroxy-2-phenylethyl)acetamide; 5-chloro-1-{2-[4-(4-hydroxyphenyl) piperazin-1-yl]-2-oxoethyl}-1,3-dihydro-2H-indol-2-one; 2-(5-chloro-2-oxo-2,3-dihydro-1H-indol-1-yl)-N-(pyridin-4-ylmethyl)acetamide; 2-(5-chloro-2-oxo-2,3-dihydro-1H-indol-1-yl)-N-[(5-methyl-2-furyl)methyl]acetamide; 2-(5-chloro-2-oxo-2,3-dihydro-1H-indol-1-yl)-N-[3-(1H-pyrazol-1-yl)propyl]acetamide; methyl 3-[(5-chloro-2-oxo-2,3-dihydro-1H-indol-1-yl]acetyl]-1,3-thiazolidine-4-carboxylate; 5-chloro-1-[2-(2,5-dihydro-1H-pyrrol-1-yl)-2-oxoethyl]-1,3-dihydro-2H-indol-2-one; 2-(5-chloro-2-oxo-2,3-dihydro-1H-indol-1-yl)-N'-(4,5-dihydro-1H-imidazol-2-yl) acetohydrazide; 2-(5-chloro-2-oxo-2,3-dihydro-1H-indol-1-yl)-N-[2-(3,4-dimethoxyphenyl)ethyl]acetamide; 2-(5-chloro-2-oxo-2,3-dihydro-1H-indol-1-yl)-N-[2-(2-chlorophenyl)etlyllacetaniide; 2-(5-chloro-2-oxo-2,3-dihydro-1H-indol-1-yl)-N-[2-(4-methylphenyl)ethyl]acetamide; 2-(5-chloro-2-oxo-2,3-dihydro-1H-indol-1-yl)-N-(2-morpholin-4-ylethyl) acetamide; 2-(5-chloro-2-oxo-2,3-dihydro-1H-indol-1-yl)-N-[2-(3,4,5,6-tetrahydro-1-benzazocin-1(2H)-yl)propyl] acetamide; 2-(5-chloro-2-oxo-2,3-dihydro-1H-indol-1-yl)-N-[2-(2-methylpiperidin-1-yl)ethyl]acetamide; 2-(5-chloro-2-oxo-2,3-dihydro-1H-indol-1-yl)-N-(2-nitrobenzyl) acetamide; 2-(5-chloro-2-oxo-2,3-dihydro-1H-indol-1-yl)-N-(3,4-dihydro-1H-isochromen-1-ylinethyl)acetamide; N-(2-chloro-6-fluorobenzyl)-2-(5-chloro-2-oxo-2,3-dihydro-1H-indol-1-yl)acetamide; N-benzyl-2-(5-chloro-2-oxo-2,3-dihydro-1H-indol-1-yl)-N-methylacetamide; 2-(5- chloro-2-oxo-2,3-dihydro-1H-indol-1-yl)-N-{2-[(trifluoromethyl)thio]benzyl}acetamide; 5-chloro-1-[2-(1,4-dioxa-8-azaspiro[4.5]dec-8-yl)-2-oxoethyl]-1,3-dihydro-2H-indol-2-one; 2-(5-chloro-2-oxo-2,3-dihydro-1H-indol-1-yl)-N-cycloheptylacetamide; 5-chloro-1-{2-[4-(2-morpholin-4-ylethyl) piperazin-1-yl]-2-oxoethyl}-1,3-dihydro-2H-indol-2-one; and 2-(5-chloro-2-oxo-2,3-dihydro-1H-indol-1-yl)-N-pyridin-3-ylacetamide.

In some embodiments, compounds useful in the methods and compositions of this invention are selected from the group consisting of: 2-(5-iodo-2-oxo-2,3-dihydro-1H-indol-1-yl)acetamide; 2-(5-chloro-2-oxo-2,3-dihydro-1H-indol-1-yl) acetamide; 2-(5,7-dibromo-2-oxo-2,3-dihydro-1H-indol-1-yl)acetamide; (2S)-2-(5-chloro-2-oxo-2,3-dihydro-1H-indol-1-yl)propanamide; 2-[2-oxo-5-(trifluoromethyl)-2,3-dihydro-1H-indol-1-yl]acetamide and 2-(5-chloro-7-fluoro-2-oxo-2,3-dihydro-1H-indol-1-yl) acetamide.

In another embodiment, compounds useful in the methods and compositions of this invention are selected from the group consisting of: 2-(5-chloro-2-oxo-2,3-dihydro-1H-indol-1-yl) acetamide and (2S)-2-(5-chloro-2-oxo-2,3-dihydro-1H-indol-1-yl)propanamide.

iv) U.S. Pat. No. 7,244,747:

A compound having the formula I or a pharmaceutically acceptable salt thereof,

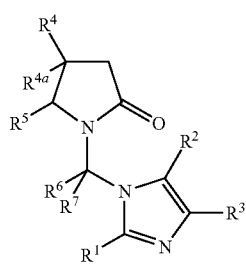

(I)

wherein $R^1$ is hydrogen, $C_{1-20}$ alkyl, $C_{3-8}$ cycloalkyl, halogen, hydroxy, alkoxy, aryloxy, ester, amido, cyano, nitro, amino, guanidine, amino derivative, alkylthio, arylthio, alkylsulfonyl, arylsulfonyl, alkylsulfinyl, arylsulfinyl, aryl or heterocycle;

$R^2$ is hydrogen, $C_{1-20}$ alkyl, alkoxy, amino, halogen, hydroxy, ester, amido, nitro, cyano, carbamate, or aryl;

$R^3$ is hydrogen, $C_{1-20}$ alkyl, alkoxy, amino, halogen, hydroxy, ester, amido, nitro, cyano, carbamate, or aryl;

or $R^2$ and $R^3$ can form together with the imidazole ring the following 1H-benzimidazole cycle

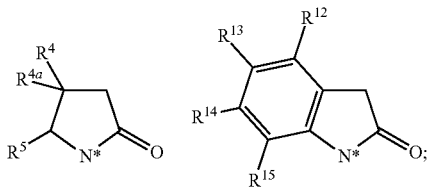

$R^4$ is hydrogen, $C_{1-20}$ alkyl, $C_{2-12}$ alkenyl, $C_{2-12}$ alkynyl, aryl, azido, alkoxycarbonylamino, arylsulfonyloxy or heterocycle;

$R^{4a}$ is hydrogen or $C_{1-20}$ alkyl;

or $R^4$ and $R^{4a}$ can form together a $C_{3-8}$ cycloalkyl;

$R^5$ is hydrogen;

or $R^4$, $R^{4a}$ and $R^5$ can form together with the 2-oxo-1-pyrrolidine ring the following 1,3-dihydro-2H-indol-2-one cycle $R^6$ is hydrogen or $C_{1-20}$ alkyl;

$R^7$ is hydrogen;

or $R^6$ and $R^7$ are linked together to form a $C_{3-6}$ cycloalkyl;

$R^8$ is hydrogen, halogen, nitro, cyano, $C_{1-20}$ alkyl or alkoxy;

$R^9$ is hydrogen, $C_{1-20}$ alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

$R^{10}$ is hydrogen, $C_{1-20}$ alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

$R^{11}$ is hydrogen, halogen, nitro, cyano, $C_{1-20}$ alkyl or alkoxy;

$R^{12}$ is hydrogen or halogen;

$R^{13}$ is hydrogen, nitro, halogen, heterocycle, amino, aryl, $C_{1-20}$ alkyl unsubstituted or substituted by halogen, or alkoxy unsubstituted or substituted by halogen;

$R^{14}$ is hydrogen, $C_{1-20}$ alkyl or halogen;

$R^{15}$ is hydrogen, $C_{1-20}$ alkyl or halogen;

with the proviso that $R^4$ is different from hydrogen when represents a group of formula

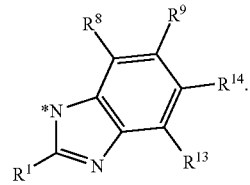

The asterisk * indicates the point of attachment of the substituents.

In a preferred embodiment, the compounds have the formula I, their tautomers, geometrical isomers (including cis and trans, Z and E isomers), enantiomers, diastereoisomers and mixtures thereof (including all possible mixtures of stereoisomers), or pharmaceutically acceptable salts thereof,

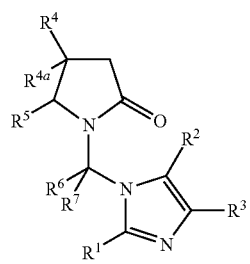

(I)

wherein $R^1$ is hydrogen, $C_{1-20}$ alkyl, $C_{3-8}$ cycloalkyl, halogen, hydroxy, ester, amido, cyano, nitro, amino, guanidine, alkylthio, alkylsulfonyl, alkylsulfinyl, aryl or heterocycle;

$R^2$ is hydrogen, $C_{1-20}$ alkyl, halogen, cyano, ester, carbamate or amido;

$R^3$ is hydrogen, cyano, $C_{1-20}$ alkyl, halogen or ester;

or $R^2$ and $R^3$ can form together with the imidazole ring the following 1H-benzimidazole cycle

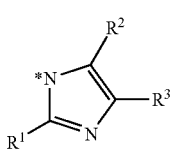 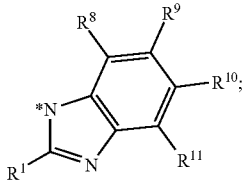

$R^4$ is hydrogen, $C_{1-20}$ alkyl, $C_{2-12}$ alkenyl or aryl;
$R^{4a}$ is hydrogen;
$R^5$ is hydrogen;
or $R^4$, $R^{4a}$ and $R^5$ can form together with the 2-oxo-1-pyrrolidine ring the following 1,3-dihydro-2H-indol-2-one cycle

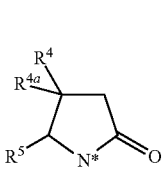 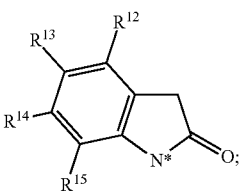

$R^6$ is hydrogen or $C_{1-20}$ alkyl;
$R^7$ is hydrogen; or $R^6$ and $R^7$ are linked together to form a $C_{3-6}$ cycloalkyl;
$R^8$ is hydrogen;
$R^9$ is hydrogen, $C_{1-20}$ alkyl, halogen or alkoxy;
$R^{10}$ is hydrogen, $C_{1-20}$ alkyl, halogen or cyano;
$R^{11}$ is hydrogen;
$R^{12}$ is hydrogen or halogen;
$R^{13}$ is hydrogen, halogen, heterocycle or $C_{1-20}$ alkyl;
$R^{14}$ is hydrogen;
$R^{15}$ is hydrogen;
with the proviso that $R^4$ is different from hydrogen when

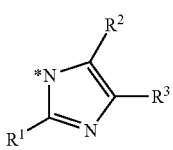

represents a group of formula

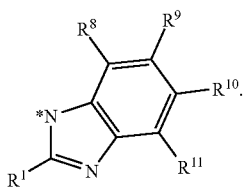

The term "alkyl", as used herein, represents saturated, monovalent hydrocarbon radicals having straight (unbranched) or branched or cyclic or combinations thereof and containing 1-20 carbon atoms, preferably 1-10 carbon atoms, more pre preferred alkyl groups have 1-3 carbon atoms. Alkyl moieties may optionally be substituted by 1 to 5 substituents independently selected from the group consisting of halogen, hydroxy, cyano, azido, aryloxy, alkoxy, alkythio, alkanoylamino, arylcarbonylamino, aminocarbonyl, methylaminocarbonyl, dimethylaminocarbonyl or aryl. Usually alkyl groups, in the present case, are methyl, ethyl, n-propyl, i-propyl, n-butyl, i-butyl, t-butyl, 1-ethylpropyl, n-heptyl, 2,4,4-trimethylpentyl, n-decyl, chloromethyl, trifluoromethyl, 2-bromo-2,2-difluoroethyl, 2,2,2-trifluoroethyl, 3,3,3-trifluoropropyl, hydroxymethyl, cyanomethyl, azidomethyl, (acetylamino)methyl, (propionylamino) methyl, (benzoylamino)methyl, (4-chlorophenoxy)methyl, benzyl, 2-phenylethyl or 2-(methylthio)ethyl. Preferred alkyl groups are methyl, ethyl, n-propyl, i-propyl, n-butyl, i-butyl, t-butyl, 1-ethylpropyl, 2,4,4-trimethylpentyl, chloromethyl, trifluoromethyl, 2,2,2-trifluoroethyl, hydroxymethyl, cyanomethyl, azidomethyl, (acetylamino)methyl, (propionylamino)methyl, (benzoylamino)methyl or 2-(methylthio)ethyl. More preferred alkyl groups are methyl, ethyl, n-propyl, i-propyl, n-butyl, azidomethyl or trifluoromethyl. Most preferred alkyl groups are methyl or n-propyl.

The term "cycloalkyl", as used herein, represents a monovalent group of 3 to 8 carbon atoms, usually 3-6 carbon atoms derived from a saturated cyclic hydrocarbon, which may be substituted by any suitable group including but not limited to one or more moieties selected from groups as described above for the alkyl groups. Preferred cycloalkyl groups are cyclopropyl and cyclohexyl.

The term "alkenyl" as used herein, represents straight, branched or cyclic unsaturated hydrocarbon radicals or combinations thereof having at least one carbon-carbon double bond, containing 2-12 carbon atoms, preferably usually 2-4 carbon atoms. Alkenyl groups are being optionally substituted with any suitable group, including but not limited to one or more moieties selected from groups as described above for the alkyl groups. Usually an alkenyl group is ethenyl (vinyl) optionally substituted by 1 to 3 halogens. Preferred alkenyl group, in the present case, is 2,2-difluorovinyl.

The term a "alkynyl" as used herein, represents straight, branched or cyclic hydrocarbon radicals or combinations thereof containing at least one carbon-carbon triple bond, containing 2-12 carbon atoms, preferably 2-6 carbon atoms, and being optionally substituted by any suitable group, including but not limited to one or more moieties selected from groups as described above for the alkyl groups. Preferably an alkynyl group is a halogenoalkynyl group (haloalkynyl group).

Groups qualified by prefixes such as "s", "i", "t" and the like (e.g. "i-propyl", "s-butyl") are branched derivatives.

The term "aryl" as used herein, is defined as phenyl optionally substituted by 1 to 4 substituents independently selected from halogen, cyano, alkoxy, alkylthio, $C_{1-3}$ alkyl or azido, preferably halogen or azido. Usually aryl groups, in the present case are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl, 3-azido-2,4-difluorophenyl or 3-azido-2,4,6-trifluorophenyl. Preferably, aryl groups are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl or 3-azido-2,4-difluorophenyl. Most preferred aryl groups are phenyl, 3-chlorophenyl, 3-fluorophenyl, 3,5-difluorophenyl, 2,3,4-trifluorophenyl, 2,4,5-trifluorophenyl, 2,3,5-trifluorophenyl, 3,4,5-trifluorophenyl or 3-azido-2,4-difluorophenyl.

The term "heterocycle", as used herein, is defined as including an aromatic or non aromatic cycloalkyl moiety as defined above, having at least one O, S and/or N atom interrupting the carbocyclic ring structure. Heterocyclic ring moieties can be optionally substituted by alkyl groups or halogens and optionally, one of the carbon of the carbocyclic ring structure may be replaced by a carbonyl. Usually heterocycles are 2-pyridyl, 3-pyridyl, 4-pyridyl, 2-furyl, 3-furyl, 2-thienyl, 3-thienyl, 2-tetrahydrofuranyl, 1H-pyrrol-2-yl, 1-methyl-1H-pyrrol-2-yl, 1H-pyrazol-2-yl, 1H-pyrazol-3-yl, 4-chloro-1-methyl-1H-pyrazol-3-yl, 5-chloro-1,3-dimethyl-1H-pyrazol-4-yl, 1,2,3-thiadiazol-4-yl, 3,5-dimethyl-4-isothiazyl, 1H-imidazol-2-yl, 1-methyl-1H-imidazol-2-yl, 4-methyl-1H-imidazol-5-yl, or 2-methyl-1,3-thiazol-4-yl. Preferred heterocycles are 1H-imidazol-2-yl, 1,2,3-thiadiazol-4-yl, 1H-pyrazol-3-yl, 2-furyl, 3-furyl, 2-thienyl, 1-methyl-1H-pyrrol-2-yl, 1H-pyrrol-2-yl.

The term "halogen", as used herein, includes an atom of chlorine, bromine, fluorine, iodine. Usually halogens are chlorine, bromine and fluorine. Preferred halogens are fluorine, bromine and chlorine.

The term "hydroxy", as used herein, represents a group of formula —OH.

The term "alkoxy", as used herein, represents a group of formula —OR$^a$ wherein R$^a$ is an alkyl group, as defined above. Preferred alkoxy group is methoxy.

The term "aryloxy", as used herein, represents a group of formula —OR$^b$ wherein R$^b$ is an aryl group, as defined above. Preferred aryloxy group is phenoxy.

The term "ester", as used herein, represents a group of formula —COOR$^c$ wherein R$^c$ is an alkyl group or aryl group, as defined above. Preferred ester group is methoxycarbonyl.

The term "amido", as used herein, represents a group of formula —CONH$_2$.

The term "amino", as used herein, represents a group of formula —NH$_2$.

The term "aminoderivative", as used herein, represents an alkylamino or an arylamino group, wherein the terms "alkyl" and "aryl" are defined as above.

The term "cyano", as used herein, represents a group of formula —CN.

The term "nitro", as used herein, represents a group of formula —NO$_2$.

The term "azido", as used herein, represents a group of formula —N$_3$.

The term "guanidine", as used herein, represents a group of formula —NHC(=NH)NH$_2$.

The term "alkylthio", as used herein, represents a group of formula —SR$^d$ wherein R$^d$ is an alkyl group, as defined above. Preferred alkylthio group is methylthio.

The term "alkylsulfonyl", as used herein, represents a group of formula —S(=O)$_2$R$^e$ wherein R$^e$ is an alkyl group, as defined above. Preferred alkylsulfonyl group is methylsulfonyl.

The term "alkylsulfinyl", as used herein, represents a group of formula —S(=O)R$^f$ wherein R$^f$ is an alkyl group, as defined above. Preferred alkylsulfinyl group is methylsulfinyl.

The term "arylthio", as used herein, represents a group of formula —SR$^g$ wherein R$^g$ is an aryl group, as defined above.

The term "arylsulfonyl", as used herein, represents a group of the formula —S(=O)$_2$R$^h$ wherein R$^h$ is an aryl group, as defined above.

The term "arylsulfinyl", as used herein, represents a group of the formula —S(=O)R$^i$ wherein R$^i$ is an aryl group, as defined above.

The term "carbamate" as used herein, represents a group of formula —N(H)C(O)OR$^j$, wherein R$^j$ is an alkyl or an aryl, as defined above. Usually carbamate groups are (propoxycarbonyl)amino or (benzyloaxycarbonyl)amino. Preferred carbamate group is (benzyloaxycarbonyl)amino.

The term "alkanoylamino" as used herein, represents a group of the formula —NHC(=O)R$^k$ wherein R$^k$ is an alkyl group, as defined above.

The term "(arylcarbonyl)amino" as used herein, represents a group of the formula —NHC(=O)R$^m$ wherein R$^m$ is an aryl group, as defined above. Preferred (arylcarbonyl)amino is benzoylamino.

Usually, R$^1$ is hydrogen; C$_{1-10}$ alkyl unsubstituted or substituted by halogen, hydroxy, cyano, methylthio, phenyl or 4-chlorophenoxy; hydroxy; C$_{3-6}$ cycloalkyl; halogen; ester; amido; nitro; cyano; amino; phenyl; alkylthio; alkylsulfonyl; alkylsulfinyl; heterocycle unsubstituted or substituted by alkyl groups; or guanidine. Preferably, R$^1$ is hydrogen; methyl; ethyl; i-propyl; n-propyl; cyclopropyl; n-butyl; i-butyl; t-butyl; 1-ethylpropyl; 2,4,4-trimethylpentyl; hydroxymethyl; chloromethyl; trifluoromethyl; 2,2,2-trifluoroethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl or 1H-imidazol-2-yl. More preferably, R$^1$ is hydrogen; methyl; ethyl; i-propyl; n-propyl; n-butyl; methylthio; nitro; cyano; amino; chloro or 1H-pyrrol-2-yl. Most preferably, R$^1$ is hydrogen; methyl; methylthio; nitro; cyano; amino or chloro.

Usually, R$^2$ is hydrogen; C$_{1-4}$ alkyl unsubstituted or substituted by hydroxy, alkanoylamino or benzoylamino; halogen; ester; cyano; alkyl carbamate; [(N-methoxy-N-methyl)amino]carbonyl. Preferably, R$^2$ is hydrogen; methyl; hydroxymethyl; (acetylamino)methyl; (propionylamino)methyl; (benzoylamino)methyl; [(benzyloxy)carbonyl]amino; chloro or cyano. More preferably, R$^2$ is hydrogen; chloro or cyano.

Usually, R$^3$ is hydrogen; C$_{1-4}$ alkyl unsubstituted or substituted by hydroxy; halogen; ester or cyano. Preferably, R$^3$ is hydrogen; hydroxymethyl; chloro; cyano. More preferably, R$^3$ is hydrogen or cyano. Most preferred R$^3$ is hydrogen.

Usually, R$^4$ is hydrogen; C$_{1-4}$ alkyl unsubstituted or substituted by halogens; C$_{2-4}$ alkenyl substituted by halogens or phenyl group unsubstituted or substituted by azido or/and halogens. Preferably, R$^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl or 3-azido-2,4,6-trifluorophenyl. More preferably, R$^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl or 3-azido-2,4-difluorophenyl. Most preferably, R$^4$ is n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl or 3-azido-2,4-difluorophenyl.

Usually, R$^{4a}$ is hydrogen.

Usually, R$^5$ is hydrogen.

Usually, R$^6$ is hydrogen or C$_{1-10}$ alkyl unsubstituted or substituted by hydroxy or azido. Preferably, R$^6$ is hydrogen or azidomethyl. More preferably R$^6$ is hydrogen.

Usually $R^7$ is hydrogen.

In other preferred embodiments, $R^6$ and $R^7$ are linked to form a cyclopropyl.

In other preferred embodiments, $R^2$ and $R^3$ can form together with the imidazole ring the following 1H-benzimidazole cycle

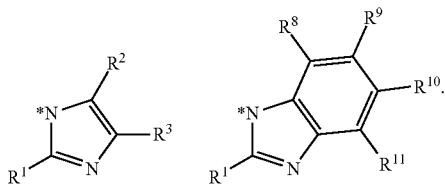

Usually, $R^8$ is hydrogen.

Usually, $R^9$ is hydrogen; halogen; $C_{1-3}$ alkyl or alkoxy. Preferably, $R^9$ is hydrogen; methyl; chloro or methoxy. More preferred $R^9$ is hydrogen.

Usually, $R^{10}$ is hydrogen; halogen; cyano; $C_{1-3}$ alkyl unsubstituted or substituted by halogens; or alkoxy. Preferably, $R^{10}$ is methyl; hydrogen; trifluoromethyl; fluoro; cyano or methoxy. More preferred $R^{10}$ is hydrogen; trifluoromethyl; fluoro or cyano.

Usually, $R^{11}$ is hydrogen.

In other preferred embodiments, $R^4$, $R^{4a}$ and $R^5$ can form together with the 2-oxo-1-pyrrolidine ring the following 1,3-dihydro-2H-indol-2-one cycle

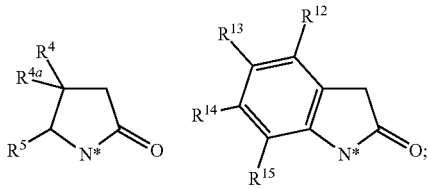

Usually, $R^{12}$ is hydrogen or halogen. Preferably $R^{12}$ is hydrogen; chloro or fluoro. More preferred $R^{12}$ is hydrogen.

Usually, $R^{13}$ is hydrogen; $C_{1-3}$ alkyl; halogen or thiazolyl unsubstituted or substituted by alkyl groups, such as methylthiazolyl. Preferably $R^{13}$ is hydrogen; chloro; bromo or methyl. Most preferred $R^{13}$ is chloro; bromo or methyl.

Usually $R^{14}$ is hydrogen.

Usually $R^{15}$ is hydrogen.

Combinations of one or more of these preferred compound groups are especially preferred.

Generally, among the embodiments, the compounds of formula I, or pharmaceutically acceptable salts thereof, are those wherein $R^1$ is selected from hydrogen; $C_{1-10}$ alkyl unsubstituted or substituted by halogen, hydroxy, cyano, methylthio, phenyl or 4-chlorophenoxy; $C_{3-6}$ cycloalkyl; halogen; ester; amido; nitro; cyano; amino; phenyl; alkylthio; alkylsulfonyl; alkylsulfinyl; heterocycle unsubstituted or substituted by alkyl group; or guanidine;

$R^2$ is selected from hydrogen; $C_{1-4}$ alkyl unsubstituted or substituted by hydroxy, alkanoylamino or benzoylamino; halogen; ester; cyano; alkyl carbamate or [(N-methoxy-N-methyl)amino]carbonyl.

$R^3$ is selected from hydrogen; $C_{1-4}$ alkyl unsubstituted or substituted by hydroxy; halogen; ester or cyano;

$R^4$ is selected from hydrogen; $C_{1-4}$ alkyl unsubstituted or substituted by halogens; $C_{2-4}$ alkenyl substituted by halogens or phenyl group unsubstituted or substituted by azido or/and halogens;

$R^{4a}$ is hydrogen;

$R^5$ is hydrogen;

$R^6$ is selected from hydrogen or $C_{1-10}$ alkyl unsubstituted or substituted by hydroxy or azido;

$R^7$ is hydrogen;

or $R^6$ and $R^7$ can be linked to form a cyclopropyl;

or $R^2$ and $R^3$ can form together with the imidazole ring the following 1H-benzimidazole cycle

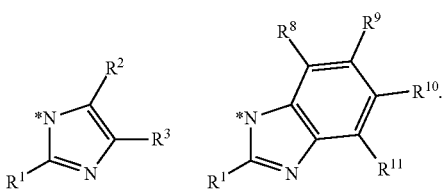

$R^8$ is hydrogen;

$R^9$ is selected from hydrogen; halogen; $C_{1-3}$ alkyl; alkoxy;

$R^{10}$ is selected from hydrogen; halogen; cyano or $C_{1-3}$ alkyl unsubstituted or substituted by halogens; or alkoxy;

$R^{11}$ is hydrogen;

or $R^4$, $R^{4a}$ and $R^5$ can form together with the 2-oxo-1-pyrrolidine ring the following 1,3-dihydro-2H-indol-2-one cycle

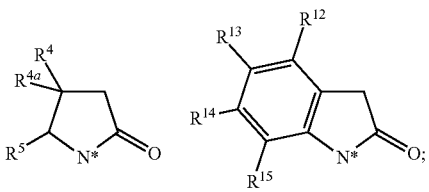

$R^{12}$ is selected from hydrogen or halogen;

$R^{13}$ is selected from hydrogen; $C_{1-3}$ alkyl; halogen; thiazolyl unsubstituted or substituted by alkyl groups, such as methylthiazolyl;

$R^{14}$ is hydrogen;

$R^{15}$ is hydrogen;

with the proviso that $R^4$ is different from hydrogen when

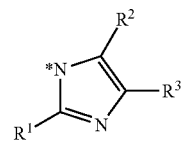

represents a group of formula

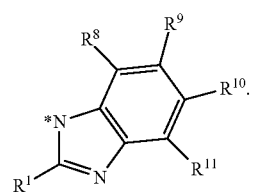

In a preferred embodiment, the compounds of formula I, or pharmaceutically acceptable salt thereof, are those wherein R¹ is selected from hydrogen; methyl; ethyl; i-propyl; n-propyl; cyclopropyl; n-butyl; i-butyl; t-butyl; 1-ethylpropyl; 2,4,4-trimethylpentyl; trifluoromethyl; 2,2,2-trifluoroethyl; hydroxymethyl; chloromethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl; or 1H-imidazol-2-yl;

R² is selected from hydrogen; methyl; hydroxymethyl; (acetylamino)methyl; (propionylamino)methyl; (benzoylamino)methyl; (benzyloxycarbonyl)amino; chloro; or cyano;

R³ is selected from hydrogen; hydroxymethyl; chloro; cyano;

or R² and R³ can form together with the imidazole ring the following 1H-benzimidazole cycle

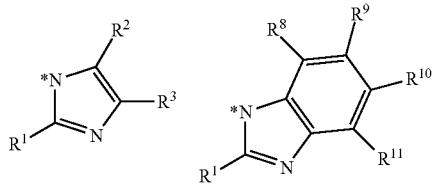

R⁸ is hydrogen;

R⁹ is selected from hydrogen; methyl; choro; methoxy;

R¹⁰ is selected from methyl; hydrogen; trifluoromethyl; fluoro; cyano; or methoxy;

R¹¹ is hydrogen;

R⁴ is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl; or 3-azido-2,4,6-trifluorophenyl.

R⁴ᵃ is hydrogen; R⁵ is hydrogen;

or R⁴, R⁴ᵃ and R⁵ can form together with the 2-oxo-1-pyrrolidine ring the following 1,3-dihydro-2H-indol-2-one cycle

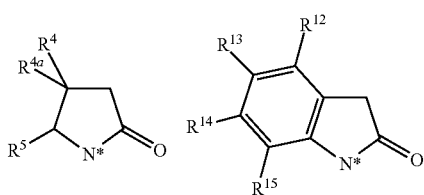

R¹² is selected from hydrogen; chloro; fluoro;

R¹³ is selected from hydrogen; chloro; bromo; methyl;

R¹⁴ is hydrogen;

R¹⁵ hydrogen;

R⁶ is selected from hydrogen; azidomethyl;

R⁷ is hydrogen;

or R⁶ and R⁷ are linked to form a cyclopropyl;

with the proviso that R⁴ is different from hydrogen when

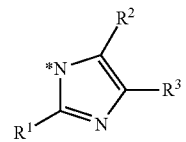

represents a group of formula

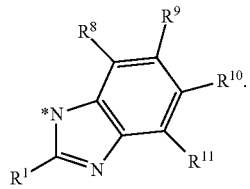

In a more preferred embodiment, the compounds of formula I, or pharmaceutically acceptable salt thereof, are those wherein R¹ is selected from hydrogen; methyl; ethyl; i-propyl; n-propyl; n-butyl; methylthio; nitro; cyano; amino; chloro; or 1H-pyrrol-2-yl;

R² is selected from hydrogen; chloro; cyano;

R³ is selected from hydrogen; cyano;

or R² and R³ can form together with the imidazole ring the following 1H-benzimidazole cycle

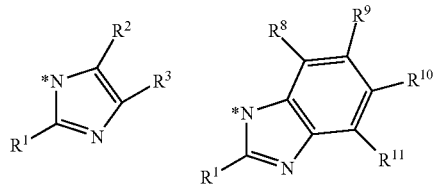

R⁸ is hydrogen;

R⁹ is hydrogen;

R¹⁰ is selected from hydrogen; trifluoromethyl; fluoro; cyano;

R¹¹ is hydrogen;

R⁴ is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; or 3-azido-2,4-difluorophenyl;

R⁴ᵃ is hydrogen;

R⁵ is hydrogen;

or R⁴, R⁴ᵃ and R⁵ can form together with the 2-oxo-1-pyrrolidine ring the following 1,3-dihydro-2H-indol-2-one cycle

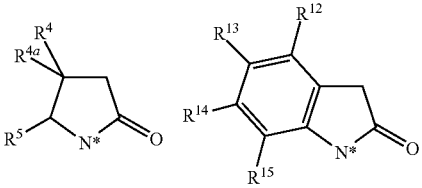

wherein
R$^{12}$ is hydrogen;
R$^{13}$ is selected from methyl; chloro; bromo;
R$^{14}$ is hydrogen;
R$^{15}$ hydrogen;
R$^6$ is hydrogen;
R$^7$ is hydrogen;
with the proviso that R$^4$ is different from hydrogen when represents a group of formula In a most preferred embodiment, the compounds of formula I, or pharmaceutically acceptable salt thereof, are those wherein
R$^1$ is selected from hydrogen; methyl; methylthio; nitro; cyano; amino; chloro;
R$^2$ is selected from hydrogen; chloro; cyano;
R$^3$ is hydrogen;
R$^4$ is selected from n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl; 3-azido-2,4-difluorophenyl;
R$^{4a}$ is hydrogen;
R$^5$ is hydrogen;
or R$^4$, R$^{4a}$ and R$^5$ can form together with the 2-oxo-1-pyrrolidine ring the following 1,3-dihydro-2H-indol-2-one cycle R$^{12}$ is hydrogen;
R$^{13}$ is selected from chloro; bromo; methyl;
R$^{14}$ is hydrogen;
R$^{15}$ hydrogen;
R$^6$ is hydrogen;
R$^7$ is hydrogen.

In some embodiments, compounds useful in the methods and compositions of this invention are selected from the group consisting of: 1-(1H-imidazol-1-ylmethyl)pyrrolidin-2-one; 1-(1H-imidazol-1-ylmethyl)-4-phenylpyrrolidin-2-one; 4-(3-azido-2,4,6-trifluorophenyl)-1-(1H-imidazol-1-ylmethyl)pyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-yl)pyrrolidin-2-one; 1-[(2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 1-[(2-phenyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-{[2-(methylsulfinyl)-1H-imidazol-1-yl]methyl}-4-propylpyrrolidin-2-one; 1-[(2-tert-butyl-1H-imidazol-1-yl)methyl]-4-propylpyrrolidin-2-one; 1-[1-(1H-imidazol-1-yl)cyclopropyl]pyrrolidin-2-one; 1-[(2-methyl-1H-imidazol-1-yl)methyl]-4-phenylpyrrolidin-2-one; 1-{[2-(methylsulfonyl)-1H-imidazol-1-yl]methyl}-propylpyrrolidin-2-one; 1-[(2-oxo-4-propylpyrrolidin-1-yl)methyl]-1H-imidazole-2-carboxamide, 4-(4-fluorophenyl)-1-(1H-imidazol-1-ylmethyl)pyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 4-(3,4-difluorophenyl)-1-(1H-imidazol-1-ylmethyl)pyrrolidin-2-one; 4-(3-chloro-4-fluorophenyl)-1-(1H-imidazol-1-ylmethyl)pyrrolidin-2-one; 4-(4-chlorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-{[2-(hydroxymethyl)-1H-imidazol-1-yl]methyl}-4-propylpyrrolidin-2-one; methyl 1-[(2-oxo-4-propylpyrrolidin-1-yl)methyl]-1H-imidazole-2-carboxylate; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(2,4-dichloro-1H-imidazol-1-yl)methyl]-4-(3,4,5-trifluorophenyl)pyrrolidin-2-one; 1-[(5-chloro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-4-carbonitrile; 1-{[2-oxo-4-(3,4,5-trifluorophenyl)pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; 1-{[2-oxo-4-(2,3,5-trifluorophenyl)pyrrolidin-1-yl]methyl}-1H-imidazole-5-carbonitrile; (−)-1-{[2-oxo-4-(2,3,4-trifluorophenyl)pyrrolidin-1-yl]methyl}-1H-imidazole-5-carbonitrile; (+)-1-{[2-oxo-4-(2,3,4-trifluorophenyl)pyrrolidin-1-yl]methyl}-1H-imidazole-5-carbonitrile; (−)-1-{[2-oxo-4-(2,3,4-trifluorophenyl)pyrrolidin-1-yl]methyl}-1H-imidazole-4-carbonitrile; (+)-1-{[2-oxo-4-(2,3,4-trifluorophenyl)-1-pyrrolidinyl]methyl}-1H-imidazole-4-carbonitrile; (−)-1-{[2-oxo-4-(3,4,5-trifluorophenyl)pyrrolidin-1-yl]methyl}-1H-imidazole-4-carbonitrile; (+)-1-{[2-oxo-4-(3,4,5-trifluorophenyl)pyrrolidin-1-yl]methyl}-1H-imidazole-4-carbonitrile; (+)-1-{[2-oxo-4-(2,4,5-trifluorophenyl)pyrrolidin-1-yl]methyl}-1H-imidazole-4-carbonitrile; (−)-1-{[2-oxo-4-(2,4,5-trifluorophenyl)pyrrolidin-1-yl]methyl}-1H-imidazole-4-carbonitrile; (−)-1-{[2-oxo-4-(2,3,5-trifluorophenyl)pyrrolidin-1-yl]methyl}-1H-imidazole-4- carbonitrile; (−)-1-{[2-oxo-4-(3,4,5-trifluorophenyl)pyrrolidin-1-yl]methyl}-1H-imidazole-5-carbonitrile; 1-{[2-oxo-4-(2,3,5-trifluorophenyl)pyrrolidin-1-yl]methyl}-1H-imidazole-5-carbonitrile; 1-{[2-oxo-4-(2,3,5-trifluorophenyl)pyrrolidin-1-yl]methyl}-1H-imidazole-5-carbonitrile; 1-[(5-methyl-2-phenyl-1H-imidazol-1-yl)methyl]-4-propylpyrrolidin-2-one; 1-[(5-methyl-1H-imidazol-1-yl)methyl]-4-propylpyrrolidin-2-one; 1-[(5-phenyl-1H-imidazol-1-yl)methyl]-4-propylpyrrolidin-2-one; 1-[(2-ethyl-5-methyl-1H-imidazol-1-yl)methyl]-4-propylpyrrolidin-2-one; 1-[(2,5-dimethyl-1H-imidazol-1-yl)methyl]-4-propylpyrrolidin-2-one; 1-[(2-chloro-1H-imidazol-1-yl)methyl]-4-(3,4,5-trifluorophenyl)pyrrolidin-2-one; 1-[2-azido-1-(1H-imidazol-1-yl)ethyl]-4-propylpyrrolidin-2-one; 1-[(4-chloro-1H-imidazol-1-yl)methyl]-4-(3,4,5-trifluorophenyl)pyrrolidin-2-one; 1-[(2-bromo-4,5-dichloro-1H-imidazol-1-yl)methyl]-4-propylpyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 1-{[5-(hydroxymethyl)-1H-imidazol-1-yl]methyl}-4-propylpyrrolidin-2-one; 1-{[4-(hydroxymethyl)-1H-imidazol-1-yl]methyl}-4-propylpyrrolidin-2-one; benzyl 1-[(2-oxo-4-propylpyrrolidin-1-yl)methyl]-1H-imidazol-5-ylcarbamat-e; N-[(1-{[2-oxo-4-(3,4,5-trifluorophenyl)pyrrolidin-1-yl]methyl}-1H-imidazol-5-yl)methyl]acetamide; N-[(1-{[2-oxo-4-(3,4,5-trifluorophenyl)pyrrolidin-1-yl]methyl}-1H-imidazol-5-yl)methyl]benzamide; N-[(1-{[2-oxo-4-(3,4,5-trifluorophenyl)pyrrolidin-1-yl]methyl}-1H-imidazol-5-yl)methyl]propanamide; 1-(1H-benzimidazol-1-ylmethyl)-4-propylpyrrolidin-2-one; 1-[(2-methyl-1H-benzimidazol-1-yl)methyl]-4-propylpyrrolidin-2-one; 4-propyl-1-[(2-propyl-1H-benzimidazol-1-yl)methyl]pyrrolidin-2-one; 1-[(2-isopropyl-1H-benzimidazol-1-yl)methyl]-4-propylpyrrolidin-2-one; 4-propyl-1-{[2-(trifluoromethyl)-1H-benzimidazol-1-yl]methyl}pyrrolidin-2-one; 1-{[2-(methylthio)-1H-benzimidazol-1-yl]methyl}-4-propylpyrrolidin-2-one; 1-[(2-amino-1H-benzimidazol-1-yl)methyl]-4-propylpyrrolidin-2-one; 1-{[2-(chloromethyl)-1H-benzimidazol-1-yl]methyl}-4-propylpyrrolidin-2-on-e; {1-[(2-oxo-4-propylpyrrolidin-1-yl)methyl]-1H-benzimidazol-2-yl}acetoni-trile; 1-[(5-methoxy-1H-benzimidazol-1-yl)methyl]-4-propylpyrrolidin-2-one-; 1-[(5-methyl-1H-benzimidazol-1-yl)methyl]-4-propylpyrrolidin-2-one; 1-[(5,6-dimethyl-1H-benzimidazol-1-yl)methyl]-4-propylpyrrolidin-2-one; 1-{[2-isopropyl-5-(trifluoromethyl)-1H-benzimidazol-1-yl]methyl}-4-propylpyrrolidin-2-one; 1-[(6-chloro-1H-benzimidazol-1-yl)methyl]-4-propylpyrrolidin-2-one; 1-[(2-oxo-4-propylpyrrolidin-1-yl)methyl]-2-propyl-1H-benzimidazole-5-car-bonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl]methyl}pyrrolidin-2-one; 1-[(5-fluoro-2-propyl-1H-benzimidazol-1-yl)methyl]-4-propylpyrrolidin-2-one; 1-{[6-methyl-2-(1H-pyrrol-2-yl)-1H-benzimidazol-1-yl]methyl}-4-pro-pylpyrrolidin-2-one; 1-[(6-methoxy-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-{[2-[2-(methylthio)ethyl]-5-(trifluoromethyl)-1H-benzimidazol-1-yl]methyl}-4-propylpyrrolidin-2-one; 1-[(5-fluoro-2-isobutyl-1H-benzimidazol-1-yl)methyl]-4-propylpyrrolidin-2-one; 1-{[5-fluoro-2-(2,4,4-trimethylpentyl)-1H-benzimidazol-1-yl]methyl}-2-cyclopropyl-1-[(2-oxo-4-propylpyrrolidin-1-yl)methyl]-1H-benzimidazole-5-carbonitrile; 1-[(2-oxo-4-propylpyrrolidin-1-yl)methyl]-2-(1H-pyrazol-3-yl)-1H-benzimidazole-5-carbonitrile; 1-[(2-cyclopropyl-5-fluoro-1H-benzimidazol-1-yl)methyl]-4-propylpyrrolidin-2-one; 1-[(5-fluoro-2-isopropyl-1H-benzimidazol-1-yl)methyl]-4-propylpyrrolidin-2-one; 1-{[2-(3-furyl)-6-methoxy-1H-benzimidazol-1-yl]methyl}-4-propylpyrrolidin-2-one; 1-[(2-cyclopropyl-6-methoxy-1H-benzimidazol-1-yl)methyl]-4-propylp-yrrolidin-2-one; 1-[(2-isopropyl-6-methoxy-1H-benzimidazol-1-yl)methyl]-4-propylpyrrolidin-2-one; 1-[(2-oxo-4-propylpyrrolidin-1-yl)methyl]-2-(1,2,3-thiadiazol-4-yl-)-1H-benzimidazole-5-carbonitrile; 1-{[2-(1H-imidazol-2-yl)-5-(trifluoromethyl)-1H-benzimidazol-1-yl]methyl}-4-propylpyrrolidin-2-one; 1-{[5-fluoro-2-(2,2,2-trifluoroethyl)-1H-benzimidazol-1-yl]methyl}-4-propylpyrrolidin-2-one; 1-{[2-(1-ethylpropyl)-6-methoxy-1H-benzimidazol-1-yl]methyl}-4-propylpyrr-olidin-2-one; 1-{[6-methoxy-2-(1-methyl-1H-pyrrol-2-yl)-1H-benzimidazol-1-yl]methyl}-4-propylpyrrolidin-2-one; 1-{[2-(2-furyl)-5-(trifluoromethyl)-1H-benzimidazol-1-yl]methyl}-4-propyl-pyrrolidin-2-one; 4-propyl-1-{[2-thien-2-yl-5-(trifluoromethyl)-1H-benzimidazol-1-yl]methyl-}pyrrolidin-2-one; 1-{[2-(3-furyl)-5-(trifluoromethyl)-1H-benzimidazol-1-yl]methyl}-4-propyl-pyrrolidin-2-one; 1-{[2-cyclopropyl-5-(trifluoromethyl)-1H-benzimidazol-1-yl]methyl}-4-propylpyrrolidin-2-one; 4-propyl-1-{[2-(1H-pyrrol-2-yl)-5-(trifluoromethyl)-1H-benzimidazol-1-yl]-methyl}pyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 4-fluoro-1-(1H-imidazol-1-ylmethyl)-1,3-dihydro-2H-indol-2-one; 4-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(2-oxo-2,3-dihydro-1H-indol-1-yl)methyl]-1H-imidazole-5-carbonitrile; and 1-[(5-chloro-2-oxo-2,3-dihydro-1H-indol-1-yl)methyl]-1H-imidazole-5-c-arbonitrile.

In some embodiments, compounds useful in the methods and compositions of this invention are selected from the group consisting of: 1-(1H-imidazol-1-ylmethyl)pyrrolidin-2-one, 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylm-ethyl)pyrrolidin-2-one; (+)-4-(3-azido-2,4-difluorophenyl)-1-(1H-imidazol-1-ylmethyl)pyrrolidin-2-one; 1-[(2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-[(2-methyl-1H-imidazol-1-yl)methyl]-4-phenylpyrrolidin-2-one; 4-(4-fluorophenyl)-1-(1H-imidazol-1-ylmethyl)pyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylm-ethyl)pyrrolidin-2-one; 4-(3,5-difluorophenyl)-1-(1H-imidazol-1-ylmethyl)pyrrolidin-2-one; 4-(3,4-difluorophenyl)-1-(1H-imidazol-1-ylmethyl)pyrrolidin-2-one; 4-(3-chloro-4-fluorophenyl)-1-(1H-imidazol-1-ylmethyl)pyrrolidin-2-one; 4-(4-chlorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(11H-imidazol-1-ylmethyl)-4-(2,3,5-trifluorophenyl)pyrrolidin-2-one; 1-(1H- imidazol-1-ylmethyl)-4-(2,4,5-trifluorophenyl)pyrrolidin-2-one; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-4-carbonitrile; 1-{[2-oxo-4-(3,4,5-trifluorophenyl)pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; (+); 1-{[2-oxo-4-(3,4,5-trifluorophenyl)pyrrolidin-1-yl]methyl}-1H-imidazole-4-carbonitrile; 1-[(2-chloro-1H-imidazol-1-yl)methyl]-4-(3,4,5-trifluorophenyl)pyrrolidin-2-one; 1-[2-azido-1-(1H-imidazol-1-yl)ethyl]-4-propylpyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl]methyl}pyrrolidin-2-one; 1-[(5-fluoro-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-[(5-fluoro-2-isopropyl-1H-benzimidazol-1-yl)methyl]-4-propylpyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbo-nitrile.

In some embodiments, compounds useful in the methods and compositions of this invention are selected from the group consisting of: 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 4-(2,2-difluorovinyl)-1-(1H-imidazol-1-ylmethyl)pyrrolidin-2-on-e; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-[(2-methyl-1H-imidazol-1-yl)methyl]-4-phenylpyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl)pyrrolidin-2-one; (+)-1-(1H-imidazol-1-ylmethyl)-4-phenylpyrrolidin-2-one; (−)-1-(1H-imidazol-1-ylmethyl)-4-phenylpyrrolidin-2-one; 1-[(2-chloro-1H-imidazol-1-yl)methyl]-4-(3,4,5-trifluorophenyl)pyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbo-nitrile.

In some embodiments, compounds useful in the methods and compositions of this invention are selected from the group consisting of: (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 4-(3-azido-2,4-difluorophenyl)-1-(1H-imidazol-1-ylmethyl)pyrrolidin-2-one.

v) International Patent Application WO 2007/065595:

Compounds having formula I, their enantiomers, diastereoisomers and mixtures thereof (including all possible mixtures of stereoisomers), or pharmaceutically acceptable salts thereof,

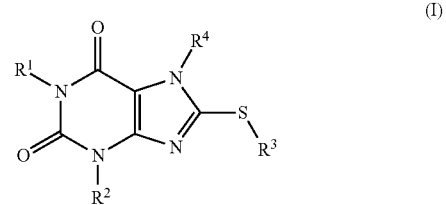

wherein
$R^1$ is hydrogen or $C_{1-6}$ alkyl;
$R^2$ is hydrogen or $C_{1-4}$ alkyl;
$R^3$ is a group of formula —$CHR^5R^6$ or a benzyl group;
$R^4$ is $C_{1-8}$ alkyl optionally substituted by alkoxycarbonyl, C3-6 cycloalkyl, aryl or heterocycle;
$R^5$ is C2-4 alkyl;
$R^6$ is C2-4 alkyl, amido or —$COOR^7$;
$R^7$ is C1-4 alkyl;

Usually when $R^3$ is a benzyl group, then $R^4$ is $C_{1-8}$ alkyl optionally substituted by alkoxycarbonyl.

Usually when $R^3$ is a group of formula —$CHR^5R^6$ then $R^4$ is $C_{1-8}$ alkyl optionally substituted by $C_{3-6}$ cycloalkyl, aryl or heterocycle.

The term "alkyl", as used herein, is a group which represents saturated, monovalent hydrocarbon radicals having straight (unbranched) or branched moieties, or combinations thereof, and containing 1-8 carbon atoms, preferably 1-6 carbon atoms; more preferably alkyl groups have 1-4 carbon atoms. Alkyl moieties may optionally be substituted by 1 to 5 substituents independently selected from the group consisting of hydroxy, alkoxy, cyano, ethynyl, alkoxycarbonyl, acyl, aryl or heterocycle. Alkyl moieties may be optionally substituted by a cycloalkyl as defined hereafter. Preferred alkyl groups are methyl, cyanomethyl, ethyl, 2-ethoxy-2-oxoethyl, 2-methoxyethyl, n-propyl, 2-oxopropyl, 3-hydroxypropyl, 2-propynyl, n-butyl, i-butyl, n-pentyl, 3-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl or (5-nitro-2-furyl)methyl. More preferred alkyl groups are methyl, ethyl, cyanomethyl, 2-methoxyethyl, n-propyl, 3-hydroxypropyl, 2-propynyl, n-butyl, 3-pentyl, n-hexyl, benzyl, 3-bromobenzyl, 3-methoxybenzyl, 3-nitrobenzyl, 3-aminobenzyl, (3,5-dimethylisoxazol-4-yl)

methyl or (5-nitro-2-furyl)methyl. Most preferred alkyl groups are methyl, ethyl, 3-methoxybenzyl, 3-nitrobenzyl or (5-nitro-2-furyl)methyl.

The term "cycloalkyl", as used herein, represents a monovalent group of 3 to 8, preferably 3 to 6 carbon atoms derived from a saturated cyclic hydrocarbon, which may be substituted by any suitable group including but not limited to one or more moieties selected from groups as described above for the alkyl groups. Preferred cycloalkyl group is cyclohexyl.

The term "aryl" as used herein, is defined as a phenyl group optionally substituted by 1 to 4 substituents independently selected from halogen, amino, nitro, alkoxy or aminosulfonyl. Preferred aryl groups are phenyl, 2-bromophenyl, 3-bromophenyl, 4-bromophenyl, 3-methoxyphenyl, 3-nitrophenyl, 3-aminophenyl or 4-(aminosulfonyl)phenyl.

The term "phenyl", as used herein, represents an aromatic hydrocarbon group of formula —$C_6H_5$.

The term "benzyl group", as used herein, represents a group of formula —$CH_2$-aryl. Preferred benzyl groups are benzyl, 2-bromobenzyl, 3-bromobenzyl, 4-bromobenzyl, 3-methoxybenzyl, 3-nitrobenzyl, 3-aminobenzyl or 4-(aminosulfonyl)benzyl. More preferred benzyl groups are benzyl, 3-bromobenzyl, 3-methoxybenzyl, 3-nitrobenzyl or 3-aminobenzyl. Most preferred alkyl groups are 3-methoxybenzyl or 3-nitrobenzyl.

The term "halogen", as used herein, represents an atom of fluorine, chlorine, bromine, or iodine. Preferred halogen is bromine.

The term "hydroxy", as used herein, represents a group of formula —OH.

The term "cyano", as used herein, represents a group of formula —CN.

The term "amino", as used herein, represents a group of formula —$NH_2$.

The term "ethynyl", as used herein, represents a group of formula —C≡CH.

The term "alkoxy", as used herein, represents a group of formula —$OR^a$ wherein $R^a$ is an alkyl group, as defined above. Preferred alkoxy group is methoxy.

The term "nitro", as used herein, represents a group of formula —$NO_2$.

The term "amido", as used herein, represents a group of formula —C(=O)NH2.

The term "acyl", as used herein, represents a group of formula —C(=O)$R^b$ wherein $R^b$ is an alkyl group, as defined here above. Preferred acyl group is acetyl (—C(=O)Me).

The term "alkoxycarbonyl (or ester)", as used herein, represents a group of formula —$COOR^c$ wherein $R^c$ is an alkyl group; with the proviso that $R^c$ does not represent an alkyl alpha-substituted by hydroxy. Preferred alkoxycarbonyl group is ethoxycarbonyl.

The term "heterocycle", as used herein, represents a 5-membered ring containing one or two heteroatoms selected from O or N. The heterocycle may be substituted by one or two $C_{1-4}$ alkyl or nitro. Preferred heterocycles are (3,5-dimethylisoxazol-4-yl) or (5-nitro-2-furyl). Most preferred heterocycle is (5-nitro-2-furyl).

Generally $R^1$ is hydrogen or $C_{1-6}$ alkyl. Usually $R^1$ is hydrogen or $C_{1-6}$ alkyl optionally substituted by hydroxy, alkoxy, cyano, ethynyl, alkoxycarbonyl or acyl. Preferably $R^1$ is hydrogen, methyl, cyanomethyl, 2-ethoxy-2-oxoethyl, 2-methoxyethyl, n-propyl, 2-oxopropyl, 2-hydroxypropyl, 2-propynyl, n-pentyl or n-hexyl. More preferably $R^1$ is hydrogen, methyl, cyanomethyl, 2-methoxyethyl, n-propyl, 3-hydroxypropyl or 2-propynyl. Most preferably $R^1$ is hydrogen.

Generally $R^2$ is hydrogen or $C_{1-4}$ alkyl. Usually $R^2$ is hydrogen or unsubstituted $C_{1-4}$ alkyl. Preferably $R^2$ is hydrogen, methyl or n-butyl. More preferably, $R^2$ is methyl.

Generally $R^3$ is a group of formula —$CHR^5R^6$ or a benzyl group. Preferably $R^3$ is 3-pentyl, 1-(aminocarbonyl)propyl, 1-(ethoxycarbonyl)propyl or 3-bromobenzyl. Most preferably $R^3$ is 1-(ethoxycarbonyl)propyl.

Generally $R^4$ is $C_{1-8}$ alkyl optionally substituted by alkoxycarbonyl, $C_{3-6}$ cycloalkyl, aryl or heterocycle. Usually $R^4$ is $C_{1-8}$ alkyl optionally substituted by cyclohexyl, phenyl, bromophenyl, aminophenyl, methoxyphenyl, nitrophenyl, aminosulfonylphenyl, 3,5-dimethylisoxazol-4-yl, 5-nitro-2-furyl or ethoxycarbonyl. Preferably $R^4$ is n-butyl, i-butyl, n-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl, (5-nitro-2-furyl)methyl or 1-(ethoxycarbonyl)propyl. More preferably $R^4$ is n-butyl, n-hexyl, benzyl, 3-bromobenzyl, 3-methoxybenzyl, 3-nitrobenzyl, 3-aminobenzyl, (3,5-dimethylisoxazol-4-yl)methyl, (5-nitro-2-furyl)methyl or 1-(ethoxycarbonyl)propyl. Most preferably $R^4$ is 3-methoxybenzyl, 3-nitrobenzyl or (5-nitro-2-furyl)methyl.

Generally $R^5$ is $C_{2-4}$ alkyl. Usually $R^5$ is unsubstituted $C_{2-4}$ alkyl. Preferably $R^5$ is ethyl.

Generally $R^6$ is $C_{2-4}$ alkyl, amido or —$COOR^7$. Usually $R^6$ is unsubstituted $C_{2-4}$ alkyl, amido or —$COOR^7$. Preferably $R^6$ is ethyl, amido or ethoxycarbonyl. Most preferably $R^6$ is ethoxycarbonyl.

Generally $R^7$ is $C_{1-4}$ alkyl. Usually $R^7$ is unsubstituted $C_{1-4}$ alkyl. Preferably, $R^7$ is ethyl.

In some embodiments, the compounds are those having formula I, and their enantiomers, diastereoisomers and mixtures thereof (including all possible mixtures of stereoisomers), or pharmaceutically acceptable salts thereof,

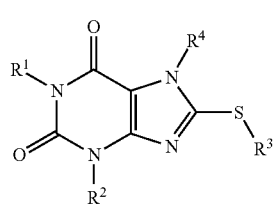

(I)

wherein
$R^1$ is hydrogen, $C_{1-6}$ alkyl optionally substituted by hydroxy, alkoxy, cyano, ethynyl, alkoxycarbonyl or acyl;
$R^2$ is hydrogen or unsubstituted $C_{1-4}$ alkyl;
$R^3$ is a group of formula —$CHR^5R^6$ or a benzyl group;
$R^4$ is $C_{1-8}$ alkyl optionally substituted by cyclohexyl, phenyl, bromophenyl, aminophenyl, methoxyphenyl, nitrophenyl, aminosulfonylphenyl, 3,5-dimethylisoxazol-4-yl, 5-nitro-2-furyl or ethoxycarbonyl;
$R^5$ is unsubstituted $C_{2-4}$ alkyl;
$R^6$ is unsubstituted $C_{2-4}$ alkyl, amido or —$COOR^7$;
$R^7$ is unsubstituted $C_{1-4}$ alkyl;
with the proviso that when $R^1$ is hydrogen, $R^2$ is methyl, $R^3$ is —$CHR^5R^6$, $R^6$ is ethoxycarbonyl and $R^5$ is ethyl, then $R^4$ is different from n-propyl, i-propyl, n-pentyl, n-heptyl, 3-bromobenzyl, 4-chlorobenzyl, 4-methylbenzyl or 2-phenylethyl.

In the above embodiment, preferably, when $R^3$ is a benzyl group, then $R^4$ is $C_{1-8}$ alkyl optionally substituted by alkoxycarbonyl.

In the above embodiment, preferably, when $R^3$ is a group of formula —$CHR^5R^6$, then $R^4$ is $C_{1-8}$ alkyl optionally substituted by $C_{3-6}$ cycloalkyl, aryl or heterocycle.

In a preferred embodiment, $R^1$ is hydrogen, methyl, cyanomethyl, 2-ethoxy-2-oxoethyl, 2-methoxyethyl, n-propyl, 2-oxopropyl, 3-hydroxypropyl, 2-propynyl, n-pentyl or n-hexyl;

$R^2$ is hydrogen, methyl or n-butyl;

$R^3$ is 3-pentyl, 1-(aminocarbonyl)propyl, 1-(ethoxycarbonyl)propyl or 3-bromobenzyl;

$R^4$ is n-butyl, i-butyl, n-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl, (5-nitro-2-furyl)methyl or 1-(ethoxycarbonyl) propyl;

with the proviso that when $R^1$ is hydrogen, $R^2$ is methyl and $R^3$ is 1-(ethoxycarbonyl)propyl, then $R^4$ is different from n-pentyl, 3-bromobenzyl or 2-phenylethyl.

In the above embodiment, preferably, when $R^3$ is 3-bromobenzyl, then $R^4$ is $C_{1-8}$ alkyl optionally substituted by alkoxycarbonyl.

In the above embodiment, preferably, when $R^3$ is 3-pentyl, 1-(aminocarbonyl)propyl or 1-(ethoxycarbonyl)propyl, then $R^4$ is different from 1-(ethoxycarbonyl)propyl.

In a more preferred embodiment, $R^1$ is hydrogen, methyl, cyanomethyl, 2-methoxyethyl, n-propyl, 3-hydroxypropyl or 2-propynyl;

$R^2$ is methyl;

$R^3$ is 3-pentyl, 1-(aminocarbonyl)propyl, 1-(ethoxycarbonyl)propyl or 3-bromobenzyl;

$R^4$ is n-butyl, n-hexyl, benzyl, 3-bromobenzyl, 3-methoxybenzyl, 3-nitrobenzyl, 3-aminobenzyl, (3,5-dimethylisoxazol-4-yl)methyl, (5-nitro-2-furyl)methyl or 1-(ethoxycarbonyl)propyl;

with the proviso that when $R^1$ is hydrogen, $R^2$ is methyl and $R^3$ is 1-(ethoxycarbonyl)propyl, then $R^4$ is different from 3-bromobenzyl.

In the above embodiment, preferably, when $R^3$ is 3-bromobenzyl, then $R^4$ is 1-(ethoxycarbonyl)propyl; In the above embodiment, preferably, when $R^3$ is 3-pentyl, 1-(aminocarbonyl)propyl or 1-(ethoxycarbonyl)propyl, then $R^4$ is different from 1-(ethoxycarbonyl)propyl;

In a most preferred embodiment, $R^1$ is hydrogen; $R^2$ is methyl; $R^3$ is 1-(ethoxycarbonyl)propyl; and $R^4$ is 3-methoxybenzyl, 3-nitrobenzyl or (5-nitro-2-furyl)methyl.

A further embodiment consists in compounds wherein $R^2$ is methyl, $R^3$ is a group of formula —$CHR^5R^6$ with $R^5$ being $C_{2-4}$ alkyl, $R^6$ being amido or —$COOR^7$ and $R^7$ being methyl or ethyl.

In some embodiments, compounds useful in the methods and compositions of this invention are selected from the group consisting of: ethyl 2-[(7-benzyl-1,3-dimethyl-2,6-dioxo-2,3,6,7-tetrahydro-1H-purin-8-yl)thio]butanoate; ethyl 2-{[7-(3-bromobenzyl)-1-(2-ethoxy-2-oxoethyl)-3-methyl-2,6-dioxo-2,3,6,7-tetrahydro-1H-purin-8-yl]thio}butanoate; ethyl 2-{[7-(3-bromobenzyl)-1-(2-methoxyethyl)-3-methyl-2,6-dioxo-2,3,6,7-tetrahydro-1H-purin-8-yl]thio}butanoate; ethyl 2-{[7-(3-bromobenzyl)-2,6-dioxo-2,3,6,7-tetrahydro-1H-purin-8-yl]thio}butanoate; ethyl 2-{[7-(3-bromobenzyl)-1,3-dimethyl-2,6-dioxo-2,3,6,7-tetrahydro-1H-purin-8-yl]thio}butanoate; ethyl 2-{[7-(2-bromobenzyl)-1,3-dimethyl-2,6-dioxo-2,3,6,7-tetrahydro-1H-purin-8-yl]thio}butanoate; ethyl 2-{[7-(3-bromobenzyl)-1-(cyanomethyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-propyl-2,3,6,7-tetrahydro-1H-purin-8-yl]thio}butanoate; ethyl 2-{[7-(3-bromobenzyl)-3-methyl-2,6-dioxo-1-(2-oxopropyl)-2,3,6,7-tetrahydro-1H-purin-8-yl]thio}butanoate; ethyl 2-{[7-(3-bromobenzyl)-1-(3-hydroxypropyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-(2-propynyl)-2,3,6,7-tetrahydro-1H-purin-8-yl]thio}butanoate; ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; ethyl 2-{[7-(3-aminobenzyl)-3-methyl-2,6-dioxo-2,3,6,7-tetrahydro-1H-purin-8-yl]thio}butanoate; ethyl 2-({7-[4-(aminosulfonyl)benzyl]-3-methyl-2,6-dioxo-2,3,6,7-tetrahydro-1H-purin-8-yl}thio)butanoate; ethyl 2-{[7-(4-bromobenzyl)-1,3-dimethyl-2,6-dioxo-2,3,6,7-tetrahydro-1H-purin-8-yl]thio}butanoate; ethyl 2-{[7-(cyclohexylmethyl)-1,3-dimethyl-2,6-dioxo-2,3,6,7-tetrahydro-1H-purin-8-yl]thio}butanoate; ethyl 2-{[1,3-dimethyl-2,6-dioxo-7-(1-phenylethyl)-2,3,6,7-tetrahydro-1H-purin-8-yl]thio}butanoate; ethyl 2-{[1,3-dimethyl-2,6-dioxo-7-(2-phenylethyl)-2,3,6,7-tetrahydro-1H-purin-8-yl]thio}butanoate; ethyl 2-({7-[(3,5-dimethylisoxazol-4-yl)methyl]-3-methyl-2,6-dioxo-2,3,6,7-tetrahydro-1H-purin-8-yl}thio)butanoate; ethyl 2-({3-methyl-7-[(5-nitro-2-furyl)methyl]-2,6-dioxo-2,3,6,7-tetrahydro-1H-purin-8-yl}thio)butanoate; ethyl 2-[(7-butyl-3-methyl-2,6-dioxo-2,3,6,7-tetrahydro-1H-purin-8-yl)thio]butanoate; ethyl 2-{[7-(3-bromobenzyl)-2,6-dioxo-2,3,6,7-tetrahydro-1H-purin-8-yl]thio}butanoate; ethyl 2-[(1,7-dihexyl-3-methyl-2,6-dioxo-2,3,6,7-tetrahydro-1H-purin-8-yl)thio]butanoate; ethyl 2-[(7-hexyl-3-methyl-2,6-dioxo-2,3,6,7-tetrahydro-1H-purin-8-yl)thio]butanoate; ethyl 2-[(3-methyl-2,6-dioxo-1,7-dipentyl-2,3,6,7-tetrahydro-1H-purin-8-yl)thio]butanoate; 2-{[7-(3-bromobenzyl)-3-methyl-2,6-dioxo-2,3,6,7-tetrahydro-1H-purin-8-yl]thio}butanamide; 2-[(7-butyl-3-methyl-2,6-dioxo-2,3,6,7-tetrahydro-1H-purin-8-yl)thio]butanamide; 7-(3-bromobenzyl)-8-[(1-ethylpropyl)thio]-3-methyl-3,7-dihydro-1H-purine-2,6-dione; ethyl 2-{8-[(3-bromobenzyl)thio]-1,3-dimethyl-2,6-dioxo-1,2,3,6-tetrahydro-7H-purin-7-yl}butanoate; and ethyl 2-[(7-isobutyl-3-methyl-2,6-dioxo-2,3,6,7-tetrahydro-1H-purin-8-yl)thio]butanoate.

In some embodiments, compounds useful in the methods and compositions of this invention are selected from the group consisting of: ethyl 2-[(7-benzyl-1,3-dimethyl-2,6-dioxo-2,3,6,7-tetrahydro-1H-purin-8-yl)thio]butanoate; ethyl 2-{[7-(3-bromobenzyl)-1-(2-methoxyethyl)-3-methyl-2,6-dioxo-2,3,6,7-tetrahydro-1H-purin-8-yl]thio}butanoate; ethyl 2-{[7-(3-bromobenzyl)-1,3-dimethyl-2,3,6,7-tetrahydro-1H-purin-8-yl]thio}butanoate; ethyl 2-{[7-(3-bromobenzyl)-1-(cyanomethyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-propyl-2,3,6,7-tetrahydro-1H-purin-8-yl]thio}butanoate; ethyl 2-{[7-(3-bromobenzyl)-1-(3-hydroxypropyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-(2-propynyl)-2,3,6,7-tetrahydro-1H-purin-8-yl]thio}butanoate; ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]

thio}butanoate; ethyl 2-{[7-(3-aminobenzyl)-3-methyl-2,6-dioxo-2,3,6,7-tetrahydro-1H-purin-8-yl]thio}butanoate; ethyl 2-({7-[(3,5-dimethylisoxazol-4-yl)methyl]-3-methyl-2,6-dioxo-2,3,6,7-tetrahydro-1H-purin-8-yl}thio)butanoate; ethyi 2-({3-methyi-7-[(5-nitro-2-furyl)methyl]-2,6-dioxo-2, 3,6,7-tetrahydro-1H-purin-8-yl}thio)butanoate; ethyl 2-[(7-butyl-3-methyl-2,6-dioxo-2,3,6,7-tetrahydro-1H-purin-8-yl)thio]butanoate; ethyl 2-[(7-hexyl-3-methyl-2,6-dioxo-2,3,6, 7-tetrahydro-1H-purin-8-yl)thio]butanoate; 2-{[7-(3-bromobenzyl)-3-methyl-2,6-dioxo-2,3,6,7-tetrahydro-1H-purin-8-yl]thio}butanamide; 7-(3-bromobenzyl)-8-[(1-ethylpropyl)thio]-3-methyl-3,7-dihydro-1H-purine-2,6-dione; and ethyl 2-{8-[(3-bromobenzyl)thio]-1,3-dimethyl-2,6-dioxo-1,2,3,6-tetrahydro-7H-purin-7-yl}butanoate.

In some embodiments, compounds useful in the methods and compositions of this invention are selected from the group consisting of: ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; and ethyl 2-({3-methyl-7-[(5-nitro-2-furyl)methyl]-2,6-dioxo-2, 3,6,7-tetrahydro-1H-purin-8-yl}thio)butanoate.

In some embodiments, the compounds are those having formula II, their enantiomers, diastereoisomers and mixtures thereof (including all possible mixtures of stereoisomers), or pharmaceutically acceptable salts:

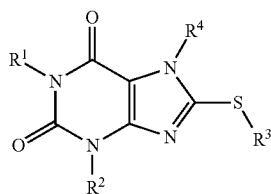

(II)

wherein R.sup.1 is hydrogen or C.sub.1-6 alkyl;
R.sup.2 is hydrogen or C.sub.1-4 alkyl;
R.sup.3 is a group of formula —CHR.sup.5R.sup.6 or a benzyl group;
R.sup.4 is C.sub.1-8 alkyl optionally substituted by alkoxycarbonyl, C.sub.3-6 cycloalkyl, aryl or heterocycle;
R.sup.5 is hydrogen or C.sub.1-4 alkyl;
R.sup.6 is C.sub.1-4 alkyl, amido or —COOR.sup.7;
R.sup.7 is C.sub.1-4 alkyl;

In the above embodiment, in some cases, when R.sup.3 is a benzyl group, then R.sup.4 is C.sub.1-8 alkyl optionally substituted by alkoxycarbonyl.

In the above embodiment, in some cases, when R.sup.3 is a group of formula —CHR.sup.5R.sup.6, then R.sup.4 is C.sub.1-8 alkyl optionally substituted by C.sub.3-6 cycloalkyl, aryl or heterocycle.

In some embodiments, the compounds are those compounds of formula II, their enantiomers, diastereoisomers and mixtures thereof (including all possible mixtures of stereoisomers), or pharmaceutically acceptable salts

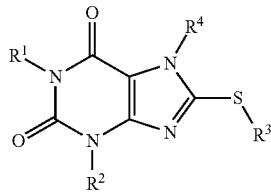

(II)

wherein
R.sup.1 is hydrogen or C.sub.1-6 alkyl;
R.sup.2 is hydrogen or C.sub.1-4 alkyl;
R.sup.3 is a group of formula —CHR.sup.5R.sup.6 or a benzyl group;
R.sup.4 is C.sub.1-8 alkyl optionally substituted by alkoxycarbonyl, C.sub.3-6 cycloalkyl, aryl or heterocycle;
R.sup.5 is hydrogen or C.sub.1-4 alkyl;
R.sup.6 is C.sub.1-4 alkyl, amido or —COOR.sup.7;
R.sup.7 is C.sub.1-4 alkyl.

In some embodiments, the compounds are compounds of formula II selected from ethyl 2-[(7-heptyl-3-methyl-2,6-dioxo-2,3,6,7-tetrahydro-1H-purin-8-yl)thio]butanoate; 7-(3-bromobenzyl)-3-methyl-8-(propylthio)-3,7-dihydro-1H-purine-2,-6-dione; ethyl 2-[(3-methyl-2,6-dioxo-7-pentyl-2,3,6,7-tetrahydro-1H-purin-8-yl)thio]but-anoate; ethyl 2-{[7-(3-bromobenzyl)-3-methyl-2,6-dioxo-2,3,6,7-tetrahydro-1H-purin-8-yl-]thio}butanoate; ethyl 2-[(3-methyl-2, 6-dioxo-7-propyl-2,3,6,7-tetrahydro-1H-purin-8-yl)thio] but-anoate; 7-(3-bromobenzyl)-8-[(3-chloro-2-hydroxypropyl)thio]-3-methyl-3,7-dihydro-1H-purine-2,6-dione; and ethyl 2-{[7-(3-bromobenzyl)-3-methyl-2,6-dioxo-2,3,6,7-tetrahydro-1H-purin-8-yl-]thio}propanoate.

In some embodiments, the compounds are compounds of formula I, their enantiomers, diastereoisomers and mixtures thereof (including all possible mixtures of stereoisomers), or pharmaceutically acceptable salts

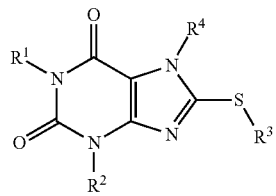

(I)

wherein
R.sup.1 is hydrogen or C.sub.1-6 alkyl;
R.sup.2 is hydrogen or C.sub.1-4 alkyl; R.sup.3 is a group of formula —CHR.sup.5R.sup.6 or a benzyl group;
R.sup.4 is C.sub.1-8 alkyl optionally substituted by alkoxycarbonyl, C.sub.3-6 cycloalkyl, aryl or heterocycle;
R.sup.5 is C.sub.2-4 alkyl;
R.sup.6 is C.sub.2-4 alkyl, amido or —COOR.sup.7;
R.sup.7 is C.sub.1-4 alkyl;

In another embodiment, the compounds are compounds having formula II, their enantiomers, diastereoisomers and mixtures thereof (including all possible mixtures of stereoisomers), or pharmaceutically acceptable salts thereof,

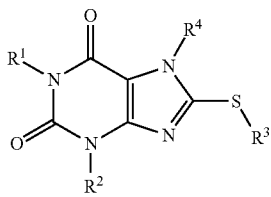

(II)

wherein
R.sup.1 is hydrogen or C.sub.1-6 alkyl;
R.sup.2 is hydrogen or C.sub.1-4 alkyl;
R.sup.3 is a group of formula —CHR.sup.5R.sup.6 or a benzyl group;

R.sup.4 is C.sub.1-8 alkyl optionally substituted by alkoxycarbonyl, C.sub.3-6 cycloalkyl, aryl or heterocycle;
R.sup.5 is hydrogen or C.sub.1-4 alkyl;
R.sup.6 is C.sub.1-4 alkyl, amido or —COOR.sup.7;
R.sup.7 is C.sub.1-4 alkyl;

vi) International Patent Application Publication No. WO2010/144712

In one embodiment, a chemical composition that includes a LEV derivative of Formula 1 or Formula 2 is disclosed.

Formula 1

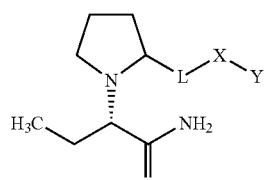

Formula 2

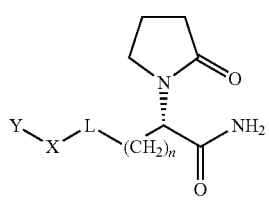

n of Formula 2 and L, X, and Y of Formulas 1 and 2 are defined as follows: a) n is an integer with a value of 0 to 8; b) L is one of the group consisting of CH2, CO, NHCO, NHCOO, CONH, NH, O, or S, and combinations thereof; c) X is an end group, an aromatic group, an aryl group, or a saturated, unsaturated, substituted, unsubstituted, straight chain, or branched chain aliphatic group having from 1 to 10 carbon and/or hetero chain atoms, the hetero chain atoms being selected from the group consisting of oxygen, nitrogen, sulfur, or phosphorus, and combinations thereof; and d) Y is optional and if present is one of a functional group selected from group consisting of alcohol amine, amide, carboxylic acid, aldehyde, ester, iminoester, isocyanate, isothiocyanate, anhydride, thiol, thiolacetone, diazonium, NHS, CO—NHS, O—NHS, maleimido; or e) Y is a Yi-Z where Yi is selected from the group consisting of COO, CO, O, CONH, NHCO, or NH and Z is an operative group.

In one embodiment of the method, the operative group of Z is selected from the group consisting of detectable labels, antigenic carriers, coupling agents, end groups, proteins, lipoproteins, glycoproteins, polypeptides, polysaccharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, and combinations thereof.

vii) International Patent Application Publication No. WO2010/002869

The present invention provides a compound of Formula I:

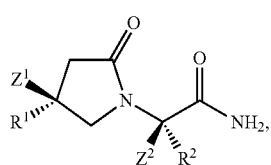

(I)

or a pharmaceutically acceptable salt thereof, wherein: each Z is independently selected from hydrogen and deuterium; R1 is an n-propyl group having zero to seven deuterium atoms; R2 is an ethyl group having zero to five deuterium atoms, and when each R has zero deuterium atoms, at least one Z is deuterium. One embodiment of this invention provides compounds of Formula I wherein R1 is selected from CD3CH2CH2-, CD3CD2CH2-, CD3CH2CD2-, CH3CH2CD2-, CH3CD2CD2-, CD3CD2CD2- or CH3CH2CH2-. In a more specific embodiment, R1 is CD3CD2CD2- or CD3CD2CH2-. In one aspect of these embodiments, Z1 and Z2 are both hydrogen. In another aspect of these embodiments, Z1 and Z2 are both deuterium. In another embodiment, R2 is selected from CH3CH2-, CD3CH2-, CH3CD2-, or CD3CD2-. In a more specific embodiment, R2 is selected from CH3CH2- or CD3CD2-. In one aspect of these embodiments, Z1 and Z2 are both hydrogen. In another aspect of these embodiments, Z1 and Z2 are both deuterium.

The R and Z variables as described above may be selected and taken together to provide more specific embodiments of this invention. For example, in one embodiment, R1 is CD3CH2CH2-, CD3CD2CH2-, CD3CH2CD2-, CH3CH2CD2-, CH3CD2CD2-, CD3CD2CD2- or CH3CH2CH2-; and R2 is selected from CH3CH2-, CD3CH2-, CH3CD2-, or CD3CD2-. In one aspect of this embodiment, R2 is CH3CH2- or CD3CD2-. [0039] In another embodiment, R1 is CD3CD2CD2- or CD3CD2CH2-; and R2 is selected from CH3CH2-, CD3CH2-, CH3CD2-, or CD3CD2-. In one aspect of this embodiment, R2 is CH3CH2- or CD3CD2-.

Examples of specific compounds of this invention include the following:

Compound 100

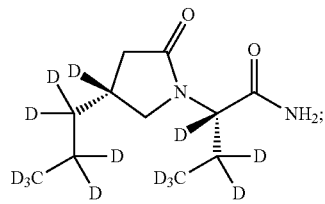

Compound 101

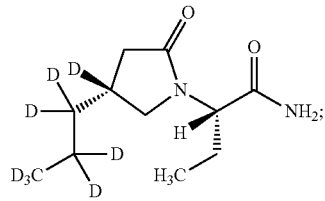

Compound 102

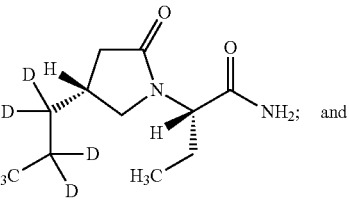

and

-continued

Compound 103

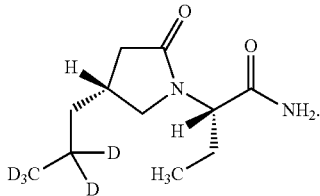

viii) 20090312333

The compounds of the present invention are those covered by formula (I), their diastereomers and mixtures, or a pharmaceutically acceptable salt thereof.

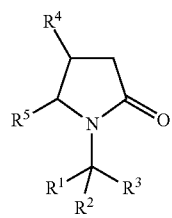
(I)

R1 is hydrogen, substituted or unsubstituted C1-12 alkyl, substituted or unsubstituted aryl or substituted or unsubstituted 3-8 membered heterocycle.
R2 is hydrogen. Alternatively, R1 and R2 may be linked together in such a way to form a C3-6 cycloalkyl.
R3 is either
(a) a substituted or unsubstituted heterocycle linked to the rest of the molecule via one of its C atoms, said heterocycle is selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl;
indolizin-3-yl;
or R3 is
(b) a substituted or unsubstituted heterocycle linked to the rest of the molecule via one of its N atoms, said heterocycle is selected from the group consisting of:
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1-yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-pyrrol-1-yl;
2-chloro-1H-benzimidazol-1-yl.
R4 in formula (I) is selected from the group comprising or consisting of hydrogen; C1-12 alkyl optionally substituted by halogen, C1-4 alkoxy, C1-4 alkylthio, azido, nitrooxy or an aryl; C2-12 alkenyl optionally substituted by halogen; C2-12 alkynyl optionally substituted by halogen; azido; alkoxycarbonylamino; arylsulfonyloxy; a substituted or unsubstituted aryl; or a 3-8 membered substituted or unsubstituted heterocycle;
In a specific embodiment R4 is hydrogen; or R4 is C1-12 alkyl or a C1-6 alkyl, optionally substituted by halogen, C1-4 alkoxy, C1-4 alkylthio, azido or nitrooxy; or R4 is C2-12 alkenyl or a C1-6 alkenyl optionally substituted by halogen; or R4 is C2-12 alkynyl or a C1-6 alkynyl optionally substituted by halogen; or R4 is alkoxycarbonylamino.
R5 is hydrogen;
Alternatively R4 may form together with R5 and the 2-oxo-1-pyrrolidine ring a 1,3-dihydro-2H-indol-2-one ring of the following structure:

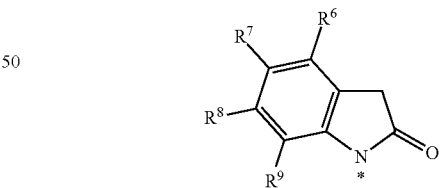

The asterisk * indicates the point of attachment of the substituents;
R6 is hydrogen or halogen.
R7 in formula (I) is selected from the group comprising or consisting of hydrogen; nitro; halogen; heterocycle; amino; aryl; C1-12 alkyl optionally substituted by at least one halogen; or C1-12 alkoxy optionally substituted by at least one halogen.
R8 in formula (I) is selected from the group comprising or consisting of hydrogen, C1-12 alkyl optionally substituted by halogen, or halogen.

R9 in formula (I) is selected from the group comprising or consisting of hydrogen, C1-12 alkyl optionally substituted by halogen, or halogen.

A further aspect of the present invention consists in compounds of formula (I) wherein
R1 and R2 are both hydrogen.
R3 is:
(a) a substituted or unsubstituted heterocycle linked to the rest of the molecule via one of its C atoms selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl;
indolizin-3-yl.
Alternatively R3 is:
(b) a substituted or unsubstituted heterocycle linked to the rest of the molecule via one of its N atoms selected from the group consisting of:
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1-yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-pyrrol-1-yl;
2-chloro-1H-benzimidazol-1-yl.
R4 in formula (I) is selected from the group comprising or consisting of hydrogen; C1-12 alkyl optionally substituted by halogen or C1-4 alkoxy; C2-12 alkenyl optionally substituted by halogen; C2-12 alkynyl optionally substituted by halogen. In a further specific embodiment R4 is n-propyl, 2,2,2-trifluoroethyl, 2-chloro-2,2-difluoroethyl, 2 bromo-2, 2-difluoroethyl, 2,2-difluorovinyl.

In another specific embodiment R4 is phenyl, 2,3,5-trifluorophenyl or 3-chloro-4-fluorophenyl.
R5 is hydrogen;
A further embodiment of the present invention consists in compounds of formula (I) wherein R4 forms together with R5a 1,3-dihydro-2H-indol-2-one ring

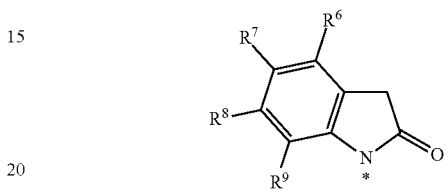

The asterisk * indicates the point of attachment of the heteroaryl alkylene substituent, and wherein
R6 is hydrogen;
R7 is chlorine;
R8 is hydrogen;
R9 is hydrogen.
A further embodiment of the present invention consists in compounds of formula (I) wherein R3 is a substituted or unsubstituted heterocycle linked to the rest of the molecule via one of its C atoms and is selected from the group consisting of:
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridin-3-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1,3-thiazol-5-yl;
[1,2,4]triazolo[4,3-b]pyridazin-8-yl;
indolizin-3-yl.
In a further specific embodiment R3 is a heterocycle linked to the rest of the molecule via one of its C atoms and is selected from the group consisting of:
imidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-pyrazol-4-yl;
1H-pyrazolo[1,5-a]pyrimidin-3-yl;

pyridin-3-yl;
1H-pyrrolo[2,3-b]pyridin-3-yl;
1H-pyrrolo[2,3-b]pyridin-4-yl;
1,3-thiazol-5-yl;

Said heterocycles are optionally substituted by e.g. a methyl, n-propyl, trifluoromethyl, cyclopropyl, bromine, chlorine, fluorine, iodine, methoxy, ethoxy, propoxy, isopropoxy, cyclopropyloxy, cyclopropylmethoxy, cyclobutylmethoxy, amino, methylamino, cyclopropylamino, cyclobutylamino, 1-pyrrolidinyl, cyano, phenyl, benzyl or 3-thienyl.

In a further specific embodiment R3 is a heterocycle linked to the rest of the molecule via one of its C atoms and is selected from the group consisting of: 6-chloro-2-cyclopropylimidazo[1,2-b]pyridazin-3-yl, 6-(cyclopropyloxy)-2-(trifluoromethyl)imidazo[1,2-b]pyridazin-3-yl, 6-propoxy-2-(trifluoromethyl)imidazo[1,2-b]pyridazin-3-yl, 6-chloroimidazo[2,1-b][1,3]thiazol-5-yl, 2,6-dichloroimidazo[2,1-b][1,3]thiazol-5-yl, 5-chloro-1H-imidazol-4-yl, 5-bromo-1H-imidazol-4-yl, 4-bromo-1H-imidazol-5-yl, 4-chloro-1H-imidazol-5-yl, 1H-imidazol-5-yl, 1-methyl-1H-imidazol-5-yl, 4-chloro-1-methyl-1H-imidazol-5-yl, 1H-pyrazol-4-yl, 1H-pyrrolo[2,3-b]pyridin-3-yl.

A further embodiment of the present invention consists in compounds of formula (I) wherein R3 is a heterocycle linked to the rest of the molecule via one of its C atoms and is a substituted or unsubstituted imidazo[1,2-a]pyridin-3-yl.

Said imidazo[1,2-a]pyridin-3-yl is optionally substituted by e.g. a methyl, cyclopropyl, bromine, chlorine, fluorine, iodine.

In a further specific embodiment R3 is a heterocycle linked to the rest of the molecule via one of its C atoms and is selected from the group consisting of: imidazo[1,2-a]pyridin-3-yl, 6-methylimidazo[1,2-a]pyridin-3-yl, 2-chloroimidazo[1,2-a]pyridin-3-yl.

A further embodiment of the present invention consists in compounds of formula (I) wherein R3 is a substituted or unsubstituted heterocycle linked to the rest of the molecule via one of its N atoms and is selected from the group consisting of:
3H-imidazo[4,5-b]pyridin-3-yl;
1H-indol-1-yl;
1H-pyrrolo[2,3-b]pyridin-1-yl;
1H-pyrrolo[3,2-b]pyridin-1-yl;
1H-pyrrol-1-yl;
2-chloro-1H-benzimidazol-1-yl.

A specific further embodiment of the present invention consists in compounds of formula (I) wherein R3 is a heterocycle linked to the rest of the molecule via one of its N atoms and is selected from the group consisting of:
3H-imidazo[4,5-b]pyridin-3-yl;
1H-pyrrolo[3,2-b]pyridin-1-yl;
1H-pyrrol-1-yl;
2-chloro-1H-benzimidazol-1-yl;

Said heterocycles may optionally be substituted by trifluoromethyl, cyclopropyl, bromine, chlorine, fluorine, methoxy or cyano.

In a further specific embodiment R3 is a heterocycle linked to the rest of the molecule via one of its C atoms and is selected from the group consisting of 6-bromo-2-chloro-3H-imidazo[4,5-b]pyridin-3-yl, 6-bromo-2-cyclopropyl-3H-imidazo[4,5-b]pyridin-3-yl, 1H-pyrrolo[3,2-b]pyridin-1-yl, 2,5-dichloro-1H-pyrrol-1-yl, 2-chloro-5-methoxy-1H-benzimidazol-1-yl, 5-bromo-2-chloro-1H-benzimidazol-1-yl or 2,5-dichloro-1H-benzimidazol-1-yl.

A further embodiment of the present invention consists in compounds of formula (I) wherein R1, R2 and R5 are hydrogen.

R4 is a C1-6 alkyl optionally substituted by halogen, a C2-6 alkenyl optionally substituted by halogen or C2-12 alkynyl optionally substituted by halogen.

R3 is selected from the group consisting of
imidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-pyrazol-4-yl;
1H-pyrazolo[1,5-a]pyrimidin-3-yl;
pyridin-3-yl;
1H-pyrrolo[2,3-b]pyridin-3-yl;
1H-pyrrolo[2,3-b]pyridin-4-yl;
1,3-thiazol-5-yl;
and optionally substituted by methyl, n-propyl, trifluoromethyl, cyclopropyl, bromine, chlorine, fluorine, iodine, methoxy, ethoxy, propoxy, isopropoxy, cyclopropyloxy, cyclopropylmethoxy, cyclobutylmethoxy, amino, methylamino, cyclopropylamino, cyclobutylamino, 1-pyrrolidinyl, cyano, phenyl, benzyl or 3-thienyl.

A further embodiment of the present invention consists in compounds of formula (I) wherein R1, R2 and R5 are hydrogen.

R4 is a C1-6 alkyl optionally substituted by halogen, a C2-6 alkenyl optionally substituted by halogen or C2-12 alkynyl optionally substituted by halogen.

R3 is selected from the group consisting of
3H-imidazo[4,5-b]pyridin-3-yl;
1H pyrrolo[3,2-b]pyridin-1-yl;
1H-pyrrol-1-yl; 2-chloro-1H-benzimidazol-1-yl;
optionally substituted by trifluoromethyl, cyclopropyl, bromine, chlorine, fluorine, methoxy or cyano.

A further embodiment of the invention consists in compounds of formula (I), their diastereomers and mixtures, or a pharmaceutically acceptable salt thereof.

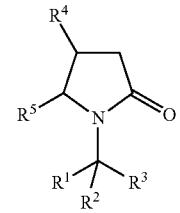

R1, R2 and R5 are hydrogen.
R3 is a substituted or unsubstituted heterocycle linked to the rest of the molecule via one of its C atoms, said heterocycle is selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;

1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl;
indolizin-3-yl;

Particularly preferred are imidazo[1,2-a]pyridin-3-yl; imidazo[1,2-a]pyrimidin-3-yl; imidazo[1,2-b]pyridazin-3-yl; 1H-imidazol-4-yl; 1H-imidazol-5-yl;
R4 is a substituted or unsubstituted phenyl moiety;

A further embodiment of the present invention consists in compounds of formula (I) wherein R1 is hydrogen or C1-12 alkyl;
R2 is hydrogen;
R3 is an aromatic 5-membered heterocycle linked to the rest of the molecule via one of its C atoms;
R4 is hydrogen, C1-12 alkyl or aryl;
R5 is hydrogen;

Alternatively, R4 can form together with R5 and the 2-oxo-1-pyrrolidine ring the following 1,3-dihydro-2H-indol-2-one cycle

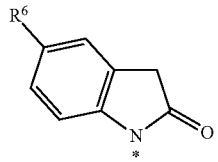

wherein the asterisk * indicates the point of attachment of the substituents;
R6 is hydrogen or halogen;

In this embodiment R4 may not be hydrogen when R3 is substituted 1H-pyrazol-5-yl. Also this embodiment does not comprise 5-(2'-oxo-1'-pyrrolidinyl)methyl-1,3,4-tricarbomethoxy-pyrazole which is disclosed in A. Padwa et al J. Org. Chem. 2000, 65, 5223-5232 without any biological activity though.

In this embodiment wherein R3 is an aromatic 5-membered heterocycle linked to the rest of the molecule via one of its C atoms, specific moieties R3 may be selected from 1,3-thiazol-5-yl, 1H-imidazol-4-yl, 1H-imidazol-5-yl, 1H-pyrazol-4-yl, 1H-pyrazol-5-yl, 2-oxo-2,3-dihydro-1,3-thiazol-5-yl, each of them being optionally substituted by 1 to 3 substituents independently selected from methyl, chlorine, bromine, amino, methylamino, dimethylamino, (2-oxo-4-propyl-pyrrolidin-1-yl)methyl, 1-pyrrolidinyl, amido, cyano, methoxy, phenyl, 4-methylphenyl-sulfonyl, benzyl or 2-(benzylamino)-2-oxoethyl.

In this embodiment, more specific moieties R3 are selected from 2-(methylamino)-1,3-thiazol-5-yl; 2-pyrrolidin-1-yl-1,3-thiazol-5-yl; 5-bromo-1H-imidazol-4-yl; 5-chloro-1H-imidazol-4-yl; 1H-imidazol-5-yl; 1-methyl-1H-imidazol-5-yl; 4-bromo-1-methyl-1H-imidazol-5-yl; 4-chloro-1H-imidazol-5-yl; 4-chloro-1-methyl-1H-imidazol-5-yl; 4-cyano-1-methyl-1H-imidazol-5-yl; 1H-pyrazol-4-yl; 3,5-dimethyl-1H-pyrazol-4-yl; 3-methyl-1H-pyrazol-4-yl.

In this embodiment, most specific moieties R3 are selected from 5-bromo-1H-imidazol-4-yl; 5-chloro-1H-imidazol-4-yl; 1H-imidazol-5-yl; 4-bromo-1-methyl-1H-imidazol-5-yl; 4-chloro-1-methyl-1H-imidazol-5-yl; 1H-pyrazol-4-yl.

Still in this embodiment, a specific moiety R1 is selected from hydrogen or ethyl.

Still in this embodiment, a specific moiety R4 is selected from hydrogen, n-propyl, 2,3,5-trifluorophenyl or phenyl.

A further embodiment of the present invention consists in compounds having the specific formula (Ia).

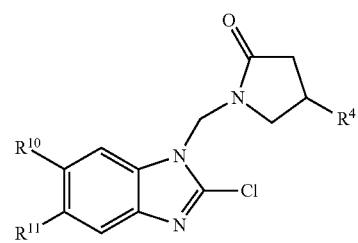

(Ia)

In formula (Ia) the substituent R10 is hydrogen; halogen; C1-4 alkyl optionally substituted by at least one halogen; C1-4 alkoxy; methoxycarbonyl; nitro; amino; alkylamino; amido; or alkanoyl-amino. Preferably R10 is hydrogen.

R11 is hydrogen; halogen; C1-4 alkyl optionally substituted by at least one halogen; C1-4 alkoxy; methoxycarbonyl; nitro; amino; alkylamino; amido; or alkanoylamino. Preferably R11 is hydrogen.

R4 is C1-4 alkyl optionally substituted by at least one halogen; or C2-4 alkenyl optionally substituted by at least one halogen. Preferably R4 is n-propyl.

Still in this aspect of the invention a specific embodiment relates to an embodiment wherein R10 is selected from hydrogen; methyl; fluorine; chlorine; bromine; methoxy; methoxycarbonyl; nitro; or trifluoromethyl, while R11 is selected from hydrogen; methyl; fluorine; chlorine; bromine; methoxy; methoxycarbonyl; nitro; or trifluoromethyl; and R3 is n-propyl.

Specific compounds of the present invention are those selected from the group consisting of:
1-[(1-methyl-1H-benzimidazol-6-yl)methyl]-4-propylpyrrolidin-2-one;
1-(1H-benzimidazol-7-ylmethyl)-4-propylpyrrolidin-2-one;
1-(imidazo[1,2-a]pyridin-3-ylmethyl)-4-propylpyrrolidin-2-one;
1-{[6-chloro-2-(4-methylphenyl)imidazo[1,2-a]pyridin-3-yl]methyl}-4-propylpyrrolidin-2-one;
1-{[2-(4-chlorophenyl)-6-methylimidazo[1,2-a]pyridin-3-yl]methyl}-4-propylpyrrolidin-2-one;
1-[(5-methylimidazo[1,2-a]pyridin-3-yl)methyl]-4-phenylpyrrolidin-2-one;

1-(imidazo[1,2-a]pyridin-3-ylmethyl)-4-phenylpyrrolidin-2-one;
1-[(6-methylimidazo[1,2-a]pyridin-3-yl)methyl]-4-propylpyrrolidin-2-one;
1-[(6-bromoimidazo[1,2-a]pyridin-3-yl)methyl]-4-propylpyrrolidin-2-one;
1-[(8-methylimidazo[1,2-a]pyridin-3-yl)methyl]-4-propylpyrrolidin-2-one;
1-[(6-iodoimidazo[1,2-a]pyridin-3-yl)methyl]-4-propylpyrrolidin-2-one;
1-{[8-chloro-6-(trifluoromethyl)imidazo[1,2-a]pyridin-3-yl]methyl}-4-propylpyrrolidin-2-one;
1-[(7-methylimidazo[1,2-a]pyridin-3-yl)methyl]-4-propylpyrrolidin-2-one;
1-[(6,8-dibromoimidazo[1,2-a]pyridin-3-yl)methyl]-4-propylpyrrolidin-2-one;
1-[(6,8-dichloroimidazo[1,2-a]pyridin-3-yl)methyl]-4-propylpyrrolidin-2-one;
1-[(6-chloroimidazo[1,2-a]pyridin-3-yl)methyl]-4-propylpyrrolidin-2-one;
1-[(2-chloroimidazo[1,2-a]pyridin-3-yl)methyl]-4-propylpyrrolidin-2-one;
1-[(2-cyclopropyl-6-fluoroimidazo[1,2-a]pyridin-3-yl)methyl]-4-(2,2-difluorovinyl)pyrrolidin-2-one;
1-[(6-chloro-2-cyclopropylimidazo[1,2-a]pyridin-3-yl)methyl]-4-(2,2-difluorovinyl)pyrrolidin-2-one;
1-(imidazo[1,2-a]pyrimidin-3-ylmethyl)-4-propylpyrrolidin-2-one;
1-{[2-(4-chlorophenyl)imidazo[1,2-a]pyrimidin-3-yl]methyl}-4-propyl pyrrolidin-2-one;
1-(imidazo[1,2-a]pyrimidin-3-ylmethyl)-4-phenylpyrrolidin-2-one;
1-[(6-chloroimidazo[1,2-a]pyrimidin-3-yl)methyl]-4-propylpyrrolidin-2-one;
1-{[6-chloro-2-(trifluoromethyl)imidazo[1,2-a]pyrimidin-3-yl]methyl}-4-propylpyrrolidin-2-one;
1-[(6-phenylimidazo[1,2-b][1,2,4]triazin-7-yl)methyl]-4-propylpyrrolidin-2-one;
1-{[6-chloro-2-(4-methylphenyl)imidazo[1,2-b]pyridazin-3-yl]methyl}-4-propylpyrrolidin-2-one;
1-{[6-chloro-2-(4-chlorophenyl)imidazo[1,2-b]pyridazin-3-yl]methyl}-4-propylpyrrolidin-2-one;
1-[(6-chloroimidazo[1,2-b]pyridazin-3-yl)methyl]-4-propylpyrrolidin-2-one;
1-[(6-chloroimidazo[1,2-b]pyridazin-3-yl)methyl]-4-phenylpyrrolidin-2-one;
1-{[6-chloro-2-(trifluoromethyl)imidazo[1,2-b]pyridazin-3-yl]methyl}-4-propylpyrrolidin-2-one;
1-{[6-chloro-2-(trifluoromethyl)imidazo[1,2-b]pyridazin-3-yl]methyl}-4-(2,3,5-trifluorophenyl)pyrrolidin-2-one;
1-{[6-chloro-2-(trifluoromethyl)imidazo[1,2-b]pyridazin-3-yl]methyl}pyrrolidin-2-one;
1-{[6-chloro-2-(trifluoromethyl)imidazo[1,2-b]pyridazin-3-yl]methyl}-4-(2,2-difluorovinyl)pyrrolidin-2-one;
1-{[6-chloro-2-(trifluoromethyl)imidazo[1,2-b]pyridazin-3-yl]methyl}-4-phenylpyrrolidin-2-one;
5-chloro-1-{[6-chloro-2-(trifluoromethyl)imidazo[1,2-b]pyridazin-3-yl]methyl}-1,3-dihydro-2H-indol-2-one;
1-{[6-methoxy-2-(trifluoromethyl)imidazo[1,2-b]pyridazin-3-yl]methyl}-4-propylpyrrolidin-2-one;
1-[(6-chloro-2-cyclopropylimidazo[1,2-b]pyridazin-3-yl)methyl]-4-propylpyrrolidin-2-one;
1-{[6-isopropoxy-2-(trifluoromethyl)imidazo[1,2-b]pyridazin-3-yl]methyl}-4-propylpyrrolidin-2-one;
1-{[6-(benzyloxy)-2-(trifluoromethyl)imidazo[1,2-b]pyridazin-3-yl]methyl}-4-propylpyrrolidin-2-one;
1-{[6-cyclopropyl-2-(trifluoromethyl)imidazo[1,2-b]pyridazin-3-yl]methyl}-4-propylpyrrolidin-2-one;
1-{[6-(dimethylamino)-2-(trifluoromethyl)imidazo[1,2-b]pyridazin-3-yl]methyl}-4-propylpyrrolidin-2-one;
4-(2,2-difluorovinyl)-1-{[6-methoxy-2-(trifluoromethyl)imidazo[1,2-b]pyridazin-3-yl]methyl}pyrrolidin-2-one;
4-(2-chloro-2,2-difluoroethyl)-1-{[6-chloro-2-(trifluoromethyl)imidazo[1,2-b]pyridazin-3-yl]methyl}pyrrolidin-2-one;
1-{[6-(methylamino)-2-(trifluoromethyl)imidazo[1,2-b]pyridazin-3-yl]methyl}-4-propylpyrrolidin-2-one;
1-{[6-hydroxy-2-(trifluoromethyl)imidazo[1,2-b]pyridazin-3-yl]methyl}-4-propylpyrrolidin-2-one;
1-{[6-(methylthio)-2-(trifluoromethyl)imidazo[1,2-b]pyridazin-3-yl]methyl}-4-propylpyrrolidin-2-one;
4-(2-bromo-2,2-difluoroethyl)-1-{[6-chloro-2-(trifluoromethyl)imidazo[1,2-b]pyridazin-3-yl]methyl}pyrrolidin-2-one;
1-{[6-(methylsulfonyl)-2-(trifluoromethyl)imidazo[1,2-b]pyridazin-3-yl]methyl}-4-propylpyrrolidin-2-one;
1-{[6-(methylsulfinyl)-2-(trifluoromethyl)imidazo[1,2-b]pyridazin-3-yl]methyl}-4-propylpyrrolidin-2-one;
1-{[6-chloro-2-(trifluoromethyl)imidazo[1,2-b]pyridazin-3-yl]methyl}-4-(2,2,2-trifluoroethyl)pyrrolidin-2-one;
1-[(6-chloro-2-cyclobutylimidazo[1,2-b]pyridazin-3-yl)methyl]-4-propylpyrrolidin-2-one;
1-{[6-chloro-2-(4-methylphenyl)imidazo[1,2-b]pyridazin-3-yl]methyl}-4-(2,2-difluorovinyl)pyrrolidin-2-one;
1-{[6-amino-2-(trifluoromethyl)imidazo[1,2-b]pyridazin-3-yl]methyl}-4-propylpyrrolidin-2-one;
1-{[6-(ethylamino)-2-(trifluoromethyl)imidazo[1,2-b]pyridazin-3-yl]methyl}-4-propylpyrrolidin-2-one;
4-propyl-1-{[6-(propylamino)-2-(trifluoromethyl)imidazo[1,2-b]pyridazin-3-yl]methyl}pyrrolidin-2-one;
4-(2-bromo-2,2-difluoroethyl)-1-{[6-(propylamino)-2-(trifluoromethyl)imidazo[1,2-b]pyridazin-3-yl]methyl}pyrrolidin-2-one;
4-(2,2-difluorovinyl)-1-{[6-(propylamino)-2-(trifluoromethyl)imidazo[1,2-b]pyridazin-3-yl]methyl}pyrrolidin-2-one;
4-(2,2-difluorovinyl)-1-{[6-methoxy-2-(4-methylphenyl)imidazo[1,2-b]pyridazin-3-yl]methyl}pyrrolidin-2-one;
4-propyl-1-{[6-pyrrolidin-1-yl-2-(trifluoromethyl)imidazo[1,2-b]pyridazin-3-yl]methyl}pyrrolidin-2-one;
4-(2-bromo-2,2-difluoroethyl)-1-{[6-methoxy-2-(trifluoromethyl)imidazo[1,2-b]pyridazin-3-yl]methyl}pyrrolidin-2-one;
1-{[6-(cyclopropylamino)-2-(trifluoromethyl)imidazo[1,2-b]pyridazin-3-yl]methyl}-4-(2,2-difluorovinyl)pyrrolidin-2-one;
1-[(6-chloro-2-cyclopropylimidazo[1,2-b]pyridazin-3-yl)methyl]-4-(2,2-difluorovinyl)pyrrolidin-2-one;
4-(2,2-difluorovinyl)-1-{[6-(isopropylamino)-2-(trifluoromethyl)imidazo[1,2-b]pyridazin-3-yl]methyl}pyrrolidin-2-one;
4-(2,2-difluorovinyl)-1-{[2-(trifluoromethyl)imidazo[1,2-b]pyridazin-3-yl]methyl}pyrrolidin-2-one;
1-{[2-cyclopropyl-6-(propylamino)imidazo[1,2-b]pyridazin-3-yl]methyl}-4-(2,2-difluorovinyl)pyrrolidin-2-one;
1-({2-cyclopropyl-6-[(2-fluoroethyl)amino]imidazo[1,2-b]pyridazin-3-yl}methyl)-4-(2,2-difluorovinyl)pyrrolidin-2-one;
1-({2-cyclopropyl-6-[(2,2-difluoroethyl)amino]imidazo[1,2-b]pyridazin-3-yl}methyl)-4-(2,2-difluorovinyl)pyrrolidin-2-one;

1-({2-cyclopropyl-6-[(2,2,2-trifluoroethyl)amino]imidazo[1,2-b]pyridazin-3-yl}methyl)-4-(2,2-difluorovinyl)pyrrolidin-2-one;
4-(2,2-difluoroethyl)-1-{[2-(trifluoromethyl)imidazo[1,2-b]pyridazin-3-yl]methyl}pyrrolidin-2-one;
1-{[2-cyclopropyl-6-(cyclopropylamino)imidazo[1,2-b]pyridazin-3-yl]methyl}-4-(2,2-difluorovinyl)pyrrolidin-2-one;
1-[(6-chloro-2-cyclobutylimidazo[1,2-b]pyridazin-3-yl)methyl]-4-(2,2-difluorovinyl)pyrrolidin-2-one;
1-[(6-chloro-2-cyclopropylimidazo[1,2-b]pyridazin-3-yl)methyl]-4-(3-chloro-4-fluorophenyl)pyrrolidin-2-one;
1-{[6-(butylamino)-2-(trifluoromethyl)imidazo[1,2-b]pyridazin-3-yl]methyl}-4-(2,2-difluorovinyl)pyrrolidin-2-one;
1-{[6-(cyclobutylamino)-2-(trifluoromethyl)imidazo[1,2-b]pyridazin-3-yl]methyl}-4-(2,2-difluorovinyl)pyrrolidin-2-one;
1-[(2-cyclopropyl-6-methoxyimidazo[1,2-b]pyridazin-3-yl)methyl]-4-(2,2-difluorovinyl)pyrrolidin-2-one;
4-(2,2-difluorovinyl)-1-{[6-ethoxy-2-(trifluoromethyl)imidazo[1,2-b]pyridazin-3-yl]methyl}pyrrolidin-2-one;
4-(2,2-difluorovinyl)-1-{[6-isopropoxy-2-(trifluoromethyl)imidazo[1,2-b]pyridazin-3-yl]methyl}pyrrolidin-2-one;
1-{[6-(cyclopropylmethoxy)-2-(trifluoromethyl)imidazo[1,2-b]pyridazin-3-yl]methyl}-4-(2,2-difluorovinyl)pyrrolidin-2-one;
1-{[6-(cyclobutylmethoxy)-2-(trifluoromethyl)imidazo[1,2-b]pyridazin-3-yl]methyl}-4-(2,2-difluorovinyl)pyrrolidin-2-one;
1-{[6-(cyclopropyloxy)-2-(trifluoromethyl)imidazo[1,2-b]pyridazin-3-yl]methyl}-4-(2,2-difluorovinyl)pyrrolidin-2-one;
4-(2,2-difluorovinyl)-1-{[6-propoxy-2-(trifluoromethyl)imidazo[1,2-b]pyridazin-3-yl]methyl}pyrrolidin-2-one;
3-{[4-(2,2-difluorovinyl)-2-oxopyrrolidin-1-yl]methyl}-2-(trifluoromethyl)imidazo[1,2-b]pyridazine-6-carbonitrile;
4-(2,2-difluorovinyl)-1-{[6-thien-3-yl-2-(trifluoromethyl)imidazo[1,2-b]pyridazin-3-yl]methyl}pyrrolidin-2-one;
4-(2,2-difluorovinyl)-1-{[6-phenyl-2-(trifluoromethyl)imidazo[1,2-b]pyridazin-3-yl]methyl}pyrrolidin-2-one;
4-(2,2-difluorovinyl)-1-{[6-methyl-2-(trifluoromethyl)imidazo[1,2-b]pyridazin-3-yl]methyl}pyrrolidin-2-one;
4-(2,2-difluorovinyl)-1-{[6-pyridin-3-yl-2-(trifluoromethyl)imidazo[1,2-b]pyridazin-3-yl]methyl}pyrrolidin-2-one;
4-propyl-1-{[2-(trifluoromethyl)-5,6,7,8-tetrahydroimidazo[1,2-b]pyridazin-3-yl]methyl}pyrrolidin-2-one;
1-[(6-methylimidazo[2,1-b][1,3,4]thiadiazol-5-yl)methyl]-4-propylpyrrolidin-2-one;
1-{[6-(4-methylphenyl)imidazo[2,1-b][1,3,4]thiadiazol-5-yl]methyl}-4-propylpyrrolidin-2-one;
1-[(2-cyclopropyl-6-phenylimidazo[2,1-b][1,3,4]thiadiazol-5-yl)methyl]-4-propylpyrrolidin-2-one;
1-[(6-methylimidazo[2,1-b][1,3]thiazol-5-yl)methyl]-4-propylpyrrolidin-2-one;
1-[(6-chloroimidazo[2,1-b][1,3]thiazol-5-yl)methyl]-4-propylpyrrolidin-2-one;
1-[(2,6-dichloroimidazo[2,1-b][1,3]thiazol-5-yl)methyl]-4-propylpyrrolidin-2-one;
1-(3H-imidazo[4,5-b]pyridin-7-ylmethyl)-4-propylpyrrolidin-2-one;
1-(3H-imidazo[4,5-b]pyridin-7-ylmethyl)-4-phenylpyrrolidin-2-one;
4-phenyl-1-[(5-phenyl-3H-imidazo[4,5-b]pyridin-7-yl)methyl]pyrrolidin-2-one;
4-phenyl-1-{[5-(trifluoromethyl)-3H-imidazo[4,5-b]pyridin-7-yl]methyl}pyrrolidin-2-one;
1-[(6-bromo-3H-imidazo[4,5-b]pyridin-7-yl)methyl]-4-propylpyrrolidin-2-one;
1-[(2-phenyl-3H-imidazo[4,5-b]pyridin-7-yl)methyl]-4-propylpyrrolidin-2-one;
1-[(5-methyl-3H-imidazo[4,5-b]pyridin-7-yl)methyl]-4-propylpyrrolidin-2-one;
1-[(2-methyl-3H-imidazo[4,5-b]pyridin-7-yl)methyl]-4-propylpyrrolidin-2-one;
4-propyl-1-{[5-(trifluoromethyl)-3H-imidazo[4,5-b]pyridin-7-yl]methyl}pyrrolidin-2-one;
1-[(6-methyl-3H-imidazo[4,5-b]pyridin-7-yl)methyl]-4-propylpyrrolidin-2-one;
1-[(6-phenyl-3H-imidazo[4,5-b]pyridin-7-yl)methyl]-4-propylpyrrolidin-2-one;
1-[1-(1H-imidazol-4-yl)propyl]pyrrolidin-2-one;
1-[(5-methyl-1H-imidazol-4-yl)methyl]pyrrolidin-2-one;
1-[(2-methyl-1H-imidazol-4-yl)methyl]pyrrolidin-2-one;
1-(1H-imidazol-4-ylmethyl)-4-propylpyrrolidin-2-one;
1-({1-[(2-oxo-4-propylpyrrolidin-1-yl)methyl]-1H-imidazol-4-yl}methyl)-4-propylpyrrolidin-2-one;
1-[(5-chloro-1H-imidazol-4-yl)methyl]-4-(2,3,5-trifluorophenyl)pyrrolidin-2-one;
1-[(5-bromo-1H-imidazol-4-yl)methyl]-4-(2,3,5-trifluorophenyl)pyrrolidin-2-one;
1-[(5-bromo-1H-imidazol-4-yl)methyl]-5-chloro-1,3-dihydro-2H-indol-2-one;
1-(1H-imidazol-5-ylmethyl)pyrrolidin-2-one;
1-[(1-methyl-1H-imidazol-5-yl)methyl]pyrrolidin-2-one;
1-methyl-5-[(2-oxopyrrolidin-1-yl)methyl]-1H-imidazole-4-carbonitrile;
1-(1H-imidazol-5-ylmethyl)-4-phenylpyrrolidin-2-one;
1-[(1-methyl-1H-imidazol-5-yl)methyl]-4-phenylpyrrolidin-2-one;
1-[(4-methoxy-1-methyl-1H-imidazol-5-yl)methyl]pyrrolidin-2-one;
1-[(1-methyl-1H-imidazol-5-yl)methyl]-4-propylpyrrolidin-2-one;
1-methyl-5-[(2-oxo-4-propylpyrrolidin-1-yl)methyl]-1H-imidazole-4-carbonitrile;
1-methyl-5-[(2-oxo-4-propylpyrrolidin-1-yl)methyl]-1H-imidazole-4-carboxamide;
N-benzyl-2-{5-[(2-oxo-4-propylpyrrolidin-1-yl)methyl]-1H-imidazol-1-yl}acetamide;
1-methyl-5-[(2-oxo-4-propylpyrrolidin-1-yl)methyl]-1H-imidazole-2-carbonitrile;
1-[(4-chloro-1H-imidazol-5-yl)methyl]-4-propylpyrrolidin-2-one;
1-methyl-5-{[2-oxo-4-(2,3,5-trifluorophenyl)pyrrolidin-1-yl]methyl}-1H-imidazole-4-carbonitrile;
1-[(4-bromo-1-methyl-1H-imidazol-5-yl)methyl]-4-propylpyrrolidin-2-one;
1-[(2,4-dichloro-1-methyl-1H-imidazol-5-yl)methyl]-4-propylpyrrolidin-2-one;
benzyl 1-methyl-5-[(2-oxo-4-propylpyrrolidin-1-yl)methyl]-1H-imidazol-2-ylcarbamate;
1-[(4-chloro-1-methyl-1H-imidazol-5-yl)methyl]-4-propylpyrrolidin-2-one;
1-[(2-chloro-1-methyl-1H-imidazol-5-yl)methyl]-4-propylpyrrolidin-2-one;
5-chloro-1-(1H-imidazol-5-ylmethyl)-1,3-dihydro-2H-indol-2-one;
1-[(2,4-dichloro-1H-imidazol-5-yl)methyl]-4-(2,3,5-trifluorophenyl)pyrrolidin-2-one;
1-[(2,4-dichloro-1-methyl-1H-imidazol-5-yl)methyl]-4-(2,3,5-trifluorophenyl)pyrrolidin-2-one;
1-[(2-chloro-1-methyl-1H-imidazol-5-yl)methyl]-4-(2,3,5-trifluorophenyl)pyrrolidin-2-one;

1-[(4-bromo-1-methyl-1H-imidazol-5-yl)methyl]-4-(2,3,5-trifluorophenyl)pyrrolidin-2-one;
5-chloro-1-[(1-methyl-1H-imidazol-5-yl)methyl]-1,3-dihydro-2H-indol-2-one;
1-[(4-chloro-1-methyl-1H-imidazol-5-yl)methyl]-4-(2,3,5-trifluorophenyl)pyrrolidin-2-one;
1-(1H-indol-2-ylmethyl)-4-propylpyrrolidin-2-one;
1-(1H-indol-3-ylmethyl)-4-propylpyrrolidin-2-one;
3-[(2-oxo-4-propylpyrrolidin-1-yl)methyl]-1H-indole-5-carbonitrile;
1-[(2-methyl-1H-indol-3-yl)methyl]-4-propylpyrrolidin-2-one;
1-[(7-methoxy-1H-indol-3-yl)methyl]-4-propylpyrrolidin-2-one;
1-[(6-nitro-1H-indol-3-yl)methyl]-4-propylpyrrolidin-2-one;
4-propyl-1-{[6-(trifluoromethyl)-1H-indol-3-yl]methyl}pyrrolidin-2-one;
1-[(5-nitro-1H-indol-3-yl)methyl]-4-propylpyrrolidin-2-one;
1-[(7-fluoro-1H-indol-3-yl)methyl]-4-propylpyrrolidin-2-one;
1-[(5-chloro-2-methyl-1H-indol-3-yl)methyl]-4-propylpyrrolidin-2-one;
1-[1H-indol-3-yl(phenyl)methyl]-4-propylpyrrolidin-2-one;
1-[1-(1H-indol-3-yl)propyl]-4-propylpyrrolidin-2-one;
1-[2-furyl(1H-indol-3-yl)methyl]-4-propylpyrrolidin-2-one;
3-[(2-oxo-4-propylpyrrolidin-1-yl)(phenyl)methyl]-1H-indole-5-carbonitrile;
1-(1H-indol-4-ylmethyl)-4-propylpyrrolidin-2-one;
1-(1H-indol-7-ylmethyl)-4-propylpyrrolidin-2-one;
1-(isoxazol-4-ylmethyl)-4-propylpyrrolidin-2-one;
1-[(1-phenyl-1H-pyrazol-4-yl)methyl]-4-(2,3,5-trifluorophenyl)pyrrolidin-2-one;
1-[(1-methyl-1H-pyrazol-4-yl)methyl]-4-(2,3,5-trifluorophenyl)pyrrolidin-2-one;
1-[(1-benzyl-1H-pyrazol-4-yl)methyl]-4-(2,3,5-trifluorophenyl)pyrrolidin-2-one;
4-(2,3,5-trifluorophenyl)-1-[(1,3,5-trimethyl-1H-pyrazol-4-yl)methyl]pyrrolidin-2-one;
4-phenyl-1-(1H-pyrazol-4-ylmethyl)pyrrolidin-2-one;
1-({1-[(4-methylphenyl)sulfonyl]-1H-pyrazol-4-yl}methyl)-4-(2,3,5-trifluorophenyl)pyrrolidin-2-one;
1-(1H-pyrazol-4-ylmethyl)-4-(2,3,5-trifluorophenyl)pyrrolidin-2-one;
1-[(5-chloro-1,3-dimethyl-1H-pyrazol-4-yl)methyl]-4-(2,3,5-trifluorophenyl)pyrrolidin-2-one;
1-[(1-chloro-1H-pyrazol-4-yl)methyl]-4-(2,3,5-trifluorophenyl)pyrrolidin-2-one;
1-[(3,5-dimethyl-1H-pyrazol-4-yl)methyl]-4-(2,3,5-trifluorophenyl)pyrrolidin-2-one;
1-[(3-methyl-1H-pyrazol-4-yl)methyl]-4-(2,3,5-trifluorophenyl)pyrrolidin-2-one;
1-[(5-amino-1,3-dimethyl-1H-pyrazol-4-yl)methyl]-4-(2,3,5-trifluorophenyl)pyrrolidin-2-one;
1-[(5-amino-1-methyl-1H-pyrazol-4-yl)methyl]-4-propylpyrrolidin-2-one;
(−)-1-(1H-pyrazol-4-ylmethyl)-4-(2,3,5-trifluorophenyl)pyrrolidin-2-one;
(+)-1-(1H-pyrazol-4-ylmethyl)-4-(2,3,5-trifluorophenyl)pyrrolidin-2-one;
1-(1H-pyrazol-4-ylmethyl)-1,3-dihydro-2H-indol-2-one;
5-chloro-1-(1H-pyrazol-4-ylmethyl)-1,3-dihydro-2H-indol-2-one;
5-chloro-1-({1-[(4-methylphenyl)sulfonyl]-1H-pyrazol-4-yl}methyl)-1,3-dihydro-2H-indol-2-one;
1-{[5-chloro-1-methyl-3-(trifluoromethyl)-1H-pyrazol-4-yl]methyl}-4-propylpyrrolidin-2-one;
1-[(5-amino-1H-pyrazol-4-yl)methyl]-4-(2,3,5-trifluorophenyl)pyrrolidin-2-one;
1-[(1-benzyl-5-chloro-1H-pyrazol-4-yl)methyl]-4-propylpyrrolidin-2-one;
1-[(1,3-dimethyl-1H-pyrazol-5-yl)methyl]-4-(2,3,5-trifluorophenyl)pyrrolidin-2-one;
1-(1H-pyrazol-5-ylmethyl)-4-(2,3,5-trifluorophenyl)pyrrolidin-2-one;
1-[(4-bromo-1-methyl-1H-pyrazol-5-yl)methyl]-4-(2,3,5-trifluorophenyl)pyrrolidin-2-one;
1-[(1-methyl-1H-pyrazol-5-yl)methyl]-4-(2,3,5-trifluorophenyl)pyrrolidin-2-one;
1-[(6-bromo-2-methylpyrazolo[1,5-a]pyrimidin-3-yl)methyl]-4-propylpyrrolidin-2-one;
1-[(2-methylpyrazolo[1,5-a]pyrimidin-3-yl)methyl]-4-propylpyrrolidin-2-one;
1-[(6-bromo-2-phenylpyrazolo[1,5-a]pyrimidin-3-yl)methyl]-4-propylpyrrolidin-2-one;
1-[(6-bromo-2-thien-2-ylpyrazolo[1,5-a]pyrimidin-3-yl)methyl]-4-propylpyrrolidin-2-one;
4-propyl-1-[(2-thien-2-ylpyrazolo[1,5-a]pyrimidin-3-yl)methyl]pyrrolidin-2-one;
1-[(6-bromo-2-cyclopropylpyrazolo[1,5-a]pyrimidin-3-yl)methyl]-4-propylpyrrolidin-2-one;
1-[(6-bromo-2-tert-butylpyrazolo[1,5-a]pyrimidin-3-yl)methyl]-4-propylpyrrolidin-2-one;
1-[(2-phenylpyrazolo[1,5-a]pyrimidin-3-yl)methyl]-4-propylpyrrolidin-2-one;
1-[(2-tert-butyl-6-cyclopropylpyrazolo[1,5-a]pyrimidin-3-yl)methyl]-4-propylpyrrolidin-2-one;
1-{[2-(2-furyl)pyrazolo[1,5-a]pyrimidin-3-yl]methyl}-4-propylpyrrolidin-2-one;
1-[(2-methyl-6-thien-2-ylpyrazolo[1,5-a]pyrimidin-3-yl)methyl]-4-propylpyrrolidin-2-one;
1-[(2-methyl-6-phenylpyrazolo[1,5-a]pyrimidin-3-yl)methyl]-4-propylpyrrolidin-2-one;
1-{[2-methyl-6-(1H-pyrrol-2-yl)pyrazolo[1,5-a]pyrimidin-3-yl]methyl}-4-propylpyrrolidin-2-one;
1-({6-[(1E)-hex-1-enyl]-2-methylpyrazolo[1,5-a]pyrimidin-3-yl}methyl)-4-propylpyrrolidin-2-one;
1-[(6-chloro-2-phenylpyrazolo[1,5-a]pyrimidin-3-yl)methyl]-4-propylpyrrolidin-2-one;
1-{[2-methyl-6-(phenylethynyl)pyrazolo[1,5-a]pyrimidin-3-yl]methyl}-4-propylpyrrolidin-2-one;
1-[(6-bromo-2-phenylpyrazolo[1,5-a]pyrimidin-3-yl)methyl]-4-(2,2-difluorovinyl)pyrrolidin-2-one;
1-[(6-hydroxy-2-methylpyrazolo[1,5-a]pyrimidin-3-yl)methyl]-4-propylpyrrolidin-2-one;
1-[(6-methyl-2-phenylpyrazolo[1,5-a]pyrimidin-3-yl)methyl]-4-propylpyrrolidin-2-one;
4-(2,2-difluorovinyl)-1-[(2-phenylpyrazolo[1,5-a]pyrimidin-3-yl)methyl]pyrrolidin-2-one;
1-[(6-methoxy-2-phenylpyrazolo[1,5-a]pyrimidin-3-yl)methyl]-4-propylpyrrolidin-2-one;
1-[(5-chloropyrazolo[1,5-a]pyrimidin-3-yl)methyl]-4-propylpyrrolidin-2-one;
4-(2,2-difluorovinyl)-1-[(5,6-dimethyl-2-phenylpyrazolo[1,5-a]pyrimidin-3-yl)methyl]pyrrolidin-2-one;
4-(2,2-difluorovinyl)-1-[(6-fluoro-5-methyl-2-phenylpyrazolo[1,5-a]pyrimidin-3-yl)methyl]pyrrolidin-2-one;
1-[(5-methoxypyrazolo[1,5-a]pyrimidin-3-yl)methyl]-4-propylpyrrolidin-2-one;
1-{[2-(4-bromophenyl)pyrazolo[1,5-a]pyrimidin-3-yl]methyl}-4-(2,2-difluorovinyl)pyrrolidin-2-one;

1-{[2-(4-fluorophenyl)pyrazolo[1,5-a]pyrimidin-3-yl]
methyl}-4-propylpyrrolidin-2-one;
4-(2,2-difluorovinyl)-1-[(6-methyl-2-phenylpyrazolo[1,5-a]
pyrimidin-3-yl)methyl]pyrrolidin-2-one;
4-(2,2-difluorovinyl)-1-[(5-methyl-2-phenylpyrazolo[1,5-a]
pyrimidin-3-yl)methyl]pyrrolidin-2-one;
4-(2,2-difluorovinyl)-1-[(2-thien-2-ylpyrazolo[1,5-a]pyrimidin-3-yl)methyl]pyrrolidin-2-one;
1-{[2-(4-chlorophenyl)-6-methylpyrazolo[1,5-a]pyrimidin-3-yl]methyl}-4-propylpyrrolidin-2-one;
1-{[2-(4-chlorophenyl)pyrazolo[1,5-a]pyrimidin-3-yl]
methyl}-4-(2,2-difluorovinyl)pyrrolidin-2-one;
1-[(6-chloro-2-phenylpyrazolo[1,5-a]pyrimidin-3-yl)
methyl]-4-(2,2-difluorovinyl)pyrrolidin-2-one;
1-{[6-chloro-2-(4-chlorophenyl)pyrazolo[1,5-a]pyrimidin-3-yl]methyl}-4-(2,2-difluorovinyl)pyrrolidin-2-one;
1-[(2-cyclopropyl-5-methylpyrazolo[1,5-a]pyrimidin-3-yl)
methyl]-4-(2,2-difluorovinyl)pyrrolidin-2-one;
1-[(5-chloro-2-cyclopropylpyrazolo[1,5-a]pyrimidin-3-yl)
methyl]-4-(2,2-difluorovinyl)pyrrolidin-2-one;
1-[(5-chloro-2,6-dimethylpyrazolo[1,5-a]pyrimidin-3-yl)
methyl]-4-(2,2-difluorovinyl)pyrrolidin-2-one;
1-[(5-bromo-1H-pyrazolo[3,4-b]pyridin-3-yl)methyl]-4-(2,
2-difluorovinyl)pyrrolidin-2-one;
4-propyl-1-(pyridin-3-ylmethyl)pyrrolidin-2-one;
(−)-1-(1-pyridin-3-ylpropyl)pyrrolidin-2-one;
5-chloro-1-[(2-fluoropyridin-3-yl)methyl]-1,3-dihydro-2H-indol-2-one;
1-[(6-chloropyridin-3-yl)methyl]-4-propylpyrrolidin-2-one;
1-{[6-(benzylamino)pyridin-3-yl]methyl}-4-propylpyrrolidin-2-one;
1-[(2-aminopyridin-3-yl)methyl]-4-propylpyrrolidin-2-one;
4-propyl-1-(1H-pyrrolo[2,3-b]pyridin-3-ylmethyl)pyrrolidin-2-one;
1-[(2-isopropyl-1H-pyrrolo[2,3-b]pyridin-3-yl)methyl]-4-propylpyrrolidin-2-one;
1-[(2-phenyl-1H-pyrrolo[2,3-b]pyridin-3-yl)methyl]-4-propylpyrrolidin-2-one;
4-propyl-1-[(2-propyl-1H-pyrrolo[2,3-b]pyridin-3-yl)
methyl]pyrrolidin-2-one;
1-[(6-bromo-1H-pyrrolo[2,3-b]pyridin-3-yl)methyl]-4-propylpyrrolidin-2-one;
1-[(1-benzoyl-6-bromo-1H-pyrrolo[2,3-b]pyridin-3-yl)
methyl]-4-propylpyrrolidin-2-one;
1-[(6-phenyl-1H-pyrrolo[2,3-b]pyridin-3-yl)methyl]-4-propylpyrrolidin-2-one;
1-[(5-bromo-1H-pyrrolo[2,3-b]pyridin-3-yl)methyl]-4-(2,2-difluorovinyl)pyrrolidin-2-one;
1-[(7-oxido-1H-pyrrolo[2,3-b]pyridin-3-yl)methyl]-4-propylpyrrolidin-2-one;
4-propyl-1-(1H-pyrrolo[2,3-b]pyridin-4-ylmethyl)pyrrolidin-2-one;
4-propyl-1-(1H-pyrrolo[2,3-b]pyridin-5-ylmethyl)pyrrolidin-2-one;
4-propyl-1-(1H-pyrrolo[2,3-c]pyridin-2-ylmethyl)pyrrolidin-2-one;
4-propyl-1-(1H-pyrrolo[2,3-c]pyridin-3-ylmethyl)pyrrolidin-2-one;
4-propyl-1-(1H-pyrrolo[3,2-b]pyridin-3-ylmethyl)pyrrolidin-2-one;
4-propyl-1-(1H-pyrrolo[3,2-c]pyridin-2-ylmethyl)pyrrolidin-2-one;
4-propyl-1-(1H-pyrrolo[3,2-c]pyridin-3-ylmethyl)pyrrolidin-2-one;
4-propyl-1-(1,3,4-thiadiazol-2-ylmethyl)pyrrolidin-2-one;
1-[(2-amino-1,3-thiazol-5-yl)methyl]pyrrolidin-2-one;
1-(1,3-thiazol-5-ylmethyl)pyrrolidin-2-one;
1-[(2-chloro-1,3-thiazol-5-yl)methyl]-4-(2,3,5-trifluorophenyl)pyrrolidin-2-one;
1-{[2-(dimethylamino)-1,3-thiazol-5-yl]methyl}-4-(2,3,5-trifluorophenyl)pyrrolidin-2-one;
1-{[2-(methylamino)-1,3-thiazol-5-yl]methyl}-4-(2,3,5-trifluorophenyl)pyrrolidin-2-one;
1-[(2-pyrrolidin-1-yl-1,3-thiazol-5-yl)methyl]-4-(2,3,5-trifluorophenyl)pyrrolidin-2-one;
5-{[2-oxo-4-(2,3,5-trifluorophenyl)pyrrolidin-1-yl]
methyl}-1,3-thiazol-2(3H)-one;
4-phenyl-1-{[3-(trifluoromethyl)[1,2,4]triazolo[4,3-b]
pyridazin-7-yl]methyl}pyrrolidin-2-one;
4-phenyl-1-[(3-phenyl[1,2,4]triazolo[4,3-b]pyridazin-7-yl)
methyl]pyrrolidin-2-one;
4-phenyl-1-{[3-(trifluoromethyl)[1,2,4]triazolo[4,3-b]
pyridazin-8-yl]methyl}pyrrolidin-2-one;
4-propyl-1-{[3-(trifluoromethyl)[1,2,4]triazolo[4,3-b]
pyridazin-8-yl]methyl}pyrrolidin-2-one;
4-phenyl-1-[(3-phenyl[1,2,4]triazolo[4,3-b]pyridazin-8-yl)
methyl]pyrrolidin-2-one;
1-[(6-chloro-3-phenyl[1,2,4]triazolo[4,3-b]pyridazin-8-yl)
methyl]-4-propylpyrrolidin-2-one;
1-[(6-chloro[1,2,4]triazolo[4,3-b]pyridazin-8-yl)methyl]-4-phenylpyrrolidin-2-one;
1-{[6-chloro-3-(trifluoromethyl)[1,2,4]triazolo[4,3-b]
pyridazin-8-yl]methyl}-4-phenylpyrrolidin-2-one;
1-[(6-chloro-3-phenyl[1,2,4]triazolo[4,3-b]pyridazin-8-yl)
methyl]-4-phenylpyrrolidin-2-one;
1-[(2-fluoroindolizin-3-yl)methyl]-4-propylpyrrolidin-2-one;
1-(1H-1,2,3-benzotriazol-1-ylmethyl)-4-propylpyrrolidin-2-one;
1-[(6-bromo-2-chloro-1H-imidazo[4,5-b]pyridin-1-yl)
methyl]-4-propylpyrrolidin-2-one;
1-[(6-bromo-2-phenyl-1H-imidazo[4,5-b]pyridin-1-yl)
methyl]-4-propylpyrrolidin-2-one;
1-(3H-imidazo[4,5-b]pyridin-3-ylmethyl)-4-propylpyrrolidin-2-one;
1-[(6-bromo-3H-imidazo[4,5-b]pyridin-3-yl)methyl]-4-propylpyrrolidin-2-one;
1-[(6-bromo-2-chloro-3H-imidazo[4,5-b]pyridin-3-yl)
methyl]-4-propylpyrrolidin-2-one;
1-[(6-bromo-2-phenyl-3H-imidazo[4,5-b]pyridin-3-yl)
methyl]-4-propylpyrrolidin-2-one;
1-[(6-bromo-2-cyclopropyl-3H-imidazo[4,5-b]pyridin-3-yl)
methyl]-4-(2,2-difluorovinyl)pyrrolidin-2-one;
1-[(3-chloro-7H-imidazo[4,5-c]pyridazin-7-yl)methyl]-4-propylpyrrolidin-2-one;
1-[(2-chloro-1H-indol-1-yl)methyl]-4-propylpyrrolidin-2-one;
1-[(5-methyl-1H-indol-1-yl)methyl]-4-propylpyrrolidin-2-one;
1-[(6-methyl-1H-indol-1-yl)methyl]-4-propylpyrrolidin-2-one;
1-[(2-phenyl-1H-indol-1-yl)methyl]-4-propylpyrrolidin-2-one;
1-[(5-fluoro-1H-indol-1-yl)methyl]-4-propylpyrrolidin-2-one;
1-[(5-bromo-1H-indol-1-yl)methyl]-4-propylpyrrolidin-2-one;
1-[(5-chloro-1H-indol-1-yl)methyl]-4-propylpyrrolidin-2-one;
1-(2,3-dihydro-1H-indol-1-ylmethyl)-4-propylpyrrolidin-2-one;
1-[(5-fluoro-2-phenyl-1H-indol-1-yl)methyl]-4-propylpyrrolidin-2-one;

1-[(2-oxo-4-propylpyrrolidin-1-yl)methyl]-1H-indole-2-carbonitrile;
1-[(2-bromo-1H-indol-1-yl)methyl]-4-propylpyrrolidin-2-one;
1-[(2,5-dichloro-1H-indol-1-yl)methyl]-4-propylpyrrolidin-2-one;
1-[(6-amino-9H-purin-9-yl)methyl]-4-propylpyrrolidin-2-one;
4-propyl-1-(9H-purin-9-ylmethyl)pyrrolidin-2-one;
1-{[6-(cyclopropylamino)-9H-purin-9-yl]methyl}-4-propylpyrrolidin-2-one;
1-{[6-(benzylamino)-9H-purin-9-yl]methyl}-4-propylpyrrolidin-2-one;
4-propyl-1-{[6-(propylamino)-9H-purin-9-yl]methyl}pyrrolidin-2-one;
1-({6-[(cyclopropylmethyl)amino]-9H-purin-9-yl}methyl)-4-propylpyrrolidin-2-one;
4-propyl-1-[(6-pyrrolidin-1-yl-9H-purin-9-yl)methyl]pyrrolidin-2-one;
1-[(5-bromo-3-phenyl-1H-pyrazolo[3,4-b]pyridin-1-yl)methyl]-4-propylpyrrolidin-2-one;
1-[(5-bromo-2H-pyrazolo[3,4-b]pyridin-2-yl)methyl]-4-propylpyrrolidin-2-one;
1-[(5-bromo-3-phenyl-2H-pyrazolo[3,4-b]pyridin-2-yl)methyl]-4-propylpyrrolidin-2-one;
1-[(2-chloro-1H-pyrrolo[2,3-b]pyridin-1-yl)methyl]-4-propylpyrrolidin-2-one;
4-propyl-1-(1H-pyrrolo[3,2-b]pyridin-1-ylmethyl)pyrrolidin-2-one;
1-(3,4-dihydroquinolin-1(2H)-ylmethyl)-4-propylpyrrolidin-2-one;
1-(8H-isothiazolo[5,4-b]indol-8-ylmethyl)-4-propylpyrrolidin-2-one;
1-(1H-1,2,4-triazol-1-ylmethyl)pyrrolidin-2-one;
1-[(2,5-dichloro-1H-pyrrol-1-yl)methyl]-4-propylpyrrolidin-2-one;
1-[(2-chloro-1H-pyrrol-1-yl)methyl]-4-propylpyrrolidin-2-one;
1-[(2-chloro-1H-benzimidazol-1-yl)methyl]-4-propylpyrrolidin-2-one;
1-[(2-chloro-1H-benzimidazol-1-yl)methyl]-4-phenylpyrrolidin-2-one;
2-chloro-1-[(2-oxo-4-propylpyrrolidin-1-yl)methyl]-1H-benzimidazole-5-carbonitrile;
2-chloro-1-[(2-oxo-4-propylpyrrolidin-1-yl)methyl]-1H-benzimidazole-6-carbonitrile;
4-propyl-1-[(2,5,6-trichloro-1H-benzimidazol-1-yl)methyl]pyrrolidin-2-one;
1-[(2-chloro-6-methoxy-1H-benzimidazol-1-yl)methyl]-4-propylpyrrolidin-2-one;
1-[(2-chloro-5-methoxy-1H-benzimidazol-1-yl)methyl]-4-propylpyrrolidin-2-one;
1-[(2-chloro-6-nitro-1H-benzimidazol-1-yl)methyl]-4-propylpyrrolidin-2-one;
1-[(2-chloro-5-nitro-1H-benzimidazol-1-yl)methyl]-4-propylpyrrolidin-2-one;
1-[(2-chloro-6-methyl-1H-benzimidazol-1-yl)methyl]-4-propylpyrrolidin-2-one;
1-[(2-chloro-1H-benzimidazol-1-yl)methyl]-4-(2,2-difluorovinyl)pyrrolidin-2-one;
1-[(6-bromo-2-chloro-1H-benzimidazol-1-yl)methyl]-4-propylpyrrolidin-2-one;
1-[(5-bromo-2-chloro-1H-benzimidazol-1-yl)methyl]-4-propylpyrrolidin-2-one;
1-[(2-chloro-6-fluoro-1H-benzimidazol-1-yl)methyl]-4-propylpyrrolidin-2-one;
1-[(2-chloro-5-fluoro-1H-benzimidazol-1-yl)methyl]-4-propylpyrrolidin-2-one;
1-[(2,6-dichloro-1H-benzimidazol-1-yl)methyl]-4-propylpyrrolidin-2-one;
1-[(2,5-dichloro-1H-benzimidazol-1-yl)methyl]-4-propylpyrrolidin-2-one;
1-{[2-chloro-6-(trifluoromethyl)-1H-benzimidazol-1-yl]methyl}-4-propylpyrrolidin-2-one;
1-{[2-chloro-5-(trifluoromethyl)-1H-benzimidazol-1-yl]methyl}-4-propylpyrrolidin-2-one;
1-[(2-chloro-1H-benzimidazol-1-yl)methyl]pyrrolidin-2-one;
1-[(2-chloro-6-hydroxy-1H-benzimidazol-1-yl)methyl]-4-propylpyrrolidin-2-one;
1-(pyridin-4-ylmethyl)pyrrolidin-2-one, and
1-[(2-chloro-5-hydroxy-1H-benzimidazol-1-yl)methyl]-4-propylpyrrolidin-2-one.

viii) U.S. Pat. No. 4,696,943

The present invention relates to the novel compound (S)-alpha-ethyl-2-oxo-1-pyrrolidineacetamide.

ix) U.S. Pat. No. 4,696,942

The present invention relates to the novel compound, (R)-alpha-ethyl-2-oxo-1-pyrrolidineacetamide x) U.S. Pat. No. 5,334,720

According to this invention we provide novel compounds of the formula I,

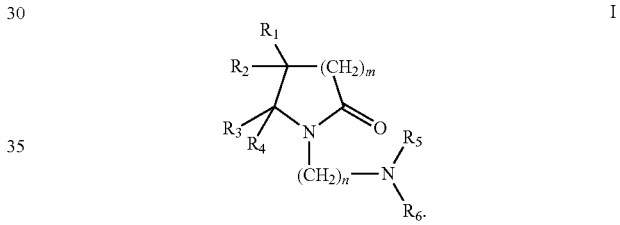

wherein, R1, R2, R3 and R4, which may be the same or different independently represent hydrogen, C1-6 alkyl, phenyl or phenyl substituted by one or more halogen, hydroxyl, nitro, amino, C1-6 alkyl or C1-C6 alkoxy groups;
R5 and R6 independently represent hydrogen, C1-C6 alkyl or C3-C6 cycloalkyl, or R5 and R6 together with the nitrogen form a C4-6 N heterocycle;
m represents an integer from 1-2; and
n represents an integer from 1-3;
provided that,
two of the substituents R1, R2, R3 and R4 independently represent phenyl or substituted phenyl and the other two independently represent hydrogen or C1-6 alkyl;
or a pharmaceutically acceptable acid addition salt thereof.

Pharmaceutically acceptable acid addition salts of the compounds of formula I include salts of mineral acids, for example, hydrohalic acids, e.g. hydrochloric or hydrobromic; organic acids, e.g. formic, acetic or lactic acids. The acid may be polybasic, for example sulphuric, fumaric, maleic or citric acid.

This invention also relates to all stereoisomeric forms and optical enantiomeric forms of the compounds of formula I.

In the compounds of formula I: alkyl groups which R1, R2, R3, R4, R5 and R6 may represent include methyl, ethyl, propyl, isopropyl, n-butyl, iso-butyl and s-butyl;
cycloalkyl groups which R5 and R6 may represent include cyclopropyl, cyclobutyl, cyclopentyl and cyclohexyl;
C1-6 alkoxy groups include methoxy, ethoxy and propoxy;

halogen groups include fluorine, chlorine, bromine or iodine;

We prefer compounds of formula I or a pharmaceutically acceptable acid addition salt thereof, in which;

R1 is hydrogen, phenyl or substituted phenyl, preferably phenyl;

R2 is hydrogen, phenyl or substituted phenyl, preferably phenyl;

R3 is hydrogen, phenyl or substituted phenyl, preferably hydrogen;

R4 is hydrogen, phenyl or substituted phenyl, preferably hydrogen;

R5 is hydrogen, C1-3 alkyl or cyclopropyl, preferably hydrogen or methyl;

R6 is hydrogen, C1-3 alkyl or cyclopropyl, preferably hydrogen or methyl;

m represents an integer from 1-2 preferably 2;

n represents an integer from 1-2, preferably 1.

We especially prefer compounds of formula I in which R1 and R2 are both phenyl.

We especially prefer compounds of formula I in which one of R5 and R6 is hydrogen and the other is hydrogen or methyl.

xi) International Patent Application Publication No. WO2005/054188

In one aspect the invention therefore provides a compound having the formula I or a pharmaceutically acceptable salt thereof,

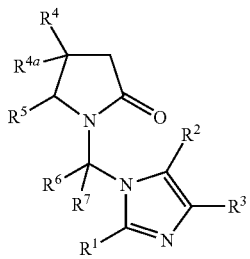

(I)

wherein

RI is hydrogen, CI-20 alkyl, C3 23 cycloalkyl, halogen, hydroxy, alkoxy, aryloxy, ester, amido, cyano, nitro, amino, guanidine, amino derivative, alkylthio, arylthio, alkylsulfonyl, arylsulfonyl, alkylsulfinyl, arylsulfinyl, aryl or heterocycle; R2 is hydrogen, C1 20 alkyl, alkoxy, amino, halogen, hydroxy, ester, amido, nitro, cyano, carbamate, or aryl;

R3 is hydrogen, C1 20 alkyl, alkoxy, amino, halogen, hydroxy, ester, amido, nitro, cyano, carbamate, or aryl;

or R2 and R3 can form together with the imidazole ring the following 1H-benzimidazole cycle

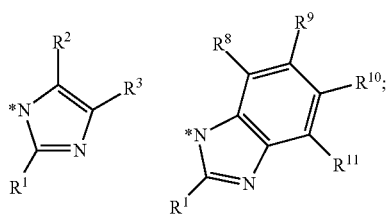

R4 is hydrogen, C1-20 alkyl, C2-12 alkenyl, C2-12 alkynyl, aryl, azido, alkoxycarbonylamino, arylsulfonyloxy or heterocycle; R4a is hydrogen or C1-20 alkyl; or R4 and R4a can form together a C3-8 cycloalkyl; R5 is hydrogen; or R4, R4a and R5 can form together with the 2-oxo-1-pyrrolidine ring the following 1,3-dihydro-2H-indol-2-one cycle

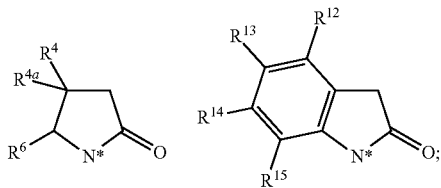

R6 is hydrogen or C1 20 alkyl; R7 is hydrogen; or R6 and R7 are linked together to form a C3-6 cycloalkyl; R8 is hydrogen, halogen, nitro, cyano, C1 20 alkyl or alkoxy; R9 is hydrogen, C1-20 alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

RIO is hydrogen, C1 20 alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

RI 1 is hydrogen, halogen, nitro, cyano, C1 20 alkyl or alkoxy; R12 is hydrogen or halogen;

R13 is hydrogen, nitro, halogen, heterocycle, amino, aryl, C1-20 alkyl unsubstituted or substituted by halogen, or alkoxy unsubstituted or substituted by halogen; R14 is hydrogen, C1-20 alkyl or halogen;

R15 is hydrogen, C1 20 alkyl or halogen;

with the proviso that R4 is different from hydrogen when

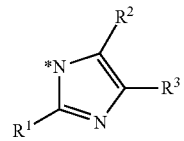

N represents a group of formula

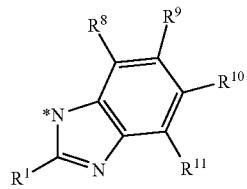

The asterisk * indicates the point of attachment of the substituents.

In a preferred embodiment, the invention concerns a compound having the formula I, their tautomers, geometrical isomers (including cis and trans, Z and E isomers), enantiomers, diastereoisomers and mixtures thereof (including all possible mixtures of stereoisomers), or pharmaceutically acceptable salts thereof,

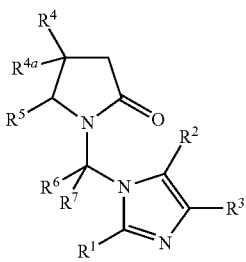 (I)

wherein
RI is hydrogen, C1-20 alkyl, C3-8 cycloalkyl, halogen, hydroxy, ester, amido, cyano, nitro, amino, guanidine, alkylthio, alkylsulfonyl, alkylsulfinyl, aryl or heterocycle; R2 is hydrogen, C1 20 alkyl, halogen, cyano, ester, carbamate or amido; R3 is hydrogen, cyano, C 1 20 alkyl, halogen or ester; or R2 and R3 can form together with the imidazole ring the following 1H-benzimidazole cycle

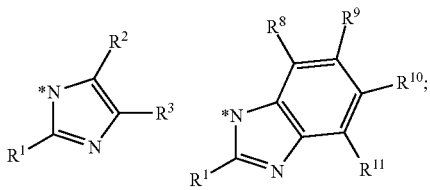

is hydrogen, C1 20 alkyl, C2 12 alkenyl or aryl; R4a is hydrogen;
R5 is hydrogen; or R4, R4a and R5 can form together with the 2-oxo-1-pyrrolidine ring the following 1,3-dihydro-2H-indol-2-one cycle

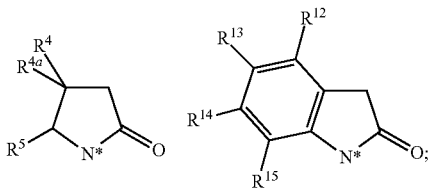

R6 is hydrogen or C 1 20 alkyl; R7 is hydrogen; or R6 and R7 are linked together to form a C3-6 cycloalkyl; R8 is hydrogen; R9 is hydrogen, C1-20 alkyl, halogen or alkoxy; RIO is hydrogen, C1 20 alkyl, halogen or cyano; R11 is hydrogen; R12 is hydrogen or halogen; R13 is hydrogen, halogen, heterocycle or C1 20 alkyl; R14 is hydrogen; R15 is hydrogen; with the proviso that R4 is different from hydrogen when

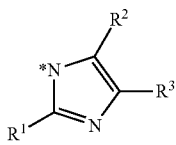

represents a group of formula

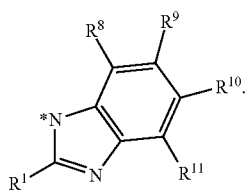

The term "alkyl", as used herein, represents saturated, monovalent hydrocarbon radicals having straight (unbranched) or branched or cyclic or combinations thereof and containing 1-20 carbon atoms, preferably 1-10 carbon atoms, more preferably 1-4 carbon atoms; most preferred alkyl groups have 1-3 carbon atoms. Alkyl moieties may optionally be substituted by 1 to 5 substituents independently selected from the group consisting of halogen, hydroxy, cyano, azido, aryloxy, alkoxy, alkylthio, alkanoylamino, arylcarbonylamino, aminocarbonyl, methylaminocarbonyl, dimethylaminocarbonyl or aryl. Usually alkyl groups, in the present case, are methyl, ethyl, n-propyl, i-propyl, n-butyl, i-butyl, t-butyl, 1-ethylpropyl, n-heptyl, 2,4,4-trimethylpentyl, n-decyl, chloromethyl, trifluoromethyl, 2-bromo-2,2-difluoroethyl, 2,2,2-trifluoroethyl, 3,3,3-trifluoropropyl, hydroxymethyl, cyanomethyl, azidomethyl, (acetylamino) methyl, (propionylamino) methyl, (benzoylamino) methyl, (4-chlorophenoxy)methyl, benzyl, 2-phenylethyl or 2-(methylthio)ethyl. Preferred alkyl groups are methyl, ethyl, n-propyl, i-propyl, n-butyl, i-butyl, t-butyl, 1-ethylpropyl, 2,4,4-trimethylpentyl, chloromethyl, trifluoromethyl, 2,2,2-trifluoroethyl, hydroxymethyl, cyanomethyl, azidomethyl, (acetylamino) methyl, (propionylamino) methyl, (benzoylamino) methyl or 2-(methylthio)ethyl. More preferred alkyl groups are methyl, ethyl, n-propyl, i-propyl, n-butyl, azidomethyl or trifluoromethyl. Most preferred alkyl groups are methyl or n-propyl.

The term "cycloalkyl", as used herein, represents a monovalent group of 3 to 8 carbon atoms, usually 3-6 carbon atoms derived from a saturated cyclic hydrocarbon, which may be substituted by any suitable group including but not limited to one or more moieties selected from groups as described above for the alkyl groups. Preferred cycloalkyl groups are cyclopropyl and cyclohexyl.

The term "alkenyl" as used herein, represents straight, branched or cyclic unsaturated hydrocarbon radicals or combinations thereof having at least one carbon-carbon double bond, containing 2-12 carbon atoms, preferably usually 2-4 carbon atoms. Alkenyl groups are being optionally substituted with any suitable group, including but not limited to one or more moities selected from groups as described above for the alkyl groups. Usually an alkenyl group is ethenyl (vinyl) optionally substituted by 1 to 3 halogens. Preferred alkenyl group, in the present case, is 2,2-difluorovinyl.

The term "alkynyl" as used herein, represents straight, branched or cyclic hydrocarbon radicals or combinations thereof containing at least one carbon-carbon triple bond, containing 2-12 carbon atoms, preferably 2-6 carbon atoms, and being optionally substituted by any suitable group, including but not limited to one or more moities selected from groups as described above for the alkyl groups. Preferably an alkynyl group is a halogenoalkynyl group (haloalkynyl group).

Groups qualified by prefixes such as "s", "i", "t" and the like (e.g. "i-propyl", "s-butyl") are branched derivatives.

The term "aryl" as used herein, is defined as phenyl optionally substituted by 1 to 4 substituents independently selected from halogen, cyano, alkoxy, alkylthio, C1 3 alkyl or azido, preferably halogen or azido. Usually aryl groups, in the present case are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl, 3-azido-2,4-difluorophenyl or 3-azido-2,4,6-trifluorophenyl. Preferably, aryl groups are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl or 3-azido-2,4-difluorophenyl. Most preferred aryl groups are phenyl, 3-chlorophenyl, 3-fluorophenyl, 3,5-difluorophenyl, 2,3,4-trifluorophenyl, 2,4,5-trifluorophenyl, 2,3,5-trifluorophenyl, 3,4,5-trifluorophenyl or 3-azido-2,4-difluorophenyl.

The term "heterocycle", as used herein, is defined as including an aromatic or non aromatic cycloalkyl moiety as defined above, having at least one O, S and/or N atom interrupting the carbocyclic ring structure. Heterocyclic ring moities can be optionally substituted by alkyl groups or halogens and optionally, one of the carbon of the carbocyclic ring structure may be replaced by a carbonyl. Usually heterocycles are 2-pyridyl, 3-pyridyl, 4-pyridyl, 2-furyl, 3-furyl, 2-thienyl, 3-thienyl, 2-tetrahydrofuranyl, 1H-pyrrol-2-yl, 1-methyl-1H-pyrrol-2-yl, 1H-pyrazol-2-yl, 1H-pyrazol-3-yl, 4-chloro-1-methyl-1H-pyrazol-3-yl, 5-chloro-1,3-dimethyl-1H-pyrazol-4-yl, 1,2,3-thiadiazol-4-yl, 3,5-dimethyl-4-isothiazyl, 1H-imidazol-2-yl, 1-methyl-1H-imidazol-2-yl, 4-methyl-1H-imidazol-5-yl, or 2-methyl-1,3-thiazol-4-yl. Preferred heterocycles are 1H-imidazol-2-yl, 1,2,3-thiadiazol-4-yl, 1H-pyrazol-3-yl, 2-furyl, 3-furyl, 2-thienyl, 1-methyl-1H-pyrrol-2-yl, 1H-pyrrol-2-yl.

The term "halogen", as used herein, includes an atom of chlorine, bromine, fluorine, iodine. Usually halogens are chlorine, bromine and fluorine. Preferred halogens are fluorine, bromine and chlorine.

The term "hydroxy", as used herein, represents a group of formula —OH.

The term "alkoxy", as used herein, represents a group of formula —ORa wherein Ra is an alkyl group, as defined above. Preferred alkoxy group is methoxy.

The term "aryloxy", as used herein, represents a group of formula —ORb wherein Rb is an aryl group, as defined above. Preferred aryloxy group is phenoxy.

The term "ester", as used herein, represents a group of formula —COORc wherein Rc is an alkyl group or aryl group, as defined above. Preferred ester group is methoxycarbonyl.

The term "amido", as used herein, represents a group of formula —CONH2.

The term "amino", as used herein, represents a group of formula —NH2.

The term "aminoderivative", as used herein, represents an alkylamino or an arylamino group, wherein the terms "alkyl" and "aryl" are defined as above.

The term "cyano", as used herein, represents a group of formula —CN.

The term "nitro", as used herein, represents a group of formula —NO2.

The term "azido", as used herein, represents a group of formula —N3.

The term "guanidine", as used herein, represents a group of formula —NHC(=NH)NH2.

The term "alkylthio", as used herein, represents a group of formula —SRd wherein Rd is an alkyl group, as defined above. One alkylthio group is methylthio.

The term "alkylsulfonyl", as used herein, represents a group of formula —S(=O)2Re wherein Re is an alkyl group, as defined above. One alkylsulfonyl group is methylsulfonyl.

The term "alkylsulfinyl", as used herein, represents a group of formula —S(=O)Rf wherein Rf is an alkyl group, as defined above. One alkylsulfinyl group is methylsulfinyl.

The term "arylthio", as used herein, represents a group of formula —SRg wherein Rg is an aryl group, as defined above.

The term "arylsulfonyl", as used herein, represents a group of the formula —S(=O)2Rh wherein Rh is an aryl group, as defined above.

The term "arylsulfinyl", as used herein, represents a group of the formula —S(=O)Ri wherein Ri is an aryl group, as defined above.

The term "carbamate" as used herein, represents a group of formula —N(H)C(O)OR1, wherein Ri is an alkyl or an aryl, as defined above. Usually carbamate groups are (propoxycarbonyl) amino or (benzyloaxycarbonyl) amino. One carbamate group is (benzyloaxycarbonyl) amino.

The term "alkanoylamino" as used herein, represents a group of the formula —NHC(=O)Rk wherein Rk is an alkyl group, as defined above.

The term "(arylcarbonyl) amino" as used herein, represents a group of the formula —NHC(=O)Rm wherein Rm is an aryl group, as defined above. One (arylcarbonyl) amino is benzoylamino.

Usually, Rl is hydrogen; C1 lo alkyl unsubstituted or substituted by halogen, hydroxy, cyano, methylthio, phenyl or 4-chlorophenoxy; hydroxy; C3-6 cycloalkyl; halogen; ester; amido; nitro; cyano; amino; phenyl; alkylthio; alkylsulfonyl; alkylsulfinyl; heterocycle unsubstituted or substituted by alkyl groups; or guanidine.

In some embodiments, Rl is hydrogen; methyl; ethyl; i-propyl; n-propyl; cyclopropyl; n-butyl; i-butyl; t-butyl; 1-ethylpropyl; 2,4,4-trimethylpentyl; hydroxymethyl; chloromethyl; trifluoromethyl; 2,2,2-trifluoroethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl or 1H-imidazol-2-yl. More preferably, Rl is hydrogen; methyl; ethyl; i-propyl; n-propyl; n-butyl; methylthio; nitro; cyano; amino; chloro or 1H-pyrrol-2-yl. Most preferably, Rl is hydrogen; methyl; methylthio; nitro; cyano; amino or chloro.

Usually, R2 is hydrogen; C1 4 alkyl unsubstituted or substituted by hydroxy, alkanoylamino or benzoylamino; halogen; ester; cyano; alkyl carbamate; [(N-methoxy-N-methyl)amino]carbonyl. Preferably, R2 is hydrogen; methyl; hydroxymethyl; (acetylamino) methyl; (propionylamino) methyl; (benzoylamino) methyl; [(benzyloxy)carbonyl] amino; chloro or cyano. In some embodiments, R2 is hydrogen; chloro or cyano.

Usually, R3 is hydrogen; C1 4 alkyl unsubstituted or substituted by hydroxy; halogen; ester or cyano. In some embodiments, R3 is hydrogen; hydroxymethyl; chloro; cyano.

In some embodiments, R3 is hydrogen or cyano. In some embodiments R3 is hydrogen.

Usually, R4 is hydrogen; C1 4 alkyl unsubstituted or substituted by halogens; C2 4 alkenyl substituted by halogens or phenyl group unsubstituted or substituted by azido or/and halogens. Preferably, R4 is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl or 3-azido-2,4,6-trifluorophenyl. More preferably, R4 is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl or 3-azido-2,4-difluorophenyl. Most preferably, R4 is n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl or 3-azido-2,4-difluorophenyl.

Usually, R4a is hydrogen.

Usually, R5 is hydrogen.

Usually, R6 is hydrogen or C1-1~0 alkyl unsubstituted or substituted by hydroxy or azido. Preferably, R6 is hydrogen or azidomethyl. More preferably R6 is hydrogen.

Usually R7 is hydrogen.

In other embodiments, R6 and R7 are linked to form a cyclopropyl.

In other embodiments, R2 and R3 can form together with the imidazole ring the following 1H-benzimidaole cycle

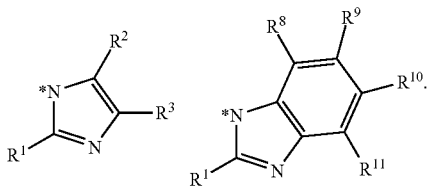

Usually, R8 is hydrogen.

Usually, R9 is hydrogen; halogen; 1-3 alkyl or alkoxy. In some embodiments, R9 is hydrogen; methyl; chloro or methoxy. In some embodiments R9 is hydrogen.

Usually, RIO is hydrogen; halogen; cyano; C1 3 alkyl unsubstituted or substituted by halogens; or alkoxy. In some embodiments, RIO is methyl; hydrogen; trifluoromethyl; fluoro; cyano or methoxy. In some embodiments R10 is hydrogen; trifluoromethyl; fluoro or cyano.

Usually, RI 1 is hydrogen.

In other embodiments, R4, R4a and R5 can form together with the 2-oxo-1-pyrrolidine ring the following 1,3-dihydro-2H-indol-2-one cycle

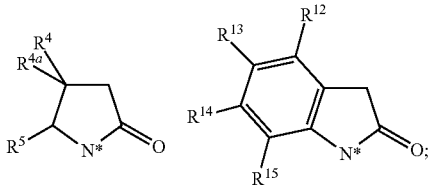

Usually, R12 is hydrogen or halogen. In some embodiments R12 is hydrogen; chloro or fluoro. In some embodiments R12 is hydrogen.

Usually, R13 is hydrogen; C1 3 alkyl; halogen or thiazolyl unsubstituted or substituted by alkyl groups, such as methylthiazolyl. In some embodiments R13 is hydrogen; chloro; bromo or methyl. In some embodiments R13 is chloro; bromo or methyl.

Usually R14 is hydrogen.

Usually, R15 is hydrogen.

In a general embodiment of the invention, the compounds of formula I, or pharmaceutically acceptable salts thereof, are those wherein RI is selected from hydrogen; C1 lo alkyl unsubstituted or substituted by halogen, hydroxy, cyano, methylthio, phenyl or 4-chlorophenoxy; C3 6 cycloalkyl; halogen; ester; amido; nitro; cyano; amino; phenyl; alkylthio; alkylsulfonyl; alkylsulfinyl; heterocycle unsubstituted or substituted by alkyl group; or guanidine; R2 is selected from hydrogen; C1-4 alkyl unsubstituted or substituted by hydroxy, alkanoylamino or benzoylamino; halogen; ester; cyano; alkyl carbamate or [(N-methoxy-N-methyl)amino]carbonyl.

R3 is selected from hydrogen; C1 4 alkyl unsubstituted or substituted by hydroxy; halogen; ester or cyano; R4 is selected from hydrogen; C1 4 alkyl unsubstituted or substituted by halogens; C2 4 alkenyl substituted by halogens or phenyl group unsubstituted or substituted by azido or/and halogens;

R4a is hydrogen; R5 is hydrogen; R6 is selected from hydrogen or C1-10 alkyl unsubstituted or substituted by hydroxy or azido;

R7 is hydrogen; or R6 and R7 can be linked to form a cyclopropyl; or R2 and R3 can form together with the imidazole ring the following 1H-benzimidazole cycle

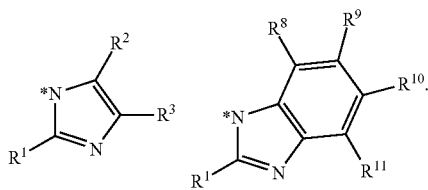

R8 is hydrogen; R9 is selected from hydrogen; halogen; C1-3 alkyl; alkoxy;

R10 is selected from hydrogen; halogen; cyano or Cil alkyl unsubstituted or substituted by halogens; or alkoxy; R1 is hydrogen; or R4, R4a and R5 can form together with the 2-oxo-1-pyrrolidine ring the following 1,3-dihydro-2H-indol-2-one cycle

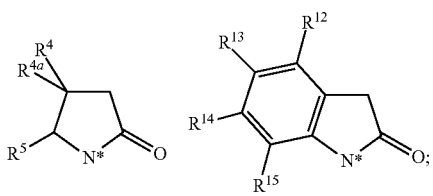

R12 is selected from hydrogen or halogen; R13 is selected from hydrogen; CI-3 alkyl; halogen; thiazolyl unsubstituted or substituted by alkyl groups, such as methylthiazolyl; R14 is hydrogen; R15 is hydrogen; with the proviso that R4 is different from hydrogen when

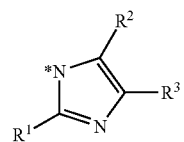

represents a group of formula

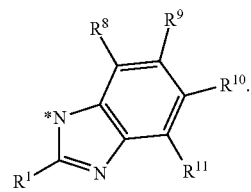

In an embodiment of the invention, the compounds of formula I, or pharmaceutically acceptable salt thereof, are those wherein RI is selected from hydrogen; methyl; ethyl; i-propyl; n-propyl; cyclopropyl; n-butyl; i-butyl; t-butyl; 1-ethylpropyl; 2,4,4-trimethylpentyl; trifluoromethyl; 2,2,2-trifluoroethyl; hydroxymethyl; chloromethyl; cyanomethyl; 2-(methylthio) ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl; or 1H-imidazol-2-yl; R2 is selected from hydrogen; methyl; hydroxymethyl; (acetylamino) methyl; (propionylamino) methyl; (benzoylamino) methyl; (benzyloxycarbonyl) amino; chloro; or cyano; R3 is selected from hydrogen; hydroxymethyl; chloro; cyano; or R2 and R3 can form together with the imidazole ring the following 1H-benzimidazole cycle

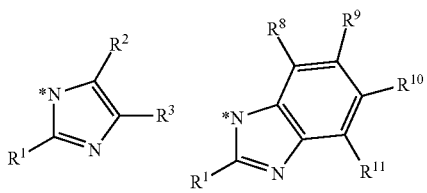

R8 is hydrogen; R9 is selected from hydrogen; methyl; choro; methoxy;
R10 is selected from methyl; hydrogen; trifluoromethyl; fluoro; cyano; or methoxy; R is hydrogen; R4 is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl; or 3-azido-2,4,6-trifluorophenyl. R4a is hydrogen; R5 is hydrogen; or R4, R4a and R5 can form together with the 2-oxo-1-pyrrolidine ring the following 1,3-dihydro-2H-indol-2-one cycle

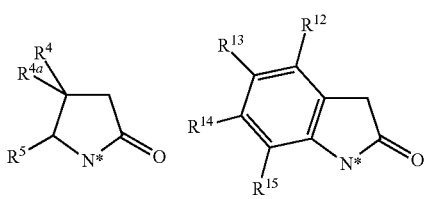

R12 is selected from hydrogen; chloro; fluoro; R13 is selected from hydrogen; chloro; bromo; methyl; R14 is hydrogen; R15 hydrogen; R6 is selected from hydrogen; azidomethyl; R7 is hydrogen; or R6 and R7 are linked to form a cyclopropyl; with the proviso that R4 is different from hydrogen when

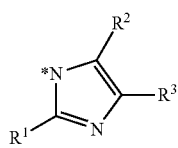

represents a group of formula

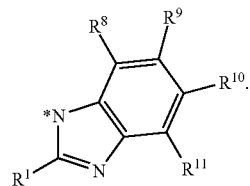

In one embodiment of the invention, the compounds of formula I, or pharmaceutically acceptable salt thereof, are those wherein RI is selected from hydrogen; methyl; ethyl; i-propyl; n-propyl; n-butyl; methylthio; nitro; cyano; amino; chloro; or 1H-pyrrol-2-yl; R2 is selected from hydrogen; chloro; cyano; R3 is selected from hydrogen; cyano; or R2 and R3 can form together with the imidazole ring the following 1H-benzimidazole cycle

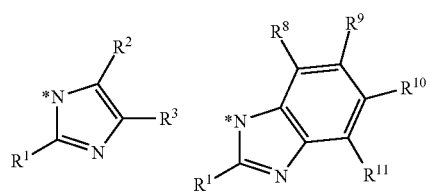

R8 is hydrogen; R9 is hydrogen;
R10 is selected from hydrogen; trifluoromethyl; fluoro; cyano;
RI 1 is hydrogen; R4 is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; or 3-azido-2,4-difluorophenyl; R4a is hydrogen; R5 is hydrogen; or R4, R4a and R5 can form together with the 2-oxo-1-pyrrolidine ring the following 1,3-dihydro-2H-indol-2-one cycle

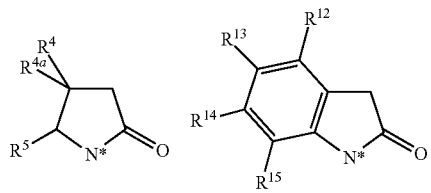

wherein R12 is hydrogen; R13 is selected from methyl; chloro; bromo; R14 is hydrogen; R15 hydrogen; R6 is hydrogen; R7 is hydrogen; with the proviso that R4 is different from hydrogen when

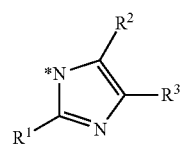

R11 represents a group of formula

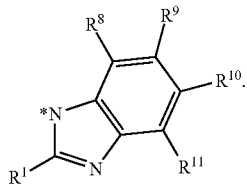

In one embodiment of the invention, the compounds of formula I, or pharmaceutically acceptable salt thereof, are those wherein
RI is selected from hydrogen; methyl; methylthio; nitro; cyano; amino; chloro; R2 is selected from hydrogen; chloro; cyano; R3 is hydrogen; R4 is selected from n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl; 3-azido-2,4-difluorophenyl; R4a is hydrogen;
R5 is hydrogen; or R4, R4a and R5 can form together with the 2-oxo-1-pyrrolidine ring the following 1,3-dihydro-2H-indol-2-one cycle

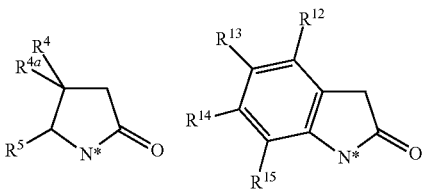

R12 is hydrogen; R13 is selected from chloro; bromo; methyl; R14 is hydrogen; R15 hydrogen; R6 is hydrogen; R7 is hydrogen.

In some embodiments, compounds are: 1-(1H-imidazol-1-ylmethyl) pyrrolidin-2-one; 1-(1H-imidazol-1-ylmethyl)-4-phenylpyrrolidin-2-one; 4-(3-azido-2,4,6-trifluorophenyl)-1-(1H-imidazol-1-ylmethyl) pyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl) pyrrolidin-2-one; (+)-4-(3-azido-2,4-difluorophenyl)-1-(1H-imidazol-1-ylmethyl) pyrrolidin-2-one; 1-[(2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 1-[(2-phenyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl) pyrrolidin-2-one; 4-(3-chlorophenyl)-1-(1H-imidazol-1-ylmethyl) pyrrolidin-2-one; 1-{[2-(methylthio)-1H-imidazol-1-yl]methyl}-4-propylpyrrolidin-2-one; 1-{[2-(methylsulfinyl)-1H-imidazol-1-yl]methyl}-4-propylpyrrolidin-2-one; 1-[(2-tert-butyl-1H-imidazol-1-yl)methyl]-4-propylpyrrolidin-2-one; 1-[1-(1H-imidazol-1-yl)cyclopropyl]pyrrolidin-2-one; 1-[(2-methyl-1H-imidazol-1-yl)methyl]-4-phenylpyrrolidin-2-one; 1-{[2-(methylsulfonyl)-1H-imidazol-1-yl]methyl}-4-propylpyrrolidin-2-one; 1-[(2-oxo-4-propylpyrrolidin-1-yl)methyl]-1H-imidazole-2-carboxamide; 4-(4-fluorophenyl)-1-(1H-imidazol-1-ylmethyl)pyrrolidin-2-one; 1-(1H-imidazol-1-ylmethyl)-4-(3,4,5-trifluorophenyl) pyrrolidin-2-one; 4-(3-fluorophenyl)-1-(1H-imidazol-1-ylmethyl) pyrrolidin-2-one; 4-(3,5-difluorophenyl)-1-(1H-imidazol-1-ylmethyl) pyrrolidin-2-one; 4-(3,4-difluorophenyl)-1-(1H-imidazol-1-ylmethyl) pyrrolidin-2-one; 4-(3-chloro-4-fluorophenyl)-1-(1H-imidazol-1-ylmelthyl) pyrrolidin-2-one; 4-(4-chlorophenyl)-1-(1H-imidazol-1-ylmelthyl) pyrrolidin-2-one; 1-(1H-imidazol-1-ylmethyl)-4-(2,3,4-trifluorophenyl) pyrrolidin-2-one; 1-(1H-imidazol-1-ylmethyl)-4-(2,3,5-trifluorophenyl) pyrrolidin-2-one; 1-(1H-imidazol-1-ylmethyl)-4-(2,4,5-trifluorophenyl) pyrrolidin-2-one; 1-{[2-(hydroxymethyl)-1H-imidazol-1-yl]methyl}-4-propylpyrrolidin-2-one; methyl 1-[(2-oxo-4-propylpyrrolidin-1-yl)methyl]-1H-imidazole-2-carboxylate; 1-[(2-nitro-1H-imidazol-1-yl)methyl]-4-(3,4,5-trifluorophenyl)pyrrolidin-2-one; 1-{[2-oxo-4-(3,4,5-trifluorophenyl) pyrrolidin-1-yl]methyl}-1H-imidazole-2-carbonitrile; 1-[(2-amino-1H-imidazol-1-yl)methyl]-4-propylpyrrolidin-2-one; 1-[(2,4-dichloro-1H-imidazol-1-yl)methyl]-4-(3,4,5-trifluorophenyl) pyrrolidin-2-one; 1-[(5-chloro-1H-imidazol-1-yl)methyl]-4-(3,4,5-trifluorophenyl) pyrrolidin-2-one; 1-{[2-oxo-4-(3,4,5-trifluorophenyl) pyrrolidin-1-yl]methyl}-1H-imidazole-4-carbonitrile; 1-{[2-oxo-4-(3,4,5-trifluorophenyl) pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; 1-{[2-oxo-4-(2,3,5-trifluorophenyl) pyrrolidin-1-yl]methyl}-1H-imidazole-5-carbonitrile; (−)-1-{[2-oxo-4-(2,3,4-trifluorophenyl) pyrrolidin-1-yl]methyl}-1H-imidazole-5-carbonitrile; (+)-1-{[2-oxo-4-(2,3,4-trifluorophenyl) pyrrolidin-1-yl]methyl}-1H-imidazole-5-carbonitrile; (−)-1-{[2-oxo-4-(2,3,4-trifluorophenyl) pyrrolidin-1-yl]methyl}-1H-imidazole-4-carbonitrile; (+)-1-{[2-oxo-4-(2,3,4-trifluorophenyl)-1-pyrrolidinyl]methyl}-1H-imidazole-4-carbonitrile; (−)-1-{[2-oxo-4-(3,4,5-trifluorophenyl) pyrrolidin-1-yl]methyl}-1H-imidazole-4-carbonitrile; (+)-1-{[2-oxo-4-(3,4,5-trifluorophenyl) pyrrolidin-1-yl]methyl}-1H-imidazole-4-carbonitrile; (+)-1-{[2-oxo-4-(2,4,5-trifluorophenyl) pyrrolidin-1-yl]methyl}-1H-imidazole-4-carbonitrile; (−)-1-{[2-oxo-4-(2,4,5-trifluorophenyl) pyrrolidin-1-yl]methyl}-1H-imidazole-4-carbonitrile; (−)-1-{[2-oxo-4-(2,3,5-trifluorophenyl) pyrrolidin-1-ylmethyl}-1H-imidazole-4-carbonitrile; (−)-1-{[2-oxo-4-(3,4,5=trifluorophenyl) pyrrolidin-1-yl]methyl}-1H-imidazole-5-carbonitrile; 1-{[2-oxo-4-(2,3,5-trifluorophenyl) pyrrolidin-1-yl]methyl}-1H-imidazole-5-carbonitrile; 1-{[2-oxo-4-(2,3,5-trifluorophenyl) pyrrolidin-methyl]-1H-imidazole-5-carbonitrile; 1-[(5-methyl-2-phenyl-1H-imidazol-1-yl)methyl]-4-propylpyrrolidin-2-one; 1-[(5-methyl-1H-imidazol-1-yl)methyl]-4-propylpyrrolidin-2-one; 1-[(5-phenyl-1H-imidazol-1-yl)methyl]-4-propylpyrrolidin-2-one; 1-[(2-ethyl-5-methyl-1H-imidazol-1-yl)methyl]-4-propylpyrrolidin-2-one; 1-[(2,5-dimethyl-1H-imidazol-1-yl)methyl]-4-propylpyrrolidin-2-one; 1-[(2-chloro-1H-imidazol-1-yl)methyll-4-(3,4,5-trifluorophenyl) pyrrolidin-2-one; 1-[2-azido-1-(1H-imidazol-1-yl)ethyl]-4-propylpyrrolidin-2-one; 1-[(4-chloro-1H-imidazol-1-yl)methyl]-4-(3,4,5-trifluorophenyl) pyrrolidin-2-one; 1-[(2-bromo-4,5-dichloro-1H-imidazol-1-yl)methyl]-4-propylpyrrolidin-2-one; 1-[(2-chloro-1H-imidazol-1-yl)methyl]-4-propylpyrrolidin-2-one; (+)-1-1[2-oxo-4-(3,4,5-trifluorophenyl) pyrrolidin-1-yl]methyl}-1H-imidazole-5-carbonitrile; 1-{[5-(hydroxymethyl)-1H-imidazol-1-yl]methyl}-4-propylpyrrolidin-2-one; 1-{[4-(hydroxymethyl)-1H-imidazol-1-yl]methyl}-4-propylpyrrolidin-2-one; benzyl 1-[(2-oxo-4-propylpyrrolidin-1-yl)methyl]-1H-imidazol-5-ylcarbamate; N-[(1-{[2-oxo-4-(3,4,5-trifluorophenyl) pyrrolidin-1-yl]

methyl}-1H-imidazol-5-yl)methyl]acetamide; N-[(1-{[2-oxo-4-(3,4,5-trifluorophenyl) pyrrolidin-1-yl]methyl}-1H-imidazol-5-yl)methyl]benzamide; N-1 (1-1[2-oxo-4-(3,4,5-trifluorophenyl)pyrroldin-1-yl]methyl}-1H-imidazol-5-yl) methyl]propanamide; 1-(1H-benzimidazol-1-ylmethyl)-4-propylpyrrolidin-2-one; 1-[(2-methyl-1H-benzimidazol-1-yl)methyl]-4-propylpyrrolidin-2-one; 4-propyl-1-[(2-propyl-1H-benzimidazol-1-yl)methyl]pyrrolidin-2-one; 1-[(2-isopropyl-1H-benzimidazol-1-yl)methyl]-4-propylpyrrolidin-2-one; 4-propyl-1-{[2-(trifluoromethyl)-1H-benzimidazol-1-yl]methyl}pyrrolidin-2-one; 1-{[2-(methylthio)-1H-benzimidazol-1-yl]methyl}-4-propylpyrrolidin-2-one; 1-[(2-amino-1H-benzimidazol-1-yl)methyl]-4-propylpyrrolidin-2-one; 1-{[2-(chloromethyl)-1H-benzimidazol-1-yl]melthyl}-4-propylpyrrolidin-2-one; {1-[(2-oxo-4-propylpyrrolidin-1-yl)methyl]-1H-benzimidazol-2-yl}acetonitrile; 1-[(5-methoxy-1H-benzimidazol-1-yl) methyl]-4-propylpyrrolidin-2-one; 1-[(5-methyl-1H-benzimidazol-1-yl)methyl]-4-propylpyrrolidin-2-one; 1-[(5, 6-dimethyl-1H-benzimidazol-1-yl)methyl]-4-propylpyrrolidin-2-one; 1-{[2-isopropyl-5-(trifluoromethyl)-1H-benzimidazol-1-yl]methyl}-4-propylpyrrolidin-2-one; 1-[(6-chloro-1H-benzimidazol-1-yl)methyl]-4-propylpyrrolidin-2-one; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl] methyl}pyrrolidin-2-one; 1-[(5-fluoro-2-propyl-1H-benzimidazol-1-yl)methyl]-4-propylpyrrolidin-2-one; 1-{[6-methyl-2-(1H-pyrrol-2-yl)-1H-benzimidazol-1-yl]methyl}-4-propylpyrrolidin-2-one; 1-[(6-methoxy-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-{[2-[2-(methylthio)ethyl]-5-(trifluoromethyl)-1H-benzimidazol-1-yl]methyl}-4-propylpyrrolidin-2-one; 1-[(5-fluoro-2-isobutyl-1H-benzimidazol-1-yl)methyl]-4-propylpyrrolidin-2-one; 1-{[5-fluoro-2-(2,4,4-trimethylpentyl)-1H-benzimidazol-1-yl] methyl}-4-propylpyrrolidin-2-one; 2-cyclopropyl-1-[(2-oxo-4-propylpyrrolidin-1-yl)methyl]-1H-benzimidazole-5-carbonitrile; 1-[(2-oxo-4-propylpyrrolidin-1-yl)methyl]-2-(1H-pyrazol-3-yl)-1H-benzimidazole-5-carbonitrile; 1-[(2-cyclopropyl-5-fluoro-1H-benzimidazol-1-yl)methyl]-4-propylpyrrolidin-2-one; 1-[(5-fluoro-2-isopropyl-1H-benzimidazol-1-yl)methyl]-4-propylpyrrolidin-2-one; 1-{[2-(3-furyl)-6-methoxy-1H-benzimidazol-1-ylmethyl}-4-propylpyrrolidin-2-one; 1-[(2-cyclopropyl-6-methoxy-1H-benzimidazol-1-yl)methyl]-4-propylpyrrolidin-2-one; 1-[(2-isopropyl-6-methoxy-1H-benzimidazol-1-yl)methyl]-4-propylpyrrolidin-2-one; 1-[(2-oxo-4-propylpyrrolidin-1-yl)methyl]-2-(1,2,3-thiadiazol-4-yl)-1H-benzimidazole-5-carbonitrile; 1-{[2-(1H-imidazol-2-yl)-5-(trifluoromethyl)-1H-benzimidazol-1-yl]methyl}-4-propylpyrrolidin-2-one; 1-{[5-fluoro-2-(2,2,2-trifluoroethyl)-1H-benzimidazol-1-yl] methyl}-4-propylpyrrolidin-2-one; 1-{[2-(1-ethylpropyl)-6-methoxy-1H-benzimidazol-1-yl]methyl}-4-propylpyrrolidin-2-one; 1-{[6-methoxy-2-(1-methyl-1H-pyrrol-2-yl)-1H-benzimidazol-1-yl]methyl}-4-propylpyrrolidin-2-one; 1-{[2-(2-furyl)-5-(trifluoromethyl)-1H-benzimidazol-1-yl] methyl}-4-propylpyrrolidin-2-one; 4-propyl-1-{[2-thien-2-yl-5-(trifluoromethyl)-1H-benzimidazol-1-yl] melthyl}pyrrolidin-2-one; 1-1[2-(3-furyl)-5-(trifluoromethyl)-1H-benzimidazol-1-yl]methyl}-4-propylpyrrolidin-2-one; 1-{[2-cyclopropyl-5-(trifluoromethyl)-1H-benzimidazol-1-yl]methyl}-4-propylpyrrolidin-2-one; 4-propyl-1-{[2-(1H-pyrrol-2-yl)-5-(trifluoromethyl)-1H-benzimidazol-1-yl]methyl}pyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 4-fluoro-1-(1H-imidazol-1-ylmethyl)-1,3-dihydro-2H-indol-2-one; 4-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(2-oxo-2,3-dihydro-1H-indol-1-yl)methyl]-1H-imidazole-5-carbonitrile; and 1-[(5-chloro-2-oxo-2,3-dihydro-1H-indol-1-yl)methyl]-1H-imidazole-5-carbonitrile.

In some embodiments, compounds are: 1-(1H-imidazol-1-ylmethyl) pyrrolidin-2-one, 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl) pyrrolidin-2-one; (+)-4-(3-azido-2,4-difluorophenyl)-1-(1H-imidazol-1-ylmethyl) pyrrolidin-2-one; 1-[(2-ethyl-1H-imidazol-1-yl)methyl]-4-propylpyrrolidin-2-one; 1-[(2-isopropyl-1H-imidazol-1-yl) methyl]-4-propylpyrrolidin-2-one; 1-[(2-methyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2, 2-difluorovinyl)-1-(1H-imidazol-1-ylmethyl) pyrrolidin-2-one; 4-(3-chlorophenyl)-1-(1H-imidazol-1-ylmethyl) pyrrolidin-2-one; 1-{[2-(methylthio)-1H-imidazol-1-yl] methyl}-4-propylpyrrolidin-2-one; 1-[(2-methyl-1H-imidazol-1-yl)methyl]-4-phenylpyrrolidin-2-one; 4-(4-fluorophenyl)-1-(1H-imidazol-1-ylmethyl) pyrrolidin-2-one; 1-(1H-imidazol-1-ylmethyl)-4-(3,4,5-trifluorophenyl) pyrrolidin-2-one; 4-(3-fluorophenyl)-1-(1H-imidazol-1-ylmethyl) pyrrolidin-2-one; 4-(3,5-difluorophenyl)-1-(1H-imidazol-1-ylmethyl) pyrrolidin-2-one; 4-(3,4-difluorophenyl)-1-(1H-imidazol-1-ylmethyl) pyrrolidin-2-one; 4-(3-chloro-4-fluorophenyl)-1-(1H-imidazol-1-ylmethyl) pyrrolidin-2-one; 4-(4-chlorophenyl)-1-(1H-imidazol-1-ylmethyl) pyrrolidin-2-one; 1-(1H-imidazol-1-ylmethyl)-4-(2,3,4-trifluorophenyl) pyrrolidin-2-one; 1-(1H-imidazol-1-ylmethyl)-4-(2,3,5-trifluorophenyl) pyrrolidin-2-one; 1-(1H-imidazol-1-ylmethyl)-4-(2,4,5-trifluorophenyl) pyrrolidin-2-one; 1-[(2-nitro-1H-imidazol-1-yl)methyl]-4-(3,4,5-trifluorophenyl) pyrrolidin-2-one; 1-{[2-oxo-4-(3,4,5-trifluorophenyl) pyrrolidin-1-yl]methyl}-1H-imidazole-2-carbonitrile; 1-[(2-amino-1H-imidazol-1-yl)methyl]-4-propylpyrrolidin-2-one; 1-1 (5-chloro-1H-imidazol-1-yl)methyl]-4-(3,4,5-trifluorophenyl) pyrrolidin-2-one; 1-{[2-oxo-4-(3,4,5-trifluorophenyl) pyrrolidin-1-yl]methyl}-1H-imidazole-4-carbonitrile; 1-{[2-oxo-4-(3,4,5-trifluorophenyl) pyrrolidin-1-yl] methyl}-1H-imidazole-5-carbonitrile; (+)-1-(1H-imidazol-1-ylmethyl)-4-phenylpyrrolidin-2-one; (+1-(1H-imidazol-1-ylmethyl)-4-phenylpyrrolidin-2-one; (+); 1-{[2-oxo-4-(3,4, 5-trifluorophenyl) pyrrolidin-1-yl]methyl}-1H-imidazole-4-carbonitrile; 1-[(2-chloro-1H-imidazol-1-yl)methyl]-4-(3,4, 5-trifluorophenyl) pyrrolidin-2-one; 1-[2-azido-1-(1H-imidazol-1-yl)ethyl]-4-propylpyrrolidin-2-one; 1-[(2-chloro-1H-imidazol-1-yl)methyl]-4-propylpyrrolidin-2-one; (+)-1-1[2-oxo-4-(3,4,5-trifluorophenyl) pyrrolidin-1-yl] methyl}-1H-imidazole-5-carbonitrile; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl]methyl}pyrrolidin-2-one; 1-[(5-fluoro-2-propyl-1H-benzimidazol-1-yl) methyl]-4-propylpyrrolidin-2-one; 2-butyl-1-[(2-oxo-4-propylpyrrolidin-1-yl)methyl]-1H-benzimidazole-5- carbonitrile; 1-[(5-fluoro-2-isopropyl-1H-benzimidazol-1-yl)methyl]-4-propylpyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbonitrile.

In some embodiments, compounds are: 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl) pyrrolidin-2-one; (+)-4-(3-azido-2,4-difluorophenyl)-1-(1H-imidazol-1-ylmethyl) pyrrolidin-2-one; 4-(2,2-difluorovinyl)-1-(1H-imidazol-1-ylmethyl) pyrrolidin-2-one; 4-(3-chlorophenyl)-1-(1H-imidazol-1-ylmethyl) pyrrolidin-2-one; 1-{[2-(methylthio)-1H-imidazol-1-yl]methyl}-4-propylpyrrolidin-2-one; 1-[(2-methyl-1H-imidazol-1-yl)methyl]-4-phenylpyrrolidin-2-one; 1-(1H-imidazol-1-ylmethyl)-4-(3,4,5-trifluorophenyl) pyrrolidin-2-one; 4-(3-fluorophenyl)-1-(1H-imidazol-1-ylmethyl) pyrrolidin-2-one; 4-(3,5-difluoromethyl)-1-(1H-imidazol-1-ylmethyl) pyrrolidin-2-one; 1-(1H-imidazol-1-ylmethyl)-4-(2,3,4-trifluorophenyl) pyrrolidin-2-one; 1-(1H-imidazol-1-ylmethyl)-4-(2,3,5-trifluorophenyl) pyrrolidin-2-one; 1-H-imidazol-1-ylmethyl)-4-(2,4,5-trifluorophenyl) pyrrolidin-2-one; 1-[(2-nitro-1H-imidazol-1-yl)methyl]-4-(3,4,5-trifluorophenyl) pyrrolidin-2-one; 1-{[2-oxo-4-(3,4,5-trifluorophenyl) pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl) pyrrolidin-2-one; (+)-1-(1H-imidazol-1-ylmethyl)-4-phenylpyrrolidin-2-one; (−)-1-(1H-imidazol-1-ylmethyl)-4-phenylpyrrolidin-2-one; 1-[(2-chloro-1H-imidazol-1-yl)methyl]-4-(3,4,5-trifluorophenyl) pyrrolidin-2-one 1-[(2-chloro-1H-imidazol-1-yl)methyl]-4-propylpyrrolidin-2-one; (+)-1-1[2-oxo-4-(3,4,5-trifluorophenyl) pyrrolidin-1-yl]methyl}-1H-imidazole-5-carbonitrile; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbonitrile.

Some compounds are: (−)-4-(3-azido-2,4-difluorophenyl)-1-(1H-imidazol-1-ylmethyl) pyrrolidin-2-one; (+)-4-(3-azido-2,4-difluorophenyl)-1-(1H-imidazol-1-ylmethyl) pyrrolidin-2-one; 4-(3-azido-2,4-difluorophenyl)-1-(1H-imidazol-1-ylmethyl) pyrrolidin-2-one.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

Some of the compounds of formula I may also exist in tautomeric forms. Such forms although not explicity indicated in the above formula are intended to be included within the scope of the present invention.

In another preferred embodiment, the present invention concerns also compounds of formula IA and their tautomeric form IB

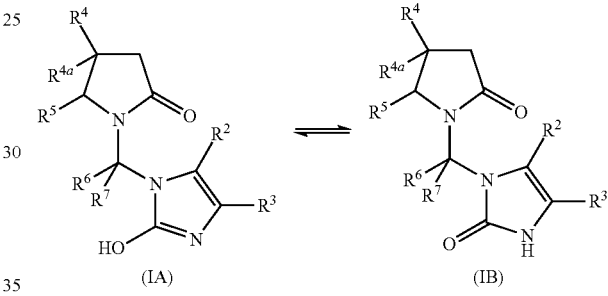

(IA)     (IB)

With respect to the present invention reference to a compound or compounds is intended to encompass that compound in each of its possible isomeric forms and mixtures thereof, unless the particular isomeric form is referred to specifically. Compounds according to the present invention may exist in different polymorphic forms. Although not explicitly indicated in the above formula, such forms are intended to be included within the scope of the present invention.

The invention also includes within its scope pro-drug forms of the compounds of formula I and its various sub-scopes and sub-groups.

xii) U.S. Patent Application Publication No. 20090018148

In one aspect the invention provides compounds having formula I, their enantiomers, diastereoisomers and mixtures thereof (including all possible mixtures of stereoisomers), or pharmaceutically acceptable salts thereof,

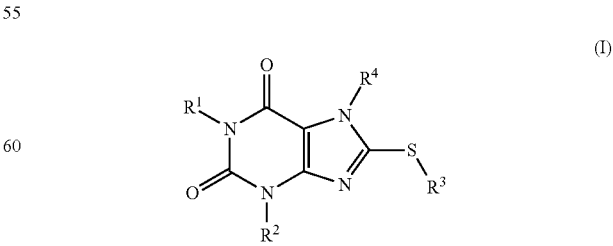

wherein
R1 is hydrogen or C1-6 alkyl;
R2 is hydrogen or C1-4 alkyl;

R3 is a group of formula —CHR5R6 or a benzyl group;
R4 is C1-8 alkyl optionally substituted by alkoxycarbonyl, C3-6 cycloalkyl, aryl or heterocycle;
R5 is C2-4 alkyl;
R6 is C2-4 alkyl, amido or —COOR7;
R7 is C1-4 alkyl;

In one aspect, the invention provides compounds:
When R1 is hydrogen, R2 is methyl, R3 is —CHR5R6, R6 is ethoxycarbonyl and R5 is ethyl, then R4 is different from methyl, n-propyl, i-propyl, n-pentyl, n-heptyl, 3-bromobenzyl, 4-chlorobenzyl, 4-methylbenzyl or 2-phenylethyl;

When R1 is hydrogen, R2 is methyl, R3 is benzyl, then R4 is different from i-propyl, n-butyl, 3-methylbutyl, benzyl, phenylethyl-, or 3-phenylpropyl; When R1 and R2 are methyl, R3 is benzyl, R4 is different from methyl, 3-methylbutyl, benzyl, 3-phenylpropyl or 4-chlorophenylmethyl; Finally 8-(2-chloro-benzylsulfanyl)-3-methyl-7-octyl-3,7-dihydro-purine-2,6-dione is considered.

Usually when R3 is a benzyl group, then R4 is C1-8 alkyl optionally substituted by alkoxycarbonyl.

Usually when R3 is a group of formula —CHR5R6, then R4 is C1-8 alkyl optionally substituted by C3-6 cycloalkyl, aryl or heterocycle.

The term "alkyl", as used herein, is a group which represents saturated, monovalent hydrocarbon radicals having straight (unbranched) or branched moieties, or combinations thereof, and containing 1-8 carbon atoms, preferably 1-6 carbon atoms; more preferably alkyl groups have 1-4 carbon atoms. Alkyl moieties may optionally be substituted by 1 to 5 substituents independently selected from the group consisting of hydroxy, alkoxy, cyano, ethynyl, alkoxycarbonyl, acyl, aryl or heterocycle. Alkyl moieties may be optionally substituted by a cycloalkyl as defined hereafter. Preferred alkyl groups according to the present invention are methyl, cyanomethyl, ethyl, 2-ethoxy-2-oxoethyl, 2-methoxyethyl, n-propyl, 2-oxopropyl, 3-hydroxypropyl, 2-propynyl, n-butyl, i-butyl, n-pentyl, 3-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl or (5-nitro-2-furyl)methyl. More preferred alkyl groups are methyl, ethyl, cyanomethyl, 2-methoxyethyl, n-propyl, 3-hydroxypropyl, 2-propynyl, n-butyl, 3-pentyl, n-hexyl, benzyl, 3-bromobenzyl, 3-methoxybenzyl, 3-nitrobenzyl, 3-aminobenzyl, (3,5-dimethylisoxazol-4-yl)methyl or (5-nitro-2-furyl)methyl. Most preferred alkyl groups are methyl, ethyl, 3-methoxybenzyl, 3-nitrobenzyl or (5-nitro-2-furyl)methyl.

The term "cycloalkyl", as used herein, represents a monovalent group of 3 to 8, preferably 3 to 6 carbon atoms derived from a saturated cyclic hydrocarbon, which may be substituted by any suitable group including but not limited to one or more moieties selected from groups as described above for the alkyl groups. Preferred cycloalkyl group according to the present invention is cyclohexyl.

The term "aryl" as used herein, is defined as a phenyl group optionally substituted by 1 to 4 substituents independently selected from halogen, amino, nitro, alkoxy or aminosulfonyl. Preferred aryl groups are phenyl, 2-bromophenyl, 3-bromophenyl, 4-bromophenyl, 3-methoxyphenyl, 3-nitrophenyl, 3-aminophenyl or 4-(aminosulfonyl)phenyl.

The term "phenyl", as used herein, represents an aromatic hydrocarbon group of formula —C6H5.

The term "benzyl group", as used herein, represents a group of formula —CH2-aryl. Preferred benzyl groups are benzyl, 2-bromobenzyl, 3-bromobenzyl, 4-bromobenzyl, 3-methoxybenzyl, 3-nitrobenzyl, 3-aminobenzyl or 4-(aminosulfonyl)benzyl. More preferred benzyl groups are benzyl, 3-bromobenzyl, 3-methoxybenzyl, 3-nitrobenzyl or 3-aminobenzyl. In some embodiments alkyl groups are 3-methoxybenzyl or 3-nitrobenzyl.

The term "halogen", as used herein, represents an atom of fluorine, chlorine, bromine, or iodine. In some embodiments the halogen is bromine.

The term "hydroxy", as used herein, represents a group of formula —OH.

The term "cyano", as used herein, represents a group of formula —CN.

The term "amino", as used herein, represents a group of formula —NH2.

The term "ethynyl", as used herein, represents a group of formula —C≡CH.

The term "alkoxy", as used herein, represents a group of formula —ORa wherein Ra is an alkyl group, as defined above. In some embodiments the alkoxy group is methoxy.

The term "nitro", as used herein, represents a group of formula —NO2.

The term "amido", as used herein, represents a group of formula —C(=O)NH2.

The term "acyl", as used herein, represents a group of formula —C(=O)Rb wherein Rb is an alkyl group, as defined here above. In some embodiments the acyl group is acetyl (—C(=O)Me).

The term "alkoxycarbonyl (or ester)", as used herein, represents a group of formula —COORc wherein Rc is an alkyl group; with the proviso that Rc does not represent an alkyl alpha-substituted by hydroxy. In some embodiments the alkoxycarbonyl group is ethoxycarbonyl.

The term "heterocycle", as used herein, represents a 5-membered ring containing one or two heteroatoms selected from O or N. The heterocycle may be substituted by one or two C1-4 alkyl or nitro. In some embodiments the heterocycles are (3,5-dimethylisoxazol-4-yl) or (5-nitro-2-furyl). Most preferred heterocycle is (5-nitro-2-furyl).

Generally R1 is hydrogen or C1-6 alkyl. Usually R1 is hydrogen or C1-6 alkyl optionally substituted by hydroxy, alkoxy, cyano, ethynyl, alkoxycarbonyl or acyl. In some embodiments R1 is hydrogen, methyl, cyanomethyl, 2-ethoxy-2-oxoethyl, 2-methoxyethyl, n-propyl, 2-oxopropyl, 3-hydroxypropyl, 2-propynyl, n-pentyl or n-hexyl. In some embodiments R1 is hydrogen, methyl, cyanomethyl, 2-methoxyethyl, n-propyl, 3-hydroxypropyl or 2-propynyl. In some embodiments R1 is hydrogen.

Generally R2 is hydrogen or C1-4 alkyl. Usually R2 is hydrogen or unsubstituted C1-4 alkyl. In some embodiments R2 is hydrogen, methyl or n-butyl. In some embodiments, R2 is methyl.

Generally R3 is a group of formula —CHR5R6 or a benzyl group. In some embodiments R3 is 3-pentyl, 1-(aminocarbonyl)propyl, 1-(ethoxycarbonyl)propyl or 3-bromobenzyl. In some embodiments R3 is 1-(ethoxycarbonyl)propyl.

Generally R4 is C1-8 alkyl optionally substituted by alkoxycarbonyl, C3-6 cycloalkyl, aryl or heterocycle. Usually R4 is C1-8 alkyl optionally substituted by cyclohexyl, phenyl, bromophenyl, aminophenyl, methoxyphenyl, nitrophenyl, aminosulfonylphenyl, 3,5-dimethylisoxazol-4-yl, 5-nitro-2-furyl or ethoxycarbonyl. In some embodiments R4 is n-butyl, i-butyl, n-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl, (5-nitro-2-furyl)methyl or 1-(ethoxycarbonyl)propyl. In some embodiments R4 is n-butyl, n-hexyl, benzyl, 3-bromobenzyl, 3-methoxybenzyl, 3-nitrobenzyl, 3-aminobenzyl, (3,5-dimethylisoxazol-4-yl)methyl, (5-nitro-2-furyl)methyl or 1-(ethoxycarbonyl)propyl. In some embodiments R4 is 3-methoxybenzyl, 3-nitrobenzyl or (5-nitro-2-furyl)methyl.

Generally R5 is C2-4 alkyl. Usually R5 is unsubstituted C2-4 alkyl. In some embodiments R5 is ethyl.

Generally R6 is C2-4 alkyl, amido or —COOR7. Usually R6 is unsubstituted C2-4 alkyl, amido or —COOR7. In some embodiments R6 is ethyl, amido or ethoxycarbonyl. In some embodiments R6 is ethoxycarbonyl.

Generally R7 is C1-4 alkyl. Usually R7 is unsubstituted C1-4 alkyl. In some embodiments, R7 is ethyl.

Usually the invention provides compounds having formula I, their enantiomers, diastereoisomers and mixtures thereof (including all possible mixtures of stereoisomers), or pharmaceutically acceptable salts thereof,

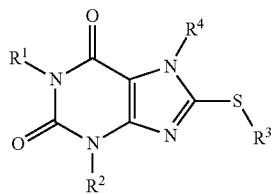

(I)

wherein
R1 is hydrogen, C1-6 alkyl optionally substituted by hydroxy, alkoxy, cyano, ethynyl, alkoxycarbonyl or acyl;
R2 is hydrogen or unsubstituted C1-4 alkyl;
R3 is a group of formula —CHR5R6 or a benzyl group;
R4 is C1-8 alkyl optionally substituted by cyclohexyl, phenyl, bromophenyl, aminophenyl, methoxyphenyl, nitrophenyl, aminosulfonylphenyl, 3,5-dimethylisoxazol-4-yl, 5-nitro-2-furyl or ethoxycarbonyl;
R5 is unsubstituted C2-4 alkyl;
R6 is unsubstituted C2-4 alkyl, amido or —COOR7;
R7 is unsubstituted C1-4 alkyl;
with the proviso that when R1 is hydrogen, R2 is methyl, R3 is —CHR5R6, R6 is ethoxycarbonyl and R5 is ethyl, then R4 is different from n-propyl, i-propyl, n-pentyl, n-heptyl, 3-bromobenzyl, 4-chlorobenzyl, 4-methylbenzyl or 2-phenylethyl.

In the above embodiment, sometimes, when R3 is a benzyl group, then R4 is C1-8 alkyl optionally substituted by alkoxycarbonyl.

In the above embodiment, sometimes, when R3 is a group of formula —CHR5R6, then R4 is C1-8 alkyl optionally substituted by C3-6 cycloalkyl, aryl or heterocycle.

In one embodiment,
R1 is hydrogen, methyl, cyanomethyl, 2-ethoxy-2-oxoethyl, 2-methoxyethyl, n-propyl, 2-oxopropyl, 3-hydroxypropyl, 2-propynyl, n-pentyl or n-hexyl;
R2 is hydrogen, methyl or n-butyl;
R3 is 3-pentyl, 1-(aminocarbonyl)propyl, 1-(ethoxycarbonyl)propyl or 3-bromobenzyl;
R4 is n-butyl, i-butyl, n-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl, (5-nitro-2-furyl)methyl or 1-(ethoxycarbonyl)propyl;

with the proviso that when R1 is hydrogen, R2 is methyl and R3 is 1-(ethoxycarbonyl)propyl, then R4 is different from n-pentyl, 3-bromobenzyl or 2-phenylethyl.

In the above embodiment, sometimes, when R3 is 3-bromobenzyl, then R4 is C1-8 alkyl optionally substituted by alkoxycarbonyl.

In the above embodiment, sometimes, when R3 is 3-pentyl, 1-(aminocarbonyl)propyl or 1-(ethoxycarbonyl)propyl, then R4 is different from 1-(ethoxycarbonyl)propyl.

In a more preferred embodiment, R1 is hydrogen, methyl, cyanomethyl, 2-methoxyethyl, n-propyl, 3-hydroxypropyl or 2-propynyl;
R2 is methyl;
R3 is 3-pentyl, 1-(aminocarbonyl)propyl, 1-(ethoxycarbonyl)propyl or 3-bromobenzyl;
R4 is n-butyl, n-hexyl, benzyl, 3-bromobenzyl, 3-methoxybenzyl, 3-nitrobenzyl, 3-aminobenzyl, (3,5-dimethylisoxazol-4-yl)methyl, (5-nitro-2-furyl)methyl or 1-(ethoxycarbonyl)propyl;
with the proviso that when R1 is hydrogen, R2 is methyl and R3 is 1-(ethoxycarbonyl)propyl, then R4 is different from 3-bromobenzyl.

In the above embodiment, sometimes, when R3 is 3-bromobenzyl, then R4 is 1-(ethoxycarbonyl)propyl;
In the above embodiment, sometimes, when R3 is 3-pentyl, 1-(aminocarbonyl)propyl or 1-(ethoxycarbonyl)propyl, then R4 is different from 1-(ethoxycarbonyl)propyl;

In one embodiment, R1 is hydrogen; R2 is methyl; R3 is 1-(ethoxycarbonyl)propyl; and R4 is 3-methoxybenzyl, 3-nitrobenzyl or (5-nitro-2-furyl)methyl.

A further embodiment consists in compounds wherein R2 is methyl, R3 is a group of formula —CHR5R6 with R5 being C2-4 alkyl, R6 being amido or —COOR7 and R7 being methyl or ethyl.

In some embodiments, compounds are ethyl 2-[(7-benzyl-1,3-dimethyl-2,6-dioxo-2,3,6,7-tetrahydro-1H-purin-8-yl)thio]butanoate; ethyl 2-{[7-(3-bromobenzyl)-1-(2-ethoxy-2-oxoethyl)-3-methyl-2,6-dioxo-2,3,6,7-tetrahydro-1H-purin-8-yl]thio}butanoate; ethyl 2-{[7-(3-bromobenzyl)-1-(2-methoxyethyl)-3-methyl-2,6-dioxo-2,3,6,7-tetrahydro-1H-purin-8-yl]thio}butanoate; ethyl 2-{[7-(3-bromobenzyl)-2,6-dioxo-2,3,6,7-tetrahydro-1H-purin-8-yl]thio}butanoate; ethyl 2-{[7-(3-bromobenzyl)-1,3-dimethyl-2,6-dioxo-2,3,6,7-tetrahydro-1H-purin-8-yl]thio}butanoate; ethyl 2-{[7-(2-bromobenzyl)-1,3-dimethyl-2,6-dioxo-2,3,6,7-tetrahydro-1H-purin-8-yl]thio}butanoate; ethyl 2-{[7-(3-bromobenzyl)-1-(cyanomethyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-propyl-2,3,6,7-tetrahydro-1H-purin-8-yl]thio}butanoate; ethyl 2-{[7-(3-bromobenzyl)-3-methyl-2,6-dioxo-1-(2-oxopropyl)-2,3,6,7-tetrahydro-1H-purin-8-yl]thio}butanoate; ethyl 2-{[7-(3-bromobenzyl)-1-(3-hydroxypropyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-(2-propynyl)-2,3,6,7-tetrahydro-1H-purin-8-yl]thio}butanoate; ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; ethyl 2-{[7-(3-aminobenzyl)-3-methyl-2,6-dioxo-2,3,6,7-tetrahydro-1H-purin-8-yl]thio}butanoate; ethyl 2-({7-[4-(aminosulfonyl)benzyl]-3-methyl-2,6-dioxo-2,3,6,7-tetrahydro-1H-purin-8-yl}thio)butanoate; ethyl 2-{[7-(4-bromobenzyl)-1,3-dimethyl-2,6-dioxo-2,3,6,7-tetrahydro-1H-purin-8-yl]thio}butanoate; ethyl 2-{[7-(cyclohexylmethyl)-1,3-dimethyl-2,6-dioxo-2,3,6,7-tetrahydro-1H-purin-8-yl]thio}butanoate; ethyl 2-{[1,3-dimethyl-2,6- dioxo-7-(1-phenylethyl)-2,3,6,7-tetrahydro-1H-purin-8-yl]thio}butanoate; ethyl 2-{[1,3-dimethyl-2,6-dioxo-7-(2-phenylethyl)-2,3,6,7-tetrahydro-1H-purin-8-yl]thio}butanoate; ethyl 2-({7-[(3,5-dimethylisoxazol-4-yl)methyl]-3-methyl-2,6-dioxo-2,3,6,7-tetrahydro-1H-purin-8-yl}thio)butanoate; ethyl 2-({3-methyl-7-[(5-nitro-2-furyl)methyl]-2,6-dioxo-2,3,6,7-tetrahydro-1H-purin-8-yl}thio)butanoate; ethyl 2-[(7-butyl-3-methyl-2,6-dioxo-2,3,6,7-tetrahydro-1H-purin-8-yl)thio]butanoate; ethyl 2-{[7-(3-bromobenzyl)-2,6-dioxo-2,3,6,7-tetrahydro-1H-purin-8-yl]thio}butanoate; ethyl 2-[(1,7-dihexyl-3-methyl-2,6-dioxo-2,3,6,7-tetrahydro-1H-purin-8-yl)thio]butanoate; ethyl 2-[(7-hexyl-3-methyl-2,6-dioxo-2,3,6,7-tetrahydro-1H-purin-8-yl)thio]butanoate; ethyl 2-[(3-methyl-2,6-dioxo-1,7-dipentyl-2,3,6,7-tetrahydro-1H-purin-8-yl)thio]butanoate; 2-{[7-(3-bromobenzyl)-3-methyl-2,6-dioxo-2,3,6,7-tetrahydro-1H-purin-8-yl]thio}butanamide; 2-[(7-butyl-3-methyl-2,6-dioxo-2,3,6,7-tetrahydro-1H-purin-8-yl)thio]butanamide; 7-(3-bromobenzyl)-8-[(1-ethylpropyl)thio]-3-methyl-3,7-dihydro-1H-purine-2,6-dione; ethyl 2-{8-[(3-bromobenzyl)thio]-1,3-dimethyl-2,6-dioxo-1,2,3,6-tetrahydro-7H-purin-7-yl}butanoate; and ethyl 2-[(7-isobutyl-3-methyl-2,6-dioxo-2,3,6,7-tetrahydro-1H-purin-8-yl)thio]butanoate.

In some embodiments compounds are: ethyl 2-[(7-benzyl-1,3-dimethyl-2,6-dioxo-2,3,6,7-tetrahydro-1H-purin-8-yl)thio]butanoate; ethyl 2-{[7-(3-bromobenzyl)-1-(2-methoxyethyl)-3-methyl-2,6-dioxo-2,3,6,7-tetrahydro-1H-purin-8-yl]thio}butanoate; ethyl 2-{[7-(3-bromobenzyl)-1,3-dimethyl-2,6-dioxo-2,3,6,7-tetrahydro-1H-purin-8-yl]thio}butanoate; ethyl 2-{[7-(3-bromobenzyl)-1-(cyanomethyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-propyl-2,3,6,7-tetrahydro-1H-purin-8-yl]thio}butanoate; ethyl 2-{[7-(3-bromobenzyl)-1-(3-hydroxypropyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-(2-propynyl)-2,3,6,7-tetrahydro-1H-purin-8-yl]thio}butanoate; ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; ethyl 2-{[7-(3-aminobenzyl)-3-methyl-2,6-dioxo-2,3,6,7-tetrahydro-1H-purin-8-yl]thio}butanoate; ethyl 2-({7-[(3,5-dimethylisoxazol-4-yl)methyl]-3-methyl-2,6-dioxo-2,3,6,7-tetrahydro-1H-purin-8-yl}thio)butanoate; ethyl 2-({3-methyl-7-[(5-nitro-2-furyl)methyl]-2,6-dioxo-2,3,6,7-tetrahydro-1H-purin-8-yl}thio)butanoate; ethyl 2-[(7-butyl-3-methyl-2,6-dioxo-2,3,6,7-tetrahydro-1H-purin-8-yl)thio]butanoate; ethyl 2-[(7-hexyl-3-methyl-2,6-dioxo-2,3,6,7-tetrahydro-1H-purin-8-yl)thio]butanoate; 2-{[7-(3-bromobenzyl)-3-methyl-2,6-dioxo-2,3,6,7-tetrahydro-1H-purin-8-yl]thio}butanamide; 7-(3-bromobenzyl)-8-[(1-ethylpropyl)thio]-3-methyl-3,7-dihydro-1H-purine-2,6-dione; and ethyl 2-{8-[(3-bromobenzyl)thio]-1,3-dimethyl-2,6-dioxo-1,2,3,6-tetrahydro-7H-purin-7-yl}butanoate.

In some embodiments compounds are: ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; and ethyl 2-({3-methyl-7-[(5-nitro-2-furyl)methyl]-2,6-dioxo-2,3,6,7-tetrahydro-1H-purin-8-yl}thio)butanoate.

The acid addition salt form of a compound of formula I that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula I containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula I or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically. Compounds according to the present invention may exist in different polymorphic forms. Although not explicitly indicated in the above formula, such forms are intended to be included within the scope of the present invention.

xiii) U.S. Pat. No. 7,465,549

In some embodiments, the compound includes optionally substituted N-alkylated 2-oxo-pyrrolidine derivatives. In some embodiments, those compounds are alkyl amides derivatives substituted on the positions 4 and/or 5 of the pyrrolidone ring.

Examples of optionally substituted N-alkylated 2-oxo-pyrrolidine derivatives include, but are not limited to, compounds such as (2S)-2-[(4S)-4-(2,2-difluorovinyl)-2-oxopyrrolidinyl]butanamide, (2S)-2-[(4R)-2-oxo-4-propylpyrrolidinyl]butanamide, (2S)-2-[(4S)-2-oxo-4-propylpyrrolidinyl]butanamide, and (2S)-2-[4-(3-azidophenyl)-2-oxopyrrolidin-1-yl]butanamide.

In some embodiments, the compounds further include optionally substituted N-alkylated 2-oxo-piperidinyl derivatives. In some embodiments, those compounds are alkyl amides derivatives substituted on the position 4 and/or 5 and/or 6 of the 2-oxo-piperidinyl ring. Examples of optionally substituted N-alkylated 2-oxo-pyrrolidine derivatives include, but are not limited to, compounds such as those referred to in international patent application PCT/EP02/05503 such as (2S)-2-[5-(iodomethyl)-2-oxo-1-piperidinyl] butanamide, (2S)-2-[5-(azidomethyl)-2-oxo-1-piperidinyl] butanamide, 2-(2-oxo-5-phenyl-1-piperidinyl]butanamide, (2S)-2-[4-(iodomethyl)-2-oxo-1-piperidinyl]butanamide, and (2S)-2-[4-(2-fluoro-2-methylpropyl)-2-oxo-1-pyrrolidinyl]butanamide.

In some embodiments, the compounds include any acetam compound of formula I, in racemic or isomeric form, or a pharmaceutically acceptable salt thereof,

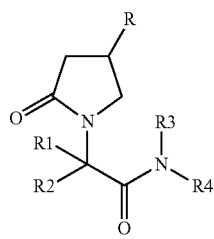

(I)

wherein
R represents hydrogen or hydroxy;
R1 and R2 represent independently hydrogen or an alkyl group of 1-4 carbon atoms; and
R3 and R4 represent independently hydrogen, an alkyl group of 1-4 carbon atoms or —(CH2)n-NR5R6 wherein n is 1, 2 or 3 and R5 and R6 represent independently hydrogen or an alkyl group of 1-4 carbon atoms.

An example of such an acetam compound includes, but is not limited to, a compound of formula I wherein R, R1, R2, R3 and R4 are hydrogen, 2-oxo-pyrrolidineacetamide, known by the generic name piracetam as described in UK Patents Nos. 1,039,113 and 1,309,692.

In some embodiments, the compounds also include optionally substituted N-alkylated 2-oxo-azepanyl derivatives. Preferably, those compounds are alkyl amides derivatives substituted on the positions 4 and/or 5 and/or 6 and/or 7 of the 2-oxo-azepanyl ring. Examples of optionally substituted N-alkylated 2-oxo-azepanyl derivatives include, but are not limited to, compounds such as those referred to in international patent application PCT/EP02/05503 such as 2-[5-(iodomethyl)-2-oxo-1-azepanyl]butanamide.

xiv) U.S. Patent Application Publication No. 2006258704

This invention provides novel compounds of the formula I

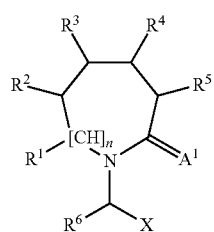

(I)

wherein
n represents 0 or 1 whereby R<1> is not existent when n=0 and R<1> is existent when n=1;
A<1> represents an oxygen or a sulfur atom;
X is —CONR<7> R<8>, —COOR<9>, —CO—R<10> or CN;
R<1> when existent, R<2>, R<3>, R<4> and R<5> are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative, provided that at least one of the substituents R chosen from R<1> when existent, R<2>, R<3>, R<4> or R<5> is not hydrogen;
R<6> is hydrogen, alkyl, aryl or —CH2-R<6a> wherein R<6a> is aryl, heterocycle, halogen, hydroxy, amino, nitro or cyano;
R<7>, R<8> and R<9> are the same or different and each is independently hydrogen, hydroxy, alkyl, aryl, heterocycle or an oxy derivative; and
R<10> is hydrogen, hydroxy, thiol, halogen, alkyl, aryl, heterocycle or a thio derivative;
their pharmaceutically acceptable salts, geometrical Isomers (including cis and trans, Z and E isomers), enantiomers, diastereoisomers and mixtures thereof (including all possible mixtures of stereoisomers).

In the above formula, at least one substituent R<1> to R<5> is different from hydrogen. Some non-substituted compounds are referred to in U.S. Pat. Nos. 5,468,733 and 5,516,759. U.S. Pat. No. 5,468,733 discloses non-ring substituted 2-oxo-1-pyrrolidinyl and 2-oxo-1-piperidinyl derivatives as inhibitors of the oncogene Ras protein. In particular, these compounds block the ability of Ras to transform normal cells to cancer cells, and therefore can be included in several chemotherapeutic compositions for treating cancer.

U.S. Pat. No. 5,516,759 discloses non-ring substituted 2-oxo-1-pyrrolidinyl, 2-oxo-1-piperidinyl and azepanyl derivatives present at the N-terminus of dodecapeptides possessing LHRH (luteinizing hormone-releasing hormone) antagonistic activity. Such LHRH antagonists are useful in the treatment of a variety of conditions in which suppression of sex steroids plays a key role including contraception, delay of puberty, treatment of benign prostatic hyperplasia a.o.

In the definitions set forth below, unless otherwise stated, R<11> and R<12> are the same or different and each is independently amido, alkyl, alkenyl, alkynyl, acyl, ester, ether, aryl, aralkyl, heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein, is defined as including —O—R<11> groups wherein R<11> is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate. The term "thio derivative", as used herein, is defined as including —S—R<11> groups wherein R<11> is as defined above except for "thio derivative". Non-limiting examples are alkylthio, alkenylthio, alkynylthio and arylthio.

The term "amino derivative", as used herein, is defined as including —NHR<11> or —NR<11>R<12> groups wherein R<11> and R<12> are as defined above. Non-limiting examples are mono- or di-alkyl-, alkenyl-, alkynyl- and arylamino or mixed amino.

The term "acyl derivative", as used herein, represents a radical derived from carboxylic acid and thus is defined as including groups of the formula R<11>—CO—, wherein R<11> is as defined above and may also be hydrogen.

Preferred are acyl derivatives of formula —COR<11> wherein R<11> is selected from hydrogen, C1-12 alkyl, C2-12 alkenyl, C2-12 alkenyl, heterocyle and aryl. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative", as used herein, is defined as including a group of the formula —SO—R<11>, wherein R<11> is as defined above except for "sulfonyl derivative". Non-limiting examples are alkylsulfonyl, alkenylsulfonyl, alkynylsulfonyl and arylsulfonyl.

The term "sulfinyl derivative", as used herein, is defined as including a group of the formula —SO—R<11>, wherein R<11> is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and generally containing 1-20 carbon atoms, most often 1 to 12 carbon atoms, preferably 1-7 carbon atoms for non-cyclic alkyl and 3-7 carbon atoms for cycloalkyl (in these two preferred cases, unless otherwise specified, "lower alkyl"), each optionally substituted by, preferably 1 to 5, substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, alkylthio, oxyester, oxyamido, heterocycle, vinyl, alkoxy (preferably C1-5), aryloxy (preferably C6-10) and aryl(preferably C6-10).

In some embodiments are alkyl groups containing 1 to 7 carbon atoms, each optionally substituted by one or more substituents selected from hydroxy, halogen, cyano, thiocyanato, alkoxy, azido, alkylthio, cyclopropyl, acyl and phenyl. Most preferred are C1-4 alkyl and C3-7 cycloalkyl, each optionally substituted by one or more hydroxy, halogen, lower alkyl or/and azido.

In some embodiments are alkyl groups are hydroxymethyl, propyl, butyl, 2,2,2-trifluoroethyl, 2-bromo-2,2-difluoroethyl, 2-chloro-2,2-difluoroethyl, 3,3,3-trifluoropropyl, cyclopropylmethyl, iodomethyl, azidomethyl, 2,2-difluoropropyl, 2-iodo-2,2-difluoroethyl.

The term "lower alkyl", as used herein, and unless otherwise specified, refers to C1 to C7 saturated straight, branched or cyclic hydrocarbon. Non limiting examples are methyl, ethyl, propyl, isopropyl, butyl, tertiobutyl, pentyl, cyclopropyl, cyclopentyl, isopentyl, neopentyl, hexyl, isohexyl, cyclohexyl, 3-methypentyl, 2,2-dimethylbutyl, optionally substituted with any suitable group, including but not limited to one or more moieties selected from groups as described above for the alkyl groups. Preferably, lower alkyl is methyl.

The term "alkenyl", as used herein, is defined as including both branched and unbranched, unsaturated hydrocarbon radicals having at least one double bond, and being optionally substituted by at least one substituent selected from the group consisting of halogen, hydroxy, thiol, amino, thiocyanato, azido, alkylthio, cycloalkyl, acyl, nitro, cyano, aryl and heterocycle.

In some embodiments are alkenyl groups are C2-C12 alkenyls, especially C2-6alkenyls, such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl and the like, optionally being substituted by one or more substituents selected from halogen, cyano, thiocyanato, azido, alkylthio, cycloalkyl, phenyl and acyl. Most preferred is vinyl, optionally substituted by one or more halogen or/and lower alkyl, and especially 2,2-difluorovinyl, 2,2-dibromovinyl and 2,2-dichlorovinyl.

The term "alkynyl" as used herein, is defined as including a monovalent branched or unbranched hydrocarbon radical containing at least one carbon-carbon triple bond, for example ethynyl, 2-propynyl (=propargyl), and the like, and being optionally substituted by at least one substituent selected from the group consisting of halogen, hydroxy, thiol, amino, nitro, cyano, aryl, heterocycle, thiocyanato, azido, alkylthio, alkyl and acyl.

In some embodiments are alkynyl groups are C2-12 alkynyl, especially C2-6 alkynyl, optionally being substituted by one or more substituents selected from halogen, cyano, thiocyanato, azido, alkylthio, acyl, aryl such as phenyl and alkyl, preferably cycloalkyl.

In some embodiments are ethynyl, propynyl and butynyl, optionally substituted by lower alkyl or/and halogen, and especially 1-propynyl, cyclopropylethynyl, 3-methyl-1-butynyl and 3,3,3-trifluoro-1-propynyl.

When present as bridging groups, alkyl, alkenyl and alkynyl represent straight- or branched chains, C1-12, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl", as used herein, is defined as including an organic radical derived from an aromatic hydrocarbon consisting of at least one ring, most often 1 to 3 rings and generally containing 6-30 carbon atoms by removal of one hydrogen, such as phenyl and naphthyl, each optionally substituted by one or more substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, C1-6-alkylthio, oxyester, oxyamido, aryl, C1-6-alkoxy, C6-10-aryloxy, C1-6-alkyl, C1-6-haloalkyl. Aryl radicals are preferably monocyclic or bicyclic containing 6-10 carbon atoms. Preferred aryl groups are phenyl and naphthyl each optionally substituted by one or more substituents independently selected from halogen, nitro, amino, azido, C1-6-alkoxy, C1-6-alkyl, C1-6-haloalkyl, sulfonyl and phenyl.

In some embodiments the aryl is phenyl, optionally substituted by one or more halogen, lower alkyl, azido or nitro, such as 3-chlorophenyl and 3-azidophenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —NO2.

The term "nitrooxy", as used herein, represents a group of the formula —ONO2.

The term "amino", as used herein, represents a group of the formula —NH2.

The term "azido", as used herein, represents a group of the formula —N3.

The term "carboxy", as used herein, represents a group of the formula —COOH.

The term "sulfonic acid", as used herein, represents a group of the formula —SO3H.

The term "sulfonamide", as used herein, represents a group of the formula —SO2NH2.

The term "ester", as used herein, is defined as including a group of formula —COO—R<11> wherein R<11> is as defined above except oxy derivative, thio derivative or amino derivative. Preferred are esters of formula —COOR<11> wherein R<11> is selected from C1-12 alkyl, C2-12 alkenyl, C2-12 alkynyl and aryl. Most preferred are esters where R<11> is a lower alkyl, especially methyl.

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —CONH2 or —CONHR<11> or —CONR<11>R<12> wherein R<11> rand R<12> are as defined above.

The term "heterocycle", as used herein, is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl, and optionally being substituted with any suitable group, including but not limited to one or more moieties selected from lower alkyl, or other groups as described above for the alkyl groups. Non-limiting examples of heterocycles are pyridyl, furyl, pyrrolyl, thienyl, isothiazolyl, triazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thiomorpholinyl, thieno(2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, 1-oxidopyridyl, phenanthridinyl, acridinyl, perimidinyl, phenanthrolinyl, phenothiazinyl, furazanyl, benzodioxolyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, sugar moieties (i.e. glucose, pentose, hexose, ribose, fructose, which may also be substituted) optionally substituted by alkyl or as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl, 8-azabicyclo(3.2.1)octanyl.

The heterocycle may be selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl. In some embodiments the heterocycle is selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl, and especially from 2- and 3-thienyl, optionally substituted by one or more halogen, acyl such as formyl, cyano and/or lower alkyl, such as methyl.

In the above definitions it is to be understood that when a substituent such as R<1>, R<2>, R<3>, R<4>, R<5>, R<7>, R<8>, R<9>, R<10> is attached to the rest of the molecule via a heteroatom or a carbonyl, a straight- or branched chain, C1-12-, preferably C1-4-alkylene or C2-12, preferably C2-4-alkenylene or -alkynylene bridge may optionally be interposed between the heteroatom or the carbonyl and the point of attachment to the rest of the molecule.

The acid addition salt form of a compound of formula (I) that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (I) containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula I and their salts can be in the form of a solvate, which is included within the scope of the present invention. Such solvates include for example hydrates, alcoholates and the like.

Many of the compounds of formula I and some of their intermediates have at least one stereogenic center in their structure. This stereogenic center may be present in a R or a S configuration, said R and S notation is used in correspondence with the rules described in Pure Appl. Chem. (1976), 45, 11-30.

The invention also relates to all stereoisomeric forms such as enantiomeric and diastereoisomeric forms of the compounds of formula I or mixtures thereof (including all possible mixtures of stereoisomers).

Furthermore, certain compounds of formula I which contain alkenyl groups may exist as Z (zusammen) or E (entgegen) isomers. In each instance, the invention includes both mixture and separate individual isomers.

Multiple substituents on the piperidinyl or the azepanyl ring can also stand in either cis or trans relationship to each other with respect to the plane of the piperidinyl or the azepanyl ring.

Some of the compounds of formula I may also exist in tautomeric forms. Such forms although not explicitly indicated in the above formula are intended to be included within the scope of the present invention.

With respect to the present invention reference to a compound or compounds is intended to encompass that compound in each of its possible isomeric forms and mixtures thereof unless the particular isomeric form is referred to specifically.

The invention also includes within its scope prodrug forms of the compounds of formula I and Its various sub-scopes and sub-groups.

The term "prodrug" as used herein includes compound forms which are rapidly transformed in vivo to the parent compound according to the invention, for example, by hydrolysis in blood. Prodrugs are compounds bearing groups which are modified by biotransformation prior to exhibiting their pharmacological action. Such groups include moieties which are readily oxidised, cyclised or cleaved, which compound after biotransformation remains or becomes pharmacologically active. For example, metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialkylsilyl (such as trimethyl- and triethylsilyl), monoesters formed with dicarboxylic acids (such as succinyl), phosphate, sulfate, sulfonate, sulfonyl, sulfinyl and the like. The compounds bearing the biotransformable groups have the advantage that they may exhibit improved bioavailability as a result of enhanced solubility and/or rate of absorption conferred upon the parent compound by virtue of the presence of the biotransformable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

The term "R substituent" refers to R<1>, R<2>, R<3>, R<4> or R<5>, independently.

According to one embodiment, the present invention relates to a compound of formula I as defined above wherein n represents 0. The compound is a 6-ring structure (2-thioxo- or 2-oxo-piperidinyl derivative) wherein R<1> is not existent since n=0, and is depicted by the formula (I-A).

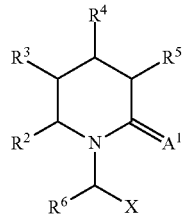

(I-A)

According to a following embodiment, the present invention relates to a compound of formula I according to the invention as defined above wherein n represents 1. The compound is a 7-ring structure (2-thioxo- or 2-oxo-azepanyl derivative) wherein R<1> is existent since n=1 and depicted by the formula (I-B).

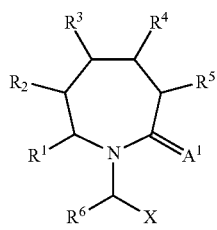

(I-B)

According to one embodiment, the invention relates to said compound as defined above wherein n=0, R<3> and/or R<4> are different from hydrogen and R<2> and R<5> represent hydrogen.

According to another embodiment, the invention relates to said compound as defined above wherein n=1, R<2>, R<3> and/or R<4> are different from hydrogen and wherein R<1> and R<5> represent hydrogen.

According to another embodiment, the invention relates to said compound as defined above wherein only one R substituent chosen from R<3> or R<4> when n=0 or from R<2>, R<3> or R<4> when n=1, is different from hydrogen and the remaining R substituent(s) is/are hydrogen. We hereby refer to a mono-substituted 2-thioxo- or 2-oxo-piperidinyl or 2-thioxo- or 2-oxo-azepanyl derivatives. According to another embodiment, the present invention relates to compounds of formula I according to the invention as defined above wherein A<1> represents an oxygen atom. We hereby refer to 2-oxo-piperidinyl or 2-oxo-azepanyl derivatives.

According to another embodiment, the present invention relates to compounds of formula I according to the invention as defined above wherein X is CONR<7>R<8>, especially CONH2. We hereby refer to amido derivatives of 2-oxo(or thioxo)-piperidinyl or 2-oxo(or thioxo)-azepanyl.

According to another embodiment, the present invention relates to compounds of formula I according to the invention as defined above wherein R<6> represents hydrogen, C1-4 alkyl, or a CH2-R<6a> group wherein R<6a> represents a heterocycle. Most preferably R<6> is a C1-4 alkyl, especially ethyl. When R<6> is ethyl we refer to 2-(2-oxo(or thioxo)-1-piperidinyl)butanamide or 2-(2-oxo(or thioxo)-1-azepanyl)butanamide derivatives.

According to another embodiment, the present invention relates to compounds of formula I according to the invention as defined above wherein the carbon atom to which R<6> is attached is of the S configuration. In case where R<6> is ethyl, A is oxygen and X is CON R<7>R<8>, we refer then to (2S)-2-(2-oxo-1-piperidinyl)butanamide or (2S)-2-(2-oxo-1-azepanyl)butanamide derivatives.

According to one embodiment, the present invention relates to a compound as defined above wherein R<2> when n=1, R<3> and R<4> are the same or different and each is independently hydrogen, halogen, nitro, nitrooxy, cyano, carboxy, amido, sulfonic acid, sulfonamide, alkyl, alkenyl, alkynyl, ester, ether, aryl, heterocycle, acyl derivative, sulfonyl derivative or sulfinyl derivative: R<1> when existent, R<2> when n=0 and R<5> are hydrogen; R<6> is hydrogen, alkyl, aryl or —CH2-R<6a> wherein R<6a> is aryl, heterocycle, halogen, hydroxy, amino, nitro or cyano; provided that, when R<6> is hydrogen, X is —CONR<7>R<8> and that the compound is neither methyl (2R)-2-[(6R)-6-methyl-2-oxoazepanyl]-3-phenylpropanoate nor methyl (2S)-2-[(4R)-4-methyl-2-oxoazepanyl]-3-phenylpropanoate.

According to this embodiment, the compound is generally such that when R<6> is benzyl, X is —COOCH3 and n=1, R<2> is different from methyl when R<3> and R<4> are both hydrogen and R<4> is different from methyl when R<2> and R<3> are both hydrogen.

According to another embodiment, the present invention relates to a compound as defined above wherein R<2> when n=1, R<3> and R<4> are the same or different and each is independently hydrogen; cyano; carboxy; amido; C1-12 alkyl, each optionally substituted by one or more substituents selected from hydroxy, halogen, cyano, thiocyanato, alkoxy, azido, alkylthio, cycloalkyl, acyl, aryl and heterocycle;

C2-12 alkenyl, each optionally substituted by one or more substituents selected from halogen, cyano, thiocyanato, azido, alkylthio, alkyl, aryl and acyl;

C2-12 alkynyl, each optionally substituted by one or more substituents selected from halogen, cyano, thiocyanato, azido, alkylthio, alkyl, aryl and acyl; acyl derivative of formula —CO—R<11>, wherein R<11> is selected from C1-12 alkyl, C2-12 alkenyl, C2-12 alkynyl, heterocycle and aryl;

ester of formula —CO—O—R<11> wherein R<11> is selected from C1-12 alkyl, C2-12 alkenyl, C2-12 alkynyl and aryl;

heterocycle selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl;

aryl, each optionally substituted by one or more substituents selected from C1-6 alkyl, C1-6 haloalkyl, C1-6 alkoxy, C1-6 alkylthio, amino, azido, sulfonyl, aryl and nitro.

According to another embodiment, the present invention relates to a compound as defined above, wherein R<2> when n=1, R<3> and R<4> are the same or different and each is independently hydrogen;

C1-7 alkyl, each optionally substituted by one or more substituents selected from hydroxy, halogen, cyano, thiocyanato, alkoxy, azido, alkyltio, cyclopropyl, acyl and phenyl;

C2-6 alkenyl, each optionally substituted by one or more substituents selected from halogen, cyano, thiocyanato, azido, alkylthio, cycloalkyl, phenyl and acyl:

C2-6 alkynyl, each optionally substituted by one or more substituents selected from halogen, cyano, thiocyanato, azido, alkylthio, cycloalkyl, phenyl and acyl: heterocycle selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl; phenyl, each optionally substitued by one or more substituents selected from C1-6 alkyl, halogen substituted alkyl, halogen, alkoxy, amino, azido, sulfonyl, phenyl and nitro.

According to another embodiment, the present invention relates to a compound as defined above wherein at least one of the R substituents chosen from the group R<2>, R<3> and R<4> when n=1 or from the group R<3> and R<4> when n=0, represents independently C1-4-alkyl or C3-7-cycloalkyl, optionally substituted by one or more halogen, hydroxy, lower alkyl and/or azido.

According to another embodiment, the present invention relates to a compound as defined above wherein at least one of the R substituents chosen from the group R<2>, R<3> and R<4> when n=1 or from the group R<3> and R<4> when n=0, represents independently vinyl, optionally substituted by one or more halogen or/and lower alkyl.

According to another embodiment, the present invention relates to a compound as defined above wherein at least one of the R substituents chosen from the group R<2>, R<3> and R<4> when n=1 or from the group R3 and R<4> when n=0, represents independently ethynyl, propynyl or butynyl, optionally substituted by one or more halogen and/or lower alkyl.

According to another embodiment, the present invention relates to a compound as defined above wherein at least one of the R substituents chosen from the group R<2>, R<3> and R<4> when n=1 or from the group R<3> and R<4> when n=0, represents independently phenyl, optionally substituted by one or more halogen, lower alkyl, azido and/or nitro.

According to another embodiment, the present invention relates to a compound as defined above wherein at least one of the R substituents chosen from the group R<2>, R<3> and R<4> when n=1 or from the group R<3> and R<4> when n=0, represents independently 2- or 3-thienyl, optionally substituted by one or more halogen, acyl, cyano or/and lower alkyl.

According to a particular embodiment, the present invention relates to a compound as defined above wherein at least one of the R substituents chosen from the group R<3>, R<4> and R<2> when n=1 or from the group R<3> and R<4> when n=0, is hydroxymethyl, propyl, butyl, 3,3,3-trifluoropropyl, 2,2,2-trifluoroethyl, cyclopropylmethyl, iodomethyl, azidomethyl, 2-thienyl, 3-thienyl, phenyl, 3-chlorophenyl, 3-azidophenyl, 2,2-difluorovinyl, 2,2-dibromovinyl, 2,2-dichlorovinyl, 2-ethynyl, 5-methyl-2-thienyl, 5-formyl-2-ethynyl, 5-cyano-2-thienyl, 3-bromo-2-thienyl, 4-methyl-2-thienyl, 3,3,3-trifluoro-1-propynyl, 1-propynyl, cyclopropylethynyl, 3-methyl-1-butynyl, 1-butynyl, 2,2-difluoropropyl, 2-chloro-2,2-difluoroethyl, 2-bromo-2,2-difluoroethyl and 2-iodo-2,2-difluoroethyl.

According to yet another embodiment, the present invention relates to a compound as defined above wherein R<1>, R<2>, R<4> and R<5> are hydrogen.

According to another embodiment, the present invention relates to a compound as defined above wherein R<1>, R<2>, R<3> and R<5> are hydrogen.

According to another embodiment, the present invention relates to a compound as defined above wherein n=1 and R<1>, R<3>, R<4> and R<5> are hydrogen.

In all the above-mentioned scopes when the carbon atom to which R<6> is attached is asymmetric it may be in the "S"-configuration.

Representative compounds of this invention as defined above are selected from the group consisting of 2-[5-(hydroxymethyl)-2-oxo-1-piperidinyl]butanamide, 2-(2-oxo-5-propyl-1-piperidinyl)butanamide, 2-12-oxo-5-(3,3,3-trifluoropropyl)-1-piperidinyl]butanamide, 2-[5-(cyclopropylmethyl)-2-oxo-1-piperidinyl]butanamide, 2-[5-(iodomethyl)-2-oxo-1-piperidinyl]butanamide, 2-[5-(azidomethyl)-2-oxo-1-piperidinyl]butanamide, 2-(2-oxo-5-phenyl-1-piperidinyl)butanamide, 2-[2-oxo-5-(2-thienyl)-1-piperidinyl]butanamide, 2-[2-oxo-5-(3-thienyl)-1-piperidinyl]butanamide, 2-[5-(3-chlorophenyl)-2-oxo-1-piperidinyl]butanamide, 2-[5-(3-azidophenyl)-2-oxo-1-piperidinyl]butanamide, 2-[5-(2,2-difluorovinyl)-2-oxo-1-piperidinyl]butanamide, 2-[5-(2,2-dibromovinyl)-2-oxo-1-piperidinyl]butanamide, 2-[5-(2,2-dichlorovinyl)-2-oxo-1-piperidinyl]butanamide, 2-(5-ethynyl-2-oxo-1-piperidinyl)butanamide, 2-[5-(5-methyl-2-thienyl)-2-oxo-1-piperidinyl]butanamide, 2-[5-(5-formyl-2-thienyl)-2-oxo-1-piperidinyl]butanamide, 2-[5-(5-cyano-2-thienyl)-2-oxo-1-piperidinyl]butanamide, 2-[5-(3-bromo-2-thienyl)-2-oxo-1-piperidinyl]butanamide, 2-[5-(4-methyl-2-thienyl)-2-oxo-1-piperidinyl]butanamide, 2-[2-oxo-5-(3,3,3-trifluoro-1-propynyl)-1-piperidinyl]butanamide, 2-[2-oxo-5-(1-propynyl)-1-piperidinyl]butanamide, 2-[5-(cyclopropylethynyl)-2-oxo-1-piperidinyl]butanamide, 2-[5-(3-methyl-1-butynyl)-2-oxo-1-piperidinyl]butanamide, 2-[5-(1-butynyl)-2-oxo-1-piperidinyl]butanamide, 2-[5-(2,2-difluoropropyl)-2-oxo 1-piperidinyl]butanamide, 2-[5-(2-chloro-2,2-difluoroethyl)-2-oxo-1-piperidinyl]butanamide, 2-[5-(2-bromo-2,2-difluoroethyl)-2-oxo-1-piperidinyl]butanamide, 2-[4-(hydroxymethyl)-2-oxo-1-piperidinyl]butanamide, 2-(2-oxo-4-propyl-1-piperidinyl)butanamide, 2-[2-oxo-4-(3,3,3- trifluoroproyl)-1-piperidinyl]butanamide, 2-14-(cyclopropylmethyl)-2-oxo-1-piperidinyl]butanamide, 2-[4-(iodomethyl)-2-oxo-1-piperldinyl]butanamide, 2-[4-(azidomethyl)-2-oxo-1-piperidinyl]butanamide, 2-(2-oxo-4-phenyl-1-piperidinyl)butanamide, 2-12-oxo-4-(2-thienyl)-1-piperidinyl]butanamide, 2-[2-oxo-4-(3-thienyl)-1-piperidinyl]butanamide, 2-[4-(3-chlorophenyl)-2-oxo-1-piperidinyl]butanamide, 2-[4-(3-azidophenyl)-2-oxo-1-piperidinyl]butanamide, 2-[4-(2,2-difluorovinyl)-2-oxo-1-piperidinyl]butanamide, 2-[4-(2,2-dibromovinyl)-2-oxo-1-piperidinyl]butanamide, 2-[4-(2,2-dichlorovinyl)-2-oxo-1-piperidinyl]butanamide, 2-(4-ethynyl-2-oxo-1-piperidinyl)butanamide, 2-[4-(5-methyl-2-thienyl)-2-oxo-1-piperidinyl]butanamide, 2-[4-(5-formyl-2-thienyl)-2-oxo-1-piperidinyl]butanamide, 2-[4-(5-cyano-2-thienyl)-2-oxo-1-piperidinyl]butanamide, 2-[4-(3-bromo-2-thienyl)-2-oxo-1-piperidinyl]butanamide, 2-[4-(4-methyl-2-thienyl)-2-oxo-1-piperidinyl]butanamide, 2-[2-oxo-4-(3,3,3-trifluoro-1-propynyl)-1-piperidinyl]butanamide, 2-[2-oxo-4-(1-propynyl)-1-piperidinyl]butanamide, 2-[4-(cyclopropylethynyl)-2-oxo-1-piperidinyl]butanamide, 2-[4-(3-methyl-1-butynyl)-2-oxo-1-piperidinyl]butanamide, 2-[4-(1-butynyl)-2-oxo-1-piperidinyl]butanamide, 2-[4-(2,2-difluoropropyl)-2-oxo-1-piperidinyl]butanamide, 2-[4-(2-chloro-2,2-difluoroethyl)-2-oxo-1-piperidinyl]butanamide, 2-14-(2-bromo-2,2-difluoroethyl)-2-oxo-1-piperidinyl]butanamide, 2-[4-(2,2,2-trifluoroethyl)-2-oxo-1-piperidinyl]butanamide, 2-[5-(hydroxymethyl)-2-oxo-1-azepanyl]butanamide, 2-(2-oxo-5-propyl-1-azepanyl)butanamide, 2-[2-oxo-5-(3,3,3-trifluoropropyl)-1-azepanyl]butanamide, 2-(5-(cyclopropylmethyl)-2-oxo-1-azepanyl]butanamide, 2-[5-(iodomethyl)-2-oxo-1-azepanyl]butanamide, 2-[5-(azidomethyl)-2-oxo-1-azepanyl]butanamide, 2-(2-oxo-5-phenyl-1-azepanyl)butanamide, 2-[2-oxo-5-(2-thienyl)-1-azepanyl]butanamide, 2-[2-oxo-5-(3-thienyl)-1-azepanyl]butanamide, 2-[5-(3-chlorophenyl)-2-oxo-1-azepanyl]butanamide, 2-[5-(3-azidophenyl)-2-oxo-1-azepanyl]butanamide, 2-[5-(2,2-difluorovinyl)-2-oxo-1-azepanyl]butanamide, 2-[5-(2,2-dibromovinyl)-2-oxo-1-azepanyl]butanamide, 2-[5-(2,2-dichlorovinyl)-2-oxo-1-azepanyl]butanamide, 2-[5-ethynyl-2-oxo-1-azepanyl]butanamide, 2-[5-(5-methyl-2-thienyl)-2-oxo-1-azepanyl]butanamide, 2-[5-(5-formyl-2-thienyl)-2-oxo-1-azepanyl]butanamide, 2-[5-(5-cyano-2-thienyl)-2-oxo-1-azepanyl]butanamide, 2-[5-(3-bromo-2-thienyl)-2-oxo-1-azepanyl]butanamide, 2-[5-(4-methyl-2-thienyl)-2-oxo-1-azepanyl]butanamide, 2-[2-oxo-5-(3,3,3-trifluoro-1-propynyl)-1-azepanyl]butanamide, 2-[2-oxo-5-(1-propynyl)-1-azepanyl]butanamide, 2-[5-(cyclopropylethynyl)-2-oxo-1-azepanyl]butanamide, 2-[5-(3-methyl-1-butynyl)-2-oxo-1-azepanyl]butanamide, 2-[5-(1-butynyl)-2-oxo-1-azepanyl]butanamide, 2-[5-(2,2-difluoropropyl)-2-oxo-1-azepanyl]butanamide, 2-[5-(2-chloro-2,2-difluoroethyl)-2-oxo-1-azepanyl]butanamide, 2-[5-(2-bromo-2,2-difluoroethyl)-2-oxo-1-azepanyl]butanamide, 2-[5-(2,2,2-trifluoroethyl)-2-oxo-1-azepanyl]butanamide, 2-[6-(hydroxymethyl)-2-oxo-1-azepanyl]butanamide, 2-(2-oxo-6-propyl-1-azepanyl)butanamide, 2-[2-oxo-6-(3,3,3-trifluoropropyl)-1-azepanyl]butanamide, 2-[6-(cyclopropylmethyl)-2-oxo-1-azepanyl]butanamide, 2-[6-(iodomethyl)-2-oxo-1-azepanyl]butanamide, 2-16-(azidomethyl)-2-oxo-1-azepanyl]butanamide, 2-(2-oxo-6-phenyl-1-azepanyl)butanamide, 2-[2-oxo-6-(2-thienyl)-1-azepanyl]butanamide, 2-[2-oxo-6-(3-thienyl)-1-azepanyl]butanamide, 2-[6-(3-chlorophenyl)-2-oxo-1-azepanyl]butanamide, 2-[6-(3-azidophenyl)-2-oxo-1-azepanyl]butanamide, 2-[6-(2,2-difluorovinyl)-2-oxo-1-azepanyl]butanamide, 2-[6-(2,2-dibromovinyl)-2-oxo-1-azepanyl]butanamide, 2-[6-(2,2-dichlorovinyl)-2-oxo-1-azepanyl]butanamide, 2-(6-ethynyl-2-oxo-1-azepanyl)butanamide, 2-[6-(5-methyl-2-thienyl)-2-oxo-1-azepanyl]butanamide, 2-[6-(5-formyl-2-thienyl)-2-oxo-1-azepanyl]butanamide, 2-[6-(5-cyano-2-thienyl)-2-oxo-1-azepanyl]butanamide, 2-[6-(3-bromo-2-thienyl)-2-oxo-1-azepanyl]butanamide, 2-[6-(4-methyl-2-thienyl)-2-oxo-1-azepanyl]butanamide, 2-[2-oxo-6-(3,3,3-trifluoro-1-propynyl)-1-azepanyl]butanamide, 2-[2-oxo-6-(1-propynyl)-1-azepanyl]butanamide, 2-[6-(cyclopropylethynyl)-2-oxo-1-azepanyl]butanamide, 2-[6-(3-methyl-1-butynyl)-2-oxo-1-azepanyl]butanamide, 2-[6-(1-butynyl)-2-oxo-1-azepanyl]butanamide, 2-[6-(2,2-difluoropropyl)-2-oxo-1-azepanyl]butanamide, 2-[6-(2-chloro-2,2-difluoroethyl)-2-oxo-1-azepanyl]butanamide, 2-[6-(2-bromo-2,2-difluoroethyl)-2-oxo-1-azepanyl]butanamide, 2-[6-(2,2,2-trifluoroethyl)-2-oxo-1-azepanyl]butanamide, 2-[4-(hydroxymethyl)-2-oxo-1-azepanyl]butanamide, 2-(2-oxo-4-propyl-1-azepanyl)butanamide, 2-[2-oxo-4-(3,3,3-trifluoropropyl)-1-azepanyl]butanamide, 2-14-(cyclopropylmethyl)-2-oxo-1-azepanyl]butanamide, 2-f4-(iodomethyl)-2-oxo-1-azepanyl]butanamide, 2-[4-(azidomethyl)-2-oxo-1-azepanyl]butanamide, 2-(2-oxo-4-phenyl-1-azepanyl)butanamide, 2-[2-oxo-4-(2-thienyl)-1-azepanyl]butanamide, 2-[2-oxo-4-(3-thienyl)-1-azepanyl]butanamide, 2-[4-(3-chlorophenyl)-2-oxo-1-azepanyl]butanamide, 2-[4-(3-azidophenyl)-2-oxo-1-azepanyl]butanamide, 2-[4-(2,2-difluorovinyl)-2-oxo-1-azepanyl]butanamide, 2-[4-(2,2-dibromovinyl)-2-oxo-1-azepanyl]butanamide, 2-[4-(2,2-dichlorovinyl)-2-oxo-1-azepanyl]butanamide, 2-(4-ethynyl-2-oxo-1-azepanyl)butanamide, 2[4-(5-methyl-2-thienyl)-2-oxo-1-azepanyl]butanamide, 2-[4-(5-formyl-2-thienyl)-2-oxo-1-azepanyl]butanamide, 2-[<4>-(5-cyano-<2>-thienyl)-2-oxo-1-azepanyl]butanamide, 2-[4-(3-bromo-2-thienyl)-2-oxo-1-azepanyl]butanamide, 2-[4-(4-methyl-2-thienyl)-2-oxo-1-azepanyl]butanamide, 2-[2-oxo-4-(3,3,3-trifluoro-1-propynyl)-1-azepanyl]butanamide, 2-[2-oxo-4-(1-propynyl)-1-azepanyl]butanamide, 2-[4-(cyclopropylethynyl)-2-oxo-1-azepanyl]butanamide, 2-[4-(3-methyl-1-butynyl)-2-oxo-1-azepanyl]butanamide, 2-[4-(1-butynyl)-2-oxo-1-azepanyl]butanamide, 2-[4-(2,2-difluoropropyl)-2-oxo-1-azepanyl]butanamide, 2-[4-(2-chloro-2,2-difluoroethyl]-2-oxo-1-azepanyl]butanamide, 2-[4-(2-bromo-2,2-difluoroethyl)-2-oxo-1-azepanyl]butanamide, 2-[4-(2,2,2-trifluoroethyl)-2-oxo-1-azepanyl]butanamide.

Results have been obtained with the following compounds:
(2S)-2-[5-(iodomethyl)-2-oxo-1-piperidinyl]butanamide,
(2S)-2-[5-(azidomethyl)-2-oxo-1-piperidinyl]butanamide,
2-(2-oxo-5-phenyl-1-piperidinyl]butanamide,
(2S)-2-[4-(iodomethyl)-2-oxo-1-piperidinyl]butanamide,
2-[5-(iodomethyl)-2-oxo-1-azepanyl]butanamide.

xv) International Patent Application Publication No. WO2008/132139

In some embodiments, the compounds are of formula (I) as follows:

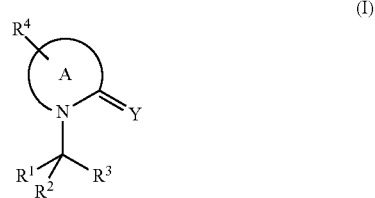

(I)

wherein

Y is O or S. In some embodiments Y is O. R1 is hydrogen or C-l.g alkyl;

R2 is hydrogen;

R3 is —CONR5R6, —COR7, an imidazolyl, an imidazopyridinyl, an imidazopyridazinyl; R5, R6 are the same or different and are independently selected from hydrogen and C-l_6 alkyl;

R7 is C<;l_6 alkyl;

A is a monocyclic or bicyclic heterocyclic moiety selected from the group consisting of imidazolidin-1-yl, 1,3-oxazolidin-3-yl, 2,5-dihydro-1H-pyrrol-1-yl, 1,3-thiazol-3(2H)-yl, 1,3-thiazolidin-3-yl, piperidin-1-yl, azepan-1-yl, 5,6-dihydro-4H-thieno[3,2-b]pyrrol-4-yl, hexahydro-4H-thieno[3,2-b]pyrrol-4-yl, 2,3-dihydro-1H-thieno[3,4-b]pyrrol-1-yl, 1,3-benzothiazol-3(2H)-yl, 1,3-benzoxazol-3(2H)-yl, pyrazolo[1,5-a]pyridin-1(2H)-yl, 3,4-dihydroisoquinolin-2(1H)-yl, 3,4-dihydroquinolin-1(2H)-yl, 1,3,4,5-tetrahydro-2H-2-benzazepin-2-yl, 1,2,4,5-tetrahydro-3H-3-benzazepin-3-yl;

R4 is either Rˆa or Rˆb depending on whether A being is a monocyclic or a bicyclic heterocycle:

where A is a monocyclic heterocyclic moiety, Rˆ is Rˆa which is selected from the group consisting of hydrogen; C-l.g alkyl optionally substituted by a substituent selected from halogen, C-1.4 alkoxy, C-1.4 alkylthio, azido, nitrooxy or an aryl; C2-6 alkenyl optionally substituted by halogen; C2-6 alkynyl optionally substituted by halogen; azido; alkoxycarbonylamino; arylsulfonyloxy; a substituted or unsubstituted aryl; or a 3-8 membered substituted or unsubstituted heterocycle; where A is a bicyclic heterocyclic moiety Rˆ is Rˆ which is selected from the group comprising or consisting of hydrogen; nitro; cyano; halogen; heterocycle; amino; aryl; C-l.g alkyl optionally substituted by at least one halogen; or C-l.g alkoxy optionally substituted by at least one halogen; In some embodiments the compounds are as follows:

For compounds where A=Y is selected from a 2-oxo-piperidin-1-yl, a 2-oxo-azepan-1-yl, a 2-oxo-1,3-benzothiazol-3(2H)-yl or a 2-oxo-1,3-benzoxazol-3(2H)-yl, R3 must be selected from an imidazolyl, an imidazopyridinyl or an imidazopyridazinyl.

For compounds where A=Y is a 5-oxoimidazolidin-1-yl, Rˆ and Rˆ are hydrogen, R3 is —CONR5R6, R5 anclR6 are as above defined, then Rˆa may not be an alkyl, aralkyl or substituted aralkyl.

Where A=Y is either of a 2-oxo-piperidin-1-yl and a 2-oxo-azepan-1-yl, Rˆ, Rˆ and Rˆa are all hydrogen, then Rˆ could not be a 2-phenylimidazo[1,2-a]pyridin-3-yl.

In a specific embodiment A=Y is selected from the list consisting of:

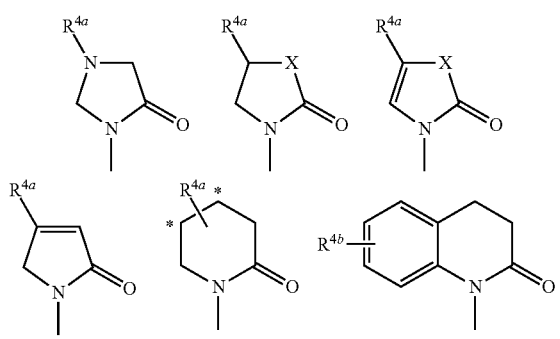

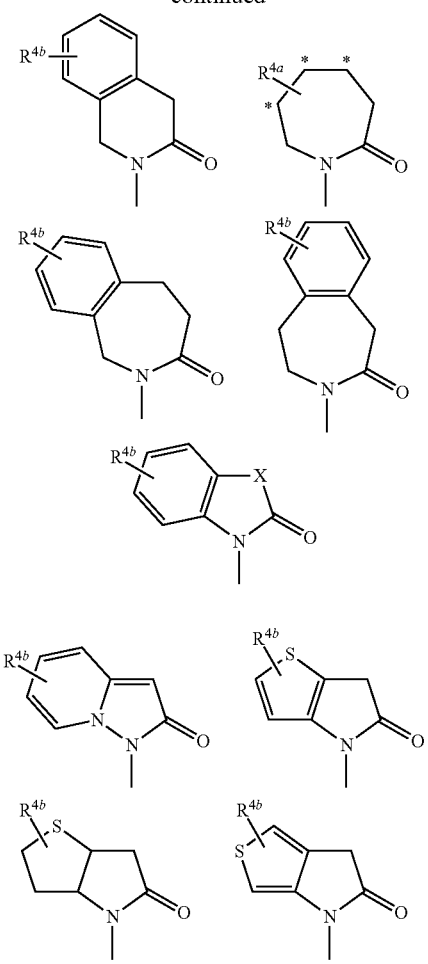

wherein X is O or S, in a more specific embodiment O; in another embodiment, X is S.

The asterisks in the above illustration indicate the attachment sites of the substituent Rˆa.

In a specific embodiment, when Rˆ is —CONR5R6 and Rˆ is C-µg alkyl, the carbon atom to which R-I and Rˆ are attached is preferably in the "S"-configuration.

In a specific embodiment Rˆ is hydrogen, methyl, ethyl and Rˆ is hydrogen. In a specific embodiment R3 is —CONH2.

In a further specific embodiment Rˆ is 1H-imidazol-1-yl, 1H-imidazol-4-yl, 1H-imidazol-5-yl, imidazo[1,2-a]pyridin-3-yl or imidazo[1,2-b]pyridazin-3-yl. In a specific embodiment Rˆa is a C-l.g alkyl which may optionally be substituted by a halogen; or a phenyl.

In another specific embodiment Rˆb is hydrogen, halogen, nitro, cyano or a C-µg alkyl optionally substituted by a halogen.

In still a further embodiment compounds may be used in the treatment of the above mentioned disorders, in particular of epilepsy, having the formula (I-E), as wells as its geometrical isomers, enantiomers, diastereomers and mixtures, or a pharmaceutically acceptable salt thereof,

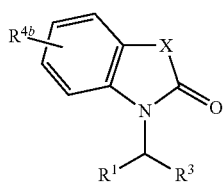

(I-E)

wherein

X is O or S;

R-I is hydrogen or C-l.g alkyl, in a more specific embodiment hydrogen;

R3 is an imidazolyl, an imidazopyridinyl, an imidazopyridazinyl; R^b is hydrogen; nitro; cyano; halogen; C-l.g alkyl optionally substituted by halogen; C-l.g alkoxy optionally substituted by halogen.

A further aspect of the present invention consists in novel compounds having the formula (I-A), their geometrical isomers, enantiomers, diastereomers and mixtures, or a pharmaceutically acceptable salt thereof,

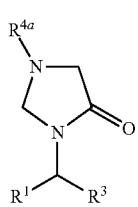

(I-A)

wherein

R1 is hydrogen or C-l.g alkyl, preferably hydrogen, methyl or ethyl; in a more specific embodiment R^ is ethyl.

R3 is —CONH2, an imidazolyl, an imidazopyridinyl, an imidazopyridazinyl, preferably R^ is —CONH2.

R^a is either hydrogen or an aryl; with the proviso that 2-(5-oxoimidazolidin-1-yl)acetamide is excluded. Preferably R^a is an aryl, e.g. a phenyl which may be substituted preferably by halogen, nitro, alkoxy, in particular by nitro.

In a particular embodiment, when R^ is —CONH2 and R^ is C-l.g alkyl, the carbon atom to which R1 and R^ are attached is preferably in the "S"-configuration.

A further aspect of the present invention consists in novel compounds having the formula (I-B1 or I-B2), their geometrical isomers, enantiomers, diastereomers and mixtures, or a pharmaceutically acceptable salt thereof,

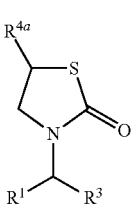

(I-B1)

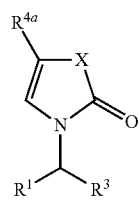

(I-B2)

wherein X in formula (I-B2) is either S or O, in a more specific embodiment S;

R1 is hydrogen or C-l.g alkyl, preferably hydrogen, methyl or ethyl; in a more specific embodiment R^ is ethyl.

R3 is —CONH2, an imidazolyl, an imidazopyridinyl, an imidazopyridazinyl; preferably R^ is —CONH2

R^a is hydrogen; C-l.g alkyl optionally substituted by halogen or C-1.4 alkoxy; an aryl; or C2.g alkenyl optionally substituted by halogen. Preferably, R^a is C-l.g alkyl optionally substituted by halogen or C2-6 alkenyl optionally substituted by halogen or an aryl. In a more specific embodiment R^a is C-l.g alkyl optionally substituted by halogen or aryl.

In a particular embodiment, when R^ is —CONH2 and R^ is C-l.g alkyl, the carbon atom to which R-I and R^ are attached is preferably in the "S"-configuration.

A further aspect of the present invention consists in novel compounds having the formula (I-B3), their geometrical isomers, enantiomers, diastereomers and mixtures, or a pharmaceutically acceptable salt thereof,

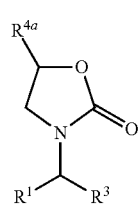

(I-B3)

wherein

R1 is either hydrogen or C-µg alkyl, preferably hydrogen, methyl or ethyl; more preferably R1 is ethyl.

R3 is —CONH2, an imidazolyl, an imidazopyridinyl, an imidazopyridazinyl;

preferably R^ is —CONH2 R^a is C-l_5 alkyl optionally substituted by halogen or C-1.4 alkoxy; an aryl; or C2_g alkenyl optionally substituted by halogen.

Preferably, R^a is C-l.g alkyl optionally substituted by halogen or C2_g alkenyl optionally substituted by halogen.

In a particular embodiment, when R^ is —CONH2 and R^ is C-l.g alkyl, the carbon atom to which R-I and R^ are attached is preferably in the "S"-configuration. A further aspect of the present invention consists in novel compounds having the formula (I-C), their geometrical isomers, enantiomers, diastereomers and mixtures, or a pharmaceutically acceptable salt thereof, (I-C)

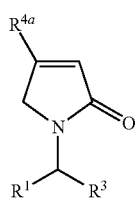

wherein
R1 is hydrogen or C-l.g alkyl, in particular hydrogen, methyl or ethyl.
R3 is —CONH2, an imidazolyl, an imidazopyridinyl, an imidazopyridazinyl; in particular Rˆ is —CONH2
Rˆa is methyl, ethyl, butyl optionally substituted by halogen or C-1.4 alkoxy, an unsubstituted phenyl or a phenyl substituted by halogen, a C-l.g alkyl optionally substituted by halogen or a C-1.4 alkoxy; or Rˆa is a C2-6 alkenyl optionally substituted by halogen. Preferably, Rˆa is methyl, optionally substituted by halogen, an unsubstituted phenyl or a phenyl substituted by halogen.

In a particular embodiment, when Rˆ is —CONH2 and Rˆ is C-l.g alkyl, the carbon atom to which R1 and Rβ are attached is preferably in the "S"-configuration.

A further aspect of the present invention consists in compounds having the formula (I-D1 or I-D2), their geometrical isomers, enantiomers, diastereomers and mixtures, or a pharmaceutically acceptable salt thereof, (I-D1)

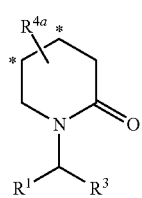

(I-D2)

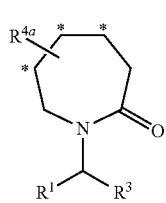

wherein
R-I is hydrogen or C-l.g alkyl, in particular hydrogen; R3 is an imidazolyl, an imidazopyridinyl or an imidazopyridazinyl. In one embodiment, Rˆ is 1H-imidazol-1-yl, 1H-imidazol-4-yl, 1H-imidazol-5-yl, imidazo[1,2-a]pyridin-3-yl or imidazo[1,2-b]pyridazin-3-yl. In a more specific embodiment, Rˆ is 1H-imidazol-1-yl, 1H-imidazol-4-yl, 1H-imidazol-5-yl, imidazo[1,2-a]pyridin-3-yl; Rˆa is hydrogen, C-l.g alkyl optionally substituted by halogen or C-1.4 alkoxy; aryl; or C2-g alkenyl optionally substituted by halogen. In a specific embodiment, Rˆa is C-l.g alkyl optionally substituted by halogen; aryl; or C2-6 alkenyl optionally substituted by halogen. In a more specific embodiment Rˆa is C-l.g alkyl optionally substituted by halogen; or aryl; e.g, propyl or phenyl; with the proviso that when Rˆ and Rˆa are hydrogen, Rˆ is not 2-phenylimidazo[1,2-a]pyridin-3-yl.

A further aspect of the present invention consists in compounds having the formula (I-F1, I-F2 or I-F3), their geometrical isomers, enantiomers, diastereomers and mixtures, or a pharmaceutically acceptable salt thereof, (I-F1)

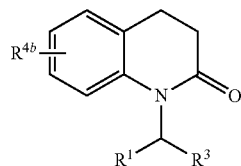

(I-F2)

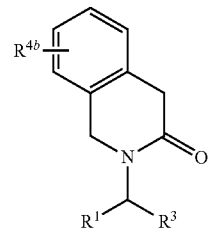

(I-F3)

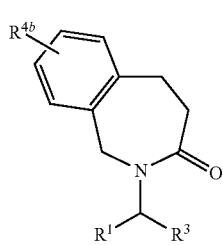

wherein
R-I is hydrogen or C-l.g alkyl, preferably hydrogen, methyl or ethyl; more preferably, Rˆ is hydrogen.
R3 is —CONH2, an imidazolyl, an imidazopyridinyl or an imidazopyridazinyl; in a more specific embodiment R3 is —CONH2, 1H-imidazol-1-yl, 1H-imidazol-4-yl, 1H-imidazol-5-yl, imidazo[1,2-a]pyridin-3-yl or imidazo[1,2-b]pyridazin-3-yl.
Rˆb is hydrogen; halogen; nitro; cyano; C1.4 alkyl optionally substituted by halogen; C-1.4 alkoxy optionally substituted by halogen. In a more specific embodiment Rˆ is hydrogen, halogen or cyano, more specifically halogen.

In a particular embodiment, when Rˆ is —CONH2 and Rˆ is C-l.g alkyl, the carbon atom to which R1 and Rβ are attached is preferably in the "S"-configuration.

A further aspect of the present invention consists in compounds having the formula (I-F4), their geometrical isomers, enantiomers, diastereomers and mixtures, or a pharmaceutically acceptable salt thereof, (I-F4)

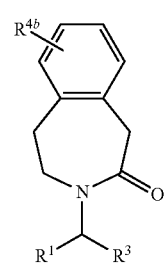

wherein
R-I is hydrogen or C-l.g alkyl, preferably hydrogen;
R3 is an imidazolyl, an imidazopyridinyl or an imidazopyridazinyl; more specifically R^ is 1H-imidazol-1-yl, 1H-imidazol-4-yl, 1H-imidazol-5-yl, imidazo[1,2-a]pyridin-3-yl or imidazo[1,2-b]pyridazin-3-yl. More specifically R^ is 1H-imidazol-4-yl or imidazo[1,2-a]pyridin-3-yl.

R^b is hydrogen; halogen; nitro; cyano; C-1.4 alkyl optionally substituted by halogen; C-1.4 alkoxy optionally substituted by halogen; specifically R^ is hydrogen, halogen or cyano.

In a particular embodiment, when R^ is —CONH2 and R^ is C-l.g alkyl, the carbon atom to which R-I and R^ are attached is preferably in the "S"-configuration.

A further aspect of the present invention consists in compounds having either of the formula (I-G1, I-G2 or I-G3), their geometrical isomers, enantiomers, diastereomers and mixtures, or a pharmaceutically acceptable salt thereof,

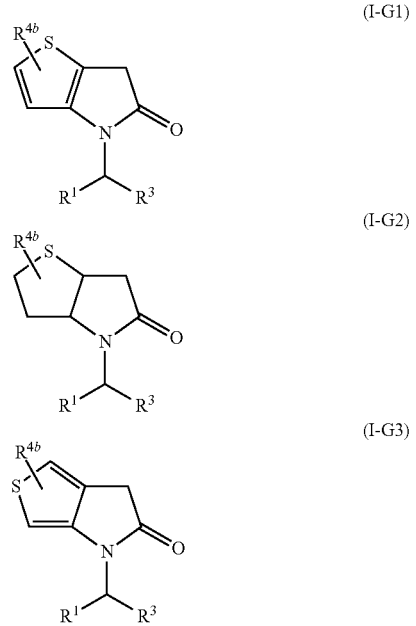

wherein
R-I is hydrogen or C-l.g alkyl; preferably hydrogen;
R3 is —CONH2, an imidazolyl, an imidazopyridinyl, an imidazopyridazinyl; in a more specific embodiment R^ is —CONH2, 1H-imidazol-1-yl, 1H-imidazol-4-yl, 1H-imidazol-5-yl, imidazo[1,2-a]pyridin-3-yl or imidazo[1,2-b]pyridazin-3-yl. In a even more specific embodiment R3 is an 1H-imidazol-4-yl or imidazo[1,2-a]pyridin-3-yl;
R4D js hydrogen; halogen; C-1.4 alkyl optionally substituted by halogen; C-1.4 alkoxy optionally substituted by halogen.

Specific compounds of the present invention are those selected from the group consisting of: (2S)-2-[3-(4-nitrophenyl)-5-oxoimidazolidin-1-yl]butanamide; (2S)-2-[3-(2,4-dinitrophenyl)-5-oxoimidazolidin-1-yl]butanamide; (25)-2-(5-oxo-3-phenylimidazolidin-1-yl)butanamide; 2-[5-(iodomethyl)-2-oxo-1,3-oxazolidin-3-yl]butanamide; 2-(2-oxo-2,5-dihydro-1H-pyrrol-1-yl)butanamide; 2-(2-oxo-4-phenyl-2,5-dihydro-1H-pyrrol-1-yl)butanamide; 2-(4-methyl-2-oxo-2,5-dihydro-1H-pyrrol-1-yl)butanamide; (2S)-2-(2-oxo-5-propyl-1,3-thiazol-3(2H)-yl)butanamide; 2-(2-oxo-5-propyl-1,3-thiazol-3(2H)-yl)propanamide; 2-(5-butyl-2-oxo-1,3-thiazolidin-3-yl)butanamide; 2-(5-butyl-2-oxo-1,3-thiazolidin-3-yl)propanamide; 2-(2-oxo-5-phenyl-1,3-thiazolidin-3-yl)propanamide; 2-(2-oxo-5-propyl-1,3-thiazolidin-3-yl)butanamide; 2-(2-oxo-5-phenyl-1,3-thiazolidin-3-yl)butanamide; 2-(2-oxo-5-propyl-1,3-thiazolidin-3-yl)propanamide; (2S)-2-[2-oxo-5-(2,2,2-trifluoroethyl)-1,3-thiazolidin-3-yl]butanamide; 1-{[6-chloro-2-(trifluoromethyl)imidazo[1,2-b]pyridazin-3-yl]methyl}piperidin-2-one; 1-(1H-imidazol-4-ylmethyl)-5-propylpiperidin-2-one; 1-(1H-imidazol-1-ylmethyl)-5-propylpiperidin-2-one; 1-(imidazo[1,2-a]pyridin-3-ylmethyl)-5-propylpiperidin-2-one; 1-(1H-imidazol-1-ylmethyl)-5-phenylpiperidin-2-one; 1-(imidazo[1,2-a]pyridin-3-ylmethyl)-5-phenylpiperidin-2-one; 1-(imidazo[1,2-a]pyridin-3-ylmethyl)-4-phenylpiperidin-2-one; 1-(1H-imidazol-1-ylmethyl)-4-phenylpiperidin-2-one; 1-(imidazo[1,2-a]pyridin-3-ylmethyl)-4-propylpiperidin-2-one; 1-(1H-imidazol-5-ylmethyl)-4-propylpiperidin-2-one; 1-(1H-imidazol-1-ylmethyl)-4-propylpiperidin-2-one; 1-{[6-chloro-2-(trifluoromethyl)imidazo[1,2-b]pyridazin-3-yl]methyl}azepan-2-one; 1-(1H-imidazol-5-ylmethyl)-5-propylazepan-2-one; 5-propyl-1-{[2-(trifluoromethyl)imidazo[1,2-a]pyridin-3-yl]methyl}azepan-2-one; 5-phenyl-1-{[2-(trifluoromethyl)imidazo[1,2-a]pyridin-3-yl]methyl}azepan-2-one; 1-(1H-imidazol-5-ylmethyl)-6-propylazepan-2-one; 1-(1H-imidazol-4-ylmethyl)-4-propylazepan-2-one; 4-(1H-imidazol-4-ylmethyl)-4,6-dihydro-5H-thieno[3,2-b]pyrrol-5-one; 2-(5-oxo-5,6-dihydro-4H-thieno[3,2-b]pyrrol-4-yl)acetamide; 4-{[2-(trifluoromethyl)imidazo[1,2-a]pyridin-3-yl]methyl}-4,6-dihydro-5H-thieno[3,2-b]pyrrol-5-one; 4-{[2-(trifluoromethyl)imidazo[1,2-a]pyridin-3-yl]methyl}hexahydro-5H-thieno[3,2-b]pyrrol-5-one; 1-(1H-imidazol-4-ylmethyl)-1H-thieno[3,4-b]pyrrol-2(3H)-one; 2-(6-chloro-2-0X0-1,3-benzothiazol-3(2H)-yl)acetamide; 6-bromo-3-(1H-imidazol-1-ylmethyl)-1,3-benzothiazol-2(3H)-one; 2-(6-bromo-2-oxo-1,3-benzothiazol-3(2H)-yl)propanamide; 2-(6-bromo-2-oxo-1,3-benzothiazol-3(2H)-yl)propanamide; 2-(6-fluoro-2-oxo-1,3-benzothiazol-3(2H)-yl)acetamide; 2-(6-methyl-2-oxo-1,3-benzothiazol-3(2H)-yl)acetamide; 6-fluoro-3-(1H-imidazol-1-ylmethyl)-1,3-benzoxazol-2(3H)-one; 1-(1H-imidazol-4-ylmethyl)pyrazolo[1,5-a]pyridin-2(1H)-one; 2-(6-chloro-3-oxo-3,4-dihydroisoquinolin-2(1H)-yl)propanamide; 5-chloro-2-(1H-imidazol-4-ylmethyl)-1,4-dihydroisoquinolin-3(2H)-one; 2-(6-chloro-2-oxo-3,4-dihydroquinolin-1(2H)-yl)acetamide; 2-(6-bromo-2-oxo-3,4-dihydroquinolin-1(2H)-yl)acetamide; 1-(1H-imidazol-4-ylmethyl)-3,4-dihydroquinolin-2(1H)-one; 2-(6-iodo-2-oxo-3,4-dihydroquinolin-1(2H)-yl)acetamide; 2-(6-cyano-2-oxo-3,4-dihydroquinolin-1(2H)-yl)acetamide; 7-chloro-2-{[2-(trifluoromethyl)imidazo[1,2-a]pyridin-3-yl]methyl}-1,2,4,5-tetrahydro-3H-2-benzazepin-3-one; 7-chloro-2-(1H-imidazol-4-ylmethyl)-1,2,4,5-tetrahydro-3H-2-benzazepin-3-one; 7-chloro-3-(1H-imidazol-4-ylmethyl)-1,3,4,5-tetrahydro-2H-3-benzazepin-2-one; and 7-chloro-3-{[2-(trifluoromethyl)imidazo[1,2-a]pyridin-3-yl]methyl}-1,3,4,5-tetrahydro-2H-3-benzazepin-2-one.

In some embodiments, compounds of the present invention are those selected from the group consisting of: 1-(1H-imidazol-4-ylmethyl)-5-propylpiperidin-2-one; 1-(1H-imidazol-1-ylmethyl)-5-propylpiperidin-2-one; 1-(imidazo[1,2-a]pyridin-3-ylmethyl)-5-propylpiperidin-2-one; 1-(1H-imidazol-1-ylmethyl)-5-phenylpiperidin-2-one; 1-(imidazo[1,2-a]pyridin-3-ylmethyl)-4-phenylpiperidin-2-one; 1-(1H-imidazol-1-ylmethyl)-4-phenylpiperidin-2-one; 1-(imidazo[1,2-a]pyridin-3-ylmethyl)-4-propylpiperidin-2-one; 1-(1H-imidazol-5-ylmethyl)-4-propylpiperidin-2-one; 1-(1H-imidazol-1-ylmethyl)-4-propylpiperidin-2-one; 1-(1H- imidazol-4-ylmethyl)-1H-thieno[3,4-b]pyrrol-2(3H)-one; 6-bromo-3-(1H-imidazol-1-ylmethyl)-1,3-benzothiazol-2 (3H)-one; 2-(6-bromo-2-oxo-1,3-benzothiazol-3(2H)-yl) propanamide; and 5-chloro-2-(1H-imidazol-4-ylmethyl)-1, 4-dihydroisoquinolin-3(2H)-one.

The following paragraphs provide definitions of the various chemical moieties that make up the compounds according to the invention and are intended to apply uniformly through-out the specification and claims unless an otherwise expressly set out definition provides a broader definition.

"C-$1_{13}$β alkyl" refers to alkyl groups having 1 to 6, or 1 to 4 carbon atoms. This term is exemplified by groups such as methyl, ethyl, n-propyl, isopropyl, n-butyl, isobutyl, tert-butyl, n-pentyl, n-hexyl, trifluoromethyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"Heterocycle" refers to a saturated or unsaturated ring system containing, in addition to carbon atoms, at least one hetero atom, such as nitrogen, oxygen and/or sulfur. "Heterocycle" includes both "heteroaryl" and "heterocycloalkyl".

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2, 3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazopyridinyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, imidazopyrimidinyl, imidazopyridazinyl, imidazothiazolyl or imidazothiadiazolyl.

"C2-6 alkenyl" refers to alkenyl groups preferably having from 2 to 6 carbon atoms and having at least 1 or 2 sites of alkenyl unsaturation. Preferable alkenyl groups include ethenyl (vinyl, —CH=CH2), n-2-propenyl (allyl, —CH2CH=CH2) and the like.

"C2-6 alkynyl" refers to alkynyl groups preferably having from 2 to 6 carbon atoms and having at least 1-2 sites of alkynyl unsaturation, preferred alkynyl groups include ethynyl (—C≡CH), propargyl (—CH2C≡CH), and the like.

"C3.8 cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopropyl, cyclobutyl, cyclopentyl, cyclohexyl, norbornyl and the like.

"Heterocycloalkyl" refers to a C3.8 cycloalkyl group according to the definition above, in which 1 to 3 carbon atoms are replaced by hetero atoms chosen from the group consisting of O, S, NR, R being defined as hydrogen or C-1.g alkyl.

"Alkoxy" refers to the group —O—R where R includes "C-µg alkyl", "C2-6 alkenyl", "C2-6 alkynyl", "C3.8 cycloalkyl", "heterocycloalkyl", "aryl", "heteroaryl".

"Amino" refers to the group —NRR' where each R, R' is independently hydrogen, "C-l.g alkyl", "C2-6 alkenyl", "C2-6 alkynyl", "C3-8 cycloalkyl", "heterocycloalkyl", "aryl", "heteroaryl", and where R and R', together with the nitrogen atom to which they are attached, can optionally form a 3-8-membered heterocycloalkyl ring.

"Amido" refers to the group —C(=O)NRR' where each R, R' is independently hydrogen, "C-|_5 alkyl", "C2-6 alkenyl", "C2-6 alkynyl", "C3.8 cycloalkyl", "heterocycloalkyl", "aryl", "heteroaryl", and where R and R', together with the nitrogen atom to which they are attached, can optionally form a 3-8-membered heterocycloalkyl ring.

"Acylamino" refers to the group —NRC(O)R' wherein R and R' are as defined hereabove for the amino group.

"Ureido" refers to the group —NR"C(O)NRR' wherein R and R' are as defined hereabove for the amino group, and $R^{11}$ is as defined hereabove. "Sulfanyl" refers to the group —SR where R is "C-l.g alkyl", "C2-6 alkenyl", "C2-6 alkynyl", "C3.8 cycloalkyl", "heterocycloalkyl", "aryl" or "heteroaryl".

"Sulfinyl" refers to the group —S(=O)R where R is "C-l.g alkyl", "C2-6 alkenyl", "C2-6 alkynyl", "C3.8 cycloalkyl", "heterocycloalkyl", "aryl" or "heteroaryl".

"Sulfonyl" refers to the group —S(=O)2R where R is "C-l.g alkyl", "C2-6 alkenyl", "C2-6 alkynyl", "C3.8 cycloalkyl", "heterocycloalkyl", "aryl" or "heteroaryl".

"Halogen" refers to fluoro, chloro, bromo and iodo atoms.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C-l.g alkyl", "C2-6 alkenyl", "C2-6 alkynyl", "cycloalkyl", "heterocycloalkyl", "amino", "amido", "acylamino", "ureido", "aryl", "heteroaryl", "alkoxy", "halogen", cyano, hydroxy, mercapto, nitro, "amido", "sulfanyl", "sulfinyl", "sulfonyl" and the like.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula (I) and their salts can be in the form of a solvate, which is included within the scope of the present invention. Such solvates include for example hydrates, alcoholates and the like.

Many of the compounds of formula (I) and some of their intermediates have at least one stereogenic center in their structure. This stereogenic center may be present in a R or a S configuration, said R and S notation is used in correspondence with the rules described in Pure Appl. Chem., 45 (1976) 11-30.

The invention also relates to all stereoisomeric forms such as enantiomeric and diastereoisomeric forms of the compounds of formula (I) or mixtures thereof (including all possible mixtures of stereoisomers). With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are intended to be included within the scope of the present invention.

Some of the compounds of formula (I) may also exist in tautomeric forms. Such forms although not explicity indicated in the above formula are intended to be included within the scope of the present invention.

The invention also includes within its scope pro-drug forms of the compounds of formula (I) and its various sub-scopes and sub-groups.

In a specific embodiment, the present invention concerns a compound selected from the group consisting of: (2S)-2-[3-(4-nitrophenyl)-5-oxoimidazolidin-1-yl]butanamide; (2S)-2-[3-(2,4-dinitrophenyl)-5-oxoimidazolidin-1-yl]butanamide; (2S)-2-(5-oxo-3-phenylimidazolidin-1-yl)butanamide; 2-[5-(iodomethyl)-2-oxo-1,3-oxazolidin-3-yl]butanamide; 2-(2-oxo-2,5-dihydro-1H-pyrrol-1-yl)butanamide; 2-(2-oxo-4-phenyl-2,5-dihydro-1H-pyrrol-1-yl)butanamide; 2-(4-methyl-2-oxo-2,5-dihydro-1H-pyrrol-1-yl)butanamide; (+)-(2S)-2-(2-oxo-4-propyl-2,5-dihydro-1H-pyrrol-1-yl)butanamide; (2S)-2-(2-oxo-5-propyl-1,3-thiazol-3(2H)-yl)butanamide; 2-(2-oxo-5-propyl-1,3-thiazol-3(2H)-yl)propanamide; 2-(5-butyl-2-oxo-1,3-thiazolidin-3-yl)butanamide; 2-(5-butyl-2-oxo-1,3-thiazolidin-3-yl)propanamide; 2-(2-oxo-5-phenyl-1,3-thiazolidin-3-yl)propanamide; 2-(2-oxo-5-propyl-1,3-thiazolidin-3-yl)butanamide; 2-(2-oxo-5-phenyl-1,3-thiazolidin-3-yl)butanamide; 2-(2-oxo-5-propyl-1,3-thiazolidin-3-yl)propanamide; (2S)-2-[2-oxo-5-(2,2,2-trifluoroethyl)-1,3-thiazolidin-3-yl]butanamide; 1-{[6-chloro-2-(trifluoromethyl)imidazo[1,2-b]pyridazin-3-yl]methyl}piperidin-2-one; 1-(1H-imidazol-4-ylmethyl)-5-propylpiperidin-2-one; 1-(1H-imidazol-1-ylmethyl)-5-propylpiperidin-2-one; 1-(imidazo[1,2-a]pyridin-3-ylmethyl)-5-propylpiperidin-2-one; 1-(1H-imidazol-1-ylmethyl)-5-phenylpiperidin-2-one; 1-(imidazo[1,2-a]pyridin-3-ylmethyl)-5-phenylpiperidin-2-one; 1-(imidazo[1,2-a]pyridin-3-ylmethyl)-4-phenylpiperidin-2-one; 1-(1H-imidazol-1-ylmethyl)-4-phenylpiperidin-2-one; 1-(imidazo[1,2-a]pyridin-3-ylmethyl)-4-propylpiperidin-2-one; 1-(1H-imidazol-5-ylmethyl)-4-propylpiperidin-2-one; 1-(1H-imidazol-1-ylmethyl)-4-propylpiperidin-2-one; 1-{[6-chloro-2-(trifluoromethyl)imidazo[1,2-b]pyridazin-3-yl]methyl}azepan-2-one; 1-(1H-imidazol-5-ylmethyl)-5-propylazepan-2-one; 5-propyl-1-{[2-(trifluoromethyl)imidazo[1,2-a]pyridin-3-yl]methyl}azepan-2-one; 1-(1H-imidazol-5-ylmethyl)-5-phenylazepan-2-one; 5-phenyl-1-{[2-(trifluoromethyl)imidazo[1,2-a]pyridin-3-yl]methyl}azepan-2-one; 1-(1H-imidazol-5-ylmethyl)-6-propylazepan-2-one; 1-(1H-imidazol-4-ylmethyl)-4-propylazepan-2-one; 4-(1H-imidazol-4-ylmethyl)-4,6-dihydro-5H-thieno[3,2-b]pyrrol-5-one; 2-(5-oxo-5,6-dihydro-4H-thieno[3,2-b]pyrrol-4-yl)acetamide; 4-{[2-(trifluoromethyl)imidazo[1,2-a]pyridin-3-yl]methyl}-4,6-dihydro-5H-thieno[3,2-b]pyrrol-5-one; 4-{[2-(trifluoromethyl)imidazo[1,2-a]pyridin-3-yl]methyl}hexahydro-5H-thieno[3,2-b]pyrrol-5-one; 1-(1H-imidazol-4-ylmethyl)-1H-thieno[3,4-b]pyrrol-2(3H)-one; 2-(6-bromo-2-oxo-1,3-benzothiazol-3(2H)-yl)acetamide; 2-(2-OXO-1,3-benzothiazol-3(2H)-yl)acetamide; 2-(6-chloro-2-oxo-1,3-benzothiazol-3(2H)-yl)acetamide; 6-bromo-3-(1H-imidazol-1-ylmethyl)-1,3-benzothiazol-2(3H)-one; 6-bromo-3-(2-oxopropyl)-1,3-benzothiazol-2(3H)-one; 2-(6-nitro-2-oxo-1,3-benzothiazol-3(2H)-yl)acetamide; 2-(6-bromo-2-oxo-1,3-benzothiazol-3(2H)-yl)propanamide; 2-(6-bromo-2-oxo-1,3-benzothiazol-3(2H)-yl)propanamide; 2-(6-fluoro-2-oxo-1,3-benzothiazol-3(2H)-yl)acetamide; 2-(6-methyl-2-oxo-1,3-benzothiazol-3(2H)-yl)acetamide; 6-fluoro-3-(1H-imidazol-1-ylmethyl)-1,3-benzoxazol-2(3H)-one; 1-(1H-imidazol-4-ylmethyl)pyrazolo[1,5-a]pyridin-2(1H)-one; 2-(6-chloro-3-oxo-3,4-dihydroisoquinolin-2(1H)-yl)propanamide; 5-chloro-2-(1H-imidazol-4-ylmethyl)-1,4-dihydroisoquinolin-3(2H)-one; 2-(6-chloro-2-oxo-3,4-dihydroquinolin-1(2H)-yl)acetamide; 2-(6-bromo-2-oxo-3,4-dihydroquinolin-1 (2H)-yl)acetamide; 1-(1H-imidazol-4-ylmethyl)-3,4-dihydroquinolin-2(1H)-one; 2-(6-iodo-2-oxo-3,4-dihydroquinolin-1(2H)-yl)acetamide; 2-(6-cyano-2-oxo-3,4-dihydroquinolin-1(2H)-yl)acetamide; 7-chloro-2-{[2-(trifluoromethyl)imidazo[1,2-a]pyridin-3-yl]methyl}-1,2,4,5-tetrahydro-3H-2-benzazepin-3-one; 7-chloro-2-(1H-imidazol-4-ylmethyl)-1,2,4,5-tetrahydro-3H-2-benzazepin-3-one; 7-chloro-3-(1H-imidazol-4-ylmethyl)-1,3,4,5-tetrahydro-2H-3-benzazepin-2-one; and 7-chloro-3-{[2-(trifluoromethyl)imidazo[1,2-a]pyridin-3-yl]methyl}-1,3,4,5-tetrahydro-2H-3-benzazepin-2-one.

xvi) UK Patent 1,039,113

The new compounds according to the present invention are N-substituted lactams of the general formula:

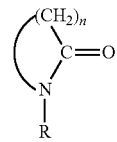

wherein N is a whole number of from 3 to 5 and R represents a

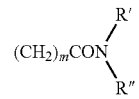

radical in which m is 0, 1 or 2 and R' is a hydrogen atom or an alkyl, cycloalkyl, alkenyl or alkynyl radical, which may contain 3 to 6 carbon atoms, or an aryl radical, and $R^{11}$ is a hydrogen atom or an alkyl radical, or both R' and R", together with the nitrogen atom to which they are attached, form a heterocyclic ring, such as 5 a pyrrolidine ring.

xvii) UK Patent 1,309,692

According to the present invention, there are provided new N-substituted lactams of the general formula:

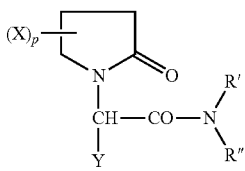

wherein X is a hydrogen atom or an alkyl, alkenyl or alkynyl radical containing 1 to 6 carbon atoms, p is a whole number of from 1 to 6, Y is a hydrogen atom or an alkyl, alkenyl or alkynyl radical containing 1 to 6 carbon atoms or a cycloalkyl radical and R' and R", which may be the same or different, are hydrogen atoms or alkyl, alkenyl, alkynyl, cycloalkyl or aryl radicals or R' and R", together with the nitrogen atom to which they are attached, form a heterocyclic radical which may contain further heteroatoms, with the proviso that at least one of the symbols X and Y is other than a hydrogen atom.

Valproate

In some embodiments, an SV2A inhibitor or its pharmaceutically acceptable salt, hydrate, solvate, polymorph or prodrug is administered in combination with valproate or its analog, derivative or pharmaceutically acceptable salt, hydrate, solvate, or polymorph or prodrug.

Analogs and derivatives of valproate useful for the methods and compositions of this invention include compounds of the formula:

wherein, independently for each occurrence:
X is —OH, $C_{1-10}$ alkoxy, —O-alkali metal, —N(R$^1$)$_2$, —SH, or —S—$C_{1-10}$ alkyl;
R is a straight chain or branched $C_{1-30}$ alkyl; and
R$^1$ is H, $C_{1-10}$ alky, $C_{2-10}$ alkenyl, $C_{2-10}$ alkynyl, aryl, or aralkyl;
provided that R may be unsubstituted or substituted by one or more —OH, $C_{1-10}$ alkoxy, —N(R$^1$)$_2$, —SH, —S—$C_{1-10}$ alkyl, or aryl.

In other embodiments, analogs and derivatives of valproate useful for the methods and compositions of this invention include compounds of the formula:

wherein, independently for each occurrence:
X is —OH, $C_{1-10}$ alkoxy, —O-alkali metal, —N(R$^1$)$_2$, —SH, or —S—$C_{1-10}$ alkyl;
R is CH[(CH$_2$)$_2$CH$_3$]$_2$; and
R$^1$ is H, $C_{1-10}$ alky, $C_{2-10}$ alkenyl, $C_{2-10}$ alkynyl, aryl, or aralkyl;
provided that R may be unsubstituted or substituted by one or more —OH, $C_{1-10}$ alkoxy, —N(R$^1$)$_2$, —SH, —S—$C_{1-10}$ alkyl, or aryl.

In other embodiments, analogs and derivatives of valproate useful for the methods and compositions of this invention include compounds of the formula:

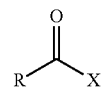

wherein, independently for each occurrence:
X is —OH, —O-alkali metal, —SH, or —NH$_2$; and
R is CH[(CH$_2$)$_2$CH$_3$]$_2$.

Methods for making the compounds of formula may be found in, for example, U.S. Pat. Nos. 4,558,070; 4,595,695; 4,654,370; 4,895,873; 4,913,906; 5,017,613; 5,019,398; 5,049,586; 5,162,573; 5,440,023; 5,856,569; 6,131,106 and 6,610,326.

Other names and descriptions of valproate are also envisioned herein, such as Depakote, Valrelease, 2-propylpentanoate, valproic acid, VPA and sodium valproate.

Methods of Treating Cognitive Impairment Associated with CNS Disorders with the Administration of an SV2A Inhibitor In one aspect, the invention provides methods and compositions for treating cognitive impairment or improving cognitive function, delaying or slowing the progression of cognitive impairment, or reducing the rate of decline of cognitive function, in a subject suffering from cognitive impairment associated with a central nervous system (CNS) disorder (e.g., age-related cognitive impairment, MCI, amnestic MCI, dementia, AD, prodromal AD, PTSD, schizophrenia, ALS and cancer therapy-related cognitive impairment), or the risk thereof in a subject in need thereof by administering an SV2A inhibitor or a pharmaceutically acceptable salt, hydrate, solvate, polymorph, or prodrug thereof. In some embodiments, the SV2A inhibitor is administered in combination with valproate or an analog, derivative or pharmaceutically acceptable salt, hydrate, solvate, polymorph, or prodrug thereof. In some embodiments, the SV2A inhibitor is selected from the group consisting of levetiracetam, seletracetam, and brivaracetam or derivatives or analogs or pharmaceutically acceptable salts, or solvates, or hydrates, or polymorphs, or prodrugs thereof. In other embodiments, the SV2A inhibitor is levetiracetam or a derivative or an analog or a pharmaceutically acceptable salt, or a solvate, or a hydrate, or a polymorph, or a prodrug thereof. In other embodiments, the SV2A inhibitor is brivaracetam or a derivative or an analog or a pharmaceutically acceptable salt, or a solvate, or a hydrate, or a polymorph, or a prodrug thereof. In other embodiments, the SV2A inhibitor is seletracetam or a derivative or an analog or a pharmaceutically acceptable salt, or a solvate, or a hydrate, or a polymorph, or a prodrug thereof. In some embodiments, the cognitive impairment is associated with age-related cognitive impairment, such as Mild Cognitive Impairment (MCI), Age-Associated Memory Impairment (AAMI), Age Related Cognitive Decline (ARCD). In one embodiment of the invention, the MCI is amnestic MCI. In some embodiments of the invention, the cognitive impairment is associated with dementia, Alzheimer's Disease (AD), prodromal AD, post traumatic stress disorder (PTSD), schizophrenia, bipolar disorder, amyotrophic lateral sclerosis, cancer-therapy-related cognitive impairment, mental retardation, Parkinson's disease, autism, compulsive. In one embodiment, the subject that suffers such cognitive impairment is a human patient. The subject may be a human or other mammal such as a non-human primate, or rodent (e.g., rat). In some embodiments, the subject is a human patient.

The use of the SV2A inhibitors and its pharmaceutically acceptable salt, hydrate, solvate or polymorph in combination with valproate or its analog, derivative or pharmaceutically acceptable salt reduces the amount of valproate necessary for the treatment of CNS disorders involving cognitive dysfunction and other affective disorders, including MCI, amnestic MCI, AAMI, ARCE, dementia, AD, PTSD, schizophrenia, bipolar disorder, amyotrophic lateral sclerosis, cancer-therapy-related cognitive impairment, mental retardation, Parkinson's disease, autism, compulsive behavior, and substance addiction. In one embodiment, the subject that suffers such cognitive impairment is a human patient, and thus the side effects caused by valproate is reduced without diminishing efficacy. Further, the efficacy of a combination of the SV2A inhibitor or its pharmaceutically acceptable salt, hydrate, solvate, polymorph, or prodrug and valproate or its analog, derivative, or pharmaceutically acceptable salt, hydrate, solvate, polymorph, or prodrug thereof exceeds the efficacy of either drug administered alone at its optimal dose and thus is an improved treatment for CNS disorders associated with cognitive impairment.

It will be appreciated that compounds and agents used in the compositions and methods of this invention preferably should readily penetrate the blood-brain barrier when peripherally administered. Compounds which cannot penetrate the blood-brain barrier, however, can still be effectively administered directly into the central nervous system, e.g., by an intraventricular or other neuro-compatible route.

As used herein, administration of an SV2A inhibitor or its pharmaceutically acceptable salt, hydrate, solvate, polymorph, or prodrug and valproate or its analog, derivative or pharmaceutically acceptable salt "in combination" includes simultaneous administration and/or administration at different times, such as sequential administration. Simultaneous administration of the SV2A inhibitor or its pharmaceutically acceptable salt, hydrate, solvate, polymorph, or prodrug and valproate or its analog, derivative or pharmaceutically acceptable salt can optionally be combined with supplemental doses of the SV2A inhibitor or its pharmaceutically acceptable salt, hydrate, solvate, polymorph, or prodrug and/or valproate or its analog, derivative or pharmaceutically acceptable salt. Simultaneous administration of drugs encompasses administration as co-formulation or, alternatively, as separate compositions.

In accordance with this invention, the SV2A inhibitor or its pharmaceutically acceptable salt, hydrate, solvate or polymorph, alone or in combination with valproate or its analog, derivative or pharmaceutically acceptable salt can be administered in an extended release form, a controlled release form, a prolonged release form, a sustained release form, a delayed release form, or a slow release form.

In accordance with this invention, the SV2A inhibitor or its pharmaceutically acceptable salt, hydrate, solvate or polymorph, alone or in combination with valproate or its analog, derivative or pharmaceutically acceptable salt can be administered to a subject via any suitable route or routes. In some embodiments, the drugs are administered orally; however, administration intravenously, subcutaneously, intraarterially, intramuscularly, intraspinally, rectally, intrathoracically, intraperitoneally, intracentricularly, or transdermally, topically, or by inhalation is also contemplated. The agents can be administered orally, for example, in the form of tablets, troches, capsules, elixirs, suspensions, syrups, wafers, or the like, prepared by art recognized procedures. In certain embodiments, the SV2A inhibitor or its pharmaceutically acceptable salt, hydrate, solvate or polymorphs, alone or in combination with valproate or its analog, derivative or pharmaceutically acceptable salt, can be administered to a subject via different routes. For example, the SV2A inhibitor its salt, solvate, hydrate, or polymorph is administered intravenously and the valproate or an analog, derivative or pharmaceutically acceptable salt, hydrate, solvate, polymorph, or prodrug thereof is administered orally.

In some embodiments, the administration is a slow or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release," "prolonged release," "sustained release," "delayed release," or "slow release" as these terms are used in the pharmaceutical sciences. In some embodiments, the extended release dosage is administered in the form of a patch or a pump. The term "Extended release dosage form" or "extended release form", as used herein, refers to a dosage form that contains one or more active ingredients, where the release of at least one of the active ingredient, when placed in water or other biological fluids or solvents, may occur over an extended period, such as a period of at least about 1 day, at least about 2 days, at least about 3 days, at least about 4 days, at least about 5 days, at least about 10 days, at least about 20 days, at least about 30 days, at least about 60 days, at least about 90 days, or at least about 150 days. In some embodiments of the present invention, only one of the SV2A inhibitor and valproate is in an extended release dosage form. In some other embodiments of the composition of the present invention, the SV2A inhibitor and valproate are each in an extended release dosage form (together in one formulation or separately in two formulations).

Dosage schedules of the agents and compositions according to the methods of the invention will vary according to the particular compound or compositions selected, the route of administration, the nature of the condition being treated, the age, and condition of the patient, the course, or stage of treatment, and will ultimately be at the discretion of the attending physician. It will be understood that the amount of the SV2A inhibitor or its pharmaceutically acceptable salt, hydrate, solvate or polymorph, alone or in combination with valproate or its analog, derivative or pharmaceutically acceptable salt that is administered will be amounts effective to produce a desired biological effect, such as beneficial results, including clinical results, e.g., an amount that normalizes neural activity in areas of the brain that exhibit abberent activity (including, but not limited to DG, CA3 and/or entorhinal cortex) and/or results in an improvement in cognitive function). It will be understood that an effective amount can be administered in more than one dose and over a course of treatment.

If administered by an implant, a device or a slow or extended release formulation, the SV2A inhibitor or its pharmaceutically acceptable salt, hydrate, solvate or polymorph, alone or in combination with valproate or its analog, derivative or pharmaceutically acceptable salt can be administered one time, or one or more times periodically throughout the lifetime of the patient as necessary. Other administration intervals intermediate to or shorter than these dosage intervals for clinical applications may also be used and may be determined by one skilled in the art following the methods of this invention.

Desired duration of administration of the SV2A inhibitor or its pharmaceutically acceptable salt, hydrate, solvate or polymorph, alone or in combination with valproate or its analog, derivative or pharmaceutically acceptable salt can be determined by routine experimentation by one skilled in the art. For example, the SV2A inhibitor or its pharmaceutically acceptable salt, hydrate, solvate or polymorph, alone or in combination with valproate or its analog, derivative or pharmaceutically acceptable salt may be administered for a period of 1-4 weeks, 1-3 months, 3-6 months, 6-12 months, 1-2 years, or more, up to the lifetime of the patient.

It is known in the art that normalization to body surface area is an appropriate method for extrapolating doses between species. The human equivalent dose (HED) for this dosage can be estimated using the following formula that accounts for differences in body surface area (see Estimating the Safe Starting Dose in Clinical Trials for Therapeutics in Adult Healthy Volunteers, December 2002, Center for Biologics Evaluation and Research):

$$\text{HED} = \text{animal dose} \times (Km \text{ animal}/Km \text{ human})$$

where the Km factor is body weight divided by body surface area (Km rat has been determined as 6, and Km human is 37; see Reagan-Saw, Nihal, Ahmad, 2007). Thus, a dosage of 10 mg/kg in rats is equivalent to 1.6 mg/kg in humans (10 mg/kg×(6/37)=1.6 mg/kg). For human subjects, to calculate a dose in mg from the dose in mg/kg, the dose in mg/kg is multiplied by a typical adult weight of 70 kg.

In certain embodiments of the invention, the dose of the SV2A inhibitor or its pharmaceutically acceptable salt, hydrate, solvate or polymorph is 0.1 to 5 mg/kg/day (which, given a typical human subject of 70 kg, is 7 to 350 mg/day).

In certain embodiments of the invention, the SV2A inhibitor or the pharmaceutically acceptable salt, hydrate, solvate, polymorph, or prodrug thereof can be administered at doses according to, for example, U.S. patent application Ser. No. 12/580,464 (Pub. No. US-2010-0099735), U.S. patent application Ser. No. 13/287,531 (Pub. No. US-2012-0046336), U.S. patent application Ser. No. 13/370,253 (Pub. No. US-2012-0214859), International Patent Application PCT/US2009/005647 (Pub. No. WO2010/044878), International Patent Application PCT/US12/24556 (Pub. No. WO2012/109491), U.S. Patent Application 61/105,847, U.S. Patent Application 61/152,631, U.S. Patent Application 61/175,536, and U.S. Patent Application 61/441,251. In certain embodiments of the invention, the SV2A inhibitor or the pharmaceutically acceptable salt, hydrate, solvate, polymorph, or prodrug thereof is administered at a daily dose of about 0.001 to 5 mg/kg, about 0.001 to 0.5 mg/kg, about 0.01 to 0.5 mg/kg, about 0.1 to 5 mg/kg, or about 1 to 2 mg/kg, or about 2 to 4 mg/kg, or about 2 to 3 mg/kg, or about 3 to 4 mg/kg, or about 0.2 to 0.4 mg/kg, or about 0.2 to 0.3 mg/kg, or about 0.3 to 0.4 mg/kg, or about 0.1 to 0.2 mg/kg, or about 0.01 to 2.5 mg/kg, or about 0.1 to 2.5 mg/kg, or about 0.4 to 2.5 mg/kg, or about 0.6 to 1.8 mg/kg, or about 0.5 to 2 mg/kg, or about 0.8 to 1.6, or about 0.8 to 3.6, or about 0.5 to 4 mg/kg, or about 0.04 to 2.5 mg/kg, or about 0.06 to 1.8 mg/kg, or about 0.05 to 3 mg/kg or about 0.08 to about 1.6 mg/kg, or about 0.08 to 3.6 or about 0.05 to 2 mg/kg, or about 0.01 to 1 mg/kg, or about 0.001 to 1 mg/kg, or about 0.5 to 5 mg/kg, or about 0.05 to 0.5 mg/kg, or about 0.8 mg/kg, or about 1.6 mg/kg, or about 3.6 mg/kg, or about 0.08 mg/kg, or about 0.16 mg/kg, or about 0.36 mg/kg. Other doses higher than, intermediate to, or less than these doses may also be used and may be determined by one skilled in the art following the methods of this invention. For repeated administrations over several days or weeks or longer, depending on the condition, the treatment is sustained until a sufficient level of cognitive function is achieved.

In certain embodiments of the invention, the dose of the SV2A inhibitor is 0.001-5 mg/kg/day (which, given a typical human subject of 70 kg, is about 0.07-350 mg/day). Doses that may be used include, but are not limited to 0.001 mg/kg/day, 0.0015 mg/kg/day, 0.002 mg/kg/day, 0.005 mg/kg/day, 0.0075 mg/kg/day, 0.01 mg/kg/day, 0.015 mg/kg/day, 0.02 mg/kg/day, 0.03 mg/kg/day, 0.04 mg/kg/day, 0.05 mg/kg/day, 0.1 mg/kg/day, 0.2 mg/kg/day, 0.3 mg/kg/day, 0.4 mg/kg/day, 0.5 mg/kg/day, 0.75 mg/kg/day, 1.0 mg/kg/day, 1.5 mg/kg/day, 2.0 mg/kg/day, 2.5 mg/kg/day, 3.0 mg/kg/day, 4.0 mg/kg/day, or 5.0 mg/kg/day. In some embodiments, the dose of the SV2A inhibitor is 0.001-0.5 mg/kg/day (which, given a typical human subject of 70 kg, is about 0.07-35 mg/day), or 0.01-0.5 mg/kg/day (which is about 0.7-35 mg/day). Other doses higher than, intermediate to, or less than these doses may also be used and may be determined by one skilled in the art following the methods of this invention.

In certain embodiments of the invention, the dose of the SV2A inhibitor is 0.1 to 5 mg/kg/day (which, given a typical human subject of 70 kg, is 7 to 350 mg/day). Doses that may be used include, but are not limited to 0.1 mg/kg/day, 0.5 mg/kg/day, 1 mg/kg/day, 1.5 mg/kg/day, 2 mg/kg/day, 2.5 mg/kg/day, 3 mg/kg/day, 4 mg/kg/day, or 5 mg/kg/day. In certain embodiments, the dose is 1-2 mg/kg/day (which, given a typical human subject of 70 kg, is 70-140 mg/day). In other embodiments of the invention, the dose of the SV2A inhibitor is 0.1 to 0.2 mg/kg/day. Other doses higher than, intermediate to, or less than these doses may also be used and may be determined by one skilled in the art following the methods of this invention.

In certain embodiments of the invention, the dose of the SV2A inhibitor is 0.01 to 2.5 mg/kg/day (which, given a typical human subject of 70 kg, is about 0.7-180 mg/day). Doses that may be used include, but are not limited to 0.01 mg/kg/day, 0.02 mg/kg/day, 0.03 mg/kg/day, 0.04 mg/kg/day, 0.06 mg/kg/day, 0.08 mg/kg/day, 0.12 mg/kg/day, 0.14 mg/kg/day, 0.16 mg/kg/day, 0.18 mg/kg/day, 0.2 mg/kg/day, 0.4 mg/kg/day, 0.6 mg/kg/day, 0.8 mg/kg/day, 1.0 mg/kg/day, 1.2 mg/kg/day, 1.4 mg/kg/day, 1.6 mg/kg/day, 1.8 mg/kg/day, 2.0 mg/kg/day, 2.2 mg/kg/day, 2.4 mg/kg/day, or 2.5 mg/kg/day. In some embodiments, the dose of the SV2A inhibitor is 0.1-2.5 mg/kg/day (which, given a typical human subject of 70 kg, is about 7-180 mg/day), 0.1-0.2 mg/kg/day (which is about 7-15 mg/day), 0.2-0.4 mg/kg/day (about 14-30 mg/day), 0.4-2.5 mg/kg/day (about 25-180 mg/day), 0.6-1.8 mg/kg/day (about 40-130 mg/day), 0.04-2.5 mg/kg/day (about 2.5-180 mg/day) or 0.06-1.8 mg/kg/day (about 4-130 mg/day). In some embodiments of the invention, the dose of the SV2A inhibitor is 40 to 130 mg, 140 to 300 mg, 200 to 300 mg or 140 to 200 mg. Other doses higher than, intermediate to, or less than these doses may also be used and may be determined by one skilled in the art following the methods of this invention.

In certain embodiments of the invention, the dose of the SV2A inhibitor is 0.0015 to 7 mg/kg/day (which, given a typical human subject of 70 kg, is about 0.1-500 mg/day). Daily doses that may be used include, but are not limited to 0.0015 mg/kg, 0.002 mg/kg, 0.0025 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.2 mg/kg, 1.4 mg/kg, 1.5 mg/kg, 1.6 mg/kg, 1.8 mg/kg, 2.0 mg/kg, 2.2 mg/kg, 2.4 mg/kg, 2.5 mg/kg, 2.6 mg/kg, 2.8 mg/kg, 3.0 mg/kg, 3.5 mg/kg, 4.0 mg/kg, 4.5 mg/kg, 5.0 mg/kg, 6.0 mg/kg, or 7.0 mg/kg; or 0.1 mg, 0.15 mg, 0.18 mg, 0.35 mg, 0.7 mg, 1.5 mg, 2.0 mg, 2.5 mg, 2.8 mg, 3.0 mg, 3.5 mg, 4.2 mg, 5 mg, 5.5 mg, 6.0 mg, 7 mg, 8 mg, 9 mg, 10 mg, 12 mg, 15 mg, 20 mg, 25 mg, 28 mg, 30 mg, 35 mg, 40 mg, 45 mg, 50 mg, 55 mg, 60 mg, 70 mg, 75 mg, 80 mg, 85 mg, 90 mg, 95 mg, 100 mg, 110 mg, 120 mg, 125 mg, 140 mg, 150 mg, 170 mg, 175 mg, 180 mg, 190 mg, 200 mg, 210 mg, 225 mg, 250 mg, 280 mg, 300 mg, 350 mg, 400 mg, or 500 mg. In some embodiments, the daily dose of SV2A inhibitor that can be used in the methods of this invention include, without limitation, 0.0015-5 mg/kg (or 0.1-350 mg for a subject of 70 kg), 0.05-4 mg/kg, 0.05-2.0 mg/kg, 0.05-1.5 mg/kg, 0.1-1.0 mg/kg, 1-5 mg/kg, 1.5-4.0 mg/kg, 1.8-3.6 mg/kg, 0.01-0.8 mg/kg, 0.01-1 mg/kg, 0.01-1.5 mg/kg, 0.01-2 mg/kg, 0.01-2.5 mg/kg, 0.01-3 mg/kg, 0.01-3.5 mg/kg, 0.01-4 mg/kg, 0.01-5 mg/kg, 0.025-0.8 mg/kg, 0.025-1 mg/kg, 0.025-1.5 mg/kg, 0.025-2 mg/kg, 0.025-2.5 mg/kg, 0.025-3 mg/kg, 0.025-3.5 mg/kg, 0.025-4 mg/kg, 0.05-0.8 mg/kg, 0.05-1 mg/kg, 0.05-1.5 mg/kg, 0.05-2 mg/kg, 0.05-2.5 mg/kg, 0.05-3 mg/kg, 0.05-3.5 mg/kg, 0.05-4 mg/kg, 0.075-0.8 mg/kg, 0.075-1 mg/kg, 0.075-1.5 mg/kg, 0.075-2 mg/kg, 0.075-2.5 mg/kg, 0.075-3 mg/kg, 0.075-3.5 mg/kg, 0.075-4 mg/kg, 0.1-0.8 mg/kg, 0.1-1 mg/kg, 0.1-1.5 mg/kg, 0.1-2 mg/kg, 0.1-2.5 mg/kg, 0.1-3 mg/kg, 0.1-3.5 mg/kg, 0.1-4 mg/kg, 0.2-0.8 mg/kg, 0.2-1 mg/kg, 0.2-1.5 mg/kg, 0.2-2 mg/kg, 0.2-2.5 mg/kg, 0.2-3 mg/kg, 0.2-3.5 mg/kg, 0.2-4 mg/kg, 0.5-0.8 mg/kg, 0.5-1 mg/kg, 0.5-1.5 mg/kg, 0.5-2 mg/kg, 0.5-2.5 mg/kg, 0.5-3 mg/kg, 0.5-3.5 mg/kg, or 0.5-4 mg/kg; or 0.7-50 mg, 0.7-75 mg, 0.7-100 mg, 0.7-150 mg, 0.7-180 mg, 0.7-225 mg, 0.7-250 mg, 0.7-280 mg, 1.8-50 mg, 1.8-75 mg, 1.8-100 mg, 1.8-150 mg, 1.8-180 mg, 1.8-225 mg, 1.8-250 mg, 1.8-280 mg, 3.5-50 mg, 3.5-75 mg, 3.5-100 mg, 3.5-150 mg, 3.5-180 mg, 3.5-225 mg, 3.5-250 mg, 3.5-280 mg, 5-50 mg, 5-75 mg, 5-100 mg, 5-150 mg, 5-180 mg, 5-225 mg, 5-250 mg, 5-280 mg, 7-50 mg, 7-75 mg, 7-100 mg, 7-150 mg, 7-180 mg, 7-225 mg, 7-250 mg, 7-280 mg, 15-50 mg, 15-75 mg, 15-100 mg, 15-150 mg, 15-180 mg, 15-225 mg, 15-250 mg, 15-280 mg, 35-50 mg, 35-75 mg, 35-100 mg, 35-150 mg, 35-180 mg, 35-225 mg, 35-250 mg, 35-280 mg, 0.1-500 mg, 3-300 mg, 3-150 mg, 3-110 mg, 7-70 mg, 70-350 mg, 100-300 mg, or 125-250 mg. Other doses higher than, intermediate to, or less than these doses may also be used and may be determined by one skilled in the art following the methods of this invention.

In certain embodiments of the invention, the interval of administration is 12 hours. In certain embodiments of the invention, the interval of administration is 24 hours. Administration at less frequent intervals, such as once every 6 hours, may also be used. In some embodiments, the SV2A inhibitor is administered at a total daily dose of 0.1 to 5 mg/kg (e.g., in the case of administration every 12 hours of a daily dose of 2 mg/kg, each administration is 1 mg/kg). In some embodiments, the SV2A inhibitor is administered every 24 hours at a daily dose of 1 to 2 mg/kg. In another embodiment, the SV2A inhibitor is administered every 24 hours at a daily dose of 0.1-0.2 mg/kg. In some embodiments, the SV2A inhibitor is administered at a daily dose of 0.01 to 2.5 mg/kg (e.g., in the case of administration every 12 hours of a daily dose of 0.8 mg/kg, each administration is 0.4 mg/kg). In some embodiments, the SV2A inhibitor is administered at a daily dose of 0.1 to 2.5 mg/kg. In some embodiments, the SV2A inhibitor is administered at a daily dose of 0.4 to 2.5 mg/kg. In some embodiments, the SV2A inhibitor is administered at a daily dose of 0.6 to 1.8 mg/kg.

In some embodiments, the selective inhibitor of SV2A is administered at a daily dose of 0.04-2.5 mg/kg. In some embodiments, the selective inhibitor of SV2A is administered at a daily dose of 0.06-1.8 mg/kg. In some embodiments, the selective inhibitor of SV2A is administered at a daily dose of 0.001-5 mg/kg. In some embodiments, the selective inhibitor of SV2A is administered at a daily dose of 0.001-0.5 mg/kg. In some embodiments, the selective inhibitor of SV2A is administered at a daily dose of 0.01-0.5 mg/kg.

In certain embodiments of the invention, the SV2A inhibitor is levetiracetam or a pharmaceutically acceptable salt, hydrate, solvate, polymorph, or prodrug thereof. The levetiracetam or its pharmaceutically acceptable salt, hydrate, solvate, polymorph, or prodrug is administered at a daily dose of about 1 to 2 mg/kg, or about 0.1 to 2.5 mg/kg, or about 0.4 to 2.5 mg/kg, or about 0.6 to 1.8 mg/kg, or about 2.0 to 3.0 mg/kg, or about 3.0 to 4.0 mg/kg, or about 2.0 to 4.0 mg/kg, or about 0.1 to 5 mg/kg, or about 70 to 140 mg, or about 7 to 180 mg, or about 25 to 180 mg, or about 40 to 130 mg, or about 140 to 300 mg, or about 200 to 300 mg, or about 140 to 200 mg, or about 7 to 350 mg.

In other embodiments, the levetiracetam or its pharmaceutically acceptable salt, hydrate, solvate, polymorph, or prodrug is administered according to one of the daily dose ranges indicated as "+" listed in Table 1 or Table 2.

TABLE 1

Daily Doses of Levetiracetam

| | Lower range | | | | |
|---|---|---|---|---|---|
| Upper range | 0.1 mg/kg | 0.4 mg/kg | 0.6 mg/kg | 1 mg/kg | 2 mg/kg | 3 mg/kg |
| 1.8 mg/kg | + | + | + | + | | |
| 2 mg/kg | + | + | + | + | | |
| 2.5 mg/kg | + | + | + | + | + | |
| 3 mg/kg | + | + | + | + | + | |
| 4 mg/kg | + | + | + | + | + | + |
| 5 mg/kg | + | + | + | + | + | + |

TABLE 2

Daily Doses of Levetiracetam in a Human Subject of 70 KG

| | Lower range | | | | |
|---|---|---|---|---|---|
| Upper range | 7 mg | 25 mg | 40 mg | 70 mg | 140 mg | 200 mg |
| 130 mg | + | + | + | + | | |
| 140 mg | + | + | + | + | | |
| 180 mg | + | + | + | + | + | |
| 200 mg | + | + | + | + | + | |
| 300 mg | + | + | + | + | + | + |
| 350 mg | + | + | + | + | + | + |

In certain embodiments of the invention, the SV2A inhibitor is levetiracetam or a pharmaceutically acceptable salt, hydrate, solvate, polymorph, or prodrug thereof. The levetiracetam or its pharmaceutically acceptable salt, hydrate, solvate, polymorph, or prodrug is administered at a daily dose of about 0.1-5 mg/kg, about 1-5 mg/kg, about 1.5-4 mg/kg, about 1.8-3.6 mg/kg, about 7-350 mg, about 70-350 mg, about 100-300 mg, or about 125-250 mg.

In certain embodiments of the invention, the SV2A inhibitor is brivaracetam or a pharmaceutically acceptable salt, hydrate, solvate, polymorph, or prodrug thereof. The brivaracetam or its pharmaceutically acceptable salt, hydrate, solvate, polymorph, or prodrug thereof is administered at a daily dose of about 0.1 to 0.2 mg/kg, or about 0.01 to 2.5 mg/kg, or about 0.04 to 2.5 mg/kg, or about 0.06 to 1.8 mg/kg, or about 0.2 to 0.4 mg/kg, or about 7 to 15 mg, or about 0.7 to 180 mg, or about 2.5 to 180 mg, or about 4.0 to 130 mg, or about 14 to 30 mg.

In other embodiments, the brivaracetam or its pharmaceutically acceptable salt, hydrate, solvate, polymorph, or prodrug is administered at a daily dose of at least 0.1 mg, 0.5 mg, 0.75 mg, 1.0 mg, 1.5 mg, or 2.0 mg, but no more than a daily dose of 2.5 mg, 5 mg, 10 mg, 15 mg, 20 mg, 25 mg, 30 mg, or 35 mg. In other embodiments, the brivaracetam or its pharmaceutically acceptable salt, hydrate, solvate, polymorph, or prodrug is administered at a daily dose of at least 0.0015 mg/kg, 0.0075 mg/kg, 0.01 mg/kg, 0.015 mg/kg, 0.02 mg/kg, or 0.03 mg/kg, but no more than a daily dose of 0.5 mg/kg, 0.4 mg/kg, 0.3 mg/kg, 0.2 mg/kg, 0.15 mg/kg, 0.1 mg/kg, 0.05 mg/kg, or 0.04 mg/kg.

In other embodiments, the brivaracetam or its pharmaceutically acceptable salt, hydrate, solvate, polymorph, or prodrug is administered according to one of the daily dose ranges indicated as "+" listed in Table 3 or Table 4. For example, the brivaracetam or the pharmaceutically acceptable salt, hydrate, solvate, polymorph, or prodrug thereof may be administered at a daily dose of 0.1-35 mg, 0.5-35 mg, 0.75-35 mg, 1.0-35 mg, 1.5-35 mg, 2.0-35 mg, 0.1-30 mg, 0.1-25 mg, 0.1-20 mg, 0.1-15 mg, 0.1-10 mg, 0.1-5 mg, 0.1-2.5 mg, 0.0015-0.5 mg/kg, 0.0075-0.5 mg/kg, 0.01-0.5 mg/kg, 0.015-0.5 mg/kg, 0.02-0.5 mg/kg, 0.03-0.5 mg/kg, 0.0015-0.4 mg/kg, 0.0015-0.3 mg/kg, 0.0015-0.2 mg/kg, 0.0015-0.15 mg/kg, 0.0015-0.1 mg/kg, 0.0015-0.05 mg/kg, or 0.0015-0.04 mg/kg.

TABLE 3

Daily Doses of Brivaracetam

| Upper range | Lower range | | | | | |
|---|---|---|---|---|---|---|
| | 0.0015 mg/kg | 0.0075 mg/kg | 0.01 mg/kg | 0.015 mg/kg | 0.02 mg/kg | 0.03 mg/kg |
| 0.04 mg/kg | + | + | + | + | + | + |
| 0.05 mg/kg | + | + | + | + | + | + |
| 0.1 mg/kg | + | + | + | + | + | + |
| 0.15 mg/kg | + | + | + | + | + | + |
| 0.2 mg/kg | + | + | + | + | + | + |
| 0.3 mg/kg | + | + | + | + | + | + |
| 0.4 mg/kg | + | + | + | + | + | + |
| 0.5 mg/kg | + | + | + | + | + | + |

TABLE 4

Daily Doses of Brivaracetam in a Human Subject of 70 KG

| Upper range | Lower range | | | | | |
|---|---|---|---|---|---|---|
| | 0.1 mg | 0.5 mg | 0.75 mg | 1.0 mg | 1.5 mg | 2.0 mg |
| 2.5 mg | + | + | + | + | + | + |
| 5 mg | + | + | + | + | + | + |
| 10 mg | + | + | + | + | + | + |
| 15 mg | + | + | + | + | + | + |
| 20 mg | + | + | + | + | + | + |
| 25 mg | + | + | + | + | + | + |
| 30 mg | + | + | + | + | + | + |
| 35 mg | + | + | + | + | + | + |

In other embodiments, the brivaracetam or its pharmaceutically acceptable salt, hydrate, solvate, polymorph, or prodrug is administered at a daily dose of at least 0.0015 mg/kg, 0.002 mg/kg, 0.0025 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, but no more than a daily dose of 1 mg/kg, 1.2 mg/kg, 1.4 mg/kg, 1.5 mg/kg, 1.6 mg/kg, 1.8 mg/kg, 2.0 mg/kg, 2.2 mg/kg, 2.4 mg/kg, 2.5 mg/kg, 2.6 mg/kg, 2.8 mg/kg, 3.0 mg/kg, 3.5 mg/kg, 4.0 mg/kg, 4.5 mg/kg, or 5.0 mg/kg. In other embodiments, the brivaracetam or its pharmaceutically acceptable salt, hydrate, solvate, polymorph, or prodrug is administered at a daily dose of at least 0.1 mg, 0.15 mg, 0.18 mg, 0.35 mg, 0.7 mg, 1.5 mg, 2.0 mg, 2.5 mg, 2.8 mg, 3.0 mg, 3.5 mg, 4.2 mg, 5 mg, 5.5 mg, 6.0 mg, 7 mg, 10 mg, 15 mg, 20 mg, 25 mg, 28 mg, 30 mg, or 35 mg but no more than a daily dose of 70 mg, 80 mg, 85 mg, 100 mg, 110 mg, 125 mg, 140 mg, 150 mg, 170 mg, 175 mg, 180 mg, 190 mg, 200 mg, 210 mg, 225 mg, 250 mg, 280 mg, 300 mg, or 350 mg. In some embodiments, the brivaracetam or the pharmaceutically acceptable salt, hydrate, solvate, polymorph, or prodrug thereof may be administered at a daily dose of 0.0015-5 mg/kg, 0.1-350 mg, 0.01-5 mg/kg, 0.7-350 mg, 0.05-4 mg/kg, 3-300 mg, 0.05-2.0 mg/kg, 3-150 mg, 0.05-1.5 mg, 3-110 mg, 0.1-1.0 mg/kg, 7-70 mg.

In other embodiments, the brivaracetam or its pharmaceutically acceptable salt, hydrate, solvate, polymorph, or prodrug is administered according to one of the daily dose ranges indicated as "+" listed in Table 5 or Table 6. For example, the brivaracetam or the pharmaceutically acceptable salt, hydrate, solvate, polymorph, or prodrug thereof may be administered at a daily dose of 0.01-0.8 mg/kg, 0.01-1 mg/kg, 0.01-1.5 mg/kg, 0.01-2 mg/kg, 0.01-2.5 mg/kg, 0.01-3 mg/kg, 0.01-3.5 mg/kg, 0.01-4 mg/kg, 0.01-5 mg/kg, 0.025-0.8 mg/kg, 0.025-1 mg/kg, 0.025-1.5 mg/kg, 0.025-2 mg/kg, 0.025-2.5 mg/kg, 0.025-3 mg/kg, 0.025-3.5 mg/kg, 0.025-4 mg/kg, 0.05-0.8 mg/kg, 0.05-1 mg/kg, 0.05-1.5 mg/kg, 0.05-2 mg/kg, 0.05-2.5 mg/kg, 0.05-3 mg/kg, 0.05-3.5 mg/kg, 0.05-4 mg/kg, 0.075-0.8 mg/kg, 0.075-1 mg/kg, 0.075-1.5 mg/kg, 0.075-2 mg/kg, 0.075-2.5 mg/kg, 0.075-3 mg/kg, 0.075-3.5 mg/kg, 0.075-4 mg/kg, 0.1-0.8 mg, 0.1-1 mg/kg, 0.1-1.5 mg/kg, 0.1-2 mg/kg, 0.1-2.5 mg/kg, 0.1-3 mg/kg, 0.1-3.5 mg/kg, 0.1-4 mg/kg, 0.2-0.8 mg/kg, 0.2-1 mg/kg, 0.2-1.5 mg/kg, 0.2-2 mg/kg, 0.2-2.5 mg/kg, 0.2-3 mg/kg, 0.2-3.5 mg/kg, 0.2-4 mg/kg, 0.5-0.8 mg/kg, 0.5-1 mg/kg, 0.5-1.5 mg/kg, 0.5-2 mg/kg, 0.5-2.5 mg/kg, 0.5-3 mg/kg, 0.5-3.5 mg/kg, or 0.5-4 mg/kg; or 0.7-50 mg, 0.7-75 mg, 0.7-100 mg, 0.7-150 mg, 0.7-180 mg, 0.7-225 mg, 0.7-250 mg, 0.7-280 mg, 1.8-50 mg, 1.8-75 mg, 1.8-100 mg, 1.8-150 mg, 1.8-180 mg, 1.8-225 mg, 1.8-250 mg, 1.8-280 mg, 3.5-50 mg, 3.5-75 mg, 3.5-100 mg, 3.5-150 mg, 3.5-180 mg, 3.5-225 mg, 3.5-250 mg, 3.5-280 mg, 5-50 mg, 5-75 mg, 5-100 mg, 5-150 mg, 5-180 mg, 5-225 mg, 5-250 mg, 5-280 mg, 7-50 mg, 7-75 mg, 7-100 mg, 7-150 mg, 7-180 mg, 7-225 mg, 7-250 mg, 7-280 mg, 15-50 mg, 15-75 mg, 15-100 mg, 15-150 mg, 15-180 mg, 15-225 mg, 15-250 mg, 15-280 mg, 35-50 mg, 35-75 mg, 35-100 mg, 35-150 mg, 35-180 mg, 35-225 mg, 35-250 mg, or 35-280 mg.

TABLE 5

Daily Doses of Brivaracetam (mg/kg)

| Upper range | Lower range | | | | | | | | |
|---|---|---|---|---|---|---|---|---|---|
| | 0.0015 | 0.01 | 0.025 | 0.04 | 0.05 | 0.075 | 0.1 | 0.2 | 0.5 |
| 0.8 | + | + | + | + | + | + | + | + | + |
| 1 | + | + | + | + | + | + | + | + | + |
| 1.5 | + | + | + | + | + | + | + | + | + |

TABLE 5-continued

Daily Doses of Brivaracetam (mg/kg)

| | Lower range | | | | | | | | |
|---|---|---|---|---|---|---|---|---|---|
| Upper range | 0.0015 | 0.01 | 0.025 | 0.04 | 0.05 | 0.075 | 0.1 | 0.2 | 0.5 |
| 2 | + | + | + | + | + | + | + | + | + |
| 2.5 | + | + | + | + | + | + | + | + | + |
| 3 | + | + | + | + | + | + | + | + | + |
| 3.5 | + | + | + | + | + | + | + | + | + |
| 4 | + | + | + | + | + | + | + | + | + |
| 5 | + | + | + | + | + | + | + | + | + |

TABLE 6

Daily Doses of Brivaracetam in a Human Subject of 70 KG (mg)

| | Lower range | | | | | | | | |
|---|---|---|---|---|---|---|---|---|---|
| Upper range | 0.1 | 0.7 | 1.8 | 3.0 | 3.5 | 5 | 7 | 15 | 35 |
| 50 | + | + | + | + | + | + | + | + | + |
| 75 | + | + | + | + | + | + | + | + | + |
| 100 | + | + | + | + | + | + | + | + | + |
| 110 | + | + | + | + | + | + | + | + | + |
| 150 | + | + | + | + | + | + | + | + | + |
| 180 | + | + | + | + | + | + | + | + | + |
| 225 | + | + | + | + | + | + | + | + | + |
| 250 | + | + | + | + | + | + | + | + | + |
| 280 | + | + | + | + | + | + | + | + | + |
| 300 | + | + | + | + | + | + | + | + | + |
| 350 | + | + | + | + | + | + | + | + | + |

In certain embodiments of the invention, the SV2A inhibitor is seletracetam or a pharmaceutically acceptable salt, hydrate, solvate, polymorph, or prodrug thereof. In some embodiments, the seletracetam or its pharmaceutically acceptable salt, hydrate, solvate, polymorph, or prodrug thereof is administered at a daily dose of at least 0.1 mg, 0.5 mg, 0.75 mg, 1.0 mg, 1.5 mg, or 2.0 mg, but no more than a daily dose of 2.5 mg, 5 mg, 10 mg, 15 mg, 20 mg, 25 mg, 30 mg, or 35 mg. In other embodiments, the seletracetam or a pharmaceutically acceptable salt, hydrate, solvate, polymorph, or prodrug thereof is administered at a daily dose of at least 0.0015 mg/kg, 0.0075 mg/kg, 0.01 mg/kg, 0.015 mg/kg, 0.02 mg/kg, or 0.03 mg/kg, but no more than a daily dose of 0.5 mg/kg, 0.4 mg/kg, 0.3 mg/kg, 0.2 mg/kg, 0.15 mg/kg, 0.1 mg/kg, 0.05 mg/kg, or 0.04 mg/kg.

In certain embodiments of the invention, the seletracetam or its pharmaceutically acceptable salt, hydrate, solvate, polymorph, or prodrug is administered according to one of the daily dose ranges indicated as "+" listed in Table 7 or Table 8. For example, the seletracetam or its pharmaceutically acceptable salt, hydrate, solvate or polymorph may be administered at a daily dose of 0.1-35 mg, 0.5-35 mg, 0.75-35 mg, 1.0-35 mg, 1.5-35 mg, 2.0-35 mg, 0.1-30 mg, 0.1-25 mg, 0.1-20 mg, 0.1-15 mg, 0.1-10 mg, 0.1-5 mg, 0.1-2.5 mg, 0.0015-0.5 mg/kg, 0.0075-0.5 mg/kg, 0.01-0.5 mg/kg, 0.015-0.5 mg/kg, 0.02-0.5 mg/kg, 0.03-0.5 mg/kg, 0.0015-0.4 mg/kg, 0.0015-0.3 mg/kg, 0.0015-0.2 mg/kg, 0.0015-0.15 mg/kg, 0.0015-0.1 mg/kg, 0.0015-0.05 mg/kg, or 0.0015-0.04 mg/kg.

TABLE 7

Daily Doses of Seletracetam

| | Lower range | | | | | |
|---|---|---|---|---|---|---|
| Upper range | 0.0015 mg/kg | 0.0075 mg/kg | 0.01 mg/kg | 0.015 mg/kg | 0.02 mg/kg | 0.03 mg/kg |
| 0.04 mg/kg | + | + | + | + | + | + |
| 0.05 mg/kg | + | + | + | + | + | + |
| 0.1 mg/kg | + | + | + | + | + | + |
| 0.15 mg/kg | + | + | + | + | + | + |
| 0.2 mg/kg | + | + | + | + | + | + |
| 0.3 mg/kg | + | + | + | + | + | + |
| 0.4 mg/kg | + | + | + | + | + | + |
| 0.5 mg/kg | + | + | + | + | + | + |

TABLE 8

Daily Doses of Seletracetam in a Human Subject of 70 KG

| | Lower range | | | | | |
|---|---|---|---|---|---|---|
| Upper range | 0.1 mg | 0.5 mg | 0.75 mg | 1.0 mg | 1.5 mg | 2.0 mg |
| 2.5 mg | + | + | + | + | + | + |
| 5 mg | + | + | + | + | + | + |
| 10 mg | + | + | + | + | + | + |
| 15 mg | + | + | + | + | + | + |
| 20 mg | + | + | + | + | + | + |
| 25 mg | + | + | + | + | + | + |
| 30 mg | + | + | + | + | + | + |
| 35 mg | + | + | + | + | + | + |

In other embodiments, the seletracetam or its pharmaceutically acceptable salt, hydrate, solvate, polymorph, or prodrug is administered at a daily dose of at least 0.0015 mg/kg, 0.002 mg/kg, 0.0025 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, but no more than a daily dose of 1 mg/kg, 1.2 mg/kg, 1.4 mg/kg, 1.5 mg/kg, 1.6 mg/kg, 1.8 mg/kg, 2.0 mg/kg, 2.2 mg/kg, 2.4 mg/kg, 2.5 mg/kg, 2.6 mg/kg, 2.8 mg/kg, 3.0 mg/kg, 3.5 mg/kg, 4.0 mg/kg, 4.5 mg/kg, or 5.0 mg/kg. In other embodiments, the seletracetam or its pharmaceutically acceptable salt, hydrate, solvate, polymorph, or prodrug is administered at a daily dose of at least 0.1 mg, 0.15 mg, 0.18 mg, 0.35 mg, 0.7 mg, 1.5 mg, 2.0 mg, 2.5 mg, 2.8 mg, 3.0 mg, 3.5 mg, 4.2 mg, 5 mg, 5.5 mg, 6.0 mg, 7 mg, 10 mg, 15 mg, 20 mg, 25 mg, 28 mg, 30 mg, or 35 mg but no more than a daily dose of 70 mg, 80 mg, 85 mg, 100 mg, 110 mg, 125 mg, 140 mg, 150 mg, 170 mg, 175 mg, 180 mg, 190 mg, 200 mg, 210 mg, 225 mg, 250 mg, 280 mg, 300 mg, or 350 mg. In some embodiments, the brivaracetam or the pharmaceutically acceptable salt, hydrate, solvate, polymorph, or prodrug thereof may be administered at a daily dose of 0.0015-5 mg/kg, 0.1-350 mg, 0.01-5 mg/kg, 0.7-350 mg, 0.05-4 mg/kg, 3-300 mg, 0.05-2.0 mg/kg, 3-150 mg, 0.05-1.5 mg/kg, 3-110 mg, 0.1-1.0 mg/kg, 7-70 mg.

In other embodiments, the seletracetam or its pharmaceutically acceptable salt, hydrate, solvate, polymorph, or prodrug is administered according to one of the daily dose ranges indicated as "+" listed in Table 9 or Table 10. For example, the seletracetam or the pharmaceutically acceptable salt, hydrate, solvate, polymorph, or prodrug thereof may be administered at a daily dose of 0.01-0.8 mg/kg, 0.01-1 mg/kg, 0.01-1.5 mg/kg, 0.01-2 mg/kg, 0.01-2.5 mg/kg, 0.01-3 mg/kg, 0.01-3.5 mg/kg, 0.01-4 mg/kg, 0.01-5 mg/kg, 0.025-0.8 mg/kg, 0.025-1 mg/kg, 0.025-1.5 mg/kg, 0.025-2 mg/kg, 0.025-2.5 mg/kg, 0.025-3 mg/kg, 0.025-3.5 mg/kg, 0.025-4 mg/kg, 0.05-0.8 mg/kg, 0.05-1 mg/kg, 0.05-1.5 mg/kg, 0.05-2 mg/kg, 0.05-2.5 mg/kg, 0.05-3 mg/kg, 0.05-3.5 mg/kg, 0.05-4 mg/kg, 0.075-0.8 mg/kg, 0.075-1 mg/kg, 0.075-1.5 mg/kg, 0.075-2 mg/kg, 0.075-2.5 mg/kg, 0.075-3 mg/kg, 0.075-3.5 mg/kg, 0.075-4 mg/kg, 0.1-0.8 mg/kg, 0.1-1 mg/kg, 0.1-1.5 mg/kg, 0.1-2 mg/kg, 0.1-2.5 mg/kg, 0.1-3 mg/kg, 0.1-3.5 mg/kg, 0.1-4 mg/kg, 0.2-0.8 mg/kg, 0.2-1 mg/kg, 0.2-1.5 mg/kg, 0.2-2 mg/kg, 0.2-2.5 mg/kg, 0.2-3 mg/kg, 0.2-3.5 mg/kg, 0.2-4 mg/kg, 0.5-0.8 mg/kg, 0.5-1 mg/kg, 0.5-1.5 mg/kg, 0.5-2 mg/kg, 0.5-2.5 mg/kg, 0.5-3 mg/kg, 0.5-3.5 mg/kg, or 0.5-4 mg/kg; or 0.7-50 mg, 0.7-75 mg, 0.7-100 mg, 0.7-150 mg, 0.7-180 mg, 0.7-225 mg, 0.7-250 mg, 0.7-280 mg, 1.8-50 mg, 1.8-75 mg, 1.8-100 mg, 1.8-150 mg, 1.8-180 mg, 1.8-225 mg, 1.8-250 mg, 1.8-280 mg, 3.5-50 mg, 3.5-75 mg, 3.5-100 mg, 3.5-150 mg, 3.5-180 mg, 3.5-225 mg, 3.5-250 mg, 3.5-280 mg, 5-50 mg, 5-75 mg, 5-100 mg, 5-150 mg, 5-180 mg, 5-225 mg, 5-250 mg, 5-280 mg, 7-50 mg, 7-75 mg, 7-100 mg, 7-150 mg, 7-180 mg, 7-225 mg, 7-250 mg, 7-280 mg, 15-50 mg, 15-75 mg, 15-100 mg, 15-150 mg, 15-180 mg, 15-225 mg, 15-250 mg, 15-280 mg, 35-50 mg, 35-75 mg, 35-100 mg, 35-150 mg, 35-180 mg, 35-225 mg, 35-250 mg, or 35-280 mg.

TABLE 9

Daily Doses of Seletracetam (mg/kg)

| Upper range | Lower range | | | | | | | | |
|---|---|---|---|---|---|---|---|---|---|
| | 0.0015 | 0.01 | 0.025 | 0.04 | 0.05 | 0.075 | 0.1 | 0.2 | 0.5 |
| 0.8 | + | + | + | + | + | + | + | + | + |
| 1 | + | + | + | + | + | + | + | + | + |
| 1.5 | + | + | + | + | + | + | + | + | + |
| 2 | + | + | + | + | + | + | + | + | + |
| 2.5 | + | + | + | + | + | + | + | + | + |
| 3 | + | + | + | + | + | + | + | + | + |
| 3.5 | + | + | + | + | + | + | + | + | + |
| 4 | + | + | + | + | + | + | + | + | + |
| 5 | + | + | + | + | + | + | + | + | + |

TABLE 10

Daily Doses of Seletracetam in a Human Subject of 70 KG (mg)

| Upper range | Lower range | | | | | | | | |
|---|---|---|---|---|---|---|---|---|---|
| | 0.1 | 0.7 | 1.8 | 3.0 | 3.5 | 5 | 7 | 15 | 35 |
| 50 | + | + | + | + | + | + | + | + | + |
| 75 | + | + | + | + | + | + | + | + | + |
| 100 | + | + | + | + | + | + | + | + | + |
| 110 | + | + | + | + | + | + | + | + | + |
| 150 | + | + | + | + | + | + | + | + | + |
| 180 | + | + | + | + | + | + | + | + | + |
| 225 | + | + | + | + | + | + | + | + | + |
| 250 | + | + | + | + | + | + | + | + | + |
| 280 | + | + | + | + | + | + | + | + | + |
| 300 | + | + | + | + | + | + | + | + | + |
| 350 | + | + | + | + | + | + | + | + | + |

The SV2A inhibitor or its pharmaceutically acceptable salt, hydrate, solvate or polymorph may be administered at a subtherapeutic dosage level when provided in combination with valproate or its analog, derivative or pharmaceutically acceptable salt, due to valproate-dependent increase in the therapeutic index of the SV2A inhibitor. In some embodiments, the increase in the therapeutic index of the SV2A inhibitor, due to the combination with valproate, is greater than the therapeutic index of the SV2A inhibitor administered in the absence of the valproate by at least about 1.5× or 2.0× or 2.5× or 3.0× or 3.5× or 4.0× or 4.5× or 5.0× or 5.5× or 6.0× or 6.5× or 7.0× or 7.5× or 8.0× or 8.5× or 9.0× or 9.5× or 10×, or greater than about 10×. In some embodiments, combinations of an SV2A inhibitor with valproate reduces the dosage of the SV2A inhibitor required for its therapeutic effect. In some embodiments of the invention, the SV2A inhibitor or the pharmaceutically acceptable salt, hydrate, solvate, polymorph, or prodrug thereof that is administered in combination with valproate or its analog, derivative or pharmaceutically acceptable salt is administered at a daily dose of about 0.001 mg/kg to 5 mg/kg, or about 0.1 to 5 mg/kg, or about 1 to 2 mg/kg, or about 0.1 to 0.2 mg/kg, or about 0.01 to 2.5 mg/kg, or about 0.1 to 2.5 mg/kg, or about 0.4 to 2.5 mg/kg, or about 0.6 to 1.8 mg/kg, or about 0.04 to 2.5 mg/kg, or about 0.06 to 1.8 mg/kg, or about 0.01 to 1 mg/kg, or about 0.001 to 1 mg/kg, or about 0.5 mg/kg to 5 mg/kg, or about 0.05 mg/kg to 0.5 mg/kg. In some embodiments, the amount of the SV2A inhibitor or the pharmaceutically acceptable salt, hydrate, solvate, polymorph, or prodrug thereof that is administered in combination with valproate or its analog, derivative or pharmaceutically acceptable salt is a subtherapeutic amount (as compared to the therapeutic dose of valproate when administered alone). Such subtherapeutic amount, may be, for example, a daily dose, administered at a daily dose of less than 5 mg/kg, less than 2.5 mg/kg, less than 2 mg/kg, less than 1.75 mg/kg, less than 1.6 mg/kg, less than 1.5 mg/kg, less than 1 mg/kg, less than 0.8 mg/kg, less than 0.6 mg/kg, less than 0.5 mg/kg, less than 0.4 mg/kg, less than 0.3 mg/kg, less than 0.2 mg/kg, less than 0.1 mg/kg, less than 0.05 mg/kg, less than 0.04 mg/kg, less than 0.03 mg/kg, less than 0.02 mg/kg, less than 0.01 mg/kg, less than 0.005 mg/kg, or less than 0.001 mg/kg.

Valproate or its analog, derivative or pharmaceutically acceptable salt may be administered at a dosage level up to conventional dosage levels. Valproate has been prescribed for treatment of epilepsy, bipolar disorder, migraine, and post-traumatic stress disorder. Valproate is also reported to be effective in treating cognitive impairment (Koh et al., 36th annual meeting of the Society for Neuroscience, Oct. 15, 2006, No. 273.14, D.3). Chronic subcutaneous administration to memory-impaired aged rats of 100 mg/kg/day sodium valproate treated their cognitive impairment and their performance in a memory test was significantly improved. This dosage results in a blood total valproate level of 10 µg/ml plasma (10 µg/ml total valproate). Treatment with chronic subcutaneous administration of 50 mg/kg/day valproate, however, was not effective.

The valproate or its analog, derivative, pharmaceutically acceptable salt, hydrate, solvate, polymorph or prodrug may be administered at dosage levels distinct from conventional levels when provided in combination with an SV2A inhibitor, due to an SV2A inhibitor-dependent increase in the valproate's therapeutic index. In some embodiments, the increase in the valproate's therapeutic index due to the combination with an SV2A inhibitor thereof is greater than the therapeutic index of the valproate administered in the absence of an SV2A inhibitor by at least about 1.5× or 2.0× or 2.5× or 3.0× or 3.5× or 4.0× or 4.5× or 5.0× or 5.5× or 6.0× or 6.5× or 7.0× or 7.5× or 8.0× or 8.5× or 9.0× or 9.5× or 10×, or greater than about 10×. In some embodiments, combinations of valproate with the SV2A inhibitor reduces the dosage of the valproate required for its therapeutic effect. In some embodiments, the amount of the valproate or its analog, derivative, pharmaceutically acceptable salt, hydrate, solvate, polymorph or prodrug administered in combination with the SV2A inhibitor is a subtherapeutic amount. In certain embodiments, the dose of valproate or its analog, derivative or pharmaceutically acceptable salt when administered in combination with an SV2A inhibitor is a dose that results in a total blood valproate of 0.5 to 5 µg/ml plasma. The doses useful for valproate or its analog, derivative or pharmaceutically acceptable salt are readily determined by those skilled in the art, using the methods of this invention.

In certain embodiments, wherein an SV2A inhibitor or its pharmaceutically acceptable salt, hydrate, solvate and polymorph is administered in combination with valproate or its analog, derivative or pharmaceutically acceptable salt, the dosage of both the SV2A inhibitor or its pharmaceutically acceptable salt, hydrate, solvate and polymorph and the valproate or its analog, derivative, pharmaceutically acceptable salt, hydrate, solvate, polymorph or prodrug, are each sub-therapeutic with respect to treating a CNS disorder with cognitive impairment when administered alone.

In some embodiments, a suitable amount of the SV2A inhibitor is administered so as to reduce the dose of the valproate (e.g., a dose required to effect a degree of cognitive function improvement or treat age-associated cognitive impairment) by at least about 20%, at least about 30%, at least about 40%, or at least about 50%, at least about 60%, at least about 70%, at least about 80%, at least about 90% or more from to the dose of valproate normally used when administered alone (i.e., individually and not in combination with other therapeutic agents or compounds). The reduction may be reflected in terms of amount administered at a given administration and/or amount administered over a given period of time (reduced frequency).

In certain embodiments of the invention, the combined administration of an SV2A inhibitor or its pharmaceutically acceptable salt, hydrate, solvate and polymorph, and valproate or its analog, derivative or pharmaceutically acceptable salt, can attain a longer or improved therapeutic effect in the subject than that attained by administering only the valproate or only the SV2A inhibitor, by at least about 1.5×, or 2.0×, or 2.5×, or 3.0×, or 3.5×, or 4.0×, or 4.5×, or 5.0×, or 5.5×, or 6.0×, or 6.5×, or 7.0×, or 7.5×, or 8.0×, or 8.5×, or 9.0×, or 9.5×, or 10×, or greater than about 10×.

In certain embodiments of the invention, the SV2A inhibitor or the pharmaceutically acceptable salt, hydrate, solvate, polymorph, or prodrug thereof is in an extended release form, a controlled release form, a prolonged release form, a sustained release form, a delayed release form, or a slow release form. In some embodiments, the SV2A inhibitor or the pharmaceutically acceptable salt, hydrate, solvate, polymorph, or prodrug thereof in an extended release form (or a controlled release form, a prolonged release form, a sustained release form, a delayed release form, or a slow release form) is formulated together with valproate or an analog, derivative, pharmaceutically acceptable salt, hydrate, solvate, polymorph, or prodrug thereof in a single formulation. In some embodiments, the SV2A inhibitor or the pharmaceutically acceptable salt, hydrate, solvate, polymorph, or prodrug thereof in an extended release form (or a controlled release form, a prolonged release form, a sustained release form, a delayed release form, or a slow release form) is formulated together with valproate or an analog, derivative, pharmaceutically acceptable salt, hydrate, solvate, polymorph, or prodrug thereof are formulated in separate formulations, which may be packaged together. In some of the above composition embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), valproate or an analog, derivative, pharmaceutically acceptable salt, hydrate, solvate, polymorph, or prodrug thereof is also in an extended release form (or a controlled release form, a prolonged release form, a sustained release form, a delayed release form, or a slow release form). In some of the above composition embodiments where the SV2A inhibitor or the pharmaceutically acceptable salt, hydrate, solvate, polymorph, or prodrug thereof is in an extended release form (or a controlled release form, a prolonged release form, a sustained release form, a delayed release form, or a slow release form), valproate or an analog, derivative, pharmaceutically acceptable salt, hydrate, solvate, polymorph, or prodrug thereof is not in an extended release form (or a controlled release form, a prolonged release form, a sustained release form, a delayed release form, or a slow release form). In some embodiments of the composition of the present invention, valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form). In some embodiments, valproate or an analog, derivative, pharmaceutically acceptable salt, hydrate, solvate, polymorph, or prodrug thereof in an extended release form (or a controlled release form, a prolonged release form, a sustained release form, a delayed release form, or a slow release form) is formulated together with the SV2A inhibitor or the pharmaceutically acceptable salt, hydrate, solvate, polymorph, or prodrug thereof in a single formulation. In some embodiments, valproate or an analog, derivative, pharmaceutically acceptable salt, hydrate, solvate, polymorph, or prodrug thereof in an extended release form (or a controlled release form, a prolonged release form, a sustained release form, a delayed release form, or a slow release form) and the SV2A inhibitor or the pharmaceutically acceptable salt, hydrate, solvate, polymorph, or prodrug thereof are formulated in separate formulations, which may be packaged together. In some of the above composition embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof is also in an extended release form (or a controlled release form, a prolonged release form, a sustained release form, a delayed release form, or a slow release form). In some of the above embodiments where valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form), the SV2A inhibitor or the pharmaceutically acceptable salt, hydrate, solvate, polymorph, or prodrug thereof is not in an extended release form (or a controlled release form, a prolonged release form, a sustained release form, a delayed release form, or a slow release form). In some embodiments, the composition is in a unit dosage form. In other embodiments, the two components of the compositions are in separate delivery forms packaged together.

Compositions of the Invention

In one aspect, the invention provides compositions comprising an SV2A inhibitor or the pharmaceutically acceptable salt, hydrate, solvate or polymorph alone or in combination with valproate or its analog, derivative or pharmaceutically acceptable salt. In some embodiments, the SV2A inhibitor and the valproate may be present in a single dosage unit (e.g., combined together in one capsule, tablet, powder, or liquid, etc.). The composition described herein can contain more than one SV2A inhibitor its pharmaceutically acceptable salt, hydrate, solvate or polymorph and/or more than one valproate or its analog, derivative or pharmaceutically acceptable salt. In some embodiments, the SV2A inhibitor and the valproate are in separate formulations packaged together.

The compositions described herein can further contain pharmaceutically acceptable excipient(s) and may contain other agents that serve to enhance and/or complement the effectiveness of the SV2A inhibitor and/or the valproate. The compositions may also contain additional agents known to be useful for treating cognitive function disorder.

The composition in the present invention may be in solid dosage forms such as capsules, tablets, dragrees, pills, lozenges, powders and granule. Where appropriate, they may be prepared with coatings such as enteric coatings or they may be formulated so as to provide controlled releases of one or more active ingredient such as sustained or prolonged release according to methods well known in the art. In certain embodiments, the composition is in form of a slow, controlled, or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release", "prolonged release", "sustained release", or "slow release", as these terms are used in the pharmaceutical sciences. In some embodiments, the extended release dosage is administered in the form of a patch or a pump. The composition may also be in liquid dosage forms including solutions, emulsions, suspensions, syrups, and elixirs. The term "extended release" used herein includes the terms "controlled release," "prolonged release," "sustained release," "delayed release," or "slow release" as these terms are used in the pharmaceutical sciences. In some embodiments, the extended release dosage is administered in the form of a patch or a pump. The term "Extended release dosage form" or "extended release form", as used herein, also refers to a dosage form that contains one or more active ingredients, where the release of at least one of the active ingredient, when placed in water or other biological fluids or solvents, may occur over an extended period, such as a period of at least about 1 day, at least about 2 days, at least about 3 days, at least about 4 days, at least about 5 days, at least about 10 days, at least about 20 days, at least about 30 days, at least about 60 days, at least about 90 days, or at least about 150 days. In some embodiments of the present invention, only one of the SV2A inhibitor and valproate is in an extended release dosage form. In some other embodiments of the composition of the present invention, the SV2A inhibitor and valproate are each in an extended release dosage form (together in one formulation or separately in two formulations).

In certain embodiments of the invention, the pharmaceutical composition comprising an SV2A inhibitor (e.g., levetiracetam, brivaracetam, or seletracetam) or a pharmaceutically acceptable salt, hydrate, solvate, polymorph, or prodrug thereof is in an extended release form, a controlled release form, a prolonged release form, a sustained release form, a delayed release form, or a slow release form.

In certain embodiments of the invention, the pharmaceutical composition comprising an SV2A inhibitor or the pharmaceutically acceptable salt, hydrate, solvate, polymorph, or prodrug thereof and valproate or an analog, derivative, pharmaceutically acceptable salt, hydrate, solvate, polymorph, or prodrug thereof is in an extended release form (or a controlled release form, a prolonged release form, a sustained release form, a delayed release form, or a slow release form). In some embodiments, the pharmaceutical composition comprising an SV2A inhibitor or a pharmaceutically acceptable salt, hydrate, solvate, polymorph, or prodrug thereof in an extended release form (or a controlled release form, a prolonged release form, a sustained release form, a delayed release form, or a slow release form) and further comprising valproate or an analog, derivative, pharmaceutically acceptable salt, hydrate, solvate, polymorph, or prodrug in an extended release form (or a controlled release form, a prolonged release form, a sustained release form, a delayed release form, or a slow release form). In some embodiments, the pharmaceutical composition comprising an SV2A inhibitor or a pharmaceutically acceptable salt, hydrate, solvate, polymorph, or prodrug thereof in an extended release form (or a controlled release form, a prolonged release form, a sustained release form, a delayed release form, or a slow release form) and further comprising valproate or an analog, derivative, pharmaceutically acceptable salt, hydrate, solvate, polymorph, or prodrug that is not an extended release form, or a controlled release form, a prolonged release form, a sustained release form, a delayed release form, or a slow release form. In some embodiments, the pharmaceutical composition comprising an SV2A inhibitor or a pharmaceutically acceptable salt, hydrate, solvate, polymorph, or prodrug thereof that is not in an extended release form (or a controlled release form, a prolonged release form, a sustained release form, a delayed release form, or a slow release form) and further comprising valproate or an analog, derivative, pharmaceutically acceptable salt, hydrate, solvate, polymorph, or prodrug that is in an extended release form, or a controlled release form, a prolonged release form, a sustained release form, a delayed release form, or a slow release form.

The compositions may be specifically formulated for administration by any suitable route as described herein and known in the art. Compositions for parental administration include sterile aqueous and nonaqueous injectable solutions, dispersions, suspensions or emulsions as well as sterile powders to be reconstituted in sterile injectable solutions or dispersions prior to use. Compositions for intraoral and oral delivery (including sublingual and buccal administration, e.g. Danckwerts et al, and oral) include but are not limited to bioadhesive polymers, tablets, patches, liquids and semisolids (see e.g., Smart et al). Compositions for respiratory delivery (pulmonary and nasal delivery) include but are not limited to a variety of pressurized metered dose inhalers, dry powder inhalers, nebulizers, aqueous mist inhalers, drops, solutions, suspensions, sprays, powders, gels, ointments, and specialized systems such as liposomes and microspheres (see e.g. Owens et al, "Alternative Routes of Insulin Delivery" and Martini et al). Compositions for transdermal delivery include but are not limited to colloids, patches, and microemulsions. Other suitable administration forms for the above and other include depot injectable formulations, suppositories, sprays, ointments, cremes, gels, inhalants, dermal patches, implants etc.

The compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Therapeutic formulations can be prepared by methods well known in the art of pharmacy, see, e.g., Goodman et al., 2001; Ansel, et al., 2004; Stoklosa et al., 2001; and Bustamante, et al., 1993.

In certain embodiments of the invention, a composition containing an SV2A inhibitor or its pharmaceutically acceptable salt, hydrate, solvate or polymorph comprises the SV2A inhibitor in an amount of 0.07-60 mg, 0.07-350 mg, 25-60 mg, 25-125 mg, 50-250 mg, 5-140 mg, 0.7-180 mg, 125-240 mg, 3-50 mg, or 3-60 mg. In some embodiments, a composition containing an SV2A inhibitor or its pharmaceutically acceptable salt, hydrate, solvate or polymorph comprises the SV2A inhibitor in an amount of 0.05-35 mg.

In certain embodiments of the invention, a composition containing an SV2A inhibitor or its pharmaceutically acceptable salt, hydrate, solvate or polymorph, in combination with valproate or its analog, derivative or pharmaceutically acceptable salt comprises an amount of the SV2A inhibitor or its pharmaceutically acceptable salt, hydrate, solvate or polymorph of 0.05-35 mg, 0.07-60 mg, 0.07-350 mg, 25-60 mg, 25-125 mg, 50-250 mg, 5-15 mg, 5-30 mg, 5-140 mg, 0.7-180 mg, 125-240 mg, 3-50 mg, or 0.07-50 mg, or 3-60 mg. In some embodiments, the amount of the SV2A inhibitor or the pharmaceutically acceptable salt, hydrate, solvate, polymorph, or prodrug thereof is less than 350 mg, less than 250 mg, less than 200 mg, less than 150 mg, less than 100 mg, less than 50 mg, less than 35 mg, less than 10 mg, less than 5 mg, less than 1 mg, less than 0.5 mg, less than 0.1 mg, less than 0.07 mg, or less than 0.05 mg.

In certain embodiments of the invention, a composition containing an SV2A inhibitor or its pharmaceutically acceptable salt, hydrate, solvate or polymorph, in combination with valproate or its analog, derivative or pharmaceutically acceptable salt comprises an amount of the SV2A inhibitor or its pharmaceutically acceptable salt, hydrate, solvate or polymorph of 0.1-500 mg, 0.1-300 mg, 0.7-300 mg, 3-300 mg, 3-150 mg, 3-110 mg, 7-70 mg, 7-300 mg, 70-300 mg, 100-300 mg, 125-250 mg, 0.5-50 mg, 0.5-75 mg, 0.5-100 mg, 0.5-150 mg, 0.5-200 mg, 0.5-225 mg, 0.5-250 mg, 0.5-300 mg, 1.5-50 mg, 1.5-75 mg, 1.5-100 mg, 1.5-150 mg, 1.5-200 mg, 1.5-225 mg, 1.5-250 mg, 1.5-300 mg, 3-50 mg, 3-75 mg, 3-100 mg, 3-150 mg, 3-200 mg, 3-225 mg, 3-250 mg, 3-300 mg, 5-50 mg, 5-75 mg, 5-100 mg, 5-150 mg, 5-200 mg, 5-225 mg, 5-250 mg, 5-300 mg, 7-50 mg, 7-75 mg, 7-100 mg, 7-150 mg, 7-200 mg, 7-225 mg, 7-250 mg, 7-300 mg, 15-50 mg, 15-75 mg, 15-100 mg, 15-150 mg, 15-200 mg, 15-225 mg, 15-250 mg, 15-300 mg, 30-50 mg, 30-75 mg, 30-100 mg, 30-150 mg, 30-200 mg, 30-225 mg, 30-250 mg, or 30-300 mg.

In addition to an SV2A inhibitor or its pharmaceutically acceptable salt, hydrate, solvate and polymorph, alone or in combination with valproate or its analog, derivative or pharmaceutically acceptable salt, the compositions and methods of this invention can also include other therapeutically useful agents. These other therapeutically useful agents may be administered in a single formulation, simultaneously or sequentially according to the methods of the invention.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

This invention will be better understood from the Experimental Details which follow. However, one skilled in the art will readily appreciate that the specific methods and results discussed are merely illustrative of the invention as described more fully in the embodiments which follow thereafter.

EXAMPLES

Introduction and Models of Cognitive Impairment

A variety of conditions characterized by cognitive impairment, e.g., Age-Associated Memory Impairment (AAMI), Mild Cognitive Impairment (MCI) and Age-related Cognitive Decline (ARCD) are believed to be related to aging. Others are related to disease, for example, AD. Animal models serve as an important resource for developing and evaluating treatments for such age-related cognitive impairments. Features that characterize age-related cognitive impairment in animal models typically extend to age-related cognitive impairment in humans. Efficacy in such animal models is, thus, predictive of efficacy in humans.

Of available models, a Long-Evans rat model of cognitive impairment is particularly well suited for distinguishing the difference between cognitive impairment related to illness and that related to aging. Indeed, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Rapp and Gallagher, *Proc. Natl. Acad. Sci.* 93: 9926-9930, (1996); Nicolle et al., *Neuroscience* 74: 741-756, (1996); and Nicolle et al., *J. Neurosci.* 19: 9604-9610, (1999).

We used the above-described rat model to identify individual AI and AU rats. We then conducted behavioral assessment on AI rats while administering various pharmacological treatments.

Example 1

Increased Gene Expression of SV2A in Aged-Impaired Rats

Behavioral Characterization of Young, Aged-Impaired and Aged-Unimpaired Rats in Morris Water Maze (MWM)

Behavioral tests were performed on young (4 months old) and aged (24 months old) pathogen-free male Long-Evans rats.

The MWM apparatus consists of a large, circular pool (diameter 1.53 m; height, 0.58 m) filled with water (27° C.) that is made opaque through the addition of non-toxic pigment or some other substance. In the typical "hidden platform" version of the test, rats are trained to find a camouflaged white escape platform (height, 34.5 cm) that is positioned in the center of one quadrant of the maze about 1.0 cm below the water surface. This platform can be retracted to the bottom of the tank or raised to its normal position from outside the maze during behavioral testing. The location of the platform remains constant from trial to trial. Because there are no local cues that mark the position of the platform, the rat's ability to locate it efficiently from any starting position at the perimeter of the pool depends on using information surrounding the maze. The maze is surrounded by black curtains to which white patterns are affixed to provide a configuration of spatial cues. A second platform (height 37.5 cm), with its surface painted black is elevated 2 cm above the water surface during cue training to control for factors unrelated to cognition. The behavior of a rat in the pool is recorded by a camera that is suspended 2.5 m above the center of the pool. The camera is connected to a video tracking system (HVS Image Advanced Tracker VP200) and a PC computer running HVS software developed by Richard Baker of HVS Image, Hampton, UK.

The MWM protocol is optimized for sensitivity to the effects of aging on cognition and for measures of reliable individual differences within the aged population of out-bred Long-Evans rats (Gallagher et al. *Behav. Neurosci.* 107:618-626, (1993)). Rats receive three trials per day for 8 consecutive days, using a 60 sec inter-trial interval. On each training trial, the rat is released into the maze from one of four equally spaced starting positions around the perimeter of the pool. The starting position varies from trial to trial, thus preventing the use of a response strategy (e.g., always turning left from the start location to locate the escape platform). If a rat does not locate the escape platform within 90 sec on any trial, the experimenter guides the rat to the platform, where it remains for 30 sec. Every sixth trial consists of a probe trial to assess the development of spatial bias in the maze. During these trials, the rat swims with the platform retracted to the bottom of the pool for 30 sec, at which time the platform is raised to its normal position for completion of the escape trial. At the completion of the protocol using the hidden platform, rats are assessed for cue learning using the visible platform. The location of this platform varies from trial to trial in a single session of 6 training trials.

The proximity of the animal's position with respect to the goal is used to analyze the training trial and probe trial performance. The proximity measure is obtained by sampling the position of the animal in the maze (10 times/sec) to provide a record of distance from the escape platform in 1 sec averages. For both probe trials and training trials, a correction procedure is implemented so that trial performance is relatively unbiased by differences in distance to the goal from the various start locations at the perimeter of the pool. In making this correction, the average swimming speed is calculated for each trial (path length/latency). Then, the amount of time required to swim to the goal at that speed from the start location used for the trial is removed from the record prior to computing trial performance, i.e., cumulative distance on training trials and average distance from the goal on probe trials. Thus, scores obtained using the proximity measure are designed to reflect search error, representing deviations from an optimal search, i.e. direct path to the goal and search in the immediate vicinity of that location during probe trials.

Computer records of video-tracking are compiled to provide data on each rat's performance in the maze. Measures on training trials and probe trials are analyzed by Analysis of Variance (ANOVA).

In one set of trials, the performance during training with the hidden, camouflaged platform differs between the groups of young and aged rats [$F (1, 23)=12.69$, $p<0.002$]. In this set of trials, no difference between the groups is observed for the cue training trials with a visible platform. In this set of trials, latencies to escape during cue training averaged 9.36 seconds for young and 10.60 seconds for the aged rats.

An average proximity measure on interpolated probe trials is used to calculate a spatial learning index for each individual subject as described in detail in Gallagher et al., *Behav. Neurosci.* 107:618-26, (1993). When a rat rapidly learns to search for the platform close to its position, its spatial learning index is low. Overall, in one set of trials aged rats differed from young rats [$F (1, 23)=15.18$, $p<0.001$]. Aged rats are classified as either unimpaired or impaired relative to the learning index profile of the young study population. Aged rats that fall within the normative range of young rats (index scores <241) are designated aged-unimpaired (AU). The remaining aged subjects that have index scores outside the range of young performance are designated aged-impaired (AI).

Preparation of RNA from Behaviorally Characterized Rats

Twenty-four outbred Long-Evans rats, behaviorally characterized as is described above, are killed by live decapitation to obtain fresh brain tissue. The brain is removed, and the dentate gyms hippocampal region is microdissected from 500 micron sections taken through the transverse axis of the entire hippocampal formation (both left and right hippocampi) of 24 characterized rats. There are 8 animals in each group (AI, AU, and Y).

Total RNA is isolated using Trizol reagent (Invitrogen, Carlsbad, Calif.) according to the standard protocol (homogenization in Trizol reagent followed by chloroform extraction and isopropanol precipitation). Total RNA is further purified using the RNeasy mini kit (Qiagen, Valencia, Calif.). cRNA probes are then generated from the RNA samples at the Johns Hopkins Microarray Core Facility, generally according to Affymetrix specifications.

Briefly, 5 µg of total RNA is used to synthesize first strand cDNA using oligonucleotide probes with 24 oligo-dT plus T7 promoter as primer (Proligo LLC, Boulder, Calif.), and the SuperScript Choice System (Invitrogen). Following the double stranded cDNA synthesis, the product is purified by phenol-chloroform extraction, and biotinilated anti-sense cRNA is generated through in vitro transcription using the BioArray RNA High Yield Transcript Labeling kit (ENZO Life Sciences Inc., Farmingdale, N.Y.). 15 µg of the biotinilated cRNA is fragmented at 94° C. for 35 min (100 mM Trix-acetate, pH 8.2, 500 mM KOAC, 150 mM MgOAC).

10 µg of total fragmented cRNA is hybridized to the RAT genome 230-2 Affymetrix GeneChip array for 16 hours at 45° C. with constant rotation (60 rpm).

Affymetrix Fluidics Station 450 is then used to wash and stain the chips, removing the non-hybridized target and incubating with a streptavidin-phycoerythrin conjugate to stain the biotinilated cRNA. The staining is then amplified using goat immunoglobulin-G (IgG) as blocking reagent and biotinilated anti-streptavidin antibody (goat), followed by a second staining step with a streptavidin-phycoerythrin conjugate.

For quality control of the total RNA from the samples, the Agilent Bioanalyzer, Lab on a Chip technology, is used to confirm that all the samples had optimal rRNA ratios (1:2, for 18S and 28S, respectively) and clean run patterns.

For quality control of the hybridization, chip image, and comparison between chips, the following parameters are considered: Scaling factor: related to the overall intensity of the chip, to confirm the similar signal intensity and staining through out the samples; Background: estimation of unspecific or cross-hybridization; Percentage of present calls: percentage of transcripts that are considered significantly hybridized to the chip (present) by the algorithm; Glyseraldehyde-3-phosphate dehydrogenase (GAPDH) (3'/5'): representation of the RNA integrity by measuring the ratio of 3' to 5' regions for the housekeeping gene GAPDH, its presence in the chip and a ratio close to 1 advocates for a good integrity of the target (sample); Spikes (BioB/BioC) to confirm the detection level and sensitivity after hybridization.

Data Analysis of Microarray

Fluorescence is detected using the Affymetrix G3000 GeneArray Scanner and image analysis of each GeneChip is done through the GeneChip Operating System 1.1.1 (GCOS) software from Affymetrix, using the standard default settings. All of the GeneChip arrays use short oligonucleotides for genes in an RNA sample.

For comparison between different chips, global scaling is used, scaling all probe sets to target intensity (TGT) of 150. Total number of present calls and scaling factors are similar across all chips. Further analysis for presence/absence and statistical difference is performed on a region by region basis in the following manner. Probe sets are determined to be present in a region if it had a present call in four of eight animals in a single group.

Probe sets are annotated using the Affymetrix annotation of Jun. 20, 2005, and all probe sets representing a specific gene are identified.

An ANOVA is conducted on the probe set signal values for all present probe sets by combining two groups of animals and comparing them to the third group. An "AI ANOVA" is performed, where AU group are combined with Young group and compared to AI group.

Pearsons's correlations comparing probe set signal values to learning indices were calculated for the aged animals (excluding young) across all present probe sets. As shown in FIG. 1, expression of genes encoding SV2A was significantly increased in aged-impaired (AI) individuals relative to young individuals (Y) and aged-unimpaired individuals (AU) in a set of experiments performed as above. These results show that increased SV2A expression was correlated to the development of age-related cognitive impairment.

Example 2

Effect of Levetiracetam in Aged-Impaired Rats

Morris Water Maze Results

Six Age-Impaired (AI) Long-Evans rats (as characterized above) were tested for their memory of new spatial information in the MWM, under different drug/control treatment conditions (vehicle control and two different dosage levels of levetiracetam). The MWM protocol was substantially the same as the one described in Example 1. Specifically for this study, a retention trial was performed after the training trials, as described below.

AI rats were given six training trials per training day with a 60-sec inter-trial interval between each training trial for two consecutive days. On each training trial, the rat was released in the maze from one of four equally spaced starting positions around the perimeter of the pool. If the rat did not locate the escape platform within 90 sec on any trial, the experimenter guided the rat to the platform, where it remained for 30 sec. 30 minutes to 1 hour prior to all the training trials on each training day, AI rats were pretreated with one of three drug conditions: 1) vehicle control (0.9% saline solution); 2) levetiracetam (5 m/kg/day); and 3) levetiracetam (10 mg/kg/day); through intraperitoneal (i.p.) injection. The same six AI rats were used for the entire trials so that each treatment condition was tested on all six rats. Therefore, to counterbalance any potential bias, both the location of the escape platform and the spatial cues surrounding the water maze were different in the three treatment conditions. Therefore, using one set of locations and spatial cues, two rats were treated with saline control solution, two with levetiracetam (5 m/kg/day) and two with levetiracetam (10 mg/kg/day). Using the second set of locations and spatial cues, the two rats treated with saline control solution in the first test were treated with either levetiracetam (5 m/kg/day) or levetiracetam (10 mg/kg/day), and the two rats previously treated with levetiracetam (5 m/kg/day) were treated with either saline control solution or levetiracetam (10 mg/kg/day), and the two rats previously treated with levetiracetam (10 mg/kg/day) were treated with either saline control solution or levetiracetam (5 m/kg/day). Using the last set of locations and spatial cues, the rat groupings were again switched so that each group was treated with a different condition than they had been treated previously.

After the second training day and completion of the twelve training trials (over the two days), the rat was returned to its home cage and placed in the animal housing room. After a delay of 24 hours from the last training trial, the rat was given one testing trial (the "retention trial"), which was the same MWM task as the training trials, but with the escape platform removed.

Figure 2:
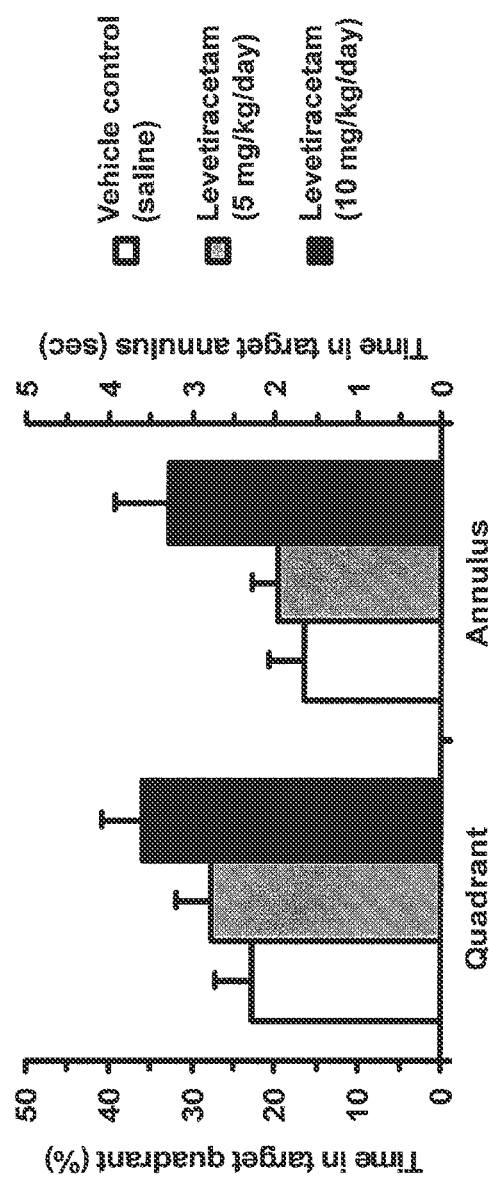
FIG. 2 depicts the effects of administering levetiracetam on the spatial memory retention of six aged-impaired rats (AI) in a Morris Water Maze (MWM) test. Three treatment conditions were employed: vehicle control, levetiracetam (5 mg/kg/day) and levetiracetam (10 mg/kg/day). The AI rats were trained for two consecutive days, with a one-time treatment prior to the training trials per day. 24 hours later, the AI rats were tested. The time the AI rats, 24 hours after treatment with the different conditions and two days of training, spent swimming in the target quadrant or the target annulus in a memory retention trial is used as a measure of spatial memory retention. The target quadrant refers to the quadrant of the maze (which is a circular pool) where the escape platform is placed during the training trials. The target annulus refers to the exact location of the escape platform during the training trials.

For the retention trial, the MWM circular pool was divided into 4 quadrants. The particular quadrant where the escape platform was placed in the training trials is referred as "target quadrant". The particular region where the platform was located in the training trials is referred as "target annulus". In the retention trial, the time the AI rats spent swimming in the target quadrant is measured and further plotted as a percentage of total swimming time. FIG. 2 displays the results of one such set of retention trials. The time the AI rats spend in the target annulus is also measured. FIG. 2 displays the results of one such set of retention trials. Time data are collected for all three drug treatment conditions.

In the retention trial, whose results are depicted in FIG. 2, the time the AI rats spent in the target quadrant was approximately 25%, which is a performance equivalent to them having no memory of the platform location. This performance did not significantly improve in the group treated with levetiractam at 5 mg/kg/day. However, the group treated with levetiractam at 10 mg/kg/day demonstrated significantly improved memory as compared to vehicle-treated controls, as indicated by a significant increase in the time spent in the target quadrant to approximately 35% of total swimming time (see FIG. 2). That level of performance is equivalent to young and age-unimpaired rats, indicating that treatment with 10 mg/kg/day levetiracetam resulted in a significant recovery of the AI rats' ability to navigate this MWM. The effectivness of the 10 mg/kg/day levetiracetam treatment was also seen in the time spent in the target annulus (see FIG. 2).

Radial Arm Maze Results

The effects of levetiracetam on the spatial memory retention of aged-impaired (AI) rats were assessed in a Radial Arm Maze (RAM) behavioral task using vehicle control and five different dosage levels of levetiracetam (1.25 mg/kg/day, 2.5 mg/kg/day, 5 mg/kg/day, 10 mg/kg/day and 20 mg/kg/day). RAM behavioral tasks were preformed on ten AI rats. All six treatment conditions were tested on all ten rats, as described above for the MWM test.

The RAM apparatus used consisted of eight equidistantly-spaced arms. An elevated maze arm (7 cm width×75 cm length) projected from each facet of an octagonal center platform (30 cm diameter, 51.5 cm height). Clear side walls on the arms were 10 cm high and were angled at 65° to form a trough. A food well (4 cm diameter, 2 cm deep) was located at the distal end of each arm. Froot Loops™ (Kellogg Company) were used as rewards. Blocks constructed of Plexiglas™ (30 cm height×12 cm width) could be positioned to prevent entry to any arm. Numerous extra maze cues surrounding the apparatus were also provided.

The AI rats were initially subjected to a pre-training test (Chappell et al. Neuropharmacology 37: 481-487, 1998). The pre-training test consisted of a habituation phase (4 days), a training phase on the standard win-shift task (18 days) and another training phase (14 days) in which a brief delay was imposed between presentation of a subset of arms designated by the experimenter (e.g., 5 arms available and 3 arms blocked) and completion of the eight-arm win-shift task (i.e., with all eight arms available).

In the habituation phase, rats were familiarized to the maze for an 8-minute session on four consecutive days. In each of these sessions food rewards were scattered on the RAM, initially on the center platform and arms and then progressively confined to the arms. After this habituation phase, a standard training protocol was used, in which a food pellet was located at the end of each arm. Rats received one trial each day for 18 days. Each daily trial terminated when all eight food pellets had been obtained or when either 16 choices were made or 15 minutes had elapsed. After completion of this training phase, a second training phase was carried out in which the memory demand was increased by imposing a brief delay during the trial. At the beginning of each trial, three arms of the eight-arm maze were blocked. Rats were allowed to obtain food on the five arms to which access was permitted during this initial 'information phase' of the trial. Rats were then removed from the maze for 60 seconds, during which time the barriers on the maze were removed, thus allowing access to all eight arms. Rats were then placed back onto the center platform and allowed to obtain the remaining food rewards during this 'retention test' phase of the trial. The identity and configuration of the blocked arms varied across trials.

The number of "errors" the AI rats made during the retention test phase was tracked. An error occurred in the trial if the rats entered an arm from which food had already been retrieved in the pre-delay component of the trial, or if it re-visited an arm in the post-delay session that had already been visited.

After completion of the pre-training test, rats were subjected to trials with more extended delay intervals, i.e., a one-hour delay, between the information phase (presentation with some blocked arms) and the retention test (presentation of all arms). During the delay interval, rats remained off to the side of the maze in the testing room, on carts in their individual home cages. AI rats were pretreated 30-40 minutes before daily trials with a one-time shot of the following six conditions: 1) vehicle control (0.9% saline solution); 2) levetiracetam (1.25 mg/kg/day); 3) levetiracetam (2.5 mg/kg/day); 4) levetiracetam (5 mg/kg/day); 5) levetiracetam (10 mg/kg/day); 6) levetiracetam (20 mg/kg/day); through intraperitoneal (i.p.) injection. Injections were given every other day with intervening washout days. Each AI rat was treated with all six conditions within 23 days of testing. To counterbalance any potential bias, drug effect was assessed using ascending-descending dose series, i.e., the dose series was given first in an ascending order and then repeated in a descending order. Therefore, each dose had two determinations.

Figure 3:
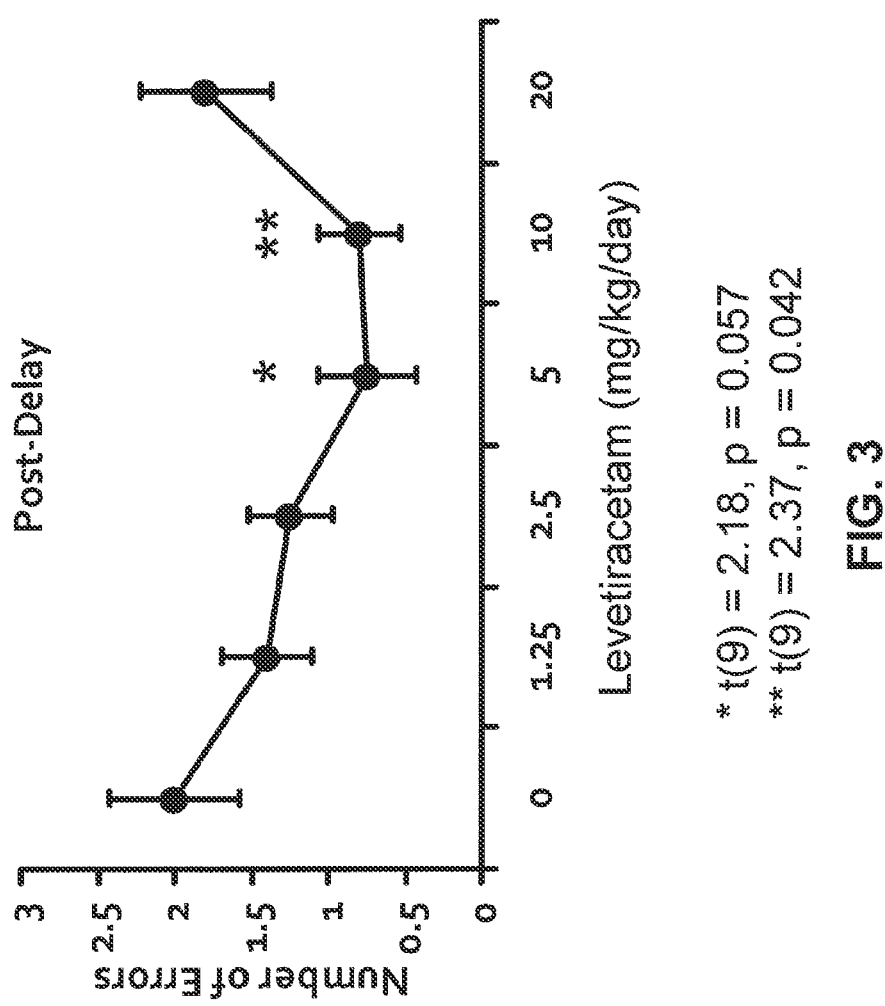
FIG. 3 depicts the effects of administering levetiracetam on the spatial memory retention of ten aged-impaired rats (AI) in an eight-arm Radial Arm Maze (RAM) test. Six treatment conditions were employed: vehicle control, levetiracetam (1.25 mg/kg), levetiracetam (2.5 mg/kg), levetiracetam (5 mg/kg), levetiracetam (10 mg/kg) and levetiracetam (20 mg/kg). In the RAM task used, there was a one-hour delay between presentation of a subset of arms (5 arms available and 3 arms blocked) and completion of the eight-arm win-shift task (eight arms available). Rats were pre-treated 30-40 minutes before daily trials with a one-time drug/control treatment. The number of errors made by the rats after the delay was used as a measure of spatial memory retention. Errors were defined as instances when rats entered an arm from which food had already been retrieved in the pre-delay component of the trial or when rats re-visited an arm in the post-delay session that had already been visited. Paired t-tests were used to compare the number of errors between different doses of levetiracetam and vehicle control.

Parametric statistics (paired t-tests) was used to compare the retention test performance of the AI rats in the one-hour delay version of the RAM task in the context of different doses of levetiracetam and vehicle control (see FIG. 3). The average numbers of errors that occurred in the trials were also significantly fewer with levetiracetam treatment of 5 mg/kg/day (average no. of errors±standard error of the mean (SEM)=0.75±0.32) and 10 mg/kg/day (average no. of errors±SEM=0.80±0.27) than using vehicle control (average no. of errors±SEM=2.00±0.42). Relative to vehicle control treatment, levetiracetam significantly improved memory performance at 5 mg/kg/day (t(9)=2.18, p=0.057) and 10 mg/kg/day (t(9)=2.37, p=0.042).

Figure 4:
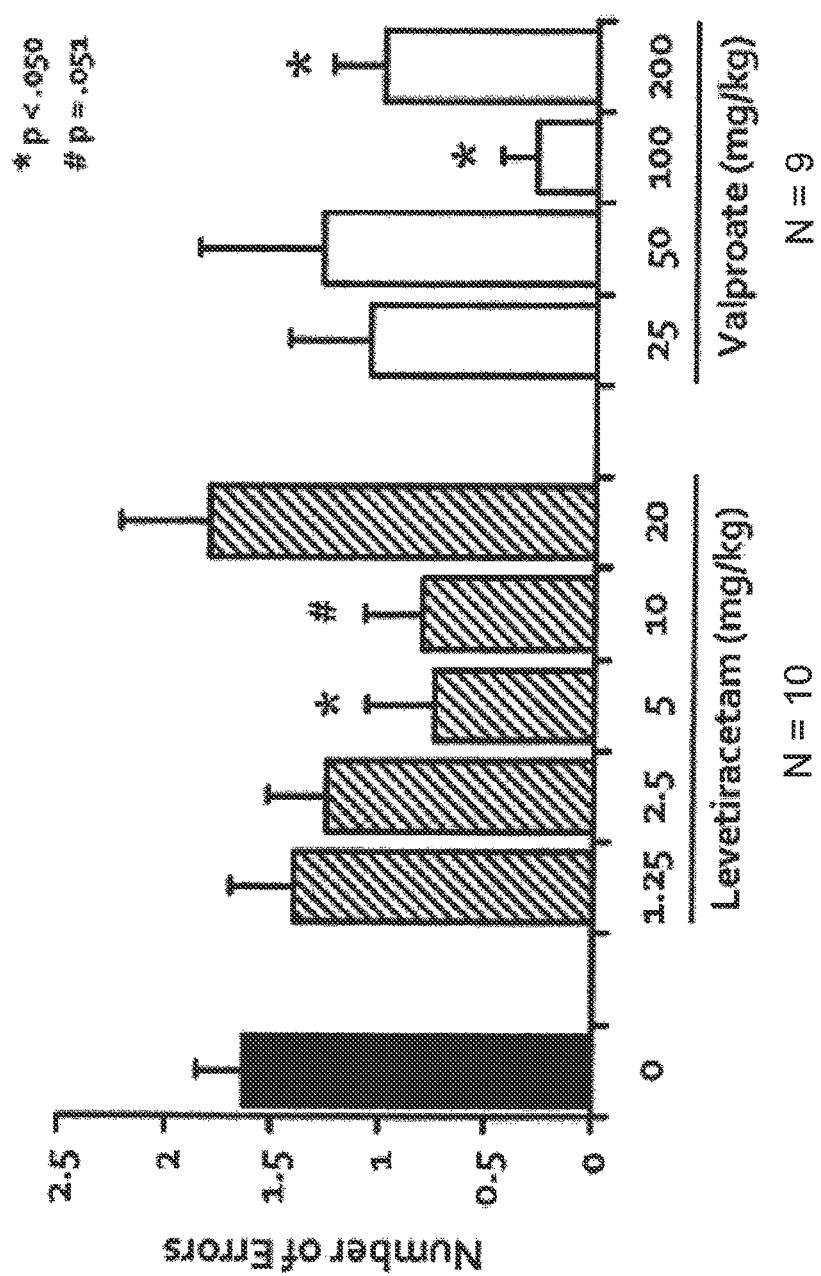
FIG. 4 depicts the effects of administering levetiracetam or valproate separately on the spatial memory retention of ten aged-impaired rats (AI) in an eight-arm Radial Arm Maze (RAM) test.
Figure 5:
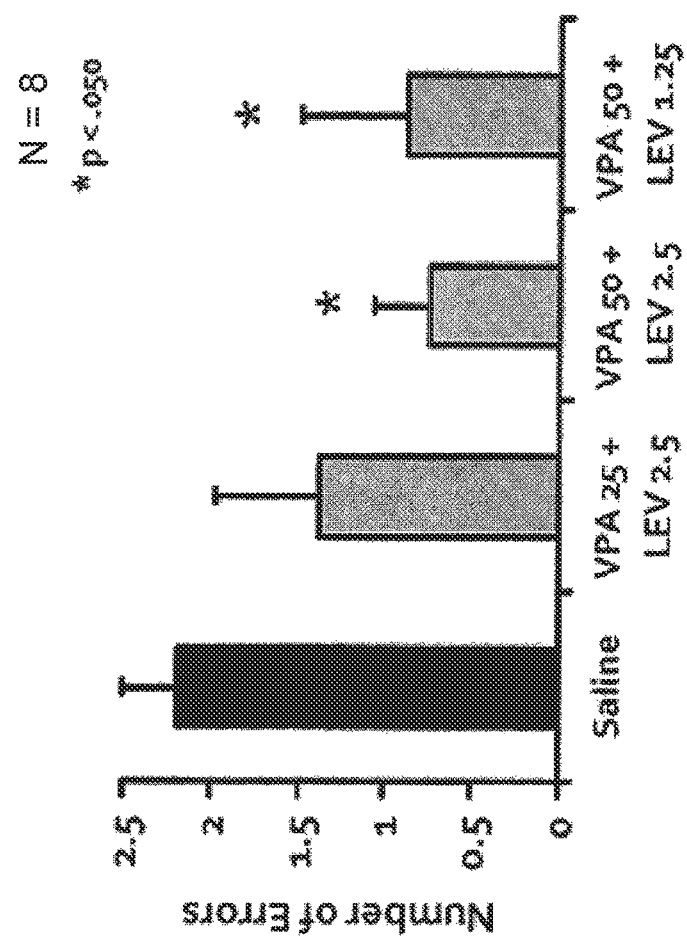
FIG. 5 depicts the effects of administering levetiracetam or valproate in combination on the spatial memory retention of ten aged-impaired rats (AI) in an eight-arm Radial Arm Maze (RAM) test.
Figure 6:
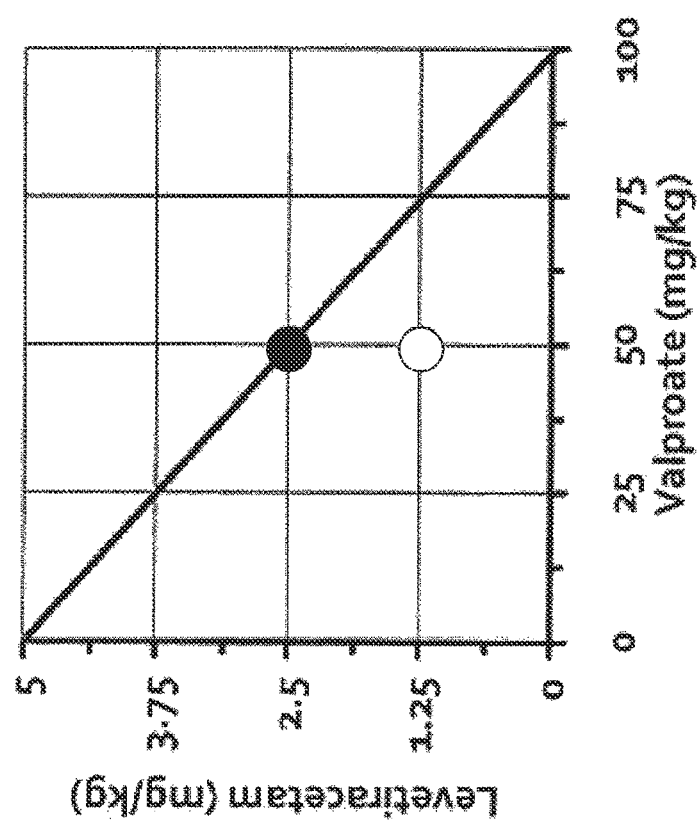
FIG. 6 shows an isobologram plotting levetiracetam dose against valproate dose. The diagonal straight line is the line of additivity, anchored on each axis by the lowest effective doses of valproate and levetiracetam when assessed individually.

The radial arm maze task was also used to evaluate the effect of a combination therapy with Levetiracetam (i.p. administration) and valproate (subcutaneous administration). Levetiracetam, on its own, was effective in reducing the number of errors by AI rats in the radial arm maze at 5-10 mg/kg doses, but not at 1.25 mg/kg or 2.5 mg/kg. Valproate, on its own, was effective at 100 mg/kg but not at 25 mg/kg or 50 mg/kg. See FIG. 4. Combining the two drugs, however, had a synergistic effect. A combined administration of 50 mg/kg valproate with 2.5 mg/kg levetiracetam, neither being an effective dose when administered individually, resulted in a reduced number of errors in the radial arm maze task. This result was also obtained at an even lower dose of 1.25 mg/kg levetiracetam combined with 50 mg/kg valproate. See FIG. 5. An isobologram of levetiracetam and valproate dosages confirmed that the effect of the combined 50 mg/kg valproate and 1.25 mg/kg levetivacetam (VPA 50+LEV 1.25; empty circle) had a synergistic (super-additive) effect. The combined 50 mg/kg valproate and 2.5 mg/kg levetivacetam (VPA 50+LEV 2.5; dark circle), on the other hand, had a simple additive effect, as indicated by its placement on the line. See FIG. 6.

To calculate the human equivalent dose (HED) for levetiracetam dosage for treatment of age-dependent cognitive impairment in humans, we employed the formula HED (mg/kg)=rat dose (mg/kg)×0.16 (see Estimating the Safe Starting Dose in Clinical Trials for Therapeutics in Adult Healthy Volunteers, December 2002, Center for Biologics Evaluation and Research). Therefore, the dosage of 5 mg/kg/day in rats is equivalent to 0.8 mg/kg/day in humans and the dosage of 10 mg/kg/day in rats is equivalent to 1.6 mg/kg/day in humans.

Example 3

Effect of Levetiracetam in Human Subjects with aMCI

A within-subjects trial of 8 weeks duration, involving 17 amnestic MCI (aMCI) subjects and 17 age-matched controls with a low dose treatment of levetiracetam is conducted. During the course of the study, each aMCI subject receives both drug and placebo treatments separately in two periods of two weeks each, with the order of treatments among different aMCI subjects counterbalanced (see FIG. 7). Age-matched control subjects treated with placebo serve as a further control. Cognitive testing and fMRI imaging data are obtained from the subjects after each two week period of drug/placebo treatment.

Participants and Clinical Characterization 17 right-handed aMCI patients are recruited from the Alzheimer's Disease Research Center (ADRC) at the Johns Hopkins Hospital and other referrals. An additional 17 right-handed healthy volunteers are recruited from the pool of control participants in the ADRC and other referrals. All participants are administered the Telephone Interview of Cognitive Status to determine if they are likely to pass the entry criteria of the study (including criteria for MRI scanning) All participants further undergo neurological, psychiatric, and neuropsychological examination using standardized instruments and methods. The psychiatric evaluation includes administration of the Structured Clinical Interview for DSM-IV Axis I Disorders and the Clinical Dementia Rating (CDR) scale. All aMCI patients have CDR scores of 0.5. Diagnosis of aMCI is based on the criteria proposed by Petersen et al. (e.g., "Mild cognitive impairment: Aging to Alzheimer's Disease," Oxford University Press, N.Y. (2003), which include a memory complaint (corroborated by an informant), impaired memory function on testing (1.5 standard deviations below norm), otherwise preserved cognitive functioning (within 1 standard deviation of norm), no decline in functional ability, and no dementia. Final aMCI diagnoses are reached by clinical consensus. Exclusion criteria include major neurological or psychiatric disorders, head trauma with loss of consciousness, history of drug abuse or dependency, and general contraindications to an MRI examination (e.g. cardiac pacemaker, aneurysm coils, claustrophobia). Each aMCI subject is required to have a study partner (i.e., an informant) who can provide information about the subject's daily function and assure that medications are taken appropriately. See FIGS. 18A and 18B.

Figure 7:
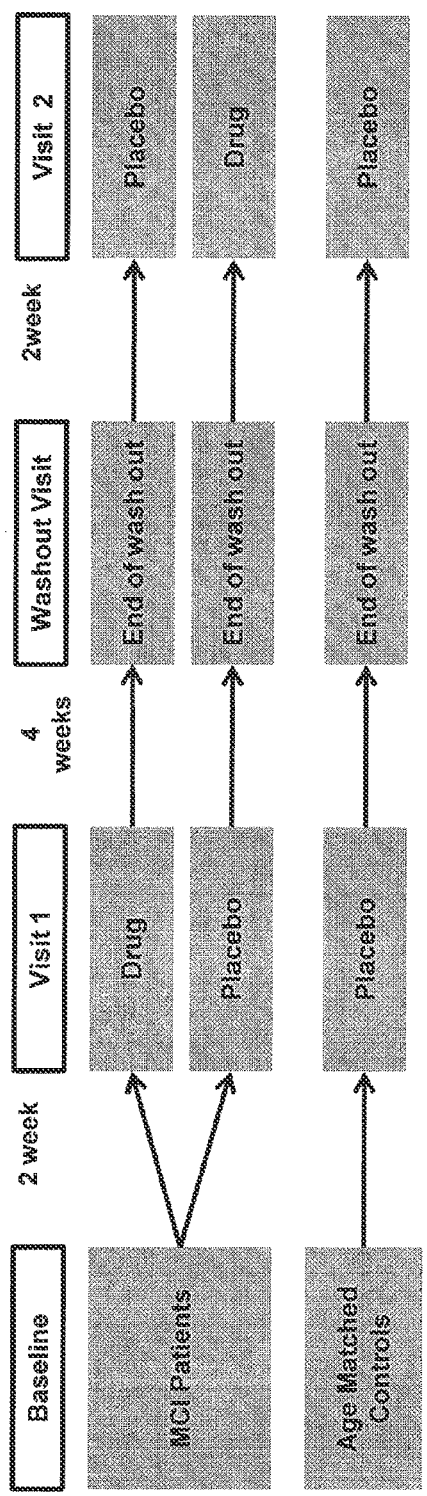
FIG. 7 depicts the experimental design of the human trials for levetiracetam treatment.

Study Visits:

The study consists of 4 visits over the course of 8 weeks (see FIG. 7). The Baseline Visit is for the purpose of performing medical, neurological, psychiatric, and neurocognitive assessments. Visits 1 and 2 are identical to the Baseline Visit but include a fMRI session. The Washout Visit, at the end of a 4 week washout period, is for the purpose of a brief clinical assessment and initiation of the second drug/placebo phase.

Baseline Visit:

At the screening visit, informed consent is obtained from the subject (and an informant in the case of MCI subjects). The subject and the informant participate in a standardized clinical interview that is used to determine the degree of the subject's functional impairment in daily life, based on the Clinical Dementia Rating (CDR) scale. The subject's medical, neurological, and psychiatric history is obtained (including a review of current medications), as well as the family history of dementia. Brief medical, neurological and psychiatric exams are conducted (including vital signs). Blood is drawn in order to perform standard laboratory tests needed to determine if the subject meets the entry criteria. The subject is re-screened for contraindications to MRI scanning, using the standard form employed at the Kirby Imaging Center. Brief cognitive testing is performed (described in section on neuropsychological assessment below). These assessments are used to determine if the subject meets the entry criteria. All of the foregoing are completed using standardized forms. If the subject meets entry criteria for the study, the subject is given the study medication (drug or placebo, randomly selected), and instructions about how it should be taken. The subject is advised about the potential for having suicidal thoughts and advised to stop taking the medication and immediately contact the study physician if this occurs.

Visit 1:

At the end of the first drug/placebo period 2 weeks after the Baseline Visit, the medical, neurological and psychiatric evaluations and cognitive testing are repeated. The subject is also clinically evaluated for suicidal ideation. Blood is drawn again to repeat the standard tests and to determine whether there are any changes related to drug treatment; the subject's blood levetiracetam level is also obtained. All medication dispensed at the Baseline Visit (drug or placebo) is collected and subject compliance with the medication regimen is assessed. The first fMRI session (with cognitive tests) is conducted on the same day, either immediately before or immediately after the clinical assessment. Subjects discontinue first period treatment at this visit.

Washout Visit:

At the end of a washout period (4 weeks) following Visit 1, the subject receives a brief medical screening, including a medical and psychiatric evaluation. Blood is drawn to obtain the blood levetiracetam level (to confirm washout). The subject is provided with new medication (drug or placebo, alternated from what was assigned in the previous treatment period) for the final phase of the study with instructions about how it should be taken.

Visit 2:

At approximately 2 weeks after the Washout Visit (i.e., 2 weeks after starting the second treatment period), the medical, neurological and psychiatric evaluations and the cognitive testing are repeated. The subject is clinically evaluated for suicidal ideation. Blood is drawn again to repeat the standard tests and to determine whether there were any changes related to drug treatment; the subject's blood levetiracetam level is also obtained. All medication dispensed at the Washout Visit is collected and subject compliance with the medication regimen is assessed. The second fMRI session (with cognitive tests) is repeated on the same day, either immediately before or immediately after the clinical assessment.

Neuropsychological Assessment

All participants undergo neuropsychological evaluation at the time of assessment for treatment efficacy (Visits 1 and 2), as well as at the Baseline Visit. The evaluation occurs outside of the scanner and includes the Buschke Selective Reminding Test (Buschke and Fuld, 1974) and the Verbal Paired Associates subtest, the Logical Memory subtest, the Visual Reproduction subtest of the Wechsler Memory Scale-Revised (WMS-R) (Wechsler, 1997), and the Benton Visual Retention Test, as these tasks are particularly sensitive to medial temporal lobe function and early memory problems (Marquis et al., 2002 and Masur et al., 1994). Additionally, subjects are asked to complete tests of more general cognitive function such as tests to assess general mental status, executive function, attention and general naming ability. All neuropsychological tests are administered by a trained research assistant during a 60-minute session. As the three neuropsychological assessments in this study occur within a time period of 8 weeks, different versions of the neuropsychological tests are used to minimize test specific practice effects. Breaks are provided to the subject as needed.

Drug Administration

As described above, the drug treatment period is the two weeks preceding Visit 1 or 2 (with the two week period preceding the other Visit being the placebo phase). For the subjects receiving the drug treatment, half a scored 250 mg tablet of levetiracetam is used to achieve a dose of 125 mg twice a day, which is approximately 3.6 mg/kg/day (assuming an average adult human weight of 70 kg).

All drug and placebo preparations are performed on a 1:1 allocation. The pharmacy randomizes patients to drug dose and condition as they enroll, and keep a list of drug assignment.

Levetiracetam is rapidly and almost completely absorbed after oral administration, and its bioavailability is not affected by food. Plasma half-life of levetiracetam is approximately 7±1 hour (expected to be 9-10 hours in elderly due to decreased renal function). Absorption is rapid, with peak plasma concentrations occurring about 1 hour following oral administration. Steady state can be achieved after 2 days of multiple twice-daily dosing.

A typical starting dose of levetiracetam in treating epilepsy in humans is 500 mg twice a day, which is approximately 14.3 mg/kg/day. The dosage is then is increased until optimal efficacy, up to 50 mg/kg/day. Thus, the dose used in this experiment is a quarter of the lowest human dose used for treating epilepsy.

Even lower dosages, e.g., of 25-60 mg twice a day, are contemplated, based on the results of previous animal studies that indicated low-dose efficacy. The highest effective doses of levetiracetam used in the animal model are 5-10 mg/kg (given acutely). The human equivalent dose (HED), calculated as described above, of this dosage for treatment of age-dependent cognitive impairment in humans is equivalent to 0.8-1.6 mg/kg/day (or 28-56 mg twice a day).

MRI Data Acquisition

Imaging data are obtained through high-resolution methods developed in the Stark laboratory. Data are collected on a Phillips 3 Tesla scanner (Eindhoven, The Netherlands) equipped with an 8-channel SENSE (Sensitivity Encoding) head coil, located at the F. M. Kirby Research Center for Functional Brain Imaging at the Kennedy Krieger Institute (Baltimore, Md.). High-resolution echo-planar images are collected using an acquisition matrix of 64×64, a repetition time of 1500 milliseconds, an echo time of 30 milliseconds, a flip angle of 70 degrees, a SENSE factor of 2, and an isotropic resolution of 1.5 mm×1.5 mm×1.5 mm with no gap. Nineteen oblique slices are acquired parallel to the principal longitudinal axis of the hippocampus and covered the entire medial temporal lobe region bilaterally. In addition to the functional runs, a whole-brain MPRAGE structural scan (parameters: 150 oblique slices, 1 mm isotropic resolution) is acquired.

Image Analysis

Data analysis is carried out using the Analysis for Functional Neuroimages (AFNI, release 2008_07_18_1710) software. Images are first co-registered to correct for within- and across-scan head motion. Acquisitions in which a significant motion event occur (more than 3 degrees of rotation or 2 mm of translation in any direction relative to prior acquisition), plus and minus one time repetition for 1.5 seconds, are excluded from the analyses. Structural anatomical data are registered to standard stereotaxic space (Talairach & Tournoux, 1988), and the same parameters are subsequently applied to the functional data. Behavioral vectors are produced to model different trial types.

The ROI-LDDMM (large deformation diffeomorphic metric mapping of the region of interest) method, a technique for cross-subject alignment, increases the power of multisubject regional fMRI studies by focusing the alignment power specifically on the ROIs (regions of interest) and not elsewhere in the brain. First, all subjects' anatomical and functional scans are normalized to the Talairach atlas using AFNI. Sub-regions of the medial temporal lobe and the hippocampus (bilateral entorhinal cortex, perirhinal cortex, parahippocampal cortex, CA3/dentate region, CA1 region, and subiculum) are segmented in three dimensions on the MPRAGE scans. The labels for the CA3 region and dentate gyms (DG) are combined. The anatomically defined ROIs are then used to calculate the ROI-LDDMM 3D vector field transformation for each subject using a customized template based on the mean of the entire sample tested as the target. The ROI-LDDMM transformations for each individual subject's ROIs are then applied to the fit coefficient maps.

Group data are analyzed using a two-way Analysis of Variance (ANOVA) with trial types and group as fixed factors, and subject as a random factor nested within group. A liberal peak threshold of $p<0.05$, along with a spatial extent threshold of 10 voxels are used to define functional ROIs on the overall F statistic. This approach, rather than using a direct pair-wise contrast, reduces voxel selection biases because any differences amongst the various conditions allowed for a voxel to be selected. This threshold is then combined with the anatomical segmentations to only include voxels inside the regions of interest. This serves to exclude voxels that does not change with any of the model's factors, effectively limiting the analysis to voxels showing any changes with task condition or group. Voxels within each functional ROI are collapsed for further analysis.

Cognitive Tests During fMRI Scans at Visits 1 and 2

Figure 10B:
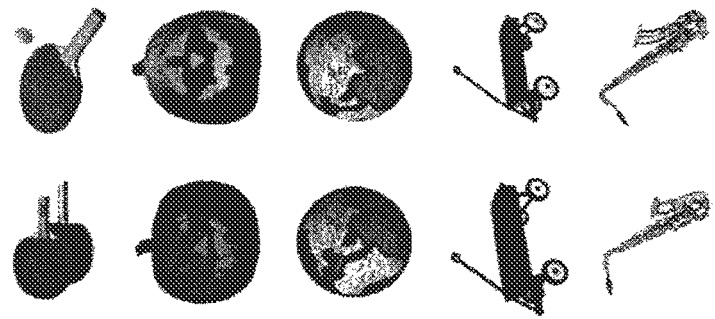
FIG. 10B shows sample pairs of similar ("lure") images.
Figure 10A:
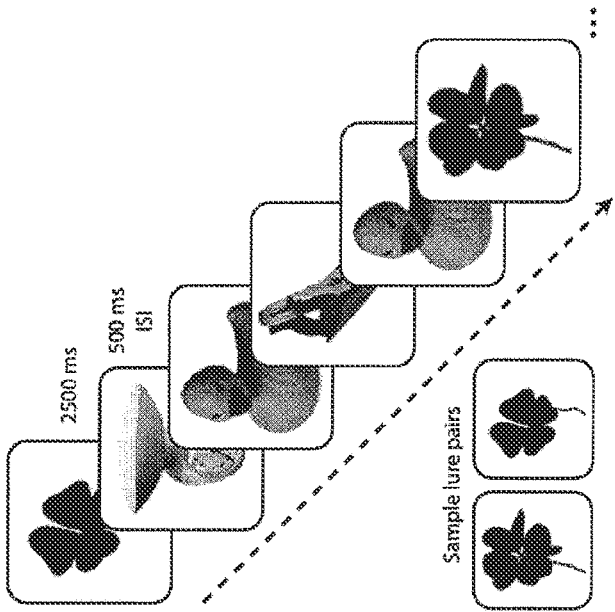
FIG. 10A depicts an example of the sequence of images shown to subjects in the explicit 3-alternative forced choice task described in Example 3.

The activity of the subject's medial temporal lobe is measured by functional MRI during the subject's participation in an explicit 3-alternative forced choice task, where participants view novel, repeated and similar ("lure") stimuli. The Psychophysics Toolbox extensions in Matlab 7.0 (The MathWorks, Natick, Mass.) is used for stimulus presentation and behavioral data collection. Stimuli are color photographs of common objects. Each participant undergoes a series of testing runs during the functional imaging sessions, each run consisting of a mix of three types of image pairs: similar pairs, identical pairs and unrelated foils. These image pairs are fully randomized throughout the run and presented individually as a series of images (see FIG. 10A). Participants are instructed to make a judgment as to whether each object seen is new, old or similar. Of critical interest are the participants' responses when presented with the second of the pair of similar objects (the "lure"; see FIG. 10B). The correct identification by the subject of lure stimuli as "similar," provides behavioral evidence of pattern separation, i.e., the separation of similar experiences into distinct non-overlapping representations. However, an incorrect indentification of lure stimuli as "old" or "new," indicates a failure of pattern separation. Identification of lure stimuli as "old" indicates that the subject focused on the similarities between the lure stimulus and the earlier-shown partner image. Identification of the lure stimulus as "new" indicates that the subject failed to recall the earlier-shown partner image altogether. Each run also contains a number of baseline trials that use a challenging perceptual discrimination task known to provide a lower and more-stable estimate of baseline activity in the medial temporal lobe (Stark & Squire, 2001 PNAS; Law et al, 2005).

A survey of the activity level of various subregions in the medial temporal lobe during the cognitive test, as measured by fMRI, shows that aMCI subjects have hyperactive DG/CA3 regions and a hypoactive entorhinal cortex during the performance of memory tasks, compared to age-matched control subjects.

Figures 8A, 8B:
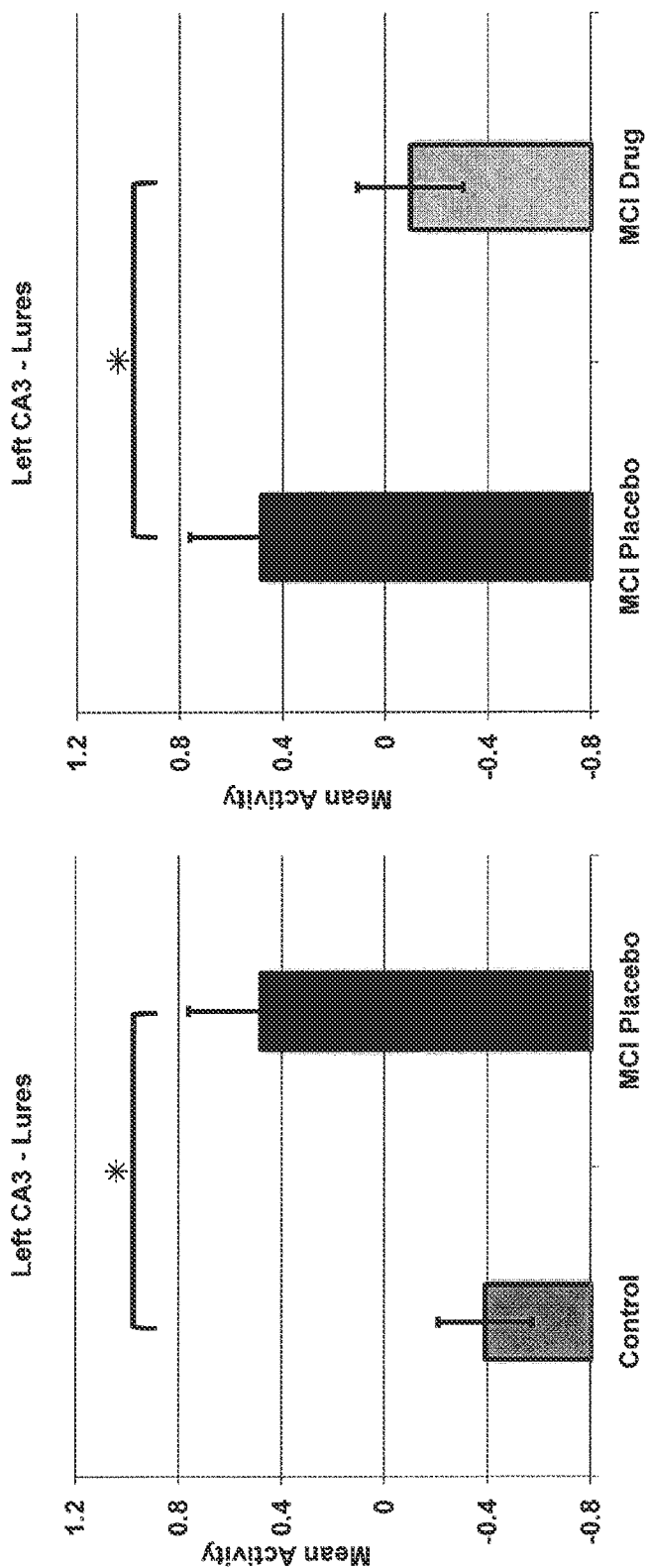
FIG. 8A depicts the average activity in the left CA3 of aMCI subjects with placebo treatment and age-matched control subjects with placebo treatment during the presentation of lure stimuli that the subject correctly identified as "similar."
FIG. 8B depicts the average activity in the left CA3 of aMCI subjects with placebo treatment or levetiracetam treatment (125 mg twice a day for two weeks) during the presentation of lure stimuli that the subject correctly identified as "similar."

We assess the level of activity in DG/CA3 during successful memory judgments in control and aMCI subjects. The mean activity is calculated from the average activity, as measured by fMRI, during the presentation of lure stimuli correctly identified by subject as "similar" that is calibrated for baseline activity. FIG. 8A shows that aMCI patients exhibit DG/CA3 hyperactivity when making these judgments ($p=0.013$). FIG. 8B, however, shows that treatment with levetiracetam reduces DG/CA3 hyper-activity in aMCI subjects ($p=0.037$). The activity level in the aMCI subject treated with the drug, in fact, is normalized to the extent that that it is statistically indistinguishable from the activity of control subjects treated with placebo. See FIG. 8C for the mean activity values shown in FIGS. 8A and 8B.

The activity level during successful memory judgments in EC is significantly lower in placebo-treated aMCI subjects compared to controls ($p=0.003$). See FIG. 9A. However, levetiracetam treatment normalizes activity in aMCI subjects in EC as well. See FIG. 9B. Levetiracetam treatment increases EC activity during memory judgments in aMCI subjects, such that it is statistically indistinguishable from placebo-treated control subjects. See FIG. 9B. See FIG. 9C for the mean activity values shown in FIGS. 9A and 9B.

Figure 11:
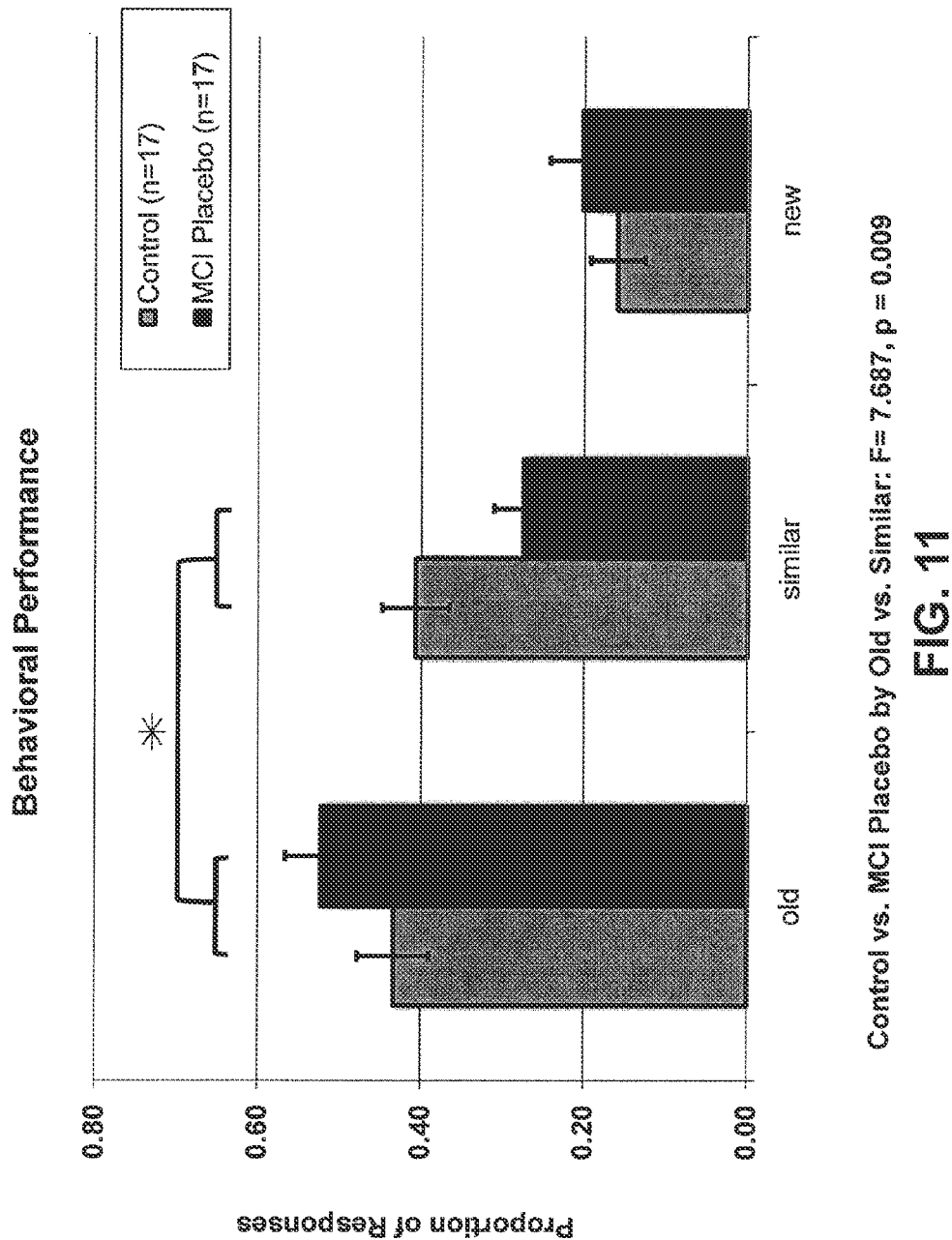
FIG. 11 shows the difference between the aMCI (placebo) subjects and age-matched control (placebo) subjects in their performance of the explicit 3-alternative forced choice task described in Example 3. Each bar represents the proportion of the subject responses (old, similar, or new) when presented with a lure image.
Figure 12:
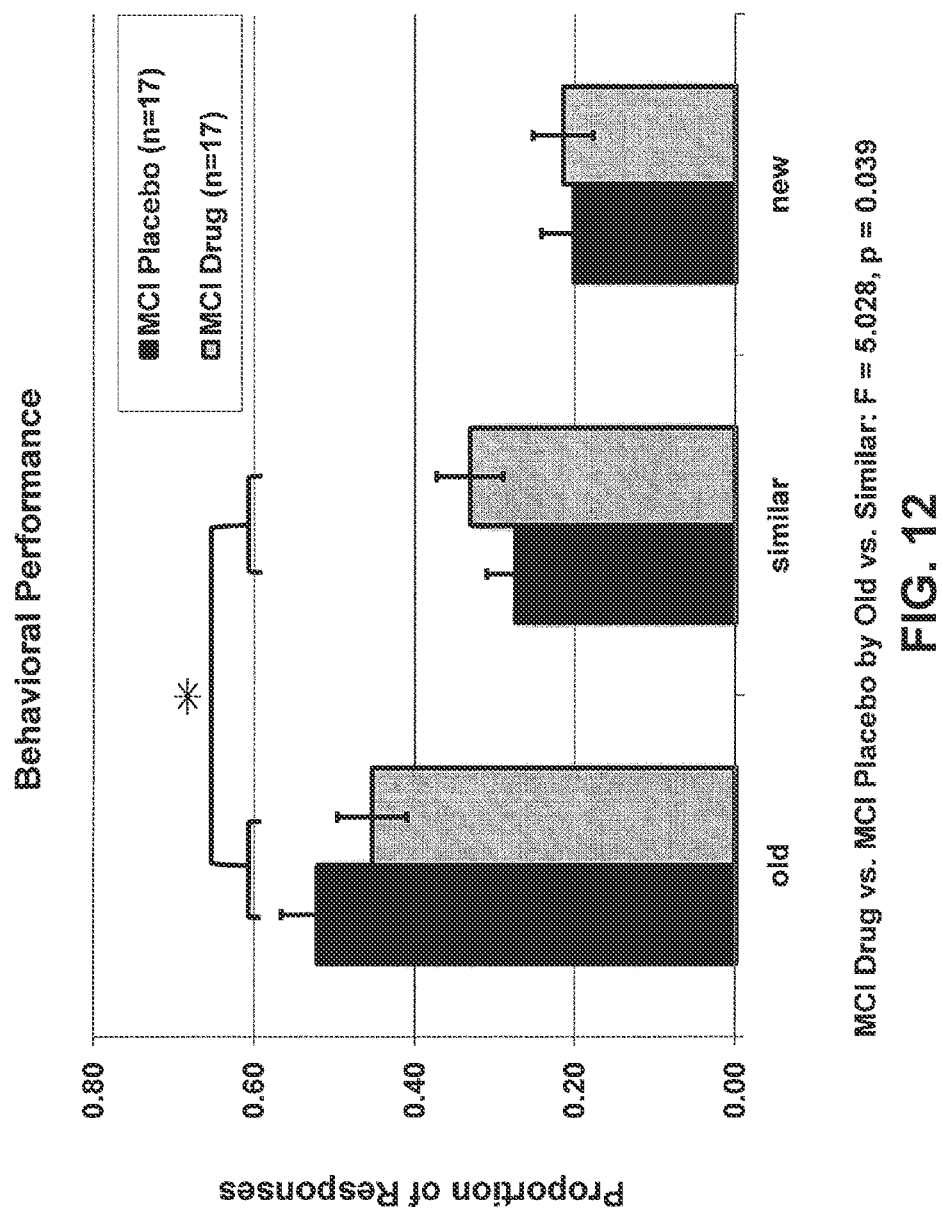
FIG. 12 shows the difference between the same aMCI subjects with placebo treatment or with levetiracetam treatment (125 mg twice a day for two weeks) in their performance of the explicit 3-alternative forced choice task described in Example 2. Each bar represents the proportion of the subjects responses (old, similar, or new) when presented with a lure image.

The normalization of DG/CA3 and EC activity during memory judgments by levetiracetam treatment is mirrored in the change seen in the aMCI subjects' performance in the cognitive task. With placebo treatment, aMCI patients perform worse than control subjects, correctly identify lure items as "similar" less often and incorrectly identifying them as "old" more often ($p=0.009$). See FIG. 11. However, the performance of aMCI subjects improves significantly under levetiracetam treatment. See FIG. 12. The interaction of more correct "similar" indenficiations with less incorrect "old" identifications under drug treatment results in a significant improvement in the performance of this memory task ($p=0.039$). See FIG. 13 for a table of the data represented in FIGS. 11 and 12.

Figures 15A, 15B:
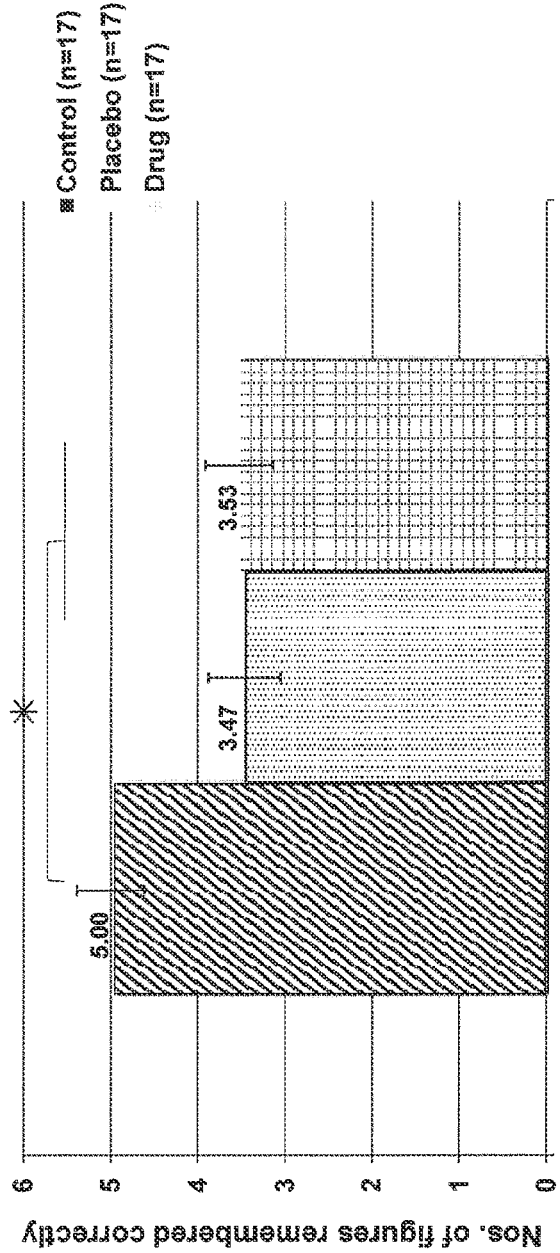
FIG. 15A shows the difference between the control (placebo) subjects and the aMCI subjects treated with placebo or with levetiracetam (125 mg twice a day for two weeks) in their performance of the Benton Visual Retention Test.
FIG. 15B is a table of the data represented in FIG. 15A.
Figures 16A, 16B:
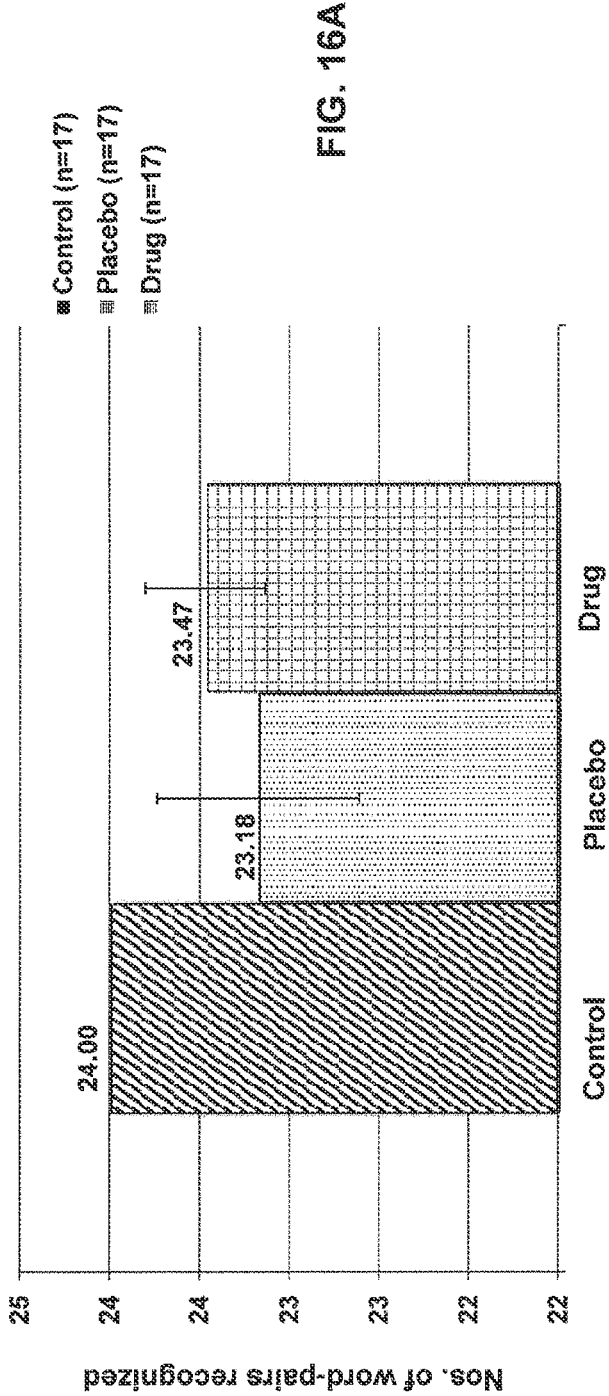
FIG. 16A shows the difference between the control (placebo) subjects and the aMCI subjects treated with placebo or with levetiracetam (125 mg twice a day for two weeks) in their performance of the Verbal Paired Associates Test—Recognition.
FIG. 16B is a table of the data represented in FIG. 16A.
Figures 17A, 17B:
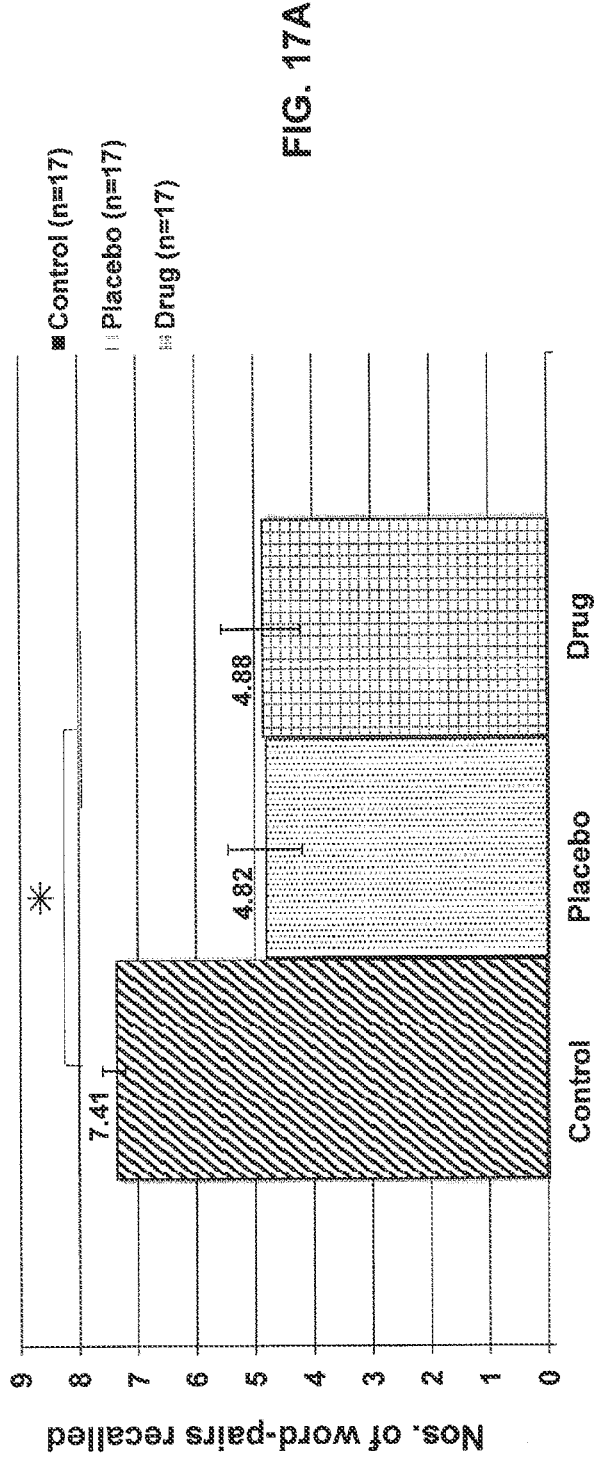
FIG. 17A shows the difference between the control (placebo) subjects and the aMCI subjects treated with placebo or with levetiracetam (125 mg twice a day for two weeks) in their performance of the Verbal Paired Associates Test—Delayed Recall.
FIG. 17B is a table of the data represented in FIG. 17A.

The performance of control-placebo subjects and aMCI subjects with drug or placebo treatment is also compared in other common cognitive tests, such as the Buschke Selective Reminding Test—Delayed Recall (FIGS. 14A and 14B), the Benton Visual Rentention Test (FIGS. 15A and 15B), Verbal Paired Associates Test—Recognition (FIGS. 16A and 16B) and Verbal Paired Associates Test—Delayed Recall (FIGS. 17A and 17B). In all of these tests, aMCI subjects treated with placebo perform worse than placebo-treated control subjects, and levetiracetam treatment fail to rescue performance in aMCI subjects.

There are a number of possible reasons why levetiracetam treatment does not help aMCI subjects with performance in these other cognitive tests. The explicit 3-alternative forced choice task done in the fMRI study is a task that is especially sensitive to DG/CA3 function. As such, the performance of the subjects in this task may be particularly attuned to the changes in DG/CA3 activity resulting from levetiracetam treatment. Further, the aMCI subjects were treated with levetiracetam for only two weeks prior to the administration of the cognitive tests. It is contemplated that a treatment duration of longer than two weeks, e.g., 16 weeks or 8 months, for the drug treatment will result in improved efficacy. Finally, comparative animal studies (see Example 1) indicate that an even lower dose would be more effective. The human dosage of 125 mg twice a day is equivalent to a rat dosage of 22.3 mg/kg/day. As is shown in Example 2 and FIG. 3, 20 mg/kg levetiracetam is too high a dose in rats, and it fails to improve the performance of AI rats in the radial maze task. The effective doses of levetiracetam used in the animal model are 5-10 mg/kg. The human equivalent dose (HED) of the optimal rat dose is 0.8-1.6 mg/kg/day. Such a dosage would result in the administration of 28-56 mg twice a day (which is substantially lower than the 125 mg twice a day used in this study). Thus, it is contemplated that aMCI subjects will exhibit a further normalization of DG/CA3 and EC activity, as well as further improved performance in cognitive tests, if they are treated with lower doses equivalent to the effective doses in rat, e.g., 25-60 mg twice a day of levetiracetam.

Example 4

Effect of Levetiracetam in Human Subjects with aMCI

A within-subjects trial of 8 weeks duration, involving 38 amnestic MCI (aMCI) subjects and 17 age-matched controls with a low dose treatment of levetiracetam is conducted. During the course of the study, each aMCI subject receives both drug and placebo treatments separately in two periods of two weeks each, with the order of treatments among different aMCI subjects counterbalanced (see FIG. 7). Age-matched control subjects treated with placebo serve as a further control. Cognitive testing and fMRI imaging data are obtained from the subjects after each two-week period of drug/placebo treatment.

Participants and Clinical Characterization 38 right-handed aMCI patients are recruited from the Alzheimer's Disease Research Center (ADRC) at the Johns Hopkins Hospital and other referrals. An additional 17 right-handed healthy volunteers are recruited from the pool of control participants in the ADRC and other referrals. All participants are administered the Telephone Interview of Cognitive Status to determine if they are likely to pass the entry criteria of the study (including criteria for MRI scanning) All participants further undergo neurological, psychiatric, and neuropsychological examination using standardized instruments and methods. The psychiatric evaluation includes administration of the Structured Clinical Interview for DSM-IV Axis I Disorders and the Clinical Dementia Rating (CDR) scale. All aMCI patients have CDR scores of 0.5. Diagnosis of aMCI is based on the criteria proposed by Petersen et al. (e.g., "Mild cognitive impairment: Aging to Alzheimer's Disease," Oxford University Press, N.Y. (2003), which include a memory complaint (corroborated by an informant), impaired memory function on testing (generally 1.5 standard deviations below the norm and at least 1 standard deviation below the norm), otherwise preserved cognitive functioning (within 1 standard deviation of norm), no decline in functional ability, and no dementia. Final aMCI diagnoses are reached by clinical consensus. Exclusion criteria include major neurological or psychiatric disorders, head trauma with loss of consciousness, history of drug abuse or dependency, and general contraindications to an MRI examination (e.g. cardiac pacemaker, aneurysm coils, claustrophobia). Each aMCI subject is required to have a study partner (i.e., an informant) who can provide information about the subject's daily function and assure that medications are taken appropriately.

Study Visits:

The study consists of 4 visits over the course of 8 weeks (see FIG. 7). The Baseline Visit is for the purpose of performing medical, neurological, psychiatric, and neurocognitive assessments. Visits 1 and 2 are identical to the Baseline Visit but include an fMRI session. The Washout Visit, at the end of a 4 week washout period, is for the purpose of a brief clinical assessment and initiation of the second drug/placebo phase.

Baseline Visit:

At the screening visit, informed consent is obtained from the subject (and an informant in the case of MCI subjects). The subject and the informant participate in a standardized clinical interview that is used to determine the degree of the subject's functional impairment in daily life, based on the Clinical Dementia Rating (CDR) scale. The subject's medical, neurological, and psychiatric history is obtained (including a review of current medications), as well as the family history of dementia. Brief medical, neurological and psychiatric exams are conducted (including vital signs). Blood is drawn in order to perform standard laboratory tests needed to determine if the subject meets the entry criteria. The subject is re-screened for contraindications to MRI scanning, using the standard form employed at the Kirby Imaging Center. Brief cognitive testing is performed (described in section on neuropsychological assessment below). These assessments are used to determine if the subject meets the entry criteria. All of the foregoing are completed using standardized forms. If the subject meets entry criteria for the study, the subject is randomly assigned to either the 62.5 mg BID or 250 mg BID study group and given the study medication (drug or placebo, randomly selected), and instructions about how it should be taken. The subject is advised about the potential for having suicidal thoughts and advised to stop taking the medication and immediately contact the study physician if this occurs.

Visit 1:

At the end of the first drug/placebo period 2 weeks after the Baseline Visit, the medical, neurological and psychiatric evaluations and cognitive testing are repeated. The subject is also clinically evaluated for suicidal ideation. Blood is drawn again to repeat the standard tests and to determine whether there are any changes related to drug treatment; the subject's blood levetiracetam level is also obtained. All medication dispensed at the Baseline Visit (drug or placebo) is collected and subject compliance with the medication regimen is assessed. The first fMRI session (with cognitive tests) is conducted on the same day, either immediately before or immediately after the clinical assessment. Subjects discontinue first period treatment at this visit.

Washout Visit:

At the end of a washout period (4 weeks) following Visit 1, the subject receives a brief medical screening, including a medical and psychiatric evaluation. Blood is drawn to obtain the blood levetiracetam level (to confirm washout). The subject is provided with new medication (drug or placebo, alternated from what was assigned in the previous treatment period) for the final phase of the study with instructions about how it should be taken.

Visit 2:

At approximately 2 weeks after the Washout Visit (i.e., 2 weeks after starting the second treatment period), the medical, neurological and psychiatric evaluations and the cognitive testing are repeated. The subject is clinically evaluated for suicidal ideation. Blood is drawn again to repeat the standard tests and to determine whether there were any changes related to drug treatment; the subject's blood levetiracetam level is also obtained. All medication dispensed at the Washout Visit is collected and subject compliance with the medication regimen is assessed. The second fMRI session (with cognitive tests) is repeated on the same day, either immediately before or immediately after the clinical assessment.

Neuropsychological Assessment

All participants undergo neuropsychological evaluation at the time of assessment for treatment efficacy (Visits 1 and 2), as well as at the Baseline Visit. The evaluation occurs outside of the scanner and includes the Buschke Selective Reminding Test (Buschke and Fuld, 1974) and the Verbal Paired Associates subtest, the Logical Memory subtest, the Visual Reproduction subtest of the Wechsler Memory Scale-Revised (WMS-R) (Wechsler, 1997), and the Benton Visual Retention Test, as these tasks are particularly sensitive to medial temporal lobe function and early memory problems (Marquis et al., 2002 and Masur et al., 1994). Additionally, subjects are asked to complete tests of more general cognitive function such as tests to assess general mental status, executive function, attention and general naming ability. All neuropsychological tests are administered by a trained research assistant during a 60-minute session. As the three neuropsychological assessments in this study occur within a time period of 8 weeks, different versions of the neuropsychological tests are used to minimize test specific practice effects. Breaks are provided to the subject as needed.

Drug Administration

As described above, the drug treatment period is the two weeks preceding Visit 1 or 2 (with the two week period preceding the other Visit being the placebo phase). For the subjects receiving the 250 mg BID (BID stands for twice daily) drug treatment, two 250 mg tablets of levetiracetam are used to achieve a dose of 250 mg twice a day, i.e., 500 mg/day, which is approximately 7.1 mg/kg/day (assuming an average adult human weight of 70 kg). For the subjects receiving the 62.5 mg BID drug treatment, a quarter of a scored 250 mg tablet of levetiracetam is used to achieve a dose of 62.5 twice a day, i.e., 125 mg/day which is approximately 1.5 mg/kg/day.

All drug and placebo preparations are performed on a 1:1 allocation. The pharmacy randomizes patients to drug dose and condition as they enroll, and keep a list of drug assignment.

Levetiracetam is rapidly and almost completely absorbed after oral administration, and its bioavailability is not affected by food. Plasma half-life of levetiracetam is approximately 7±1 hour (expected to be 9-10 hours in elderly due to decreased renal function). Absorption is rapid, with peak plasma concentrations occurring about 1 hour following oral administration. Steady state can be achieved after 2 days of multiple twice-daily dosing.

A typical starting dose of levetiracetam in treating epilepsy in humans is 500 mg twice a day, which is approximately 14.3 mg/kg/day. The dosage is then is increased until optimal efficacy, up to 50 mg/kg/day. Thus, the 250 mg BID dose (500 mg/day) used in this experiment is one-half of the lowest human dose used for treating epilepsy. The 62.5 mg BID dose (125 mg/day) is one eighth of the lowest human dose used for treating epilepsy.

MRI Data Acquisition

Imaging data are obtained through high-resolution methods developed in the Stark laboratory. Data are collected on a Philips 3 Tesla scanner (Eindhoven, The Netherlands) equipped with an 8-channel SENSE (Sensitivity Encoding) head coil, located at the F. M. Kirby Research Center for Functional Brain Imaging at the Kennedy Krieger Institute (Baltimore, Md.). High-resolution echo-planar images are collected using an acquisition matrix of 64×64, a repetition time of 1500 milliseconds, an echo time of 30 milliseconds, a flip angle of 70 degrees, a SENSE factor of 2, and an isotropic resolution of 1.5 mm×1.5 mm×1.5 mm with no gap. Nineteen oblique slices are acquired parallel to the principal longitudinal axis of the hippocampus and covered the entire medial temporal lobe region bilaterally. In addition to the functional runs, a whole-brain MPRAGE structural scan (parameters: 231 oblique slices, 0.65 mm isotropic resolution) is acquired.

Image Analysis

Data analysis is carried out using the Analysis for Functional Neuroimages (AFNI, release 2010_10_19_1028) software. Images are first co-registered to correct for within- and across-scan head motion. Acquisitions in which a significant motion event occur (more than 3 degrees of rotation or 2 mm of translation in any direction relative to prior acquisition), plus and minus one time repetition for 1.5 seconds, are excluded from the analyses. Structural anatomical data are registered to standard stereotaxic space (Talairach & Tournoux, 1988), and the same parameters are subsequently applied to the functional data. Behavioral vectors are produced to model different trial types.

The ROI-LDDMM (large deformation diffeomorphic metric mapping of the region of interest) method, a technique for cross-subject alignment, increases the power of multisubject regional fMRI studies by focusing the alignment power specifically on the ROIs (regions of interest) and not elsewhere in the brain. First, all subjects' anatomical and functional scans are normalized to the Talairach atlas using AFNI. Sub-regions of the medial temporal lobe and the hippocampus (bilateral entorhinal cortex, perirhinal cortex, parahippocampal cortex, CA3/dentate region, CA1 region, and subiculum) are segmented in three dimensions on the MPRAGE scans. The labels for the CA3 region and dentate gyms (DG) are combined. The anatomically defined ROIs are then used to calculate the vector field transformation for each subject using the Advanced Normalization Tools (ANTs) software package and a customized template based on the mean of the entire sample tested as the target. The resulting vector transformations for each individual subject's ROIs are then applied to the fit coefficient maps.

Group data are analyzed using a two-way Analysis of Variance (ANOVA) with trial types and group as fixed factors, and subject as a random factor nested within group. A liberal peak threshold of $p<0.07$, along with a spatial extent threshold of 40 voxels are used to define functional ROIs on the overall F statistic. This approach, rather than using a direct pair-wise contrast, reduces voxel selection biases because any differences amongst the various conditions allowed for a voxel to be selected. This threshold is then combined with the anatomical segmentations to only include voxels inside the regions of interest. This serves to exclude voxels that does not change with any of the model's factors, effectively limiting the analysis to voxels showing any changes with task condition or group. Voxels within each functional ROI are collapsed for further analysis.

Cognitive Tests During fMRI Scans at Visits 1 and 2

The activity of the subject's medial temporal lobe is measured by functional MRI during the subject's participation in an explicit 3-alternative forced choice task, where participants view novel, repeated and similar ("lure") stimuli. The Psychophysics Toolbox extensions in Matlab 7.0 (The MathWorks, Natick, Mass.) is used for stimulus presentation and behavioral data collection. Stimuli are color photographs of common objects. Each participant undergoes a series of testing runs during the functional imaging sessions, each run consisting of a mix of three types of image pairs: similar pairs, identical pairs and unrelated foils. These image pairs are fully randomized throughout the run and presented individually as a series of images (see FIG. 10A). Participants are instructed to make a judgment as to whether each object seen is new, old or similar. Of critical interest are the participants' responses when presented with the second of the pair of similar objects (the "lure"; see FIG. 10B). The correct identification by the subject of lure stimuli as "similar," provides behavioral evidence of pattern separation, i.e., the separation of similar experiences into distinct non-overlapping representations. However, an incorrect identification of lure stimuli as "old" or "new," indicates a failure of pattern separation. Identification of lure stimuli as "old" indicates that the subject focused on the similarities between the lure stimulus and the earlier-shown partner image. Identification of the lure stimulus as "new" indicates that the subject failed to recall the earlier-shown partner image altogether. Each run also contains a number of baseline trials that use a challenging perceptual discrimination task known to provide a lower and more-stable estimate of baseline activity in the medial temporal lobe (Stark & Squire, 2001 PNAS; Law et al, 2005).

A survey of the activity level of various subregions in the medial temporal lobe during the cognitive test, as measured by fMRI, shows that aMCI subjects have hyperactive DG/CA3 regions and a hypoactive entorhinal cortex during the performance of memory tasks, compared to age-matched control subjects.

Figures 22A, 22B:
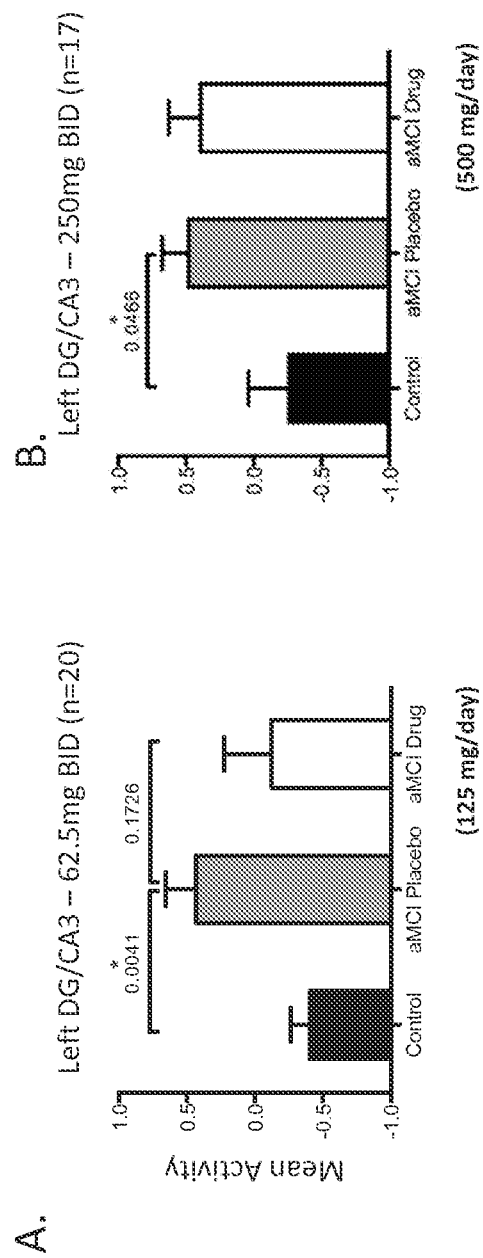
FIG. 22A and FIG. 22B depict the effects of levetiracetam on fMRI activities in Dentate Gyrus/CA3 region of aMCI patients at a dose of 62.5 mg BID and 250 mg BID.

We assess the level of activity in DG/CA3 during successful memory judgments in control and aMCI subjects. The mean activity is calculated from the average activity, as measured by fMRI, during the presentation of lure stimuli correctly identified by subject as "similar" that is calibrated for baseline activity. FIGS. 22A and 22B show that aMCI patients in both the 62.5 mg BID cohort (N=20) and 250 mg BID cohort (N=17) exhibit DG/CA3 hyperactivity when making these judgments ($p=0.0041$ and $p=0.0466$ respectively). Treatment with levetiracetam does not significantly reduce the DG/CA3 hyperactivity in aMCI subjects in the 250 mg BID or the 62.5 mg BID cohort.

Figures 23A, 23B:
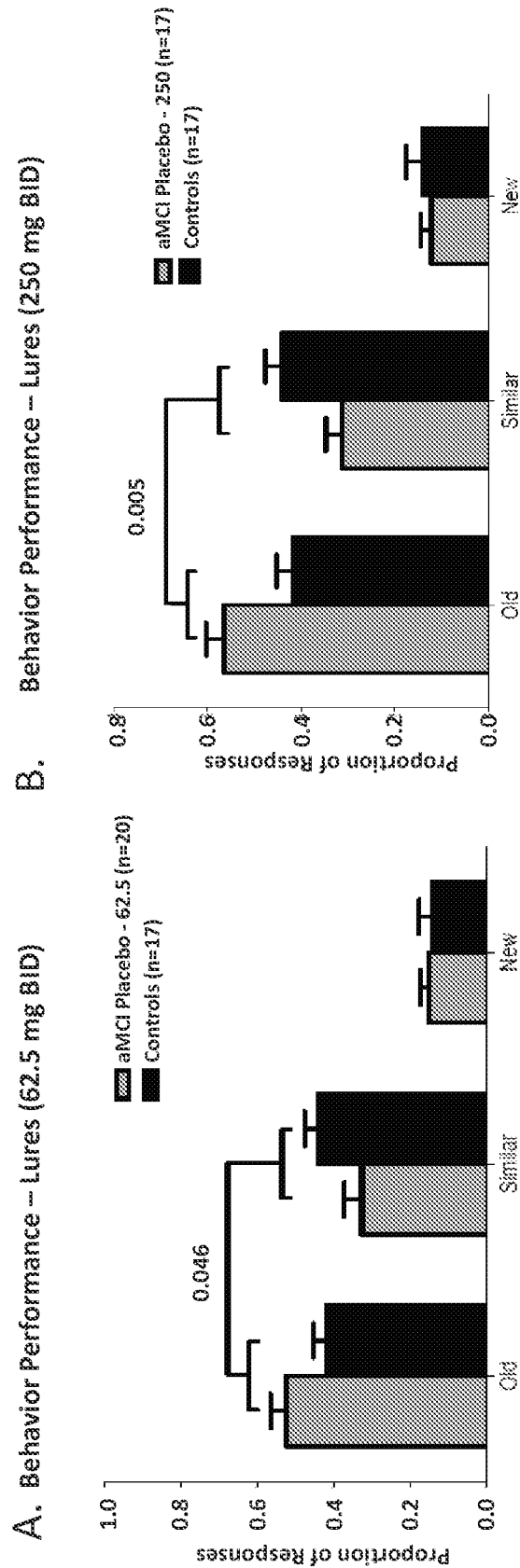
FIG. 23A and FIG. 23B show the difference between the aMCI (placebo) subjects and age-matched control (placebo) subjects in their performance of the explicit 3-alternative forced choice task described in Example 4 at a dose of 62.5 mg BID placebo and 250 mg BID placebo. Each bar represents the proportion of the subject responses (old, similar, or new) when presented with a lure image.

The level of DG/CA3 activity during memory judgments by levetiracetam treatment is mirrored in the change seen in the aMCI subjects' performance in the cognitive task. With placebo treatment, aMCI patients perform worse than control subjects, correctly identify lure items as "similar" less often and incorrectly identifying them as "old" more often in both the 62.5 mg BID cohort and the 250 mg BID cohort. See FIGS. 23A and 23B. However, the performance of aMCI subjects improves significantly under 62.5 mg BID levetiracetam treatment. See FIG. 24A. The interaction of more correct "similar" identifications with less incorrect "old" identifications under drug treatment results in a significant improvement in the performance of this memory task ($p=0.041$). The performance of aMCI subjects does not significantly improve under 250 mg BID levetiracetam treatment ($p=0.2396$). See FIG. 24B.

Example 5

Effect of Brivaracetam and Seletractam in Aged-Impaired Rats

Subjects

Aged, male Long-Evans rats were obtained at 8-9 month of age from Charles River Laboratories (Raleigh, N.C.) and housed in a vivarium at Johns Hopkins University until 24-26 month of age. Young rats obtained from the same source were housed in the same vivarium and tested at 6 month of age. All rats were individually housed at 25° C. and maintained on a 12 hr light/dark cycle. Food and water were provided ad libitum unless noted otherwise. The rats were examined for health and pathogen-free status throughout the experiments, as well as necropsies at the time of sacrifice. All procedures in the current investigations were approved by the Institutional Animal Care and Use Committee in accordance with the National Institutes of Health directive.

Background Characterization of Cognitive Status

All rats were screened in a standardized assessment of spatial cognition prior to the studies with experimental treatments. That background assessment used a well-established Morris Water Maze protocol. The MWM protocol was substantially the same as the one described in Example 1. See, also, Gallagher et al., Behav. Neurosci. 107:618-626, (1993). Briefly, the rats were trained for eight days (three trials per day) to locate a camouflaged escape platform that remained at the same location throughout training in a water maze. Every sixth trial consisted of a probe trial (free swim with no escape platform) that served to assess the development of a spatially localized search for the escape platform. During these probe trials, a learning index was generated from the proximity of the rat to the escape platform and was used to define impairment in the aged rats. The learning index is the sum of weighted proximity scores obtained during probe trials, with low scores reflecting a search near the escape platform and high scores reflecting searches farther away from the platform (Gallagher et al, 1993). Cue training (visible escape platform) occurred on the last day of training to test for sensorimotor and motivational factors independent of spatial learning. Aged rats with impaired spatial memory performance (i.e., those with learning index scores outside the young "normative" range) but successful cued training performance were characterized as Aged-Impaired rats (i.e., AI rats). The AI rats were used for the studies as described below.

Treatments

The radial arm maze experiments used acute administration of seletracetam (0-4 mg/kg), brivaracetam (0-4 mg/kg), or saline vehicle given by intraperitoneal injection (in a volume of 1 ml/kg) 30-40 min prior to test sessions. In the chronic treatment experiment, memory-impaired aged rats were implanted subcutaneously in the intrascapular region with osmotic mini-pumps (ALZET, Durect Corporation, Cupertino, Calif.) with brivaracetam (2 mg/kg/day) or saline vehicle starting two weeks prior to assessment in the water maze.

Behavioral Assessment in the Radial Arm Maze

A radial arm maze (RAM) task was used to assess effects of acute drug treatment with seletracetam and brivaracetam. This protocol allowed within-subject assessment across drugs at different doses. The radial maze consisted of eight arms projecting from each side of an octagonal center platform, with a food well located at the distal end of each arm. Plexiglas blocks could be positioned to prevent entry into any arm. Extra-maze cues were provided in the room surrounding the maze and illumination was provided by an overhead light.

Figure 19:
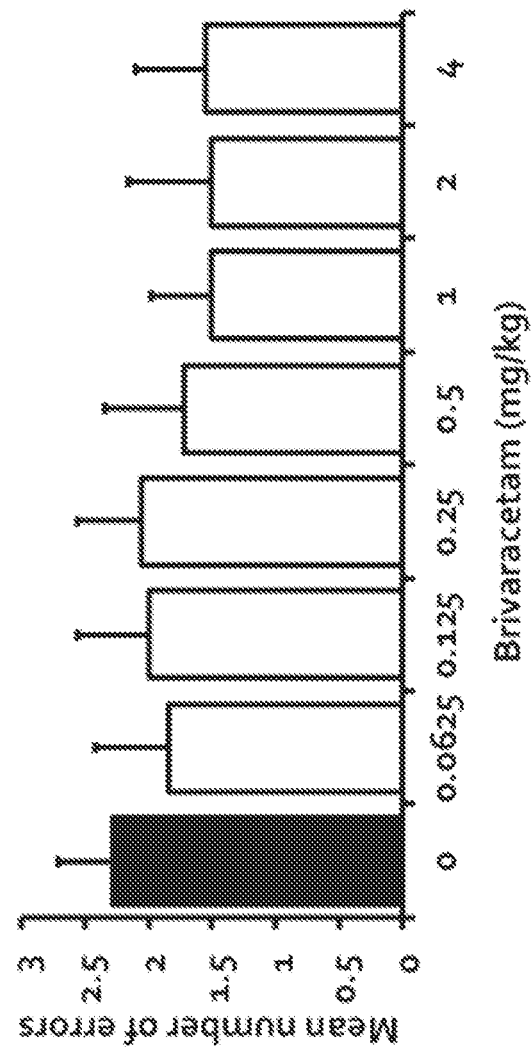
FIG. 19 depicts the effects of administering brivaracetam on the memory performance of nine aged-impaired rats in an eight-arm Radial Arm Maze task. Doses of brivaracetam administered to the AI rats include 0.0625 mg/kg, 0.125 mg/kg, 0.25 mg/kg, 0.5 mg/kg, 1 mg/kg, 2 mg/kg and 4 mg/kg. Means and SEMs for the number of errors are shown as the y-axis.
Figure 20:
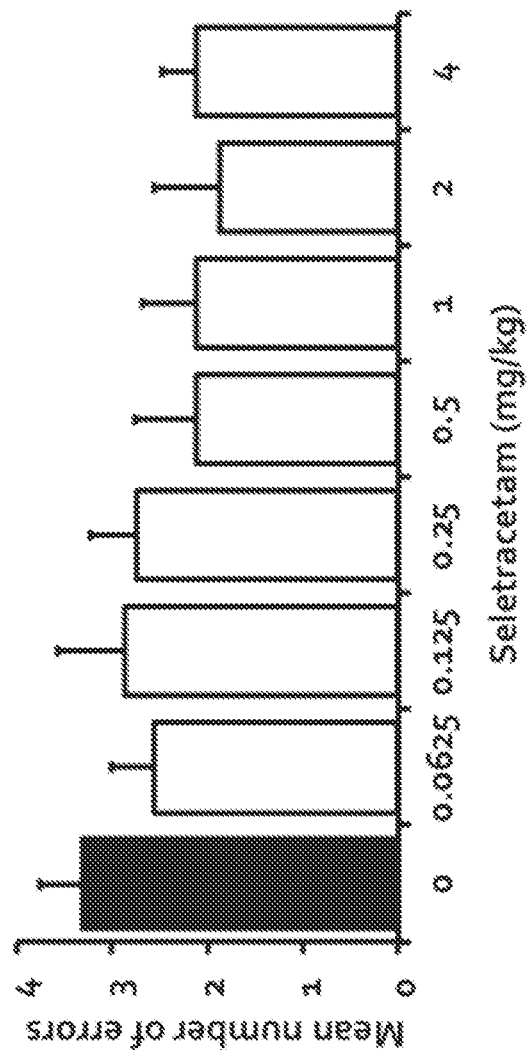
FIG. 20 depicts the effects of administering seletracetam on the memory performance of nine aged-impaired rats in an eight-arm Radial Arm Maze test. Doses of seletracetam administered to the AI rats include include 0.0625 mg/kg, 0.125 mg/kg, 0.25 mg/kg, 0.5 mg/kg, 1 mg/kg, 2 mg/kg and 4 mg/kg. Means and SEMs for the number of errors are shown as the y-axis.

Pre-training, as described in detail in Chappell et al. Neuropharmacology 37: 481-487, (1998), consisted of habituation, standard win-shift training, and win-shift training with delays interposed between information and memory test phases. Drug treatments began two days after the completion of pre-training Three arms were blocked at the beginning of each trial (information phase). The identity and configuration of the blocked arms were varied across trials. Food-deprived rats were allowed to retrieve food reward (Kellogg's Froot Loops cereal) from the five unblocked arms. The rat was then removed from the maze for 2 hr (retention interval), during which time the barriers on the blocked arms were removed allowing access to all eight arms. Rats were then placed back onto the center platform and allowed to retrieve the remaining food rewards (memory test phase). An error consisted of returning to an arm (all four paws on the arm) from which food had already been obtained. Memory-impaired aged rats (n=8 for seletracetam, and n=9 for brivaracetam) were first tested with a series of drug doses in ascending/descending order; each dose was thus tested twice, with one washout day in between each determination. The number of errors made in the retention phase after the 2-hr delay was used to assess memory performance. See FIG. 19 and FIG. 20. A series of different doses of brivaracetam was tested: 0.0625 mg/kg, 0.125 mg/kg, 0.25 mg/kg, 0.5 mg/kg, 1 mg/kg, 2 mg/kg and 4 mg/kg. A series of different doses of seletracetam was tested: 0.0625 mg/kg, 0.125 mg/kg, 0.25 mg/kg, 0.5 mg/kg, 1 mg/kg, 2 mg/kg and 4 mg/kg. As shown in FIG. 19, brivaracetam has a significant effect as a function of dose in the range tested (repeated measures ANOVA for within-subject contrasts, $F(1, 8)=6.046$, $p=0.039$). As shown in FIG. 20, seletracetam also has a significant effect as a function of dose in the range tested (repeated measures ANOVA for within-subject contrasts, $F(1, 7)=12.577$, $p=0.009$).

Behavioral Assessment in the Water Maze

Figures 21A, 21B:
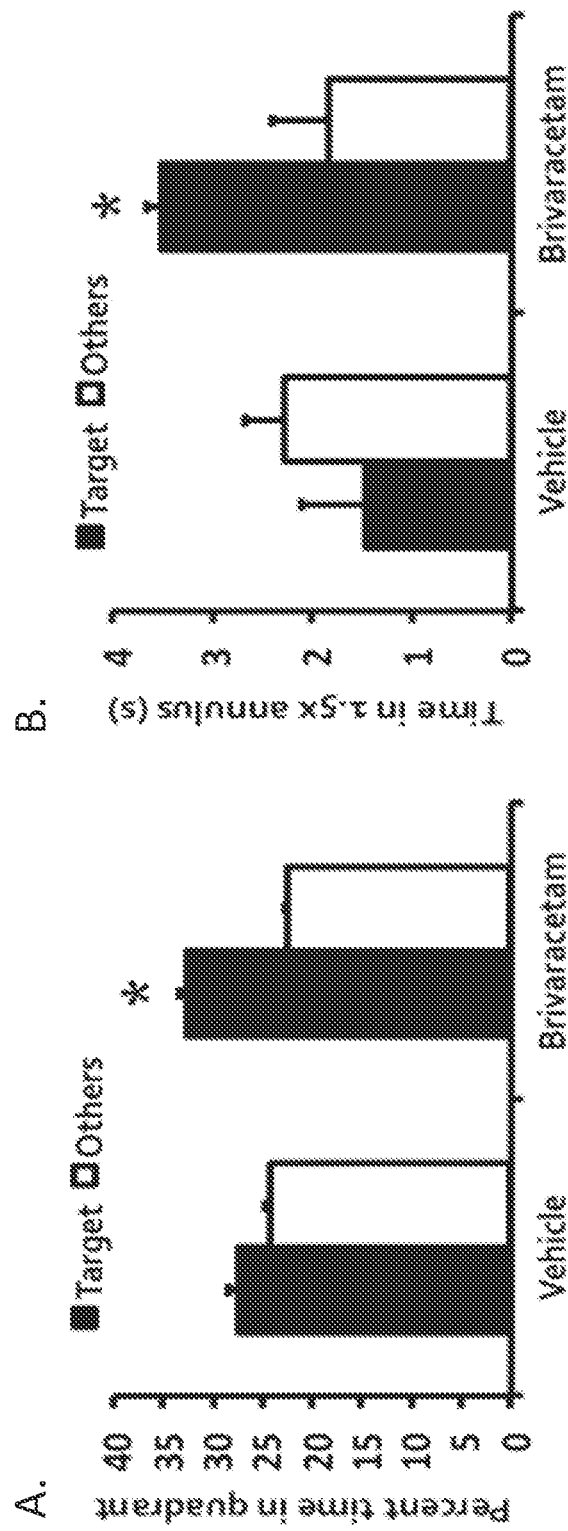
FIG. 21A and FIG. 21B depict the performance of aged-impaired rats (n=3/group) treated with brivaracetam at a dose of 2 mg/kg/day after 14 days in the water maze task. Rats treated with brivaracetam at 2 mg/kg/day (t(2)=10.000, p=0.010) but not vehicle (t(2)=1.964, p=0.188) showed a significant spatial bias for the target quadrant compared to the other controls quadrants. Brivaracetam-treated rats (2 mg/kg/day) also spent significantly more time in the target quadrant than the vehicle-treated rats, t(4)=3.881, p=0.018. Brivaracetam-treated rats (2 mg/kg/day) spent significantly more time in the target annulus (area surrounding the location of the escape platform) than the vehicle-treated rats, t(4)=3.109, p=0.036.

Rats were trained and tested in a novel water maze environment to assess the effect of drug treatment. The water maze used here was housed in a different building and was surrounded by curtains with a novel set of patterns relative to the maze used for initial assessment of cognitive status. The training protocol consisted of 6 trials per day for 2 days to locate a submerged escape platform. On each trial, a rat was released in the maze from one of four equally spaced starting positions around the perimeter of the pool. The starting position varied from trial to trial. If the rat did not locate the escape platform within 60 s on any trial, the experimenter guided and placed the rat on the platform, where it remained for 20 s. The rat was then removed from the platform and placed in a holding cage for another 40 s before the next trial. Approximately 24 hr after the last training trial, a probe test in the absence of the escape platform was given to assess spatial memory. Results of the behavior assessment in the Water Maze task were shown in FIG. 21A and FIG. 21B. Rats treated with brivaracetam at 2 mg/kg/day ($t(2)=10.000$, $p=0.010$) but not vehicle ($t(2)=1.964$, $p=0.188$) showed a significant spatial bias for the target quadrant compared to the other controls quadrants. In addition, brivaracetam-treated rats (2 mg/kg/day) spent significantly more time in the target quadrant than the vehicle-treated rats, $t(4)=3.881$, $p=0.018$. Brivaracetam-treated rats (2 mg/kg/day) spent significantly more time in the target annulus (area surrounding the location of the escape platform) than the vehicle-treated rats, $t(4)=3.109$, $p=0.036$.

Example 6

Chronic Treatment with Levetiracetam in Aged-Impaired Rats

Subjects

Aged, male Long-Evans rats were obtained at 8-9 month of age from Charles River Laboratories (Raleigh, N.C.) and housed in a vivarium at Johns Hopkins University until 24-26 month of age. Young rats obtained from the same source were housed in the same vivarium and tested at 6 month of age. All rats were individually housed at 25° C. and maintained on a 12 hr light/dark cycle. Food and water were provided ad libitum unless noted otherwise. The rats were examined for health and pathogen-free status throughout the experiments, as well as necropsies at the time of sacrifice. All procedures in the current investigations were approved by the Institutional Animal Care and Use Committee in accordance with the National Institutes of Health directive.

Background Behavioral Characterization

All rats were screened in a standardized assessment of spatial cognition prior to the studies with experimental treatments. That background assessment used a well-established Morris water maze protocol as described in Gallagher et al, 1993. Briefly, the rats were trained for eight days (three trials per day) to locate a camouflaged escape platform that remained at the same location throughout training in a water maze. Every sixth trial consisted of a probe trial (free swim with no escape platform) that served to assess the development of a spatially localized search for the escape platform. During these probe trials, a learning index was generated from the proximity of the rat to the escape platform and was used to define impairment in the aged rats. The learning index is the sum of weighted proximity scores obtained during probe trials, with low scores reflecting a search near the escape platform and high scores reflecting searches farther away from the platform (Gallagher et al, 1993). Cue training (visible escape platform) occurred on the last day of training to test for sensorimotor and motivational factors independent of spatial learning. Aged rats with impaired spatial memory performance (i.e., those with learning index scores outside the young "normative" range) but successful cued training performance were used for the studies as described below.

Surgery and Treatments

Under isoflurane anesthesia, memory-impaired aged rats were implanted subcutaneously in the intrascapular region with osmotic mini-pumps (ALZET, Durect Corporation, Cupertino, Calif.) with levetiracetam (10 mg/kg/day) or saline vehicle for four weeks prior to perfusion. Young rats, which served as controls, received either saline vehicle in mini-pumps or no implantation.

Perfusion and Tissue Preparation

At the end of the 4-week treatment period, rats were anesthetized with isoflurane and perfused transcardiacally with 0.1 M phosphate buffer saline, followed by 4% paraformaldehyde in phosphate buffer. Brains were removed and post-fixed in paraformaldehyde overnight. The brains were then moved into 4% paraformaldehyde in phosphate buffer containing 16% sucrose. The brains were then sectioned with a freezing microtome on the coronal plane at 40 µm and stored in either 4% paraformaldehyde at 4° C. for in situ hybridization or cryoprotectant at −20° C. for immunohistochemistry.

Probe Synthesis

Probe templates were synthesized as described in Haberman et al. (2008). Initial primer sequences for reelin were as follows: left, agtactcagacgtgcagtgg, right, ctcatgaagcaaagtcaa; PCR products were verified by restriction endonuclease digestion. Initial PCR products were amplified further with the same PCR primers that had been modified by the addition of T7 or SP6 RNA polymerase binding sites. PCR products containing T7 and SP6 extensions were purified by SVgel and a PCR cleanup kit (Promega). 35S-UTP labeled riboprobe was then generated using the Maxiscript kit (Ambion). The probe was then phenol/choloroform extracted and precipitated in ethanol at −80° C. The final probe was resuspended in RNase-free water and the specific activity was determined by scintillation counter.

In Situ Hybridization

In situ hybridization was carried out as described by Haberman et al., (2008). Free-floating tissue sections were washed in 0.75% glycine in 0.1M phosphate buffer two times, followed by a single wash in phosphate buffer. After that, sections were reacted in Proteinase K buffer containing 1.0 µg/ml proteinase K for 30 minutes at 37° C. Sections were then treated with acetic anhydride solution (11.3% triethanolamine, 0.25% acetic anhydride, 0.04 M acetic acid) for 10 minutes at room temperature. This was followed by two 15-minute washes in 2× sodium chloride/citrate buffer (SSC buffer; 20× concentration, 3M NaCl, 0.3M sodium citrate). Next, sections were transferred to hybridization buffer containing 20% formamide, 0.4×Denhardt's solution, 4% dextran sulfate, and 1.6×SSC) supplemented with 0.25 mg/ml tRNA, 0.33 mg/ml sheared salmon sperm DNA, 100 mM DTT, and 1×10$^7$ cpm/ml 35S-UTP-labeled probe for overnight reaction at 60° C. The following day, sections were washed at 60° C. in 4×SSC/0.01M DTT and 2×SSC/50% formamide. They were then incubated with RNase (20 µg/ml) at 37° C. for 30 min. Sections were washed with progressively decreasing concentrations of SSC before mounting on slides. Slides were dried overnight, exposed to a phosphoimager screen, and quantified by using ImageQuant (GE Healthcare). Digital images were acquired of entorhinal cortical sections from the same levels for all animals and the subregion of interest was outlined and quantified. Sections were averaged to obtain a single score for each animal.

Immunohistochemistry

Tissue was labeled with anti-SOM antiserum (Santa Cruz Biotechnology; cat. no. SC7819-P) using an established immunoperoxidase protocol and tissue sections were processed concurrently to minimize inter-replication variability (Haberman et al., 2009). The anti-SOM antiserum can detect somatostatin. Briefly, sections were washed in 0.1M phosphate-buffered saline (PBS) to remove cryoprotectant, and endogenous peroxidases were quenched in 0.3% H202 in PBS. After additional PBS washes, sections were blocked in 5% normal horse serum in PBS with 0.3% Triton. Sections were then incubated with primary antibody at a dilution of 1:1600 in PBS containing 0.15% Triton and 3% normal serum for 72 hours at 4° C. with agitation. Following primary antibody incubation, sections were washed in PBS and reacted with horse anti-goat IgG biotinylated secondary antibody (Vector Laboratories Inc., Burlingame, Calif.) diluted in PBS with 0.15% Triton and 5% normal horse serum for 45 minutes. The secondary antibody was detected with avidin-biotin complex (ABC Elite; Vector Laboratories Inc., Burlingame, Calif.) and the avidin-biotin complex was visualized with nickel-enhanced diaminobenzadine (Vector Laboratories Inc., Burlingame, Calif.). Tissue sections were mounted onto coated slides and dried, dehydrated with increasing concentrations of ethanol, cleared with xylene, and coverslipped using DPX mounting media.

Interneuron quantification was performed using a Zeiss Axioplan 2 microscope equipped with a motorized stage. All analyses were conducted blind with regards to animal age and cognitive status. The dentate hilar region was defined using the Paxinos and Watson rat brain atlas (1998). Dorsal hilar neuron counts were derived bilaterally from four matched tissue sections per animal with a 40× objective lens (Bregma −3.80 mm to −4.16 mm). Neuron counts were analyzed as the total number of hilar interneurons per hippocampal section for each rat.

Results

Figure 25:
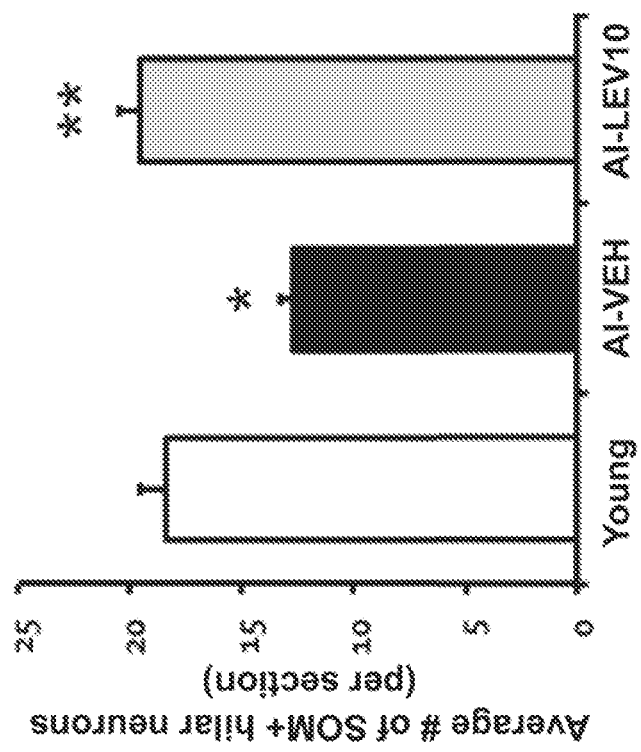
FIG. 25 shows that administering levetiracetam at a dose of 10 mg/kg/day and vehicle in osmotic minipumps for four weeks in aged-impaired rats restores sematostatin in DG hilus.

Somatostatin is a peptide hormone that regulates the endocrine system and affects neurotransmission and cell proliferation via interaction with G protein-coupled somatostatin receptors and inhibition of the release of numerous secondary hormones. Somatostatin levels in the brain have been shown to drop as low as 10-20% in association with aging and Alzheimer's disease progression. A four-week treatment with levetiracetam at a dose of 10 mg/kg/day in aged-impaired rats restores the levels of somatostatin in DG hilus. See FIG. 25. Aged-impaired rats that were administered a saline vehicle rather than drug possessed significantly lower numbers of SOM-immunoreactive hilar neurons relative to both young and levetiracetam treated aged rats ($N=18$; $F2,20=15.739$, $p<0.001$; AI-LEV vs Y, $p=0.679$; AI-LEV vs AI-VEH, $p<0.01$; AI-VEH vs Y, $p<0.001$).

Figure 26:
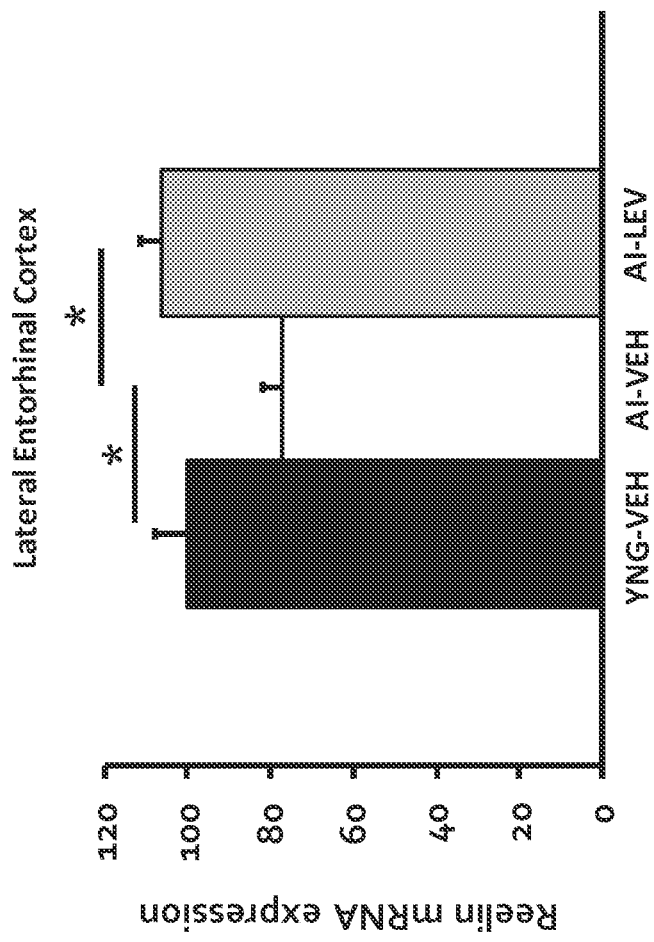
FIG. 26 shows that administering levetiracetam at a dose of 10 mg/kg/day and vehicle in osmotic minipumps for four weeks in aged-impaired rats restores reelin in Entorhinal Cortex (EC2).
Figures 27A, 27B, 27C:
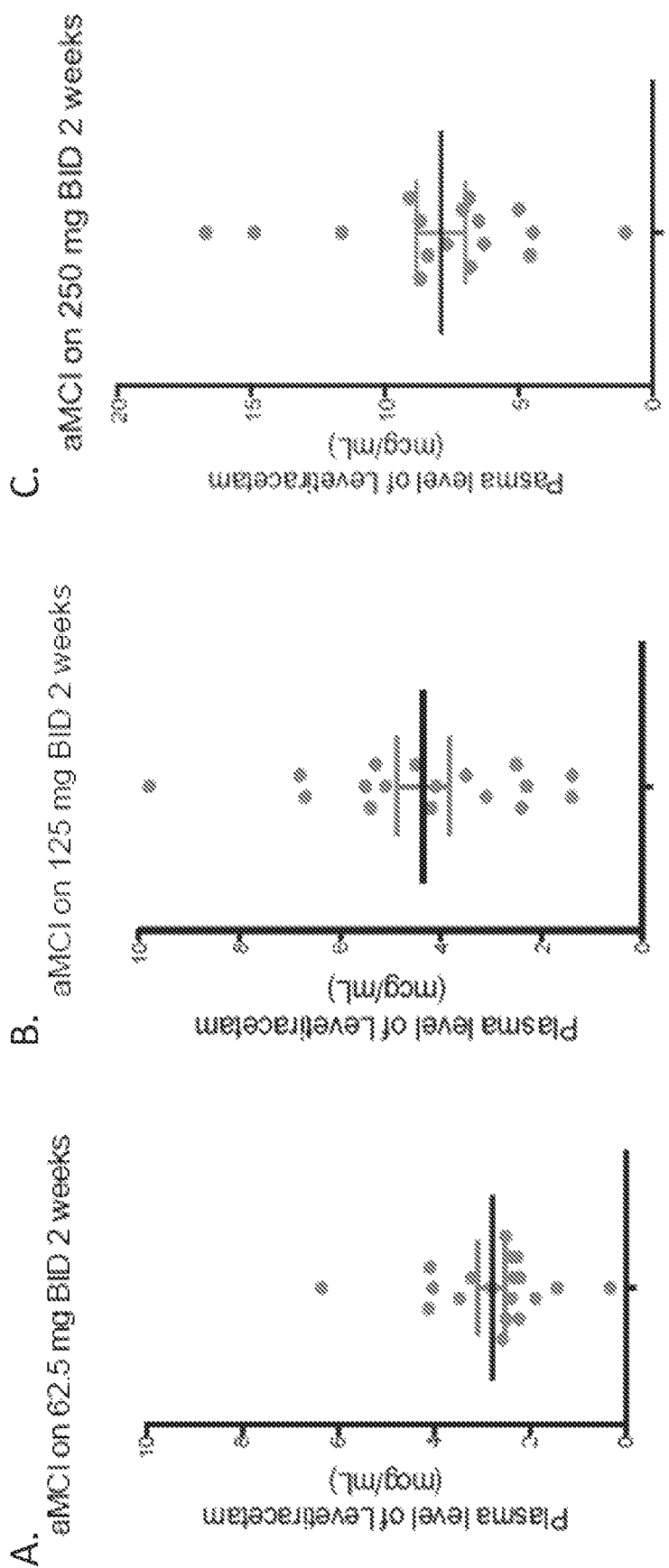
FIGS. 27A-27C depict the levetiracetam blood plasma levels for the aMCI patients at a dose of 62.5 mg BID, 125 mg BID and 250 mg BID levetiracetam.

Reelin is a large secreted extracellular matrix glycoprotein that helps regulate processes of neuronal migration and positioning in the developing brain by controlling cell-cell interactions. Reduced reelin expression in EC2 neurons has been observed in aged rats with memory loss, in hAPPJ20 AD mice, as well as in human AD brains (Chin et al. 2007; Stranahan et al. 2010). A four-week treatment with levetiracetam at a dose of 10 mg/kg/day in aged-impaired rats restores the levels of reelin in Entorhinal Cortex (EC2). See FIG. 26. A one-way ANOVA shows a significant difference among the groups, $F(2, 20)=5.035$, $p=0.017$. Additional analysis shows that reelin mRNA expression in the lateral entorhinal cortex of AI rats treated with vehicle controls (AI-VEH) is significantly lower than that of young rats, $t(13)=2.790$, $p=0.015$. Treatment with levetiracetam in AI rats at a dose of 10 mg/kg/day for 28 days (AI-LEV) significantly increased the expression of reelin, $t(13)=2.386$, $p=0.033$ (compared to AI-VEH).

Example 7

Evaluation of Levetiracetam Blood Plasma Levels

Human: in the human studies described in Examples 3 and 4, a subject's levetiracetam blood plasma level was assessed at each visit. The subject's blood was drawn by the Johns Hopkins Phlebotomy Service and analysis of levetiracetam blood plasma levels was conducted either by the Johns Hopkins Core laboratory or by MedTox Laboratories in St. Paul, Minn. for the 62.5 mg BID cohort, the 125 mg BID cohort and the 250 mg BID cohort. Upon completion of the levetiracetam treatment, subjects in the 62.5 mg BID cohort showed a mean levetiracetam blood plasma level of 2.88 mcg/ml (SEM±0.288), while levels in the 125 mg BID had 4.4 mcg/ml (SEM±0.53) and subjects in the 250 mg BID cohort showed mean levetiracetam blood plasma level of 7.9 mcg/ml (SEM±0.92). See FIGS. 27A-27C.

Rats: Blood was drawn from aged-impaired rats by cardiac puncture during perfusion after a 28-day levetiracetam treatment period and sent for analysis of levetiracetam plasma levels by MedTox Laboratories in St. Paul, Minn. Aged-impaired rats treated with 10 mg/kg/day of levetiracetam showed a mean levetiracetam blood plasma level of 3.8 mcg/ml (SEM±0.255), while those treated with 60 mg/kg/day showed a mean levetiracetam blood plasma level of 22.4 mcg/ml (SEM±3.371).

What is claimed is:

1. A method for treating cognitive impairment, for delaying or slowing the progression of said cognitive impairment, or for reducing the rate of decline of cognitive function, in a subject having or at risk of having said cognitive impairment or decline of cognitive function, the method comprising administering to said subject brivaracetam, or a pharmaceutically acceptable salt, hydrate, solvate, polymorph, or prodrug thereof, at a daily dose of 0.1 mg-350 mg, wherein the cognitive impairment or decline of cognitive function accompanies bipolar disorder, mental retardation, Parkinson's disease, autism, compulsive behavior, or substance addiction.

2. The method of claim 1, wherein the brivaracetam, or the pharmaceutically acceptable salt, hydrate, solvate, polymorph, or prodrug thereof, is administered in an extended release form.

3. The method of claim 2, wherein the extended release form is a controlled release form, a prolonged release form, a sustained release form, a delayed release form, or a slow release form.

* * * * *